United States Patent
Weiner et al.

(10) Patent No.: US 10,287,347 B2
(45) Date of Patent: *May 14, 2019

(54) TREATMENT OF CANCER WITH ANTI-LAP MONOCLONAL ANTIBODIES

(71) Applicant: The Brigham and Women's Hospital, Inc., Boston, MA (US)

(72) Inventors: Howard L. Weiner, Brookline, MA (US); Galina Gabriely, Brookline, MA (US); Andre Pires Da Cunha, Boston, MA (US); Takatoku Oida, Osaka (JP)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/649,373

(22) Filed: Jul. 13, 2017

(65) Prior Publication Data

US 2018/0030128 A1    Feb. 1, 2018

Related U.S. Application Data

(63) Continuation of application No. PCT/US2016/013408, filed on Jan. 14, 2016.

(60) Provisional application No. 62/103,401, filed on Jan. 14, 2015.

(51) Int. Cl.
| | |
|---|---|
| *A61K 39/395* | (2006.01) |
| *C07K 16/22* | (2006.01) |
| *C07K 16/28* | (2006.01) |
| *A61K 45/06* | (2006.01) |
| *C07K 16/30* | (2006.01) |
| *G01N 33/574* | (2006.01) |
| *A61K 39/00* | (2006.01) |

(52) U.S. Cl.
CPC .......... *C07K 16/22* (2013.01); *A61K 39/3955* (2013.01); *A61K 39/39558* (2013.01); *A61K 45/06* (2013.01); *C07K 16/2839* (2013.01); *C07K 16/30* (2013.01); *G01N 33/57492* (2013.01); *A61K 2039/505* (2013.01); *C07K 2317/24* (2013.01); *C07K 2317/54* (2013.01); *C07K 2317/55* (2013.01); *C07K 2317/565* (2013.01); *C07K 2317/569* (2013.01); *C07K 2317/622* (2013.01); *C07K 2317/626* (2013.01); *C07K 2317/76* (2013.01); *G01N 2333/495* (2013.01)

(58) Field of Classification Search
None
See application file for complete search history.

(56) References Cited

U.S. PATENT DOCUMENTS

| | | | |
|---|---|---|---|
| 8,198,412 B2 | 6/2012 | Kojima et al. | |
| 10,017,567 B2 | 7/2018 | Weiner et al. | |
| 2003/0068661 A1 | 4/2003 | Hockfield et al. | |
| 2005/0276802 A1 | 12/2005 | Adams et al. | |
| 2005/0276812 A1 | 12/2005 | Ebens et al. | |
| 2008/0038748 A1 | 2/2008 | Kojima et al. | |
| 2008/0206219 A1 | 8/2008 | Coussens et al. | |
| 2008/0227704 A1 | 9/2008 | Kamens et al. | |
| 2008/0280827 A1 | 11/2008 | Kojima et al. | |
| 2011/0064653 A1 | 3/2011 | Hansen et al. | |
| 2011/0070163 A1 | 3/2011 | Gonda et al. | |
| 2013/0028915 A1 | 1/2013 | Baylor et al. | |
| 2013/0071403 A1 | 3/2013 | Rolland et al. | |
| 2014/0328860 A1 | 11/2014 | Scandura et al. | |
| 2015/0033703 A1 | 2/2015 | Hyde et al. | |
| 2015/0273056 A1 | 10/2015 | Blumberg et al. | |
| 2015/0284455 A1 | 10/2015 | Springer et al. | |
| 2018/0009886 A1 | 1/2018 | Weiner et al. | |

FOREIGN PATENT DOCUMENTS

| | | |
|---|---|---|
| JP | 2006-523179 A | 10/2006 |
| JP | 2008-247900 A | 10/2008 |
| JP | 2008-289478 A | 12/2008 |
| WO | WO 02/085306 A2 | 10/2002 |
| WO | WO 2006/086469 A2 | 8/2006 |
| WO | WO 2006/116002 A2 | 11/2006 |
| WO | WO 2009/119455 A1 | 10/2009 |
| WO | WO 2010/124276 A2 | 10/2010 |
| WO | WO 2011/102483 A1 | 8/2011 |
| WO | WO 2013/134365 A1 | 9/2013 |
| WO | WO 2014/059251 A1 | 4/2014 |
| WO | WO 2014/074532 A2 | 5/2014 |
| WO | WO 2014/182676 A2 | 11/2014 |

OTHER PUBLICATIONS

Frank Immunology and Evolution of Infectious Disease, Chapter 4 "Specificity and Cross-Reactivity," Princeton University Press, 2002 (Year: 2002).*
Van Regenmortel (Journal of Immunological Methods, 1998, 216:37-48) (Year: 1998).*
Cunha et al., In vivo anti-LAP mAb enhances IL-17/IFN-γ responses and abrogates anti-CD3-induced oral tolerance. International Immunology, Feb. 2015;27(2):73-82. https://doi.org/10.1093/intimm/dxu083.
Frank, Immunology and Evolution of Infectious Disease. Chapter 4: "Specificity and Cross-Reactivity," Princeton University Press, 2002.
Maynard et al., Antibody engineering. Annu Rev Biomed Eng. 2000;2:339-76.
Oida et al., Depletion of TGF-β from fetal bovine serum. J Immunol Methods, Oct. 31, 2010;362(1-2):195-8. doi: 10.1016/j.jim.2010.09.008. Epub Sep. 15, 2010.

(Continued)

*Primary Examiner* — Laura B Goddard
*Assistant Examiner* — Meera Natarajan
(74) *Attorney, Agent, or Firm* — Wolf, Greenfield & Sacks, P.C.

(57) ABSTRACT

Described herein are compositions and methods relating to LAP-binding agents, including, for example, anti-LAP antibodies, and to their use in methods of treatment of cancer. LAP-binding agents affected both systemic and intra-tumor immunity and were shown effective to treat a broad spectrum of cancer types.

13 Claims, 67 Drawing Sheets

Specification includes a Sequence Listing.

(56) References Cited

OTHER PUBLICATIONS

Von Regenmortel et al., From absolute to exquisite specificity. Reflections on the fuzzy nature of species, specificity and antigenic sites. J Immunol Methods. Jul. 1, 1998;216(1-2):37-48.
International Search Report and Written Opinion for PCT/US2016/013408, dated May 2, 2016.
International Preliminary Report on Patentability for for PCT/US2016/013408, dated Jul. 27, 2017.
Andersson et al., CD4+ FoxP3+ regulatory T cells confer infectious tolerance in a TGF-beta-dependent manner. J Exp Med. Sep. 1, 2008;205(9):1975-81. doi: 10.1084/jem.20080308. Epub Aug. 18, 2008.
Broderick et al., Membrane-associated TGF-beta1 inhibits human memory T cell signaling in malignant and nonmalignant inflammatory microenvironments. J Immunol. Sep. 1, 2006;177(5):3082-8.
Cao et al., Granzyme B and perforin are important for regulatory T cell-mediated suppression of tumor clearance. Immunity. Oct. 2007;27(4):635-46. Epub Oct. 4, 2007.
Gerlach et al., Recurrence of hepatitis C virus after loss of virus-specific CD4(+) T-cell response in acute hepatitis C. Gastroenterology. Oct. 1999;117(4):933-41.
Mahalingam et al., CD4$^+$ T cells expressing latency-associated peptide and Foxp3 are an activated subgroup of regulatory T cells enriched in patients with colorectal cancer. PLoS One. Sep. 30, 2014;9(9):e108554. doi: 10.1371/journal.pone.0108554. eCollection 2014.
Nakamura et al., TGF-beta 1 plays an important role in the mechanism of CD4+CD25+ regulatory T cell activity in both humans and mice. J Immunol. Jan. 15, 2004;172(2):834-42.
Oida et al., Overexpression of TGF-β 1 gene induces cell surface localized glucose-regulated protein 78-associated latency-associated peptide/TGF-β. J Immunol. Sep. 15, 2010;185(6):3529-35. doi: 10.4049/jimmunol.0904121. Epub Aug. 18, 2010.
Scurr et al., Highly prevalent colorectal cancer-infiltrating LAP$^+$ Foxp3$^-$ T cells exhibit more potent immunosuppressive activity than Foxp3$^+$ regulatory T cells. Mucosal Immunol. Mar. 2014;7(2):428-39. doi: 10.1038/mi.2013.62. Epub Sep. 25, 2013.
Sun et al., Identification of human regulatory T cells in the setting of T-cell activation and anti-CTLA-4 immunotherapy on the basis of expression of latency-associated peptide. Cancer Discov. Feb. 2012;2(2):122-30. doi: 10.1158/2159-8290.CD-11-0236. Epub Dec. 27, 2011.
English Language Translation of International Preliminary Report on Patentability for PCT/JP2011/053559 dated Sep. 18, 2012.
Redacted Royalty Report generated by BioLegend, Inc. for Brigham & Women's Hospital and Summary of disclosure to patent office. Mar. 2013. 2 pages.
Ali et al., Latency associated peptide has in vitro and in vivo immune effects independent of TGF-β1. PLoS ONE. 2008;3(4):e1914. 9 pages.
U.S. Appl. No. 15/649,235, filed Jul. 13, 2017, Weiner et al.
PCT/US2016/013408, May 2, 2016, International Search Report and Written Opinion.
PCT/US2016/013408, Jul. 27, 2017, International Preliminary Report on Patentability.
Extended European Search Report for EP 16737879.3, dated May 29, 2018.
[No Author Listed] Biolegend: "Ultra-LEAF™ Purified anti-mouse/human LAP (TGF-[beta] 1) Antibody."
Almagro et al., Humanization of antibodies. Front Biosci. Jan. 1, 2008;13:1619-33.
Chen et al., Latency-associated peptide identifies a novel CD4+ CD25+ regulatory T cell subset with TGFbeta-mediated function and enhanced suppression of experimental autoimmune encephalomyelitis. J Immunol. Jun. 1, 2008;180(11):7327-37.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.
Gabriely et al., Targeting latency-associated peptide promotes antitumor immunity. Sci Immunol. May 19, 2017;2(11). pii: eaaj1738. doi: 10.1126/sciimmunol.aaj1738.
Gray et al., Optimising anti-tumour CD8 T-cell responses using combinations of immunomodulatory antibodies. Eur J Immunol. Sep. 20008;38(9):2499-511. doi: 10.1002/eji.200838208.
Leger et al., Molecular Medicine and Medicinal Chemistry, Jan. 1, 2011. Chapter 1: "Humanization of Antibodies" pp. 1-23.
Mahalingam et al., LAP+CD4+ T cells are suppressors accumulated in the tumor sites and associated with the progression of colorectal cancer. Clin Cancer Res. Oct. 1, 2012;18(19):5224-33. doi: 10.1158/1078-0432.CCR-12-0211. Epub Aug. 9, 2012.
Oida et al., TGF-β induces surface LAP expression on murine CD4 T cells independent of Foxp3 induction. PLoS One. Nov. 24, 2010;5(11):e15523. doi: 10.1371/journal.pone.0015523.
Santegoets et al., Monitoring regulatory T cells in clinical samples: consensus on an essential marker set and gating strategy for regulatory T cell analysis by flow cytometry. Cancer Immunol Immunother. Oct. 2015;64(10):1271-86. doi: 10.1007/s00262-015-1729-x. Epub Jun. 28, 2015.
Shah et al., Neutralisation of TGF-beta 1 and TGF-beta 2 or exogenous addition of TGF-beta 3 to cutaneous rat wounds reduces scarring. J Cell Sci. Mar. 1995;108 ( Pt 3):985-1002.
EP 16737879.3, May 29, 2018, Extended European Search Report.

\* cited by examiner

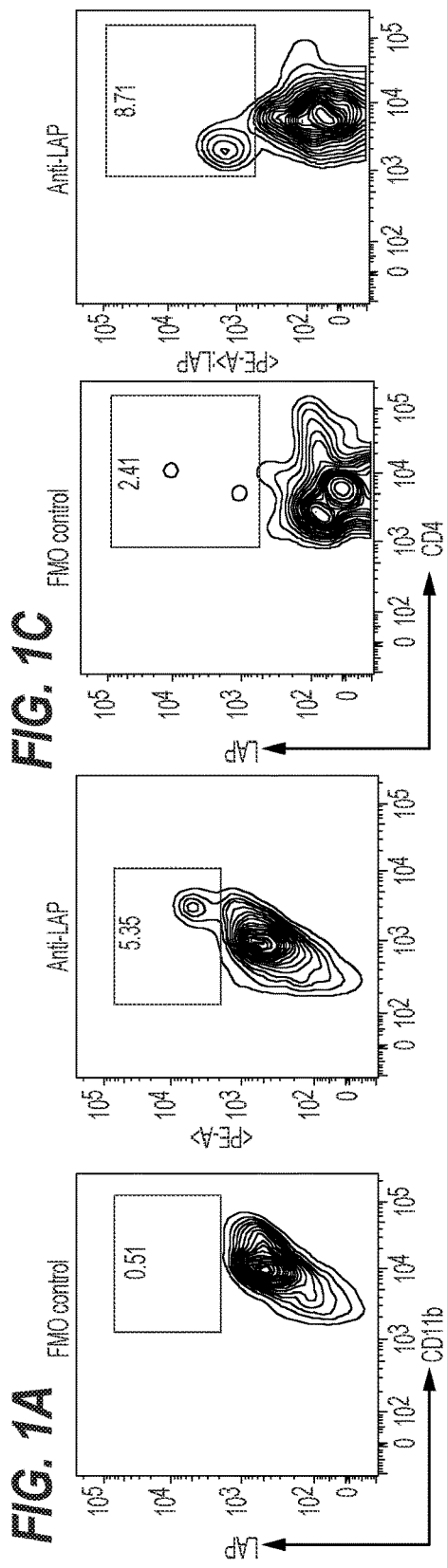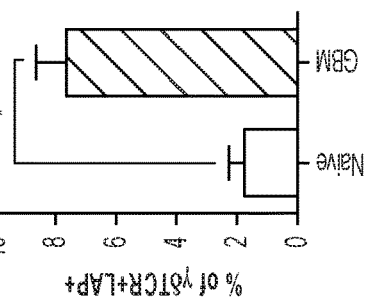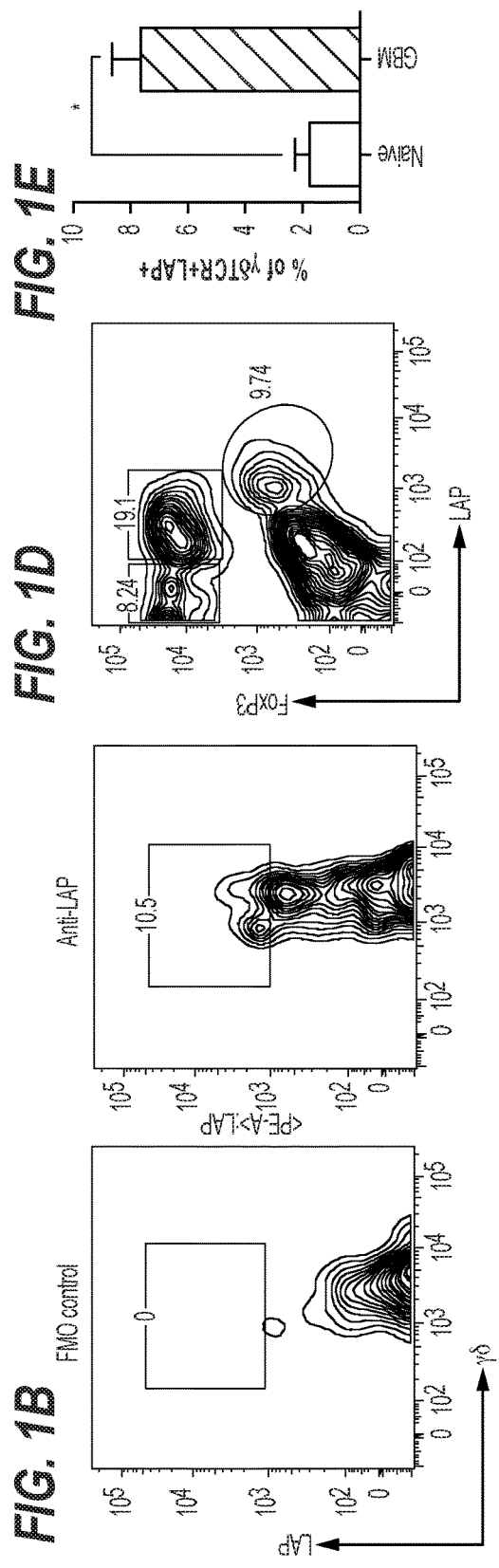

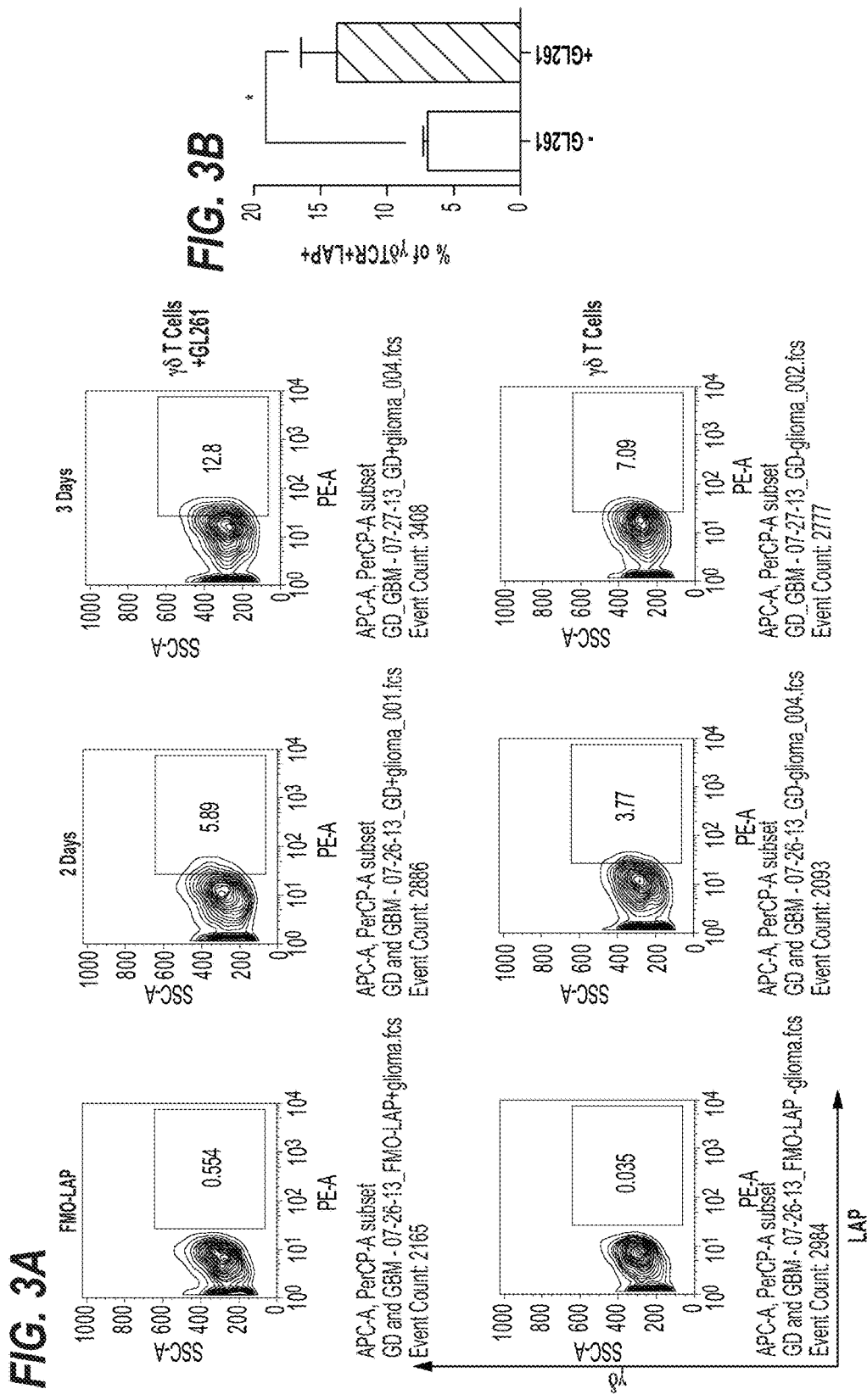

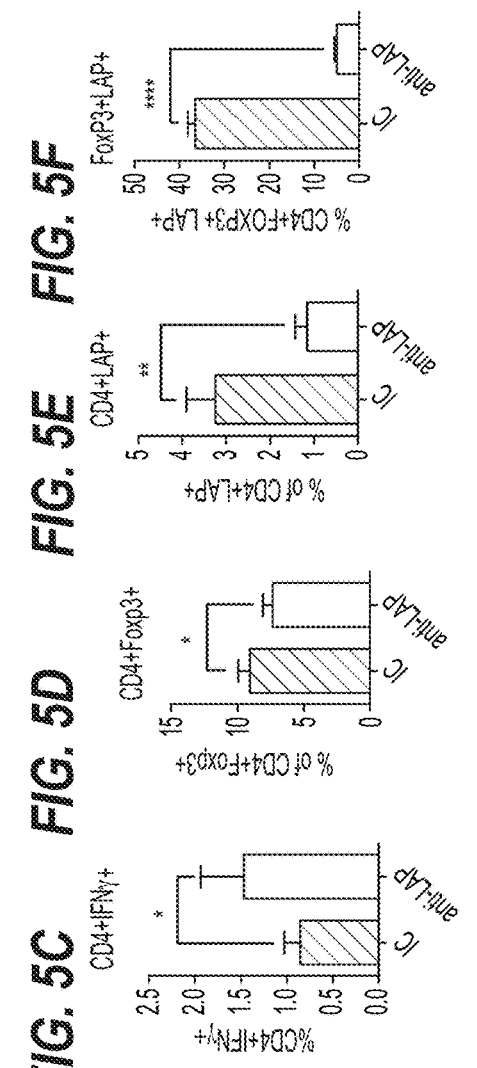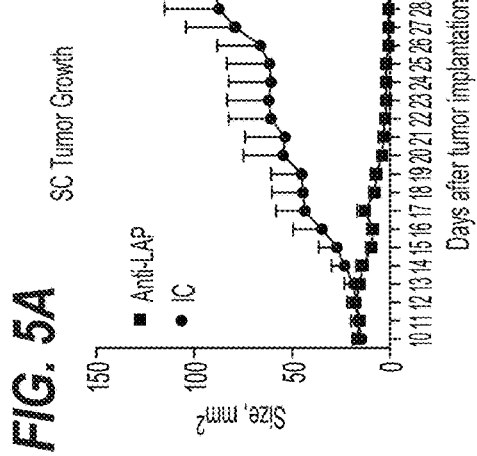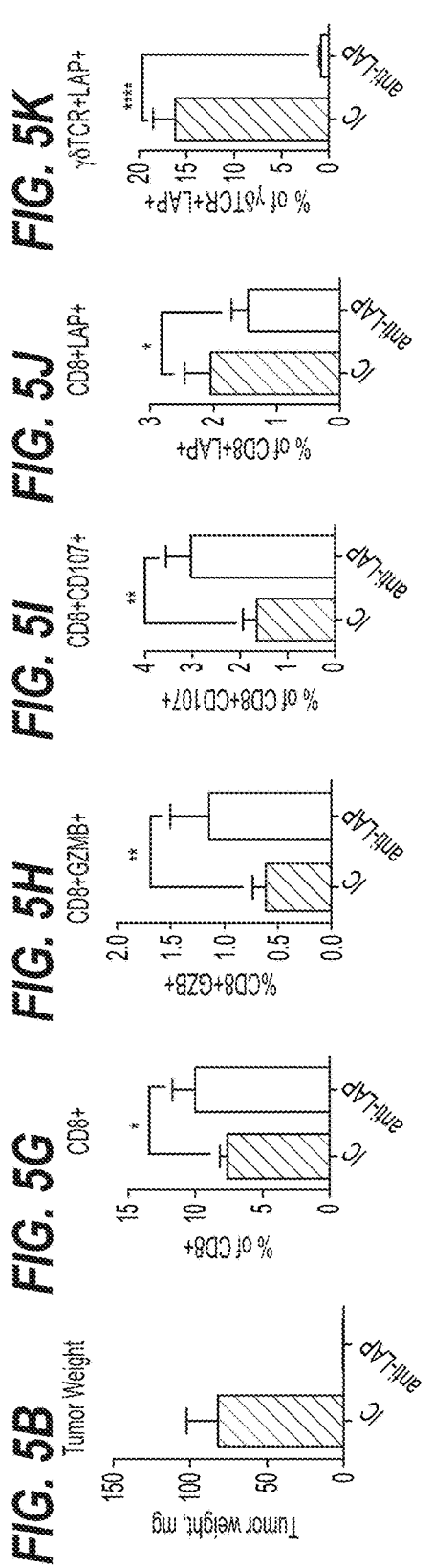

SC GBM Model

SC GBM Model

SC GBM Model

Naïve mice

Naïve mice

SC GBM Model

SC GBM Model

SC GBM Model

INC GBM Model

INC GBM Model

INC GBM Model

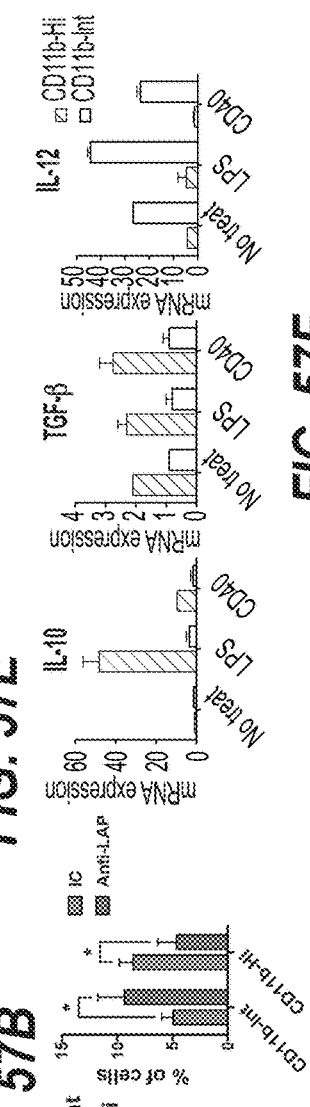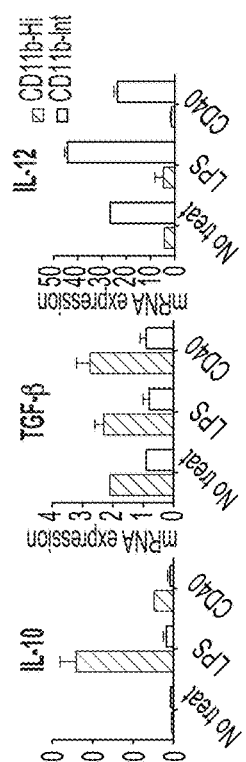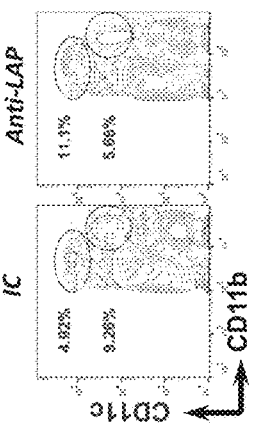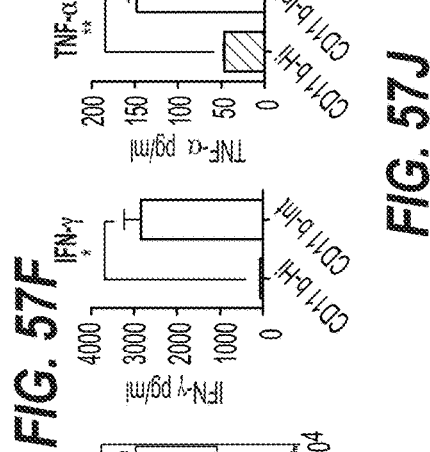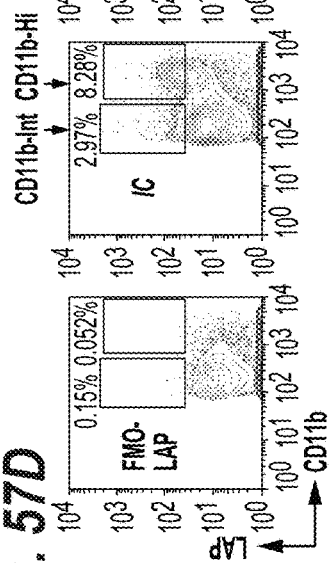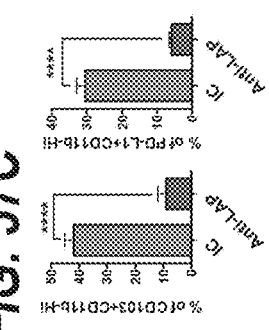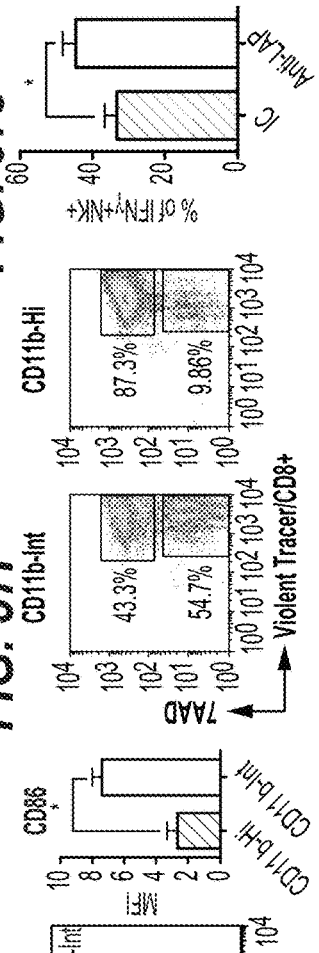

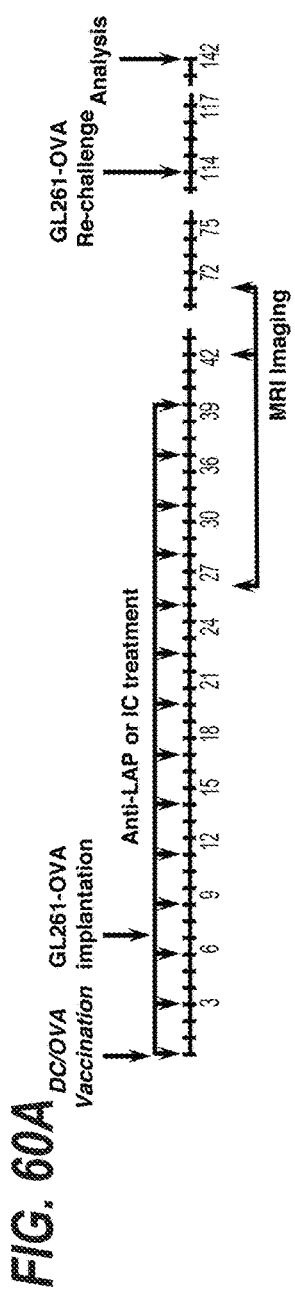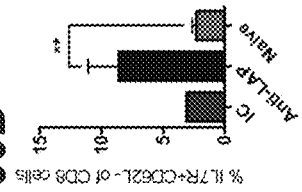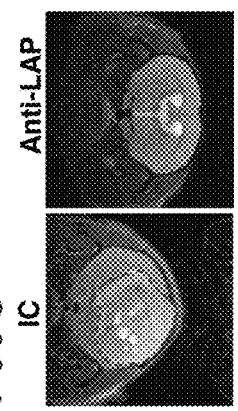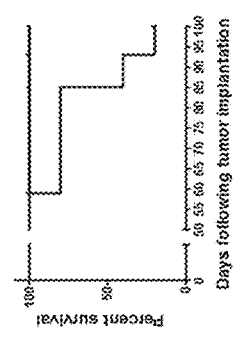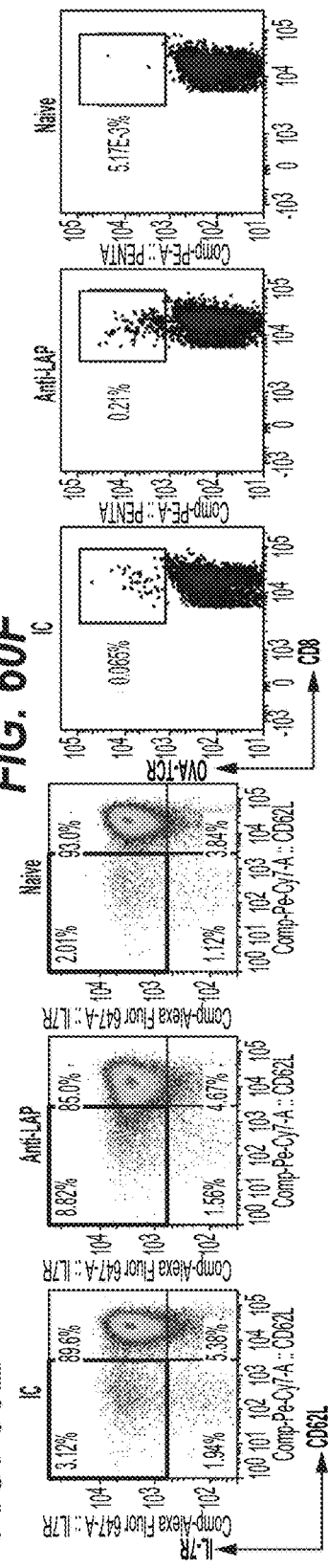
FIG. 60A, FIG. 60B, FIG. 60C, FIG. 60D, FIG. 60E, FIG. 60F B16-OVA Model

FIG. 66

SEQUENCE LISTING

```
<160> NUMBER OF SEQ ID NOS: 31

<210> SEQ ID NO 1
<211> LENGTH: 249
<212> TYPE: PRT
<213> ORGANISM: Homo sapiens

<400> SEQUENCE: 1

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140
```

```
Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
            165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
            195                 200                 205

Gly Phe Thr Thr Gly Arg Arg Gly Asp Leu Ala Thr Ile His Gly Met
            210                 215                 220

Asn Arg Pro Phe Leu Leu Met Ala Thr Pro Leu Glu Arg Ala Gln
225                 230                 235                 240

His Leu Gln Ser Ser Arg His Arg Arg
            245

<210> SEQ ID NO 2
<211> LENGTH: 282
<212> TYPE: PRT
<213> ORGANISM: Homo sapiens

<400> SEQUENCE: 2

Leu Ser Thr Cys Ser Thr Leu Asp Met Asp Gln Phe Met Arg Lys Arg
1               5                   10                  15

Ile Glu Ala Ile Arg Gly Gln Ile Leu Ser Lys Leu Lys Leu Thr Ser
            20                  25                  30

Pro Pro Glu Asp Tyr Pro Glu Pro Glu Glu Val Pro Pro Glu Val Ile
            35                  40                  45

Ser Ile Tyr Asn Ser Thr Arg Asp Leu Leu Gln Glu Lys Ala Ser Arg
50                  55                  60

Arg Ala Ala Ala Cys Glu Arg Glu Arg Ser Asp Glu Glu Tyr Tyr Ala
65                  70                  75                  80

Lys Glu Val Tyr Lys Ile Asp Met Pro Pro Phe Phe Pro Ser Glu Asn
            85                  90                  95

Ala Ile Pro Pro Thr Phe Tyr Arg Pro Tyr Phe Arg Ile Val Arg Phe
            100                 105                 110

Asp Val Ser Ala Met Glu Lys Asn Ala Ser Asn Leu Val Lys Ala Glu
            115                 120                 125

Phe Arg Val Phe Arg Leu Gln Asn Pro Lys Ala Arg Val Pro Glu Gln
            130                 135                 140

Arg Ile Glu Leu Tyr Gln Ile Leu Lys Ser Lys Asp Leu Thr Ser Pro
145                 150                 155                 160

Thr Gln Arg Tyr Ile Asp Ser Lys Val Val Lys Thr Arg Ala Glu Gly
            165                 170                 175

Glu Trp Leu Ser Phe Asp Val Thr Asp Ala Val His Glu Trp Leu His
            180                 185                 190

His Lys Asp Arg Asn Leu Gly Phe Lys Ile Ser Leu His Cys Pro Cys
            195                 200                 205

Cys Thr Phe Val Pro Ser Asn Asn Tyr Ile Ile Pro Asn Lys Ser Glu
            210                 215                 220

Glu Leu Glu Ala Arg Phe Ala Gly Ile Asp Gly Thr Ser Thr Tyr Thr
225                 230                 235                 240

Ser Gly Asp Gln Lys Thr Ile Lys Ser Thr Arg Lys Lys Asn Ser Gly
            245                 250                 255

Lys Thr Pro His Leu Leu Leu Met Leu Leu Pro Ser Tyr Arg Leu Glu
            260                 265                 270
```

```
Ser Gln Gln Thr Asn Arg Arg Lys Lys Arg
        275                 280

<210> SEQ ID NO 3
<211> LENGTH: 277
<212> TYPE: PRT
<213> ORGANISM: Homo sapiens

<400> SEQUENCE: 3

Leu Ser Thr Cys Thr Thr Leu Asp Phe Gly His Ile Lys Lys Lys Arg
1               5                   10                  15

Val Glu Ala Ile Arg Gly Gln Ile Leu Ser Lys Leu Arg Leu Thr Ser
            20                  25                  30

Pro Pro Glu Pro Thr Val Met Thr His Val Pro Tyr Gln Val Leu Ala
        35                  40                  45

Leu Tyr Asn Ser Thr Arg Glu Leu Leu Glu Glu Met His Gly Glu Arg
    50                  55                  60

Glu Glu Gly Cys Thr Gln Glu Asn Thr Glu Ser Glu Tyr Tyr Ala Lys
65                  70                  75                  80

Glu Ile His Lys Phe Asp Met Ile Gln Gly Leu Ala Glu His Asn Glu
                85                  90                  95

Leu Ala Val Cys Pro Lys Gly Ile Thr Ser Lys Val Phe Arg Phe Asn
            100                 105                 110

Val Ser Ser Val Glu Lys Asn Arg Thr Asn Leu Phe Arg Ala Glu Phe
        115                 120                 125

Arg Val Leu Arg Val Pro Asn Pro Ser Ser Lys Arg Asn Glu Gln Arg
    130                 135                 140

Ile Glu Leu Phe Gln Ile Leu Arg Pro Asp Glu His Ile Ala Lys Gln
145                 150                 155                 160

Arg Tyr Ile Gly Gly Lys Asn Leu Pro Thr Arg Gly Thr Ala Glu Trp
                165                 170                 175

Leu Ser Phe Asp Val Thr Asp Thr Val Arg Glu Trp Leu Leu Arg Arg
            180                 185                 190

Glu Ser Asn Leu Gly Leu Glu Ile Ser Ile His Cys Pro Cys His Thr
        195                 200                 205

Phe Gln Pro Asn Gly Asp Ile Leu Glu Asn Ile His Glu Val Met Glu
    210                 215                 220

Ile Lys Phe Lys Gly Val Asp Asn Glu Asp Asp His Gly Arg Gly Asp
225                 230                 235                 240

Leu Gly Arg Leu Lys Lys Gln Lys Asp His His Asn Pro His Leu Ile
                245                 250                 255

Leu Met Met Ile Pro Pro His Arg Leu Asp Asn Pro Gly Gln Gly Gly
            260                 265                 270

Gln Arg Lys Lys Arg
        275

<210> SEQ ID NO 4
<211> LENGTH: 249
<212> TYPE: PRT
<213> ORGANISM: Mus musculus

<400> SEQUENCE: 4

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30
```

```
Pro Pro Ser Gln Gly Glu Val Pro Gly Pro Leu Pro Glu Ala Val
        35                  40                  45

Leu Ala Leu Tyr Asn Ser Thr Arg Asp Arg Val Ala Gly Glu Ser Ala
 50                  55                  60

Asp Pro Glu Pro Glu Pro Glu Ala Asp Tyr Tyr Ala Lys Glu Val Thr
 65                  70                  75                  80

Arg Val Leu Met Val Asp Arg Asn Asn Ala Ile Tyr Glu Lys Thr Lys
                 85                  90                  95

Asp Ile Ser His Ser Ile Tyr Met Phe Phe Asn Thr Ser Asp Ile Arg
                100                 105                 110

Glu Ala Val Pro Glu Pro Leu Leu Ser Arg Ala Glu Leu Arg Leu
                115                 120                 125

Gln Arg Leu Lys Ser Ser Val Glu Gln His Val Glu Leu Tyr Gln Lys
130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
                180                 185                 190

His Cys Ser Cys Asp Ser Lys Asp Asn Lys Leu His Val Glu Ile Asn
                195                 200                 205

Gly Ile Ser Pro Lys Arg Arg Gly Asp Leu Gly Thr Ile His Asp Met
                210                 215                 220

Asn Arg Pro Phe Leu Leu Leu Met Ala Thr Pro Leu Glu Arg Ala Gln
225                 230                 235                 240

His Leu His Ser Ser Arg His Arg Arg
                245

<210> SEQ ID NO 5
<211> LENGTH: 282
<212> TYPE: PRT
<213> ORGANISM: Mus musculus

<400> SEQUENCE: 5

Leu Ser Thr Cys Ser Thr Leu Asp Met Asp Gln Phe Met Arg Lys Arg
 1               5                  10                  15

Ile Glu Ala Ile Arg Gly Gln Ile Leu Ser Lys Leu Lys Leu Thr Ser
                 20                  25                  30

Pro Pro Glu Asp Tyr Pro Glu Pro Asp Glu Val Pro Pro Glu Val Ile
            35                  40                  45

Ser Ile Tyr Asn Ser Thr Arg Asp Leu Leu Gln Glu Lys Ala Ser Arg
 50                  55                  60

Arg Ala Ala Ala Cys Glu Arg Glu Arg Ser Asp Glu Glu Tyr Tyr Ala
 65                  70                  75                  80

Lys Glu Val Tyr Lys Ile Asp Met Pro Ser His Leu Pro Ser Glu Asn
                 85                  90                  95

Ala Ile Pro Pro Thr Phe Tyr Arg Pro Tyr Phe Arg Ile Val Arg Phe
                100                 105                 110

Asp Val Ser Thr Met Glu Lys Asn Ala Ser Asn Leu Val Lys Ala Glu
                115                 120                 125

Phe Arg Val Phe Arg Leu Gln Asn Pro Lys Ala Arg Val Ala Glu Gln
130                 135                 140

Arg Ile Glu Leu Tyr Gln Ile Leu Lys Ser Lys Asp Leu Thr Ser Pro
```

```
                145                 150                 155                 160
        Thr Gln Arg Tyr Ile Asp Ser Lys Val Val Lys Thr Arg Ala Glu Gly
                        165                 170                 175
        Glu Trp Leu Ser Phe Asp Val Thr Asp Ala Val Gln Glu Trp Leu His
                        180                 185                 190
        His Lys Asp Arg Asn Leu Gly Phe Lys Ile Ser Leu His Cys Pro Cys
                        195                 200                 205
        Cys Thr Phe Val Pro Ser Asn Asn Tyr Ile Ile Pro Asn Lys Ser Glu
        210                 215                 220
        Glu Leu Glu Ala Arg Phe Ala Gly Ile Asp Gly Thr Ser Thr Tyr Ala
        225                 230                 235                 240
        Ser Gly Asp Gln Lys Thr Ile Lys Ser Thr Arg Lys Lys Thr Ser Gly
                        245                 250                 255
        Lys Thr Pro His Leu Leu Leu Met Leu Leu Pro Ser Tyr Arg Leu Glu
                        260                 265                 270
        Ser Gln Gln Ser Ser Arg Arg Lys Lys Arg
                        275                 280
```

<210> SEQ ID NO 6
<211> LENGTH: 277
<212> TYPE: PRT
<213> ORGANISM: Mus musculus

<400> SEQUENCE: 6

```
        Leu Ser Thr Cys Thr Thr Leu Asp Phe Gly His Ile Lys Lys Lys Arg
        1               5                   10                  15
        Val Glu Ala Ile Arg Gly Gln Ile Leu Ser Lys Leu Arg Leu Thr Ser
                        20                  25                  30
        Pro Pro Glu Pro Ser Val Met Thr His Val Pro Tyr Gln Val Leu Ala
                        35                  40                  45
        Leu Tyr Asn Ser Thr Arg Glu Leu Leu Glu Glu Met His Gly Glu Arg
                        50                  55                  60
        Glu Glu Gly Cys Thr Gln Glu Thr Ser Glu Ser Glu Tyr Tyr Ala Lys
        65                  70                  75                  80
        Glu Ile His Lys Phe Asp Met Ile Gln Gly Leu Ala Glu His Asn Glu
                        85                  90                  95
        Leu Ala Val Cys Pro Lys Gly Ile Thr Ser Lys Val Phe Arg Phe Asn
                        100                 105                 110
        Val Ser Ser Val Glu Lys Asn Gly Thr Asn Leu Phe Arg Ala Glu Phe
                        115                 120                 125
        Arg Val Leu Arg Val Pro Asn Pro Ser Ser Lys Arg Thr Glu Gln Arg
                        130                 135                 140
        Ile Glu Leu Phe Gln Ile Leu Arg Pro Asp Glu His Ile Ala Lys Gln
        145                 150                 155                 160
        Arg Tyr Ile Gly Gly Lys Asn Leu Pro Thr Arg Gly Thr Ala Glu Trp
                        165                 170                 175
        Leu Ser Phe Asp Val Thr Asp Thr Val Arg Glu Trp Leu Leu Arg Arg
                        180                 185                 190
        Glu Ser Asn Leu Gly Leu Glu Ile Ser Ile His Cys Pro Cys His Thr
                        195                 200                 205
        Phe Gln Pro Asn Gly Asp Ile Leu Glu Asn Val His Glu Val Met Glu
                        210                 215                 220
        Ile Lys Phe Lys Gly Val Asp Asn Glu Asp Asp His Gly Arg Gly Asp
        225                 230                 235                 240
```

Leu Gly Arg Leu Lys Lys Gln Lys Asp His Asn Pro His Leu Ile
                245                 250                 255

Leu Met Met Ile Pro Pro His Arg Leu Asp Ser Pro Gly Gln Gly Ser
            260                 265                 270

Gln Arg Lys Lys Arg
        275

<210> SEQ ID NO 7
<211> LENGTH: 417
<212> TYPE: DNA
<213> ORGANISM: Artificial Sequence
<220> FEATURE:
<223> OTHER INFORMATION: Synthetic polynucleotide

<400> SEQUENCE: 7
atgaagttgt ggctgaactg gatttccctt gtaacacttt taaatgatat ccagtgtgag     60
gtgaagctgg tggagtctgg aggaggcttg gtacagcctg ggggttctct gagtctctcc    120
tgtgcagctt ctggattcac cttcactgat tactacatga gctgggtccg ccagcctcca    180
gggaaggcac ttgagtggtt gggttttatt agaaacaaac taatggtta cacaacagag    240 tacagtgcat ctgtgaaggg tcggttcacc atctccagag ataattccca aagcatcctc    300
tatcttcaaa tgaatgtcct gagagctgag gacagtgcca cttattactg tgcaagatat    360
acgggggggg gttactttga ctactggggc caaggcacca ctctcacagt ctcctca      417

<210> SEQ ID NO 8
<211> LENGTH: 139
<212> TYPE: PRT
<213> ORGANISM: Artificial Sequence
<220> FEATURE:
<223> OTHER INFORMATION: Synthetic polypeptide

<400> SEQUENCE: 8

Met Lys Leu Trp Leu Asn Trp Ile Phe Leu Val Thr Leu Leu Asn Asp
1               5                   10                  15

Ile Gln Cys Glu Val Lys Leu Val Glu Ser Gly Gly Gly Leu Val Gln
            20                  25                  30

Pro Gly Gly Ser Leu Ser Leu Ser Cys Ala Ala Ser Gly Phe Thr Phe
        35                  40                  45

Thr Asp Tyr Tyr Met Ser Trp Val Arg Gln Pro Pro Gly Lys Ala Leu
    50                  55                  60

Glu Trp Leu Gly Phe Ile Arg Asn Lys Pro Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Asn Val Leu Arg Ala Glu Asp Ser
            100                 105                 110

Ala Thr Tyr Tyr Cys Ala Arg Tyr Thr Gly Gly Gly Tyr Phe Asp Tyr
        115                 120                 125

Trp Gly Gln Gly Thr Thr Leu Thr Val Ser Ser
    130                 135

<210> SEQ ID NO 9
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 9

```
Asp Tyr Tyr Met Ser
1               5

<210> SEQ ID NO 10
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 10

Phe Ile Arg Asn Lys Pro Asn Gly Tyr Thr Thr Glu Tyr Ser Ala Ser
1               5                   10                  15

Val Lys Gly

<210> SEQ ID NO 11
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 11

Tyr Thr Gly Gly Gly Tyr Phe Asp Tyr
1               5

<210> SEQ ID NO 12
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 12
atgatgtcct ctgctcagtt ccttggtctc ctgttgctct gttttcaagg taccagatgt      60
gatatccaga tgacacagac tacatcctcc ctgtctgcct ctctgggaga cagactcacc     120
atcagttgca gggcaagtca ggacattagc aattatttaa actggtatca gcagaaacca     180
gatggaactg ttaaactcct gatctactac acatcaagat acactcagg  agtcccatca     240 aggttcagtg gcagtgggtc tggaacagat tattctctca ccattagcaa cctggagcaa     300
gcagatattg ccacttactt ttgccaacag ggtgatacac ttccgtggac gttcggtgga     360
ggcaccaagc tggaaatcaa a                                               381

<210> SEQ ID NO 13
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 13

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
                20                  25                  30

Ala Ser Leu Gly Asp Arg Leu Thr Ile Ser Cys Arg Ala Ser Gln Asp
            35                  40                  45

Ile Ser Asn Tyr Leu Asn Trp Tyr Gln Gln Lys Pro Asp Gly Thr Val
        50                  55                  60

Lys Leu Leu Ile Tyr Tyr Thr Ser Arg Leu His Ser Gly Val Pro Ser
```

```
                65                  70                  75                  80
Arg Phe Ser Gly Ser Gly Ser Gly Thr Asp Tyr Ser Leu Thr Ile Ser
                        85                  90                  95
Asn Leu Glu Gln Ala Asp Ile Ala Thr Tyr Phe Cys Gln Gln Gly Asp
                   100                 105                 110
Thr Leu Pro Trp Thr Phe Gly Gly Thr Lys Leu Glu Ile Lys
               115                 120                 125

<210> SEQ ID NO 14
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 14

Arg Ala Ser Gln Asp Ile Ser Asn Tyr Leu Asn
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 15

Tyr Thr Ser Arg Leu His Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 16

Gln Gln Gly Asp Thr Leu Pro Trp Thr
1               5

<210> SEQ ID NO 17
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 17

Glu Val Lys Leu Val Glu Ser Gly Gly Gly Leu Val Gln Pro Gly Gly
1               5                   10                  15
Ser Leu Ser Leu Ser Cys Ala Ala Ser Gly Phe Thr Phe Thr
            20                  25                  30

<210> SEQ ID NO 18
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 18

Trp Val Arg Gln Pro Pro Gly Lys Ala Leu Glu Trp Leu Gly
1               5                   10
```

```
<210> SEQ ID NO 19
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 19

Arg Phe Thr Ile Ser Arg Asp Asn Ser Gln Ser Ile Leu Tyr Leu Gln
1               5                   10                  15

Met Asn Val Leu Arg Ala Glu Asp Ser Ala Thr Tyr Tyr Cys Ala Arg
            20                  25                  30

<210> SEQ ID NO 20
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 20

Trp Gly Gln Gly Thr Thr Leu Thr Val Ser Ser
1               5                   10

<210> SEQ ID NO 21
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 21

Asp Ile Gln Met Thr Gln Thr Thr Ser Ser Leu Ser Ala Ser Leu Gly
1               5                   10                  15

Asp Arg Leu Thr Ile Ser Cys
            20

<210> SEQ ID NO 22
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 22

Trp Tyr Gln Gln Lys Pro Asp Gly Thr Val Lys Leu Leu Ile Tyr
1               5                   10                  15

<210> SEQ ID NO 23
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 23

Gly Val Pro Ser Arg Phe Ser Gly Ser Gly Ser Gly Thr Asp Tyr Ser
1               5                   10                  15

Leu Thr Ile Ser Asn Leu Glu Gln Ala Asp Ile Ala Thr Tyr Phe Cys
            20                  25                  30

<210> SEQ ID NO 24
<211> LENGTH: 10
<212> TYPE: PRT
<213> ORGANISM: Artificial Sequence
```

<220> FEATURE:
<223> OTHER INFORMATION: Synthetic polypeptide

<400> SEQUENCE: 24

Phe Gly Gly Gly Thr Lys Leu Glu Ile Lys
1               5                   10

<210> SEQ ID NO 25
<211> LENGTH: 390
<212> TYPE: PRT
<213> ORGANISM: Homo sapiens

<400> SEQUENCE: 25

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

```
Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
        370                 375                 380

Arg Ser Cys Lys Cys Ser
385                 390

<210> SEQ ID NO 26
<211> LENGTH: 390
<212> TYPE: PRT
<213> ORGANISM: Mus musculus

<400> SEQUENCE: 26

Met Pro Pro Ser Gly Leu Arg Leu Leu Pro Leu Leu Leu Pro Leu Pro
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65              70                  75                  80

Tyr Asn Ser Thr Arg Asp Arg Val Ala Gly Glu Ser Ala Asp Pro Glu
            85                  90                  95

Pro Glu Pro Glu Ala Asp Tyr Tyr Ala Lys Glu Val Thr Arg Val Leu
            100                 105                 110

Met Val Asp Arg Asn Asn Ala Ile Tyr Glu Lys Thr Lys Asp Ile Ser
            115                 120                 125

His Ser Ile Tyr Met Phe Phe Asn Thr Ser Asp Ile Arg Glu Ala Val
        130                 135                 140

Pro Glu Pro Pro Leu Leu Ser Arg Ala Glu Leu Arg Leu Gln Arg Leu
145             150                 155                 160

Lys Ser Ser Val Glu Gln His Val Glu Leu Tyr Gln Lys Tyr Ser Asn
            165                 170                 175

Asn Ser Trp Arg Tyr Leu Gly Asn Arg Leu Leu Thr Pro Thr Asp Thr
            180                 185                 190

Pro Glu Trp Leu Ser Phe Asp Val Thr Gly Val Val Arg Gln Trp Leu
        195                 200                 205

Asn Gln Gly Asp Gly Ile Gln Gly Phe Arg Phe Ser Ala His Cys Ser
        210                 215                 220

Cys Asp Ser Lys Asp Asn Lys Leu His Val Glu Ile Asn Gly Ile Ser
225                 230                 235                 240

Pro Lys Arg Arg Gly Asp Leu Gly Thr Ile His Asp Met Asn Arg Pro
            245                 250                 255

Phe Leu Leu Leu Met Ala Thr Pro Leu Glu Arg Ala Gln His Leu His
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
        290                 295                 300

Asp Leu Gly Trp Lys Trp Ile His Glu Pro Lys Gly Tyr His Ala Asn
305                 310                 315                 320
```

```
Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
            340                 345                 350

Ser Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
            370                 375                 380

Arg Ser Cys Lys Cys Ser
385             390

<210> SEQ ID NO 27
<211> LENGTH: 412
<212> TYPE: PRT
<213> ORGANISM: Homo sapiens

<400> SEQUENCE: 27

Met Lys Met His Leu Gln Arg Ala Leu Val Val Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Lys Arg Val Glu Ala Ile Arg Gly Gln Ile Leu
            35                  40                  45

Ser Lys Leu Arg Leu Thr Ser Pro Pro Glu Pro Thr Val Met Thr His
        50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
            85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
            115                 120                 125

Ser Lys Val Phe Arg Phe Asn Val Ser Ser Val Glu Lys Asn Arg Thr
        130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
            165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
            195                 200                 205

Arg Glu Trp Leu Leu Arg Arg Glu Ser Asn Leu Gly Leu Glu Ile Ser
            210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
            245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
            275                 280                 285

Asp Asn Pro Gly Gln Gly Gly Gln Arg Lys Lys Arg Ala Leu Asp Thr
```

```
                290                 295                 300
Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
                340                 345                 350

Ser Ala Asp Thr Thr His Ser Thr Val Leu Gly Leu Tyr Asn Thr Leu
                355                 360                 365

Asn Pro Glu Ala Ser Ala Ser Pro Cys Cys Val Pro Gln Asp Leu Glu
                370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410

<210> SEQ ID NO 28
<211> LENGTH: 412
<212> TYPE: PRT
<213> ORGANISM: Mus musculus

<400> SEQUENCE: 28

Met Lys Met His Leu Gln Arg Ala Leu Val Leu Ala Leu Leu Asn
1               5                   10                  15

Leu Ala Thr Ile Ser Leu Ser Leu Ser Thr Cys Thr Thr Leu Asp Phe
                20                  25                  30

Gly His Ile Lys Lys Arg Val Glu Ala Ile Arg Gly Gln Ile Leu
                35                  40                  45

Ser Lys Leu Arg Leu Thr Ser Pro Pro Glu Pro Ser Val Met Thr His
50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Thr Ser
                85                  90                  95

Glu Ser Glu Tyr Tyr Ala Lys Glu Ile His Lys Phe Asp Met Ile Gln
                100                 105                 110

Gly Leu Ala Glu His Asn Glu Leu Ala Val Cys Pro Lys Gly Ile Thr
                115                 120                 125

Ser Lys Val Phe Arg Phe Asn Val Ser Ser Val Glu Lys Asn Gly Thr
                130                 135                 140

Asn Leu Phe Arg Ala Glu Phe Arg Val Leu Arg Val Pro Asn Pro Ser
145                 150                 155                 160

Ser Lys Arg Thr Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
                180                 185                 190

Thr Arg Gly Thr Ala Glu Trp Leu Ser Phe Asp Val Thr Asp Thr Val
                195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Val His Glu Val Met Glu Ile Lys Phe Lys Gly Val Asp Asn Glu
                245                 250                 255
```

```
Asp Asp His Gly Arg Gly Asp Leu Gly Arg Leu Lys Lys Gln Lys Asp
                260                 265                 270

His His Asn Pro His Leu Ile Leu Met Met Ile Pro Pro His Arg Leu
            275                 280                 285

Asp Ser Pro Gly Gln Gly Ser Gln Arg Lys Lys Arg Ala Leu Asp Thr
        290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
            340                 345                 350

Ser Ala Asp Thr Thr His Ser Thr Val Leu Gly Leu Tyr Asn Thr Leu
        355                 360                 365

Asn Pro Glu Ala Ser Ala Ser Pro Cys Cys Val Pro Gln Asp Leu Glu
370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410

<210> SEQ ID NO 29
<211> LENGTH: 442
<212> TYPE: PRT
<213> ORGANISM: Homo sapiens

<400> SEQUENCE: 29

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Thr Val Cys Pro Val Val Thr Thr Pro Ser Gly Ser Val
        115                 120                 125

Gly Ser Leu Cys Ser Arg Gln Ser Gln Val Leu Cys Gly Tyr Leu Asp
    130                 135                 140

Ala Ile Pro Pro Thr Phe Tyr Arg Pro Tyr Phe Arg Ile Val Arg Phe
145                 150                 155                 160

Asp Val Ser Ala Met Glu Lys Asn Ala Ser Asn Leu Val Lys Ala Glu
                165                 170                 175

Phe Arg Val Phe Arg Leu Gln Asn Pro Lys Ala Arg Val Pro Glu Gln
            180                 185                 190

Arg Ile Glu Leu Tyr Gln Ile Leu Lys Ser Lys Asp Leu Thr Ser Pro
        195                 200                 205

Thr Gln Arg Tyr Ile Asp Ser Lys Val Val Lys Thr Arg Ala Glu Gly
    210                 215                 220
```

Glu Trp Leu Ser Phe Asp Val Thr Asp Ala Val His Glu Trp Leu His
225                 230                 235                 240

His Lys Asp Arg Asn Leu Gly Phe Lys Ile Ser Leu His Cys Pro Cys
                245                 250                 255

Cys Thr Phe Val Pro Ser Asn Asn Tyr Ile Ile Pro Asn Lys Ser Glu
            260                 265                 270

Glu Leu Glu Ala Arg Phe Ala Gly Ile Asp Gly Thr Ser Thr Tyr Thr
        275                 280                 285

Ser Gly Asp Gln Lys Thr Ile Lys Ser Thr Arg Lys Lys Asn Ser Gly
    290                 295                 300

Lys Thr Pro His Leu Leu Leu Met Leu Leu Pro Ser Tyr Arg Leu Glu
305                 310                 315                 320

Ser Gln Gln Thr Asn Arg Arg Lys Lys Arg Ala Leu Asp Ala Ala Tyr
                325                 330                 335

Cys Phe Arg Asn Val Gln Asp Asn Cys Cys Leu Arg Pro Leu Tyr Ile
            340                 345                 350

Asp Phe Lys Arg Asp Leu Gly Trp Lys Trp Ile His Glu Pro Lys Gly
        355                 360                 365

Tyr Asn Ala Asn Phe Cys Ala Gly Ala Cys Pro Tyr Leu Trp Ser Ser
    370                 375                 380

Asp Thr Gln His Ser Arg Val Leu Ser Leu Tyr Asn Thr Ile Asn Pro
385                 390                 395                 400

Glu Ala Ser Ala Ser Pro Cys Cys Val Ser Gln Asp Leu Glu Pro Leu
                405                 410                 415

Thr Ile Leu Tyr Tyr Ile Gly Lys Thr Pro Lys Ile Glu Gln Leu Ser
            420                 425                 430

Asn Met Ile Val Lys Ser Cys Lys Cys Ser
            435                 440

<210> SEQ ID NO 30
<211> LENGTH: 414
<212> TYPE: PRT
<213> ORGANISM: Mus musculus

<400> SEQUENCE: 30

Met His Tyr Cys Val Leu Ser Thr Phe Leu Leu Leu His Leu Val Pro
1               5                   10                  15

Val Ala Leu Ser Leu Ser Thr Cys Ser Thr Leu Asp Met Asp Gln Phe
                20                  25                  30

Met Arg Lys Arg Ile Glu Ala Ile Arg Gly Gln Ile Leu Ser Lys Leu
            35                  40                  45

Lys Leu Thr Ser Pro Pro Glu Asp Tyr Pro Glu Pro Asp Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Ser His Leu
            100                 105                 110

Pro Ser Glu Asn Ala Ile Pro Pro Thr Phe Tyr Arg Pro Tyr Phe Arg
        115                 120                 125

Ile Val Arg Phe Asp Val Ser Thr Met Glu Lys Asn Ala Ser Asn Leu
    130                 135                 140

Val Lys Ala Glu Phe Arg Val Phe Arg Leu Gln Asn Pro Lys Ala Arg

```
                145                 150                 155                 160
Val Ala Glu Gln Arg Ile Glu Leu Tyr Gln Ile Leu Lys Ser Lys Asp
                    165                 170                 175

Leu Thr Ser Pro Thr Gln Arg Tyr Ile Asp Ser Lys Val Val Lys Thr
                180                 185                 190

Arg Ala Glu Gly Glu Trp Leu Ser Phe Asp Val Thr Asp Ala Val Gln
                    195                 200                 205

Glu Trp Leu His His Lys Asp Arg Asn Leu Gly Phe Lys Ile Ser Leu
                210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                    245                 250                 255

Ser Thr Tyr Ala Ser Gly Asp Gln Lys Thr Ile Lys Ser Thr Arg Lys
                260                 265                 270

Lys Thr Ser Gly Lys Thr Pro His Leu Leu Leu Met Leu Leu Pro Ser
                275                 280                 285

Tyr Arg Leu Glu Ser Gln Gln Ser Ser Arg Arg Lys Lys Arg Ala Leu
                290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
                    325                 330                 335

Glu Pro Lys Gly Tyr Asn Ala Asn Phe Cys Ala Gly Ala Cys Pro Tyr
                340                 345                 350

Leu Trp Ser Ser Asp Thr Gln His Thr Lys Val Leu Ser Leu Tyr Asn
                355                 360                 365

Thr Ile Asn Pro Glu Ala Ser Ala Ser Pro Cys Cys Val Ser Gln Asp
                370                 375                 380

Leu Glu Pro Leu Thr Ile Leu Tyr Tyr Ile Gly Asn Thr Pro Lys Ile
385                 390                 395                 400

Glu Gln Leu Ser Asn Met Ile Val Lys Ser Cys Lys Cys Ser
                    405                 410

<210> SEQ ID NO 31
<211> LENGTH: 310
<212> TYPE: PRT
<213> ORGANISM: Homo sapiens

<400> SEQUENCE: 31

Leu Ser Thr Cys Ser Thr Leu Asp Met Asp Gln Phe Met Arg Lys Arg
1               5                   10                  15

Ile Glu Ala Ile Arg Gly Gln Ile Leu Ser Lys Leu Lys Leu Thr Ser
                20                  25                  30

Pro Pro Glu Asp Tyr Pro Glu Pro Glu Glu Val Pro Pro Glu Val Ile
                35                  40                  45

Ser Ile Tyr Asn Ser Thr Arg Asp Leu Leu Gln Glu Lys Ala Ser Arg
            50                  55                  60

Arg Ala Ala Ala Cys Glu Arg Glu Arg Ser Asp Glu Glu Tyr Tyr Ala
65                  70                  75                  80

Lys Glu Val Tyr Lys Ile Asp Met Pro Pro Phe Phe Pro Ser Glu Thr
                85                  90                  95

Val Cys Pro Val Val Thr Thr Pro Ser Gly Ser Val Gly Ser Leu Cys
                100                 105                 110
```

-continued

```
Ser Arg Gln Ser Gln Val Leu Cys Gly Tyr Leu Asp Ala Ile Pro Pro
        115             120             125

Thr Phe Tyr Arg Pro Tyr Phe Arg Ile Val Arg Phe Asp Val Ser Ala
    130             135             140

Met Glu Lys Asn Ala Ser Asn Leu Val Lys Ala Glu Phe Arg Val Phe
145             150             155                         160

Arg Leu Gln Asn Pro Lys Ala Arg Val Pro Glu Gln Arg Ile Glu Leu
            165             170             175

Tyr Gln Ile Leu Lys Ser Lys Asp Leu Thr Ser Pro Thr Gln Arg Tyr
            180             185             190

Ile Asp Ser Lys Val Val Lys Thr Arg Ala Glu Gly Glu Trp Leu Ser
        195             200             205

Phe Asp Val Thr Asp Ala Val His Glu Trp Leu His His Lys Asp Arg
        210             215             220

Asn Leu Gly Phe Lys Ile Ser Leu His Cys Pro Cys Cys Thr Phe Val
225             230             235                         240

Pro Ser Asn Asn Tyr Ile Ile Pro Asn Lys Ser Glu Glu Leu Glu Ala
                245             250             255

Arg Phe Ala Gly Ile Asp Gly Thr Ser Thr Tyr Thr Ser Gly Asp Gln
            260             265             270

Lys Thr Ile Lys Ser Thr Arg Lys Lys Asn Ser Gly Lys Thr Pro His
        275             280             285

Leu Leu Leu Met Leu Leu Pro Ser Tyr Arg Leu Glu Ser Gln Gln Thr
        290             295             300

Asn Arg Arg Lys Lys Arg
305             310
```

TREATMENT OF CANCER WITH ANTI-LAP MONOCLONAL ANTIBODIES

CROSS-REFERENCE TO RELATED APPLICATION

This application claims priority under 35 U.S.C. §§ 120 and 365(c) to and is a continuation of international PCT Application, PCT/US2016/013408, filed Jan. 14, 2016, which claims benefit under 35 U.S.C. § 119(e) of U.S. Provisional Application No. 62/103,401, filed Jan. 14, 2015, the contents of each of which is herein incorporated by reference in its entirety.

GOVERNMENT SUPPORT

This invention was made with government support under Grant Number NS090163 awarded by the National Institutes of Health. The Government has certain rights in the invention.

TECHNICAL FIELD

The technical field relates to anti-LAP antibodies and methods for treating cancer.

BACKGROUND

According to the data from the World Health Organization, ten million people around the world were diagnosed with cancer in 2000, and six million died from it. Moreover, statistics indicate that the cancer incidence rate is on the rise around the globe. In the United States, for example, projections indicate that fifty percent of those alive today will be diagnosed with some form of cancer at some point in their lives.

Cancer therapies include radiation, surgery, cytotoxic chemotherapeutic agents, treatments aimed at increasing cancer-specific immune responses, and combinations of such approaches. Recent approaches to cancer therapy have focused on actively harnessing a patient's immune response to target cancer cells using a variety of approaches, including immunization with tumor antigens, inhibition or removal of suppressive/regulatory immune cell populations, and activation of exhausted immune cell populations.

SUMMARY

LAP or latency-associated peptide results from the separation of the N-terminal protein portion of TGF-β. LAP is secreted and can be found in the extracellular matrix. In addition, LAP can also be expressed on platelets. Importantly, as described herein, LAP is found on activated regulatory T cells. The compositions and methods described herein are based, in part, on the discoveries that tumor growth is lower and mice survive longer when treated with anti-LAP antibodies, and that the anti-LAP antibodies described herein act, in part, by preventing or inhibiting TGF-β signaling (including by blocking the release of TGF-β from the LAP/TGF-b complex) and/or depleting both activated CD4+ and CD8+ regulatory T cell populations. More specifically, as shown herein, anti-LAP antibody treatment affected both systemic and intra-tumor immunity as follows: (1) Tumors were infiltrated by increased numbers of cytotoxic CD8+ T cells and intra-tumor Foxp3 Tregs were decreased. CD4+ and CD8+ intra-tumor T cells had decreased expression of PD-1, LAG3 and CD103. (2) In the periphery, CD4+ and CD8+ T cells, expressing IFN-γ and granzyme B, were increased, respectively whereas CD103+ T cells were decreased. Finally, there were reduced numbers of tolerogenic dendritic cells expressing CD103 and PD-L1, whereas MHC II was elevated on splenic myeloid cells. Anti-LAP antibodies showed efficacy in various cancer models, including a GBM model, a melanoma model, and a colon carcinoma model, and similar intra-tumor and peripheral immune effects were observed, indicating broad applicability of this approach for cancer therapy. Thus, as demonstrated herein, anti-LAP antibody strongly influences systemic and intra-tumor immune responses by activating both innate and adaptive immunity and overcomes the mechanisms suppressing tumor-specific immunity. In conclusion, anti-LAP antibody as monotherapy or combined with conventional anti-tumor modalities represents a novel immunotherapeutic approach for the treatment of cancer.

Accordingly, described herein is an isolated anti-LAP antibody or antigen-binding fragment thereof that specifically binds to LAP comprising one or more heavy and light chain complimentarity determining regions (CDRs) selected from the group consisting of: a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16.

In one embodiment, the isolated anti-LAP antibody or antigen-binding fragment thereof comprises the heavy chain complimentarity determining regions (CDRs): a) a heavy chain CDR1 having the amino acid sequence of SEQ ID NO: 9; b) a heavy chain CDR2 having the amino acid sequence of SEQ ID NO: 10; and c) a heavy chain CDR3 having the amino acid sequence of SEQ ID NO: 11.

In another embodiment, the isolated anti-LAP antibody or antigen-binding fragment thereof comprises the light chain complimentarity determining regions (CDRs): a) a light chain CDR1 having the amino acid sequence of SEQ ID NO: 14; b) a light chain CDR2 having the amino acid sequence of SEQ ID NO: 15; and c) a light chain CDR3 having the amino acid sequence of SEQ ID NO: 16.

In another embodiment, the isolated anti-LAP antibody or antigen-binding fragment thereof comprises the complimentarity determining regions (CDRs): a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; c) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16.

In another embodiment, the isolated anti-LAP antibody or antigen-binding fragment thereof comprises a heavy chain having the amino acid sequence of SEQ ID NO: 8.

In another embodiment, the isolated anti-LAP antibody or antigen-binding fragment thereof comprises a light chain having the sequence of SEQ ID NO: 13.

In another embodiment, the isolated anti-LAP antibody or antigen-binding fragment thereof comprises a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16.

In another embodiment, the isolated anti-LAP antibody or antigen-binding fragment comprises one or more heavy chain complimentarity determining regions (CDRs) selected from the group consisting of: a) a heavy chain CDR1 having the amino acid sequence of SEQ ID NO: 9; b) a heavy chain CDR2 having the amino acid sequence of SEQ ID NO: 10; and c) a heavy chain CDR3 having the amino acid sequence of SEQ ID NO: 11.

In another embodiment, the isolated anti-LAP antibody or antigen-binding fragment comprises one or more light chain complimentarity determining regions (CDRs) selected from the group consisting of: a) a light chain CDR1 having the amino acid sequence of SEQ ID NO: 14; b) a light chain CDR2 having the amino acid sequence of SEQ ID NO: 15; and c) a light chain CDR3 having the amino acid sequence of SEQ ID NO: 16.

The antibody for any aspect described herein can be a monoclonal antibody. In certain embodiments, the antibody of any aspect described herein is a chimeric, CDR-grafted, humanized, composite human or fully human antibody or dual antibody or antigen-binding fragment thereof. In other embodiments of any aspect described herein, the antibody fragment is a Fab fragment, a Fab' fragment, a Fd fragment, a Fd' fragment, a Fv fragment, a dAb fragment, a F(ab')$_2$ fragment, a single chain fragment, a diabody, or a linear antibody. In another embodiment of any aspect described herein, the antibody or antigen-binding fragment thereof comprises a human acceptor framework. The monoclonal antibody upon which any of these embodiments is based can include, for example, the monoclonal antibody produced by a hybridoma clone selected from the group designated TW4-9E7, TW4-5A8, TW4-4E5, TW4-12B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9.

Also described is a composition comprising a LAP-binding agent and an inhibitor of TGF-β signaling.

In one embodiment, the LAP-binding agent comprises an anti-LAP antibody or antigen-binding fragment thereof. In another embodiment, the antibody is a monoclonal antibody. In another embodiment, the antibody is chimeric, CDR-grafted, humanized or fully human. In another embodiment, the antibody comprising one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16.

In another embodiment, the inhibitor of TGF-β signaling is selected from the group consisting of an antibody or antigen-binding fragment thereof that binds TGF-β or a receptor therefor, a double-stranded RNA or nucleic acid encoding a double-stranded RNA, an aptamer, and a small molecule. Antibodies that specifically bind and inhibit signaling by TGF-β and TGF-β receptors are known in the art and include commercially available antibodies. Double stranded RNAs that specifically target TGF-β and/or TGF-β receptors via RNA interference are also known in the art and commercially available. Small molecule inhibitors of TGF-b signaling are known in the art and include, for example, 4-[4-(1,3-benzodioxol-5-yl)-5-pyridin-2-yl-1H-imidazol-2-yl]benzamide (SB431542), N-(oxan-4-yl)-4-[4-(5-pyridin-2-yl-1H-pyrazol-4-yl)pyridin-2-yl]benzamide (GW788388), 4-[3-(2-Pyridinyl)-1H-pyrazol-4-yl]-quinoline (LY364947), and 2-(3-(6-methylpyridin-2-yl)-1H-pyrazol-4-yl)-1,5-naphthyridine ("ALK5 Inhibitor II").

Also described is a composition comprising a LAP-binding agent and an immunomodulatory or chemotherapeutic agent.

In one embodiment, the LAP-binding agent comprises an antibody or antigen-binding fragment thereof. In another embodiment, the antibody or antigen-binding fragment thereof is a monoclonal antibody or antigen-binding fragment thereof. In certain embodiments, the antibody or antigen-binding fragment thereof is chimeric, CDR-grafted, humanized or fully human. In another embodiment, the antibody comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16.

In another embodiment, the immunomodulatory agent comprises an immune checkpoint modulator Immune checkpoint protein receptors and their ligands (referred to herein collectively as checkpoint proteins) mediate suppression of T cell mediated cytotoxicity and are often expressed by tumors or on anergic T cells in the tumor microenvironment and permit the tumor to evade immune attack. Inhibitors of the activity of immunosuppressive checkpoint protein receptors and their ligands can overcome the immunosuppressive tumor environment to permit cytotoxic T cell attack of the tumor. Examples of immune checkpoint proteins include, but are not limited to PD-1, PD-L1, PDL2, CTLA4, LAG3, TIM3, TIGIT, and CD103. Modulation, including inhibition, of the activity of such proteins can be accomplished by an immune checkpoint modulator, which can include, for example, antibodies, aptamers, small molecules and soluble versions of checkpoint receptor proteins, among others, that target the checkpoint proteins. PD-1-targeting inhbitors include the approved drug agents pembrolizumab and nivolumab, and ipilimumab is an approved CTLA-4 inhibitor. Antibodies specific for PD-L1, PD-L2, LAG3, TIM3, TIGIT and CD103 are known and/or commercially available and can also be produced by those of skill in the art.

Immunomodulatory agents include, in addition to immune checkpoint modulators, agents that facilitate or mediate antigen presentation that promotes a cell-mediated immune response. Such immunomodulators can include, for example, a tumor antigen vaccine. A tumor antigen vaccine can include a preparation comprising a particular tumor antigen or set of known tumor antigens, with or without a subject's own dendritic cells or an adjuvant. Alternatively, a tumor antigen vaccine can comprise a relatively crude preparation of tumor cell antigens from a patient's tumor, which, when exposed ex vivo to dendritic cells generated in vitro from a patient's cells can permit T cell-mediated attack of the tumor when the dendritic cell vaccine is introduced to the patient. In one embodiment, then, an immunomodulatory agent comprises a tumor antigen vaccine. In another embodiment, the tumor antigen vaccine comprises a dendritic cell tumor antigen vaccine.

Also described herein is an antibody or antigen-binding fragment thereof that binds to LAP when complexed with TGF-β and inhibits release of TGF-β from the LAP/TGF-β complex. In one embodiment, the antibody or antigen-binding fragment binds an epitope formed by the binding of LAP to TGF-β. In another embodiment, the antibody or antigen-binding fragment is a monoclonal antibody or antigen-binding fragment thereof, and can include, for example, a chimeric, CDR-grafted, humanized or fully human antibody or antigen-binding fragment thereof. In another embodiment, the antibody or antigen-binding fragment thereof comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16. The antibody or antigen-binding fragment thereof encompasses the antibody produced, for example, by the hybridoma clone TW7-28G11. The antibody or antigen-binding fragment thereof can also encompass the antibody produced, for example, by any of the other anti-LAP hybridoma clones described herein.

Also described herein are pharmaceutical compositions comprising a LAP-binding agent or an antibody that specifically binds LAP, including, for example, human LAP, as described herein, and a pharmaceutically acceptable carrier. For any composition administered to an individual in need thereof in a method as described herein, the amount of the composition will be a "therapeutically effective amount" as that term is defined herein.

Also described herein is method of decreasing the number or activity of a population of LAP+ T Regulatory cells in a subject, the method comprising administering a LAP-binding agent to the subject, whereby the number or activity of the LAP+ T regulatory cell population is decreased.

As used herein, the terms "regulatory T cells" or "T regulatory cells" or "Tregs" refer to any population of CD4+ or CD8+ T cells that inhibits or suppresses the activation, proliferation and/or effector functions of other immune cells, including other CD4+ and CD8+ T cells, and helps to maintain self-tolerance. Tregs are also sometimes referred to in older literature as suppressor T cells. CD4+CD25+ FoxP3+ Tregs are a population of regulatory T cells derived from the thymus and are a relatively homogeneous population until they migrate to the periphery, where a subpopulation can develop phenotypic characteristics similar to conventional memory and effector T cells. Cells of this subpopulation can migrate to lymphoid and non-lymphoid tissues to maintain proper immune homeostasis. Peripherally-derived or so-called induced Tregs are a population of regulatory T cells that can develop from conventional CD4+ CD25−FoxP3− T cells in the periphery. CD4+ Tregs are generally CD4+ and FoxP3+, although the marker profiles can vary depending upon source—for example, thymically-derived Tregs express high levels of the marker Helios, while induced Tregs do not. Not all induced Tregs express CD25 or FoxP3. Unlike conventional T cells, some Treg cells express both GARP and LAP/TGFβ transiently on their cell surface upon T cell receptor activation. CD103+CD8+ Tregs are a population of regulatory T cells that mediate antigen-specific suppression by production of the cytokines IL-10 and/or TGF-β and/or by a direct inhibitory action on dendritic cells. Exemplary assays for identifying and/or characterizing the function of regulatory T cell populations are known in the art and are described, for example, in Collison and Vignali, In Vitro Treg Suppression Assays, METHODS IN MOLECULAR BIOLOGY (CLIFTON, N.J.). JANUARY 2011, the contents of which are herein incorporated by reference in their entireties. Typically, regulatory T cell function is identified by measuring suppression of proliferation in vitro, ex vivo, or in vivo. For example, an exemplary basic type of in vitro Treg suppression assay is one where Treg function is measured in the absence of antigen-presenting cells (APCs). This assay includes only two cell types, the target Tconv and Tregs, which are mixed together at various ratios, typically starting at a 2:1 ratio and stimulated using anti-CD3 and anti-CD28, for example, using beads. Suppressive function of the Treg population is determined by measuring cellular proliferation, using, for example, a thymidine incorporation assay or using a fluorescent dye-based assay, such as a carboxyfluorescein succinimidyl ester (CFSE) dilution assay.

As reported herein, a population of Tregs of particular interest is LAP+ Tregs, which can accumulate in tumor tissues, among other sites. As reported herein, a LAP-binding agent can decrease the number or activity of LAP+ Tregs, including the number or activity of tumor-infiltrated or tumor-associated Tregs. Reduction of the immunosuppression mediated by LAP+ Tregs can permit effective immune attack of the tumor. In one embodiment, the LAP-binding agent can be an antibody or antigen-binding fragment thereof. In one embodiment, the antibody can be a monoclonal antibody or antigen-binding fragment thereof. In another embodiment, the antibody or antigen-binding fragment thereof can be chimeric, CDR-grafted, humanized or fully human. In another embodiment, the antibody or antigen-binding fragment thereof comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16. The antibody or antigen-binding fragment thereof encompasses the antibody produced, for example, by the hybridoma clone TW7-28G11. The antibody or antigen-binding fragment thereof can also encompass the antibody produced, for example, by any of the other anti-LAP hybridoma clones described herein. While unconjugated antibody can be effective, in one embodiment, the LAP-binding agent can be conjugated to a cytotoxic or chemotherapeutic agent or drug.

Not only are LAP+ Tregs reduced by administering a LAP-binding agent, but FoxP3+ Tregs are also reduced. Thus, also described herein is a method of decreasing the number of FoxP3+ regulatory T cells in a tumor, the method comprising administering a LAP-binding agent to the subject. As with other aspects described herein, in one embodiment, the LAP-binding agent can be an antibody or antigen-binding fragment thereof. In one embodiment, the antibody can be a monoclonal antibody or antigen-binding fragment thereof. In another embodiment, the antibody or antigen-binding fragment thereof can be chimeric, CDR-grafted, humanized or fully human. In another embodiment, the antibody or antigen-binding fragment thereof comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16. The antibody or antigen-binding fragment thereof encompasses the antibody produced, for example, by the hybridoma clone TW7-28G11. The antibody or antigen-binding fragment thereof can also encompass the antibody produced, for example, by any of the other anti-LAP hybridoma clones described herein. While unconjugated antibody can be effective, in one embodiment, the LAP-binding agent can be conjugated to a cytotoxic or chemotherapeutic agent or drug.

Also described herein is a method of decreasing the number or activity of tumor-infiltrated immunosuppressive T cells in a tumor, the method comprising administering a LAP-binding agent to a subject with a tumor comprising tumor-infiltrated immunosuppressive T cells, whereby the number or activity of such cells is decreased. In one embodiment, the LAP-binding agent can be an antibody or antigen-binding fragment thereof. In one embodiment, the antibody can be a monoclonal antibody or antigen-binding fragment thereof. In another embodiment, the antibody or antigen-binding fragment thereof can be chimeric, CDR-grafted, humanized or fully human. In another embodiment, the antibody or antigen-binding fragment thereof comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16. The antibody or antigen-binding fragment thereof encompasses the antibody produced, for example, by the hybridoma clone TW7-28G11. The antibody or antigen-binding fragment thereof can also encompass the antibody produced, for example, by any of the other anti-LAP hybridoma clones described herein. While unconjugated antibody can be effective, in one embodiment, the LAP-binding agent can be conjugated to a cytotoxic or chemotherapeutic agent or drug.

Where LAP-binding agents are demonstrated herein to reduce immunosuppressive T cell populations, including immunosuppressive T cells associated with or infiltrated within tumor tissue, it follows that tumor specific immunity can be increased using a LAP-binding agent as described herein. Thus, this provides a method of increasing tumor-specific immunity comprising administering a therapeutically effective amount of a LAP-binding agent to a subject in need thereof. This also provides a method of treating a cancer or tumor where LAP expression and/or activity is associated with suppression of cancer- or tumor-specific immunity, the method comprising administering a therapeutically effective amount of a LAP-binding agent to a subject in need thereof. In these aspects, as in others described herein, the LAP-binding agent administered can include, for example, an antibody or antigen-binding fragment thereof. In one embodiment, the antibody can be a monoclonal antibody or antigen-binding fragment thereof. In another embodiment, the antibody or antigen-binding fragment thereof can be chimeric, CDR-grafted, humanized or fully human. In another embodiment, the antibody or antigen-binding fragment thereof comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16. The antibody or antigen-binding fragment thereof encompasses the antibody produced, for example, by the hybridoma clone TW7-28G11. The antibody or antigen-binding fragment thereof can also encompass the antibody produced, for example, by any of the other anti-LAP hybridoma clones described herein. While unconjugated antibody can be effective, in one embodiment, the LAP-binding agent can be conjugated to a cytotoxic or chemotherapeutic agent or drug.

As described herein, it was discovered that treatment with a LAP-binding agent not only reduces the number of LAP+ and FoxP3+ Tregs in a tumor, it also increases the number of CD8+ cytotoxic T cells in a tumor. Thus, also described herein is a method of increasing the number of CD8+ cytotoxic T cells in a tumor, the method comprising administering, to a subject with a tumor, a LAP-binding agent. In this aspect, as in others described herein, the LAP-binding agent administered can include, for example, an antibody or antigen-binding fragment thereof. In one embodiment, the antibody can be a monoclonal antibody or antigen-binding fragment thereof. In another embodiment, the antibody or antigen-binding fragment thereof can be chimeric, CDR-grafted, humanized or fully human. In another embodiment, the antibody or antigen-binding fragment thereof comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16. The antibody or antigen-binding fragment thereof encompasses the antibody produced, for example, by the hybridoma clone TW7-28G11. The antibody or antigen-binding fragment thereof can also encompass the antibody produced, for example, by any of the other anti-LAP hybridoma clones described herein. While unconjugated antibody can be effective, in one embodiment, the LAP-binding agent can be conjugated to a cytotoxic or chemotherapeutic agent or drug.

In addition to effects on the number and/or activity of CD8+ cytotoxic T cells, it was also discovered that treatment with a LAP-binding agent can increase the population of peripheral CD4+ T cells expressing IFNγ. Thus, also described herein is a method of increasing peripheral CD4+

T cells expressing IFNγ in a subject in need thereof, the method comprising administering a LAP-binding agent to the subject. Measurement of IFNγ production or secretion by CD4+ T cells is known to those of skill in the art and/or described elsewhere herein. In this aspect, as in others described herein, the LAP-binding agent administered can include, for example, an antibody or antigen-binding fragment thereof. In one embodiment, the antibody can be a monoclonal antibody or antigen-binding fragment thereof. In another embodiment, the antibody or antigen-binding fragment thereof can be chimeric, CDR-grafted, humanized or fully human. In another embodiment, the antibody or antigen-binding fragment thereof comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16. The antibody or antigen-binding fragment thereof encompasses the antibody produced, for example, by the hybridoma clone TW7-28G11. The antibody or antigen-binding fragment thereof can also encompass the antibody produced, for example, by any of the other anti-LAP hybridoma clones described herein. While unconjugated antibody can be effective, in one embodiment, the LAP-binding agent can be conjugated to a cytotoxic or chemotherapeutic agent or drug.

Also described herein is a method of inhibiting expression of an immunosuppressive factor or marker by CD8+ and/or CD4+ T cells in a tumor, the method comprising administering a LAP-binding agent to a subject with a tumor Immunosuppressive factors or markers produced by CD8+ and CD4+ T cells in a tumor include, for example, PD-1, LAG3 and CD103, among others, and inhibit T cell proliferation or responsiveness to stimulation, including, for example, T cell receptor stimulation or antigen stimulation. In this aspect, as in others described herein, the LAP-binding agent administered can include, for example, an antibody or antigen-binding fragment thereof. In one embodiment, the antibody can be a monoclonal antibody or antigen-binding fragment thereof. In another embodiment, the antibody or antigen-binding fragment thereof can be chimeric, CDR-grafted, humanized or fully human. In another embodiment, the antibody or antigen-binding fragment thereof comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16. The antibody or antigen-binding fragment thereof encompasses the antibody produced, for example, by the hybridoma clone TW7-28G11. The antibody or antigen-binding fragment thereof can also encompass the antibody produced, for example, by any of the other anti-LAP hybridoma clones described herein. While unconjugated antibody can be effective, in one embodiment, the LAP-binding agent can be conjugated to a cytotoxic or chemotherapeutic agent or drug.

It was also found that administering a tumor antigen or tumor antigen vaccine in conjunction with a LAP-binding agent promoted an anti-tumor immune response. This approach can supplement, for example, tumor antigen vaccine therapeutic approaches. Thus, also described herein is a method of promoting an anti-tumor immune response, the method comprising vaccinating a subject in need of treatment for a tumor with a tumor antigen and administering a LAP-binding agent to the subject. Tumor antigens, and tumor antigen vaccines are known in the art and described elsewhere herein. In this aspect, as in others described herein, the LAP-binding agent administered can include, for example, an antibody or antigen-binding fragment thereof. In one embodiment, the antibody can be a monoclonal antibody or antigen-binding fragment thereof. In another embodiment, the antibody or antigen-binding fragment thereof can be chimeric, CDR-grafted, humanized or fully human. In another embodiment, the antibody or antigen-binding fragment thereof comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16. The antibody or antigen-binding fragment thereof encompasses the antibody produced, for example, by the hybridoma clone TW7-28G11. The antibody or antigen-binding fragment thereof can also encompass the antibody produced, for example, by any of the other anti-LAP hybridoma clones described herein. While unconjugated antibody can be effective, in one embodiment, the LAP-binding agent can be conjugated to a cytotoxic or chemotherapeutic agent or drug.

While cancer treatment with immune checkpoint inhibitors can be effective in overcoming the immunosuppression exploited by tumors to avoid immune attack, some types of cancer are, or can become, refractory to treatment with checkpoint inhibitors. For example, certain cancers, including certain glioblastomas, melanomas and colorectal carcinomas, among others, tend to be refractory to treatment with inhibitors of PD-1 and its receptors. Treatment with a LAP-binding agent can be effective to promote an anti-tumor immune response in these cancers, and it is contemplated that such treatment can also restore or establish sensitivity of such cancers to the checkpoint inhibitor(s). Thus, described herein is a method of treating cancer that is refractory to treatment with an immune checkpoint inhibitor, the method comprising administering to a subject having such cancer a LAP-binding agent. In this aspect, as in others described herein, the LAP-binding agent administered can include, for example, an antibody or antigen-binding fragment thereof. In one embodiment, the antibody can be a monoclonal antibody or antigen-binding fragment thereof. In another embodiment, the antibody or antigen-binding fragment thereof can be chimeric, CDR-grafted, humanized or fully human. In another embodiment, the antibody or antigen-binding fragment thereof comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16. The antibody or antigen-binding fragment thereof encompasses the antibody produced, for example, by the hybridoma clone TW7-28G11. The antibody or antigen-binding fragment thereof can also encompass the antibody produced, for example, by any of the other anti-LAP hybridoma clones described herein. While unconjugated antibody can be effective, in one embodiment, the LAP-binding agent can be conjugated to a cytotoxic or chemotherapeutic agent or drug. In one embodiment, the method further comprises administering an immune checkpoint inhibitor, which can include, but is not limited to a checkpoint inhibitor to which the cancer was refractory. In one embodiment, the cancer is a glioblastoma, colorectal carcinoma or a melanoma. In one embodiment, the cancer is refractory to a PD-1 or PD-L1 inhibitor before treatment with the LAP-binding agent.

Where it is demonstrated herein that treatment with a LAP-binding agent can be effective for overcoming tumor immunosuppression, also described herein are methods in which patients are selected for treatment and/or for expected or predicted treatment efficacy on the basis of the presence (detection) and/or amount (quantitative detection) of LAP+ Tregs present in a patient's tumor. It follows that if LAP+ Tregs are present and/or present in significant number relative to a reference, the patient will be more likely to respond to treatment with a LAP-binding agent as described herein. Thus, also described herein is a method for identifying or selecting a patient with a tumor that is likely to respond to therapy with a LAP-binding agent, the method comprising analyzing a tumor sample from a subject to determine the presence of LAP+ T regulatory cells, and, if LAP+ T regulatory cells are present or are present in significant number relative to a reference. If the patient's tumor has LAP+ Tregs or has, for example, a significant number relative to a reference, the patient is identified a having a tumor likely to respond to treatment with a LAP-binding agent. For such patients, the method can further comprise treatment, comprising administering to the subject a LAP-binding agent, thereby promoting an anti-tumor immune response. As one example, the reference can be the number of LAP+ Treg cells present in a tumor known to have been effectively treated with a LAP-binding agent. In this embodiment, if the number of LAP+ Treg cells in a patient's tumor is, for example, at least 20% or more of such a reference (i.e., in a significant number relative to the reference, as that term is used herein), the patient would be more likely to respond to treatment with a LAP-binding agent than if the number in the patient's tumor were below that level. If the patient's tumor is found not to have LAP+ Tregs or is found to have a considerably lower level of LAP+ Tregs relative to a reference, treatment with a LAP-binding agent, it may still be possible that treatment with a LAP-binding agent will facilitate treatment, but it is less likely than where the level is higher. In such instances, the patient is identified as less likely to respond to a LAP-binding agent, and other therapeutic approaches such as administering an immunomodulatory or anti-tumor agent other than a LAP-binding agent to the patient can be considered or carried out. Non-limiting examples of such therapeutic approaches can include, for example, administering an immune checkpoint inhibitor, a chemotherapeutic agent and/or gamma radiation.

In this aspect, as in others described herein, the LAP-binding agent administered can include, for example, an antibody or antigen-binding fragment thereof. In one embodiment, the antibody can be a monoclonal antibody or antigen-binding fragment thereof. In another embodiment, the antibody or antigen-binding fragment thereof can be chimeric, CDR-grafted, humanized or fully human. In another embodiment, the antibody or antigen-binding fragment thereof comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16. The antibody or antigen-binding fragment thereof encompasses the antibody produced, for example, by the hybridoma clone TW7-28G11. The antibody or antigen-binding fragment thereof can also encompass the antibody produced, for example, by any of the other anti-LAP hybridoma clones described herein. While unconjugated antibody can be effective, in one embodiment, the LAP-binding agent can be conjugated to a cytotoxic or chemotherapeutic agent or drug.

It was also discovered that markers of memory T cells are up-regulated following treatment of tumors using a LAP-binding agent. Thus, also described herein is a method of promoting the formation of memory T cells specific for an antigen of interest in a subject in need thereof, the method comprising administering a LAP-binding agent and the antigen of interest to the subject. In one embodiment, treatment with a LAP-binding agent results in increased CD44+ and/or increased IL7R+ T cells. It is contemplated that this approach can provide benefit not only in promoting and maintaining memory for a response to tumor antigen, but also for promoting and maintaining memory for a response to an infectious pathogen. The antigen of interest, which can be a purified antigen or a more crude antigen preparation such as a whole tumor antigen preparation, can be administered on its own, with an adjuvant, or in the form of a dendritic cell vaccine. In this aspect, as in others described herein, the LAP-binding agent administered can include, for example, an antibody or antigen-binding fragment thereof. In one embodiment, the antibody can be a monoclonal antibody or antigen-binding fragment thereof. In another embodiment, the antibody or antigen-binding fragment thereof can be chimeric, CDR-grafted, humanized or fully human. In another embodiment, the antibody or antigen-binding fragment thereof comprises one or more, two or more, three or more, four or more, five or more, or all six of the heavy and light chain complimentarity determining regions (CDRs) including a) a heavy chain CDR1 having the amino acid sequence of SEQ ID NO: 9; b) a heavy chain CDR2 having the amino acid sequence of SEQ ID NO: 10; c) a heavy chain CDR3 having the amino acid sequence of SEQ ID NO: 11; d) a light chain CDR1 having the amino acid sequence of SEQ ID NO: 14; e) a light chain CDR2 having the amino acid sequence of SEQ ID NO: 15; and f) a light chain CDR3 having the amino acid sequence of SEQ ID NO: 16. The antibody or antigen-binding fragment thereof encompasses the antibody produced, for example, by the hybridoma clone TW7-28G11. The antibody or antigen-binding fragment thereof can also encompass the antibody produced, for example, by any of the other anti-LAP hybridoma clones described herein. While unconjugated antibody can be effective, in one embodiment, the LAP-binding agent can be conjugated to a cytotoxic or chemotherapeutic agent or drug.

Also described herein is the use of a LAP-binding agent for:

the treatment of a disease or disorder characterized by or involving an undesirable number or activity of LAP+ T regulatory cells;

the treatment of cancer by decreasing the number or activity of tumor-infiltrated immunosuppressive T cells in a tumor, the use comprising administering a LAP-binding agent to a subject with a tumor comprising tumor-infiltrated immunosuppressive T cells, whereby the number or activity of such cells is decreased;

the treatment of cancer by increasing tumor-specific immunity, the use comprising administering a therapeutically effective amount of a LAP-binding agent to a subject in need thereof;

the treatment of a cancer or tumor where LAP expression and/or activity is associated with suppression of cancer- or tumor-specific immunity, the use comprising administering a therapeutically effective amount of a LAP-binding agent to a subject in need thereof;

the treatment of a cancer or tumor by increasing the number of CD8+ cytotoxic T cells in a tumor, the usecomprising administering, to a subject with a tumor, a LAP-binding agent;

the treatment of a cancer or tumor by increasing peripheral CD4+ T cells expressing IFNγ in a subject in need thereof, the use comprising administering a LAP-binding agent to the subject;

the treatment of a cancer or tumor by increasing peripheral CD8+ T cells expressing granzyme B in a subject in need thereof, the use comprising administering a LAP-binding agent to the subject;

the treatment of a cancer or tumor by decreasing the number of FoxP3+ regulatory T cells in a tumor, the use comprising administering a LAP-binding agent to the subject;

the treatment of a cancer or tumor by inhibiting expression of an immunosuppressive factor by CD8+ and/or CD4+ T cells in a tumor, the use comprising administering a LAP-binding agent to a subject with a tumor;

promoting an anti-tumor immune response, the use comprising vaccinating a subject in need of treatment for a tumor with a tumor antigen and administering a LAP-binding agent to the subject;

treating cancer that is refractory to treatment with an immune checkpoint inhibitor, the use comprising administering to a subject having such cancer a LAP-binding agent;

treating cancer, the use comprising analyzing a tumor sample from a subject to determine the presence of LAP+ T regulatory cells, and, if LAP+ T regulatory cells are present, administering to the subject a LAP-binding agent, thereby promoting an anti-tumor immune response;

promoting the formation of memory T cells specific for an antigen of interest for the treatment of cancer or an infection in a subject, the use comprising administering a LAP-binding agent and the antigen of interest to the subject.

In each of the aspects described herein, the LAP-binding agent can be, for example, one that specifically binds a LAP molecule having the sequence set forth in any one of SEQ ID NOs: 1-3.

In one embodiment of each of the aspects described herein, the antibody or antigen-binding fragment thereof can be, for example, one that binds a LAP ligand interaction site. The LAP ligand interaction site can be, for example, a site that interacts with mature TGFβ, a site that interacts with integrins, and/or a site that interacts with latent TGFβ binding protein (LTBP).

In one embodiment of each of the aspects described herein, the LAP-binding agent binds LAP complexed with TGF-β and inhibits release of TGF-β from the complex.

In one embodiment of each of the aspects described herein, the monoclonal antibody is one produced by any one of the hybridoma clones selected from TW4-9E7, TW4-5A8, TW4-3E5, TW4-4E5, TW4-12B12, TW4-13B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9.

In one embodiment of each of the aspects described herein, the LAP-binding agent is a small molecule inhibitor, agent, or compound.

In one embodiment of each of the aspects described herein, the LAP-binding agent is an RNA or DNA aptamer that binds or physically interacts with LAP.

In one embodiment of each of the methods described herein, the subject has or has been diagnosed with cancer.

In one embodiment of each of the methods described herein, the subject has or has been diagnosed with a brain tumor, a melanoma, or colorectal cancer. In one embodiment, the brain tumor is a glioblastoma.

In one embodiment of each of the therapeutic methods described herein the method further comprises administering an anti-cancer therapy, chemotherapeutic or immunomodulatory agent to the subject. In one embodiment, the immunomodulatory agent comprises an immune checkpoint inhibitor. In one embodiment, the immune checkpoint inhibitor binds to one or more of the following: PD1, PDL1, PDL2, CTLA4, LAG3, TIM3, TIGIT and/or CD103. In one embodiment, the immune checkpoint inhibitor is a PD1, PDL1, and/or PDL2 inhibitory agent selected from pembrolizumab; nivolumab; MK-3475; MPDL3280A; MEDI0680; MEDI4736; AMP-224; and MSB0010718C.

In one embodiment of each of the therapeutic methods described herein, the methods further comprise administering a chemotherapeutic agent to the subject.

In one embodiment of each of the therapeutic methods described herein, the method further comprises administering a tumor or cancer antigen to the subject. In one embodiment, the method comprises administering a LAP-binding agent concurrently or in combination with dendritic cell (DC) vaccination.

In one embodiment of each of the therapeutic methods described herein, the LAP-binding agent is an isolated antibody or antigen-binding fragment thereof as described herein or a pharmaceutical composition comprising such an antibody or antigen-binding fragment thereof.

DEFINITIONS

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

As used herein, the term "LAP binding agent" refers to a molecule or agent that specifically binds LAP and significantly modulates the interaction between LAP and any of its ligands or molecules that interact with LAP and consequently modulates their resultant biological or functional activity in vitro, in situ, and/or in vivo, including activity of downstream pathways mediated by LAP signaling, such as, for example, TGF-β release from the small latent complex or latent complex, LAP-mediated inhibition of immune responses and LAP-mediated inhibition of anti-tumor immune responses. Exemplary LAP binding agents contemplated for use in the various aspects and embodiments described herein include, but are not limited to, antibodies or antigen-binding fragments thereof that specifically bind to one or more amino acid residues or epitopes on LAP involved in the binding and/or interactions of LAP and TGF-β, including an epitope formed when TGF-β is bound to LAP, LAP and integrins, and/or LAP and LTBP, and/or modulate LAP homodimerization and/or binding; small molecule agents that target or specifically bind to one or more amino acid residues or epitopes on LAP involved in the binding and/or interactions of LAP and TGFβ, LAP and integrins, and/or LAP and LTBP, and/or LAP and GARP, and/or modulate LAP homodimerization and/or binding; and RNA or DNA aptamers that bind to one or more amino acid residues or epitopes on LAP involved in the binding and/or interactions of LAP and TGFβ, LAP and integrins, and/or LAP and LTBP, and/or modulate LAP homodimerization and/or binding. In preferred embodiments of the aspects described herein, a LAP binding agent specifically binds LAP and inhibits or blocks TGF-β release from the small latent complex or latent complex.

As used herein, a LAP binding agent has the ability to modulate the interaction between LAP and TGF-β, LAP and integrins, and/or LAP and LTBP, and/or modulate LAP homodimerization and/or their resultant biological or functional activity in vitro, in situ, and/or in vivo by at least 5%, at least 10%, at least 20%, at least 30%, at least 40%, at least 50%, at least 60%, at least 70%, at least 80%, at least 90%, at least 95%, at least 98%, at least 99%, or more, relative to the interaction and/or activity in the absence of the LAP binding agent. At a minimum, a LAP binding agent as described herein blocks tumor-induced immune suppression in a cancer model, such as a subcutaneous mouse glioma model, and leads to higher expression of IFNγ on CD4+ T cells, reduced numbers and/or activity of regulatory CD4+ T cells, increased numbers and/or infiltration of cytotoxic CD8+ T cells to the tumor, decreased tumor size, and/or increased survival in said model.

"Modulating an interaction between LAP and TGF-β/integrins/latent TGF-β binding protein/LAP," or "impacting an interaction between LAP and TGF-β/integrins/latent TGF-β binding protein/LAP" as used interchangeably herein, generally means either modulating, i.e., increasing or decreasing, the interaction between or binding of LAP and TGF-β/integrins/latent TGF-β binding protein/LAP by at least 5%, at least 10%, at least 25%, at least 50%, at least 60%, at least 70%, at least 80%, at least 90%, at least 95%, at least 98%, or more, compared to the interaction between LAP and TGF-β/integrins/latent TGF-β binding protein/LAP under the same conditions but without the presence of a LAP binding agent. In preferred embodiments of the aspects described herein, a LAP binding agent modulates the interaction between LAP and TGF-β, such that release of TGF-β from the small latent complex is inhibited or blocked, and/or reduces the number of and/or activity of regulatory CD4+ and/or CD8+ T cells.

As used herein, "increasing tumor-specific immunity" refers to directly increasing or amplifying the immune response directed against a cancer or a tumor and/or removing suppression of the immune response against a cancer or a tumor, and includes, but is not limited to, for example, increasing the recognition of cancer-specific antigens; increasing the number and/or activity of tumour infiltrating lymphocytes (e.g., CD4 and CD8 T cells) and/or tumor-infiltrating innate immune cells, such as natural killer cells, natural killer T cells, macrophages and dendritic cells to the tumor site; increasing or amplifying cytokine and/or chemokine production at the tumor/cancer site, such as IFNγ, CXCL10, CXCL9 and CXCL11, IL-17, IL-12; decreasing/suppressing immune inhibitory molecules, such as LAG3 and PD1; decreasing/suppressing regulatory cell populations such as T regulatory cells, including Foxp3+ CD4 T cells and CD103+CD8 T cells etc. In this context and others herein, "increasing" refers at a minimum to a statistically significant increase, preferably at least 10% or more relative to a reference.

As used herein, the phrase "a cancer or tumor where LAP expression and/or activity is associated with suppression of cancer- or tumor-specific immunity" refers to those cancers/tumors in which expression and/or activity of LAP has been determined to correlate with a suppression of the cancer or tumor-specific immunity. In other words, a cancer or tumor where expression and/or activity of LAP correlates with decreased recognition of cancer-specific antigens; lack or reduction in the number and/or activity of tumour infiltrating lymphocytes (e.g., CD4 and CD8 T cells) and/or tumor-infiltrating innate immune cells, such as natural killer cells, natural killer T cells, macrophages and dendritic cells to the tumor site; decreased or absent cytokine and/or chemokine production at the tumor/cancer site, such as IFNγ, CXCL10, CXCL9 and CXCL11, IL-17, IL-12; increased expression of immune inhibitory molecules, such as LAG3 and PD1; increased presence of regulatory cell populations such as T regulatory cells, including Foxp3+CD4 T cells and CD103+ CD8 T cells, for example.

As used herein, antibodies or antigen-binding fragments thereof include monoclonal, human, humanized or chimeric antibodies, single chain antibodies, Fab fragments, F(ab') fragments, fragments produced by a Fab expression library, and/or antigen-binding fragments of any of the above. Antibodies also refer to immunoglobulin molecules and immunologically active portions of immunoglobulin molecules, i.e., molecules that contain antigen or target binding sites or "antigen-binding fragments." The immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art.

The terms "antibody fragment" or "antigen-binding fragment" include, without limitation: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) a dAb fragment (Ward et al., Nature 341, 544-546 (1989)) which consists of a $V_H$ domain or a $V_L$ domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$—$C_H1$-$V_H$-$C_H1$) which, together with complementary light chain polypeptides, form a pair of antigen binding regions (Zapata et al. Protein Eng. 8(10):1057-1062 (1995); and U.S. Pat. No. 5,641,870); and modified versions of any of the foregoing that retain antigen-binding activity (e.g., modified by the covalent attachment of polyalkylene glycol (e.g., polyethylene glycol, polypropylene glycol, polybutylene glycol) or other suitable polymer).

As used herein, an "epitope" can be formed both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin $V_H$/$V_L$ pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein.

The terms "specificity," "specifically binds," or "specific for" refers to the number of different types of antigens or antigenic determinants to which a particular antibody or antigen-binding fragment thereof can bind. Accordingly, an antibody or antigen-binding fragment thereof as defined herein is said to be "specific for" a first target or antigen compared to a second target or antigen when it binds to the first antigen with an affinity (as described herein, and suitably expressed, for example as a $K_D$ value) that is at least 50 times, such as at least 100 times, and preferably at least 1000 times, and up to 10,000 times or more better than the affinity with which said amino acid sequence or polypeptide binds to another target or polypeptide. Preferably, when an antibody or antigen-binding fragment thereof is "specific for" a target or antigen, compared to another target or antigen, it can bind said target or antigen, but not the other target or antigen.

As used herein, "small molecule inhibitors" include, but are not limited to, small peptides or peptide-like molecules, soluble peptides, and synthetic non-peptidyl organic or inorganic compounds. A small molecule inhibitor or antagonist can have a molecular weight of any of about 100 to about 20,000 daltons (Da), about 500 to about 15,000 Da, about 1000 to about 10,000 Da

BRIEF DESCRIPTION OF THE FIGURES

FIGS. 1A-1E demonstrate LAP expression on immune cells in GBM. Mononuclear cells were isolated following percoll gradient separation from intracranial GBM. The levels of surface LAP expression were determined on myeloid cells (FIG. 1A), γδ T cells (FIG. 1B), and CD4 T cells (FIG. 1C). Coexpression of LAP and FoxP3 was examined on CD4 T cells in GBM (FIG. 1D). FIG. 1E. Expression of LAP on γδ T cells in the spleen of GBM mice. *p<0.05

FIG. 3A-3B demonstrate induction of LAP expression on γδ T cells by glioma. LAP-γδ T cells were grown alone or co-cultured with GL261 glioma cells. Two and three days later, LAP expression was analyzed on γδ T cells. Representative results for both time points (FIG. 3A) and statistical analysis for three days incubation (FIG. 3B) are shown. *p<0.05

FIGS. 5A-5K demonstrate that Anti-LAP treatment eliminates sub-cutaneous glioma growth and activates the immune system. GL261 glioma cells were implanted in the flanks of C57BL/6 mice and treated with anti-LAP or isotype-matched control (IC) antibodies. Following anti-LAP treatment tumors shrunk (FIGS. 5A and 5B), peripheral Th1 responses increased (FIG. 5C), regulatory T cells decreased (FIGS. 5D-5F, 5K), CTL responses were up-regulated (FIGS. 5G-5J). *p<0.05, p<0.01, **p<0.0001

FIG. 52 depicts a sequence alignment and comparison between all human LAP isoforms.

FIG. 53 depicts a sequence alignment and comparison between all mouse LAP isoforms.

FIG. 54 depicts a sequence alignment and comparison between all human and mouse proTGF-β isoforms. SEQ ID NOs: 25-30 are disclosed in order of their appearance.

FIGS. 55A, 55B: melanoma, B16; FIGS. 55C-55F: intracranial GBM, FIGS. 55G, 55H: subcutaneous glioblastoma, GL261; FIGS. 55I-55N colorectal carcinoma (CRC) (FIGS. 55I-55K: AOM/DSS CRC, FIGS. 55L-55N: subcutaneous CRC). Mice were treated with TW7-28G11: FIGS. 55A, 55B, 55G, 55I-55N; and 16B4: FIGS. 55C-55F, 55H.

FIGS. 57A-57J depict effects of anti-LAP antibodies on innate immune responses in the spleen. FIGS. 57A, 57B show accumulation of CD11b-int/CD11c-hi cells and decrease in CD11b-hi/CD11c-int in the spleen after anti-LAP treatment. Expression of CD103 and PD-L1 is decreased with anti-LAP treatment (FIG. 57C). LAP is mainly expressed on CD11b-hi cells (FIG. 57D). CD11b-hi cells express increased levels of immunosuppressive cytokines, TGF-b and IL-10, and reduced expression of a proinflammatory cytokine, IL-12 as compared to CD11b-int (FIG. 57E). Co-culture of CD11b-int with CD8+ T cells promotes the expression of proinflammatory cytokines (FIG. 57F). Expression of antigen-presentation markers, MHCII (FIG. 87G) and CD86 (FIG. 57H) is higher on CD11b-int than on CD11b-hi. CD11b-hi cells are not able to support CD8+ T cell growth in vitro (FIG. 57I). Anti-LAP treatment leads to the accumulation of NK cells expressing IFN-g (FIG. 57J). Mice were treated with TW7-16B4.

FIG. 58A shows that anti-LAP treatment reduces the number of LAP+CD4+ T cells in vivo. Melanoma (B16)-bearing mice were treated with TW7-28G11 clone of anti-LAP and counted with non-competing TW7-16B4 clone. Mice were treated with TW7-28G11. FIG. 58B shows that LAP+CD4+ T cells express increased levels of suppression markers. FIG. 58C demonstrates that LAP+CD4+ T cells posses suppressive abilities. FIG. 58D shows that anti-LAP diminishes the suppressive abilities of LAP+CD4+ T cells.

FIGS. 60A-60C demonstrate that anti-LAP treatment combined with dendritic cell (DC) vaccination protects mice from GBM. Mice were prevaccinated with ovalbumin loaded DCs and treated with anti-LAP. A week later, the mice were implanted with GL261-OVA glioma cells intracranially and mice survival and tumor growth were followed thereafter. FIGS. 60D-60F demonstrate increased accumulation of tumor-specific CD8+ memory cells after anti-LAP treatment. Mice were treated with the TW7-16B4 anti-LAP clone.

Figure 66:
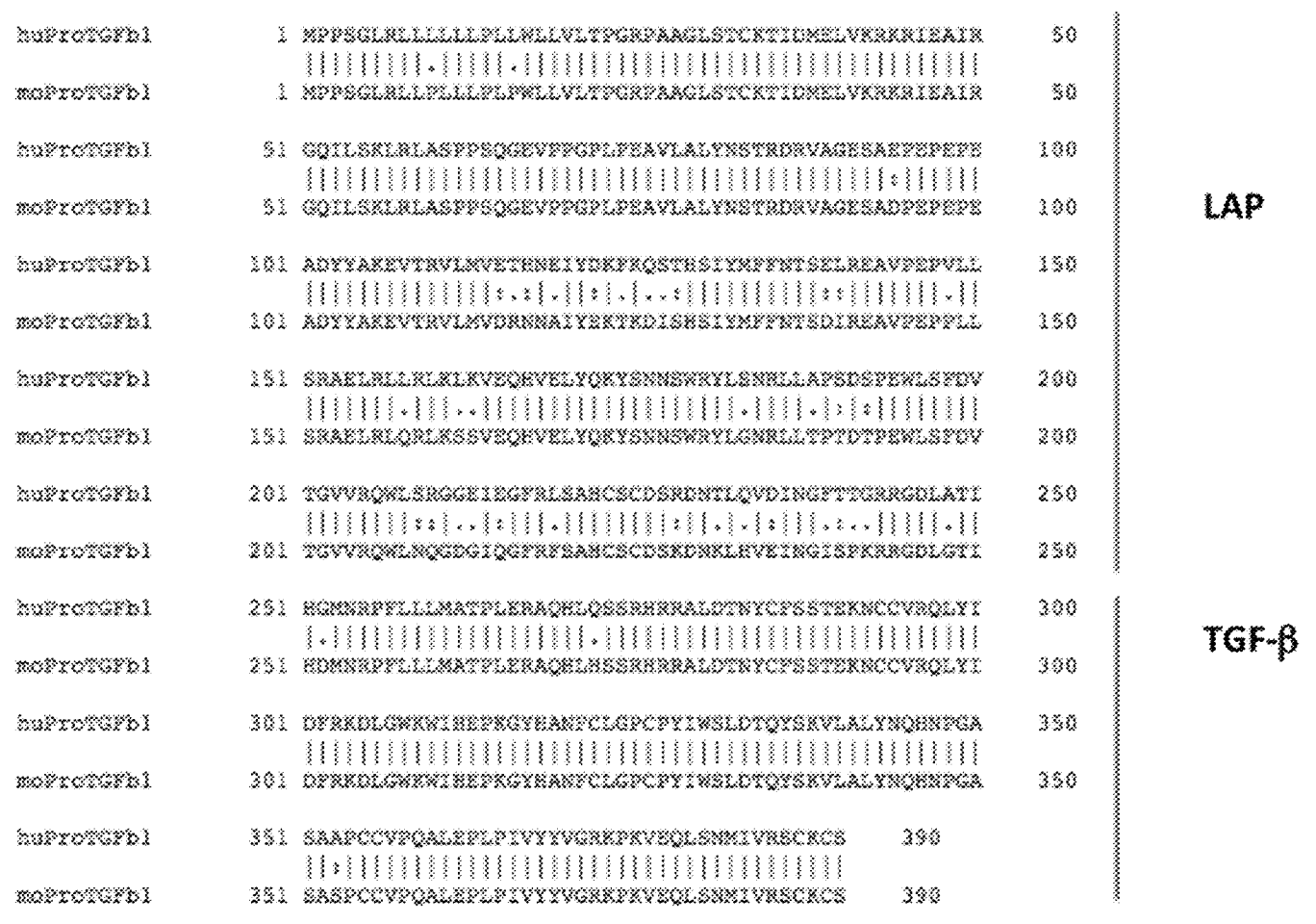

FIG. 66 depicts similarity between mouse and human proTGF-β protein sequences.

DETAILED DESCRIPTION

Figure 2A:
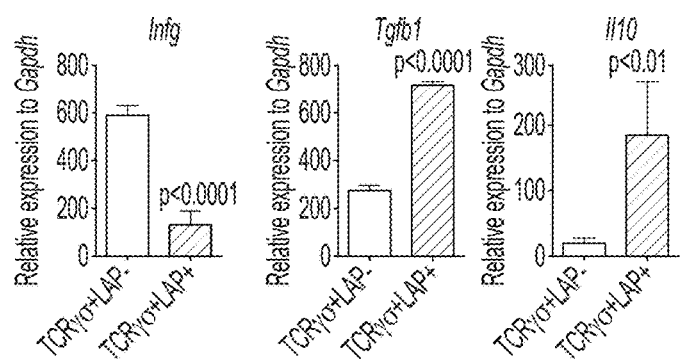
FIGS. 2A-2D demonstrate that LAP+γδ T cells exhibit immune suppressive properties. Expression of inflammatory cytokines was analyzed on LAP- and LAP+γδ T cells in naïve mice by qRT-PCR (FIG. 2A) and flow cytometry (FIG. 2B). LAP+γδ T cells suppress T cell proliferation (FIG. 2C) and induce FoxP3 expression (FIG. 2D) in naïve mice.

Compositions and methods are provided that relate to the discoveries described herein that tumor growth is lower and mice survive longer when treated with anti-LAP antibodies, and that the anti-LAP antibodies described herein block TGF-β release and deplete suppressive regulatory T cell populations, including CD4+LAP+ T cells and CD8+CD103+ T cells. Anti-LAP antibodies were tested in various cancer models, including a glioblastoma model, a melanoma model, and a colorectal cancer model, and similar intra-tumor and peripheral immune effects were observed, as described herein. Thus, as demonstrated herein, treatment with an anti-LAP antibody that acts, in part, by blocking TGF-β release and depleting suppressive CD4+ T cells, strongly influences systemic and intra-tumor immune responses by activating both innate and adaptive immunity and overcomes the mechanisms suppressing tumor-specific immunity.

LAP and LAP Binding Agents

LAP and TGF-β are translated as one precursor polypeptide that undergoes intracellular cleavage by furin, resulting in the separation of the N-terminal LAP protein portion from TGF-β. TGF-β is immediately reassembled non-covalently with LAP by forming a small latent complex (SLC) that retains TGF-β in its inactive form deposited on the cell surface bound to GARP receptor or embedded into the extracellular matrix following SLC binding to the latent TGF-β-binding protein 1 (LTBP-1). TGF-β must be released from its latent form by a specific signal to initiate signal transduction. This mechanism is believed to allow immediate availability and fast release of the active cytokine when needed and explains why TGF-β, different from other cytokines, is constitutively expressed but silent in many tissues.

The transforming growth factor beta (TGFβ) protein family consists of three distinct isoforms found in mammals (TGFβ1, TGFβ2, and TGFβ3). The TGFβ proteins activate and regulate multiple gene responses that influence disease states, including cell proliferative, inflammatory, and cardiovascular conditions. TGFβ is a multifunctional cytokine originally named for its ability to transform normal fibroblasts to cells capable of anchorage-independent growth. The TGFβ molecules are produced primarily by hematopoietic and tumor cells and can regulate, i.e., stimulate or inhibit, the growth and differentiation of cells from a variety of both normal and neoplastic tissue origins (Sporn et al., Science, 233: 532 (1986)), and stimulate the formation and expansion of various stromal cells.

The TGFβs are known to be involved in many proliferative and non-proliferative cellular processes such as cell proliferation and differentiation, embryonic development, extracellular matrix formation, bone development, wound healing, hematopoiesis, and immune and inflammatory responses. See e.g., Pircher et al, Biochem. Biophys. Res. Commun., 136: 30-37 (1986); Wakefield et al., Growth Factors, 1: 203-218 (1989); Roberts and Sporn, pp 419-472 in Handbook of Experimental Pharmacology eds M. B. Sporn & A. B. Roberts (Springer, Heidelberg, 1990); Massague et al., Annual Rev. Cell Biol., 6: 597-646 (1990); Singer and Clark, New Eng. J. Med., 341: 738-745 (1999). Also, TGFβ is used in the treatment and prevention of diseases of the intestinal mucosa (WO 2001/24813). TGFβ is also known to have strong immunosuppressive effects on various immunologic cell types, including cytotoxic T lymphocyte (CTL) inhibition (Ranges et al., J. Exp. Med., 166: 991, 1987), Espevik et al., J. Immunol., 140: 2312, 1988), depressed B cell lymphopoiesis and kappa light-chain expression (Lee et al., J. Exp. Med., 166: 1290, 1987), negative regulation of hematopoiesis (Sing et al., Blood, 72: 1504, 1988), down-regulation of HLA-DR expression on tumor cells (Czarniecki et al., J. Immunol., 140: 4217, 1988), and inhibition of the proliferation of antigen-activated B lymphocytes in response to B-cell growth factor (Petit-Koskas et al., Eur. J. Immunol., 18: 111, 1988). See also U.S. Pat. No. 7,527,791.

TGF-β isoform expression in cancer is complex and variable with different combinations of TGFβ isoforms having different roles in particular cancers. See e.g., U.S. Pat. No. 7,927,593. For example, TGF-β1 and TGF-β3 may play a greater role in ovarian cancer and its progression than TGFβ2; while TGF-β1 and TGF-β2 expression is greater in higher grade chondrosarcoma tumors than TGF-β3. In human breast cancer, TGF-β1 and TGF-β3 are highly expressed, with TGF-β3 expression appearing to correlate with overall survival—patients with node metastasis and positive TGFβ3 expression have poor prognostic outcomes. However, in colon cancer, TGF-β1 and TGF-β2 are more highly expressed than TGF-β3 and are present at greater circulating levels than in cancer-free individuals. In gliomas, TGF-β2 is important for cell migration.

As used herein, "Latency associated peptide" or "LAP" refers: to the amino-terminal domain of the human TGF-β1 precursor peptide having the amino acid sequence LSTCKTIDMELVKRKRIEAIRGQILSKLRLASPPSQGEVPPGPLPEAVLALYNSTRDRVAGESAEP EPEPEADYYAKEVTRVLMVETHNEIYDKFKQSTHSIYMFFNTSELREAVPEPVLLSRAELRLLRL KLKVEQHVELYQKYSNNSWRYLSNRLLAPSDSPEWLSFDVTGVVRQWLSRGGEIEGFRLSAHC SCDSRDNTLQVDINGFTTGRRGDLATIHGMNRPFLLLMATPLERAQHLQSSRHRR (SEQ ID NO: 1), as described by, e.g., amino acids 30-278 of NP_000651.3; to the amino-terminal domain of the human TGF-β2 precursor peptide having the amino acid sequence LSTCSTLDMDQFMRKRIEAIRGQILSKLKLTSPPEDYPEPEEVPPEVISIYNSTRDLLQEKASRRAA ACERERSDEEYYAKEVYKIDMPPFFPSENAIPPTFYRPYFRIVRFDVSAMEKNASNLVKAEFRVF RLQNPKARVPEQRIELYQILKSKDLTSPTQRYIDSKVVKTRAEGEWLSFDVTDAVHEWLHHKD RNLGFKISLHCPCCTFVPSNNYIIPNKSEELEARFAGIDGTSTYTSGDQKTIKSTRKKNSGKTPHLL LMLLPSYRLESQQTNRRKKR (SEQ ID NO: 2), as described by, e.g., amino acids 21-302 of NP_001129071.1; to the amino-terminal domain of the human TGF-β3 precursor peptide having the amino acid sequence LSTCTTLDFGHIKKKRVEAIRGQILSKLRLTSPPEPTVMTHVPYQVLALYNSTRELLEEMHGERE EGCTQENTESEYYAKEIHKFDMIQGLAEHNELAVCPKGITSKVFRFNVSSVEKNRTNLFRAEFR VLRVPNPSSKRNEQRIELFQILRPDEHIAKQRYIGGKNLPTRGTAEWLSFDVTDTVREWLLRRES NLGLEISIHCPCHTFQPNGDILENIHEVMEIKFKGVDNEDDHGRGDLGRLKKQKDHHNPHLILM MIPPHRLDNPGQGGQRKKR (SEQ ID NO: 3), as described by, e.g., amino acids 24-300 of NP_003230.1; to the amino-terminal domain of the mouse TGF-β1 precursor peptide having the amino acid sequence LSTCKTIDMELVKRKRIEAIRGQILSKLRLASPPSQGEVPPGPLPEAVLALYNSTRDRVAGESADP EPEPEADYYAKEVTRVLMVDRNNAIYEKTKDISHSIYMFFNTSDIREAVPEPPLLSRAELRLQRL KSSVEQHVELYQKYSNNSWRYLGNRLLTPTDTPEWLSFDVTGVVRQWLNQGDGIQGFRFSAH CSCDSKDNKLHVEINGISPKRRGDLGTIHDMNRPFLLLMATPLERAQHLHSSRHRR (SEQ ID NO: 4), as described by, e.g., amino acids 30-278 of NP_035707.1; to the amino-terminal domain of the mouse TGF-β2 precursor peptide having the amino acid sequence LSTCSTLDMDQFMRKRIEAIRGQILSKLKLTSPPEDYPEPDEVPPEVISIYNSTRDLLQEKASRRA AACERERSDEEYYAKEVYKIDMPSHLPSENAIPPTFYRPYFRIVRFDVSTMEKNASNLVKAEFRV FRLQNPKARVAEQRIELYQILKSKDLTSPTQRYIDSKVVKTRAEGEWLSFDVTDAVQEWLHHK DRNLGFKISLHCPCCTFVPSNNYIIPNKSEELEARFAGIDGTSTYASGDQKTIKSTRKKTSGKTPH LLLMLLPSYRLESQQSSRRKKR (SEQ ID NO: 5), as described by, e.g., amino acids 21-302 of NP_033393.2; to the amino-terminal domain of the mouse TGF-β3 precursor peptide having the amino acid sequence LSTCTTLDFGHIKKKRVEAIRGQILSKLRLTSPPEPSVMTHVPYQVLALYNSTRELLEEMHGERE EGCTQETSESEYYAKEIHKFDMIQGLAEHNELAVCPKGITSKVFRFNVSSVEKNGTNLFRAEFRV LRVPNPSSKRTEQRIELFQILRPDEHIAKQRYIGGKNLPTRGTAEWLSFDVTDTVREWLLRRESN LGLEISIHCPCHTFQPNGDILENVHEVMEIKFKGVDNEDDHGRGDLGRLKKQKDHHNPHLILM M IPPHRLDSPGQGSQRKKR (SEQ ID NO: 6), as described by, e.g., amino acids 24-298 of NP_033394.2; together with any other naturally occurring allelic, splice variants, and processed forms thereof. The term "LAP" is also used, in some embodiments, to refer to truncated forms or fragments of the LAP polypeptide. Reference to any such forms of LAP can be identified in the application, e.g., by "LAP(215-217)." Specific residues of LAP can be referred to as, for example, "LAP (194)," "amino acid 194 of SEQ ID NO: 1," or "Cys 194 of LAP of SEQ ID NO: 1."

In some embodiments, LAP can exist as a homodimer of LAP molecules. Sequences of LAP polypeptides are known for a number of species, e.g. human and mouse LAP. Agents that physically interact with, bind to, or sterically occlude ligand binding to their interaction sites can be used to inhibit LAP activity.

LAP contains important residues necessary for the interaction with binding partners, e.g., TGFβ. Cysteines at positions 194 and 196 of SEQ ID NOs: 1 and 4, 206 and 208 of SEQ ID NOs: 2 and 5, and 204 and 206 of SEQ ID NOs: 3 and 6 are important in the intermolecular disulphide bond between two LAPs. Their mutation to serine renders the molecule "active" (Sanderson et al., Proc. Natl. Acad. Sci. USA, 92, 2572-2576 (1995); Brunner et al, Mol. Endocrinol. 6, 1691-1700 (1992); Brunner et al, J. Biol. Chem, 264, 13660-13664 (1989); which are incorporated by reference herein in their entireties). The RGD/SGD motif at positions 215-217 of SEQ ID NOs: 1 and 4, 241-243 of SEQ ID NOs: 2 and 5, and 238-240 of SEQ ID NOs: 3 and 6 facilitates the interaction with integrins (Munger et al, Mol Biol Cell, 9:2627-2638 (1998; DerynckR, TIBS, 19, 548-553 (1994); which are incorporated by reference herein in their entireties). Cysteine at position 4 of SEQ ID NOs: 1-6 is important for the disulphide bridge with the third cysteine-rich repeat of LTBP (Saharinen et al. The EMBO Journal, 15, 245-253 (1996)). Nucleic acid encoding TGFβ is described in U.S. Pat. No. 5,801,231. The foregoing references are incorporated by reference herein in their entireties.

Provided herein are compositions and methods based, in part, on the discovery that tumor growth is lower and mice survive longer when treated with anti-LAP antibodies, and that the effects of the anti-LAP antibodies described herein were based, in part, on their ability to inhibit the release of TGF-β from the small latent complex (SLC) comprising LAP that retains TGF-β in its inactive form, and/or to reduce the number of regulatory CD4+ T cells. As shown herein, anti-LAP antibody treatment also affected both systemic and intra-tumor immunity as follows. Tumors were infiltrated by increased numbers of cytotoxic CD8+ T cells and intra-tumor Foxp3 Tregs were decreased. CD4+ and CD8+ intra-tumor T cells had decreased expression of PD-1, LAG3 and CD103. In the periphery, CD4+ and CD8+ T cells, expressing IFN-γ and granzyme B, were increased, respectively whereas CD103+ T cells were decreased. Finally, there were reduced numbers of tolerogenic dendritic cells expressing CD103 and PD-L1 whereas MHC II was elevated on splenic myeloid cells. The anti-LAP antibodies described herein strongly influence systemic and intra-tumor immune responses by activating both innate and adaptive immunity and overcome the mechanisms suppressing tumor-specific immunity. Without wishing to be bound or limited by theory, this activity may involve sequestering active TGF-β by preventing its release from the SLC and/or reducing the number of regulatory CD4+ T cells. Given their demonstrated activities against a range of tumor types, anti-LAP antibodies as described herein can be used as a monotherapy or combined with other anti-tumor modalities, such as, for example, anti-PD1 antibodies, other agents targeting tumor immunosuppression and/or other anti-cancer therapies, and represent a novel immunotherapeutic approach for the treatment of cancers.

Accordingly, provided herein, in some aspects, are compositions and methods to treat cancer and tumors where LAP expression and/or activity is associated with suppression of cancer- or tumor-specific immunity, comprising administering a therapeutically effective amount of a LAP binding agent to a subject in need thereof. Such binding agents can be used to modulate the interaction between LAP and TGFβ, such that TGFβ is not released from the small latent complex, and/or inhibit/block interaction between LAP and another LAP molecule, i.e., inhibit/block homodimerization. In particular, in preferred embodiments of the aspects described herein, such LAP binding agents can be used to inhibit or block release of TGFβ from the small latent complex comprising LAP and mature TGFβ, thus sequestering mature TGFβ.

In some embodiments of the methods described herein, a LAP binding agent can bind a LAP molecule having the sequence set forth in any one of SEQ ID NOs: 1-6. In some embodiments of the methods described herein, a LAP binding agent can bind a LAP molecule having the sequence set forth in any one of SEQ ID NOs: 1-3. In some embodiments of the methods described herein, a LAP binding agent can bind a conserved region shared between the sequences set forth in any of SEQ ID NOs: 1-3. In some embodiments, a LAP binding agent can bind an epitope derived from any of SEQ ID NOs: 1-6 and a LAP interacting protein, such as TGFβ. In some such embodiments, where the LAP binding agent binds an epitope derived from any of SEQ ID NOs: 1-6 and TGFβ, binding of the LAP binding agent to the epitope inhibits or blocks release of TGFβ from the small latent complex.

In some embodiments, a LAP binding agent for use in the compositions and methods described herein can bind or physically interact with a LAP ligand interaction site, e.g. a site that interacts with mature TGFβ, a site that interacts with integrins, and/or a site that interacts with LTBP. Non-limiting examples of such sites include R189 of SEQ ID NOs: 1 and 4, R196 of SEQ ID NOs: 2 and 5, and R192 of SEQ ID NOs: 3 and 6 (see, e.g. McGowan et al. The Journal of Clinical Endocrinology and Metabolism 2003 88:3321-6; which is incorporated by reference herein in its entirety). Accordingly, in some embodiments of the compositions and methods described herein, a LAP binding agent binds or physically interacts with R189 of SEQ ID NOs: 1 and 4, R196 of SEQ ID NOs: 2 and 5, and/or R192 of SEQ ID NOs: 3 and 6. In some embodiments of the compositions and methods described herein, a LAP binding agent binds or physically interacts with amino acids 215-217 of SEQ ID NOs: 1 and 4, amino acids 241-243 of SEQ ID NOs: 2 and 5, and/or amino acids 238-240 of SEQ ID NOs: 3 and 6. In some embodiments of the methods described herein, a LAP binding agent binds or physically interacts with Cys4 of any of SEQ ID NOs: 1-6.

In some embodiments of the aspects described herein, a LAP binding agent for use in the compositions and methods described herein can bind or interact with a LAP homodimerization site, i.e., a site that interacts with another LAP molecule. Accordingly, in some embodiments of the aspects described herein, a LAP binding agent binds or physically interacts with Cys194 and/or Cys196 of SEQ ID NOs: 1 and 4, Cys206 and/or Cys208 of SEQ ID NOs: 2 and 5, and/or Cys204 and/or Cys206 of SEQ ID NOs: 3 and 6.

As used herein, the term "LAP binding agent" refers to a molecule or agent that specifically binds LAP and significantly modulates the interaction between LAP and any of its ligands or molecules that interact with LAP and consequently modulates their resultant biological or functional activity in vitro, in situ, and/or in vivo, including activity of downstream pathways mediated by LAP signaling, such as, for example, TGF-β release from the small latent complex or latent complex, LAP-mediated inhibition of immune responses and LAP-mediated inhibition of anti-tumor immune responses. Exemplary LAP binding agents contemplated for use in the various aspects and embodiments described herein include, but are not limited to, antibodies or antigen-binding fragments thereof that specifically bind to one or more amino acid residues or epitopes on LAP involved in the binding and/or interactions of LAP and TGF-β, LAP and integrins, and/or LAP and LTBP, and/or modulate LAP homodimerization and/or binding; small molecule agents that target or specifically bind to one or more amino acid residues or epitopes on LAP involved in the binding and/or interactions of LAP and TGFβ, LAP and integrins, and/or LAP and LTBP, and/or modulate LAP homodimerization and/or binding; and RNA or DNA aptamers that bind to one or more amino acid residues or epitopes on LAP involved in the binding and/or interactions of LAP and TGFβ, LAP and integrins, and/or LAP and LTBP, and/or modulate LAP homodimerization and/or binding. In preferred embodiments of the aspects described herein, a LAP binding agent specifically binds LAP and inhibits or blocks TGF-β release from the small latent complex or latent complex.

As used herein, a LAP binding agent has the ability to modulate the interaction between LAP and TGF-β, LAP and integrins, and/or LAP and LTBP, and/or modulate LAP homodimerization and/or their resultant biological or functional activity in vitro, in situ, and/or in vivo by at least 5%, at least 10%, at least 20%, at least 30%, at least 40%, at least 50%, at least 60%, at least 70%, at least 80%, at least 90%, at least 95%, at least 98%, at least 99%, or more, relative to the interaction and/or activity in the absence of the LAP binding agent. At a minimum, a LAP binding agent as described herein blocks tumor-induced immune suppression in a mouse cancer model, such as a subcutaneous mouse glioma model. This activity leads to higher expression of IFNγ on CD4+ T cells, reduced numbers and/or activity of regulatory CD4+ T cells, increased numbers and/or infiltration of cytotoxic CD8+ T cells to the tumor, decreased tumor size, and/or increased survival in the mouse subcutaneous glioma model.

"Modulating an interaction between LAP and TGF-β/integrins/latent TGF-β binding protein/LAP," or "impacting an interaction between LAP and TGF-β/integrins/latent TGF-β binding protein/LAP" as used interchangeably herein, generally means either modulating, i.e., increasing or decreasing, the interaction between or binding of LAP and TGF-β/integrins/latent TGF-β binding protein/LAP by at least 5%, at least 10%, at least 25%, at least 50%, at least 60%, at least 70%, at least 80%, at least 90%, at least 95%, at least 98%, or more, compared to the interaction between LAP and TGF-β/integrins/latent TGF-β binding protein/LAP under the same conditions but without the presence of a LAP binding agent as described herein. In preferred embodiments of the aspects described herein, a LAP binding agent modulates the interaction between LAP and TGF-β, such that release of TGF-β from the small latent complex is inhibited or blocked, and/or reduces the number of and/or activity of regulatory CD4+ T cells.

Some LAP binding reagents, such as anti-LAP antibodies are known in the art. See, e.g., Ali et al. PLOS ONE 2008:e1914; which is incorporated by reference herein in its entirety. Further examples of anti-LAP antibody reagents are described in U.S. Pat. No. 8,198,412 and U.S. Patent Publication No. 2008/0206219; which are incorporated by reference herein in their entireties.

In some embodiments of the aspects described herein, an anti-LAP antibody or antigen-binding fragment thereof for use in the compositions and methods described herein can bind or physically interact with a LAP ligand interaction site, e.g., a site that interacts with mature TGF-β, a site that interacts with integrins, and/or a site that interacts with LTBP. In some embodiments of the aspects described herein, an anti-LAP antibody or antigen-binding fragment thereof for use in the compositions and methods described herein binds or physically interacts with an epitope of LAP that exists when LAP is bound to latent TGF-β. In some embodiments of the aspects described herein, an anti-LAP antibody or antigen-binding fragment thereof for use in the compositions and methods described herein binds both mouse and human LAP.

In some embodiments of the aspects described herein, an anti-LAP antibody or antigen-binding fragment thereof binds or physically interacts with R189 of SEQ ID NOs: 1 and 4, R196 of SEQ ID NOs: 2 and 5, and/or R192 of SEQ ID NOs: 3 and 6. In some embodiments of the aspects described herein, an anti-LAP antibody or antigen-binding fragment thereof binds or physically interacts with amino acids 215-217 of SEQ ID NOs: 1 and 4, amino acids 241-243 of SEQ ID NOs: 2 and 5, and/or amino acids 238-240 of SEQ ID NOs: 3 and 6. In some embodiments of the aspects described herein, an anti-LAP antibody or antigen-binding fragment thereof binds or physically interacts with Cys4 of any of SEQ ID NOs: 1-6.

In some embodiments of the aspects described herein, an anti-LAP antibody or antigen-binding fragment thereof for use in the compositions and methods described herein can bind or physically interact with a LAP homodimerization site, i.e., a site that interacts with another LAP molecule. Accordingly, in some embodiments of the aspects described herein, an anti-LAP antibody or antigen-binding fragment thereof binds or physically interacts with Cys194 and/or Cys196 of SEQ ID NOs: 1 and 4, Cys206 and/or Cys208 of SEQ ID NOs: 2 and 5, and/or Cys204 and/or Cys206 of SEQ ID NOs: 3 and 6.

Antibodies or antigen-binding fragments thereof that are specific for or that selectively bind LAP, suitable for use in the compositions and for practicing the methods described herein are preferably monoclonal, and can include, but are not limited to, human, humanized, CDR grafted, or chimeric antibodies, comprising single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain antigen or target binding sites or "antigen-binding fragments." The immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art. The term "antibody" is intended to refer to immunoglobulin molecules consisting of 4 polypeptide chains, two heavy (H) chains and two light (L) chains. The chains are usually linked to one another via disulfide bonds. Each heavy chain is composed of a variable region of said heavy chain (abbreviated here as HCVR or $V_H$) and a constant region of said heavy chain. The heavy chain constant region consists of three domains CH1, CH2 and CH3. Each light chain is composed of a variable region of said light chain (abbreviated here as LCVR or $V_L$) and a constant region of said light chain. The light chain constant region consists of a CL domain. The $V_H$ and $V_L$ regions can be further divided into hypervariable regions referred to as complementarity-determining regions (CDRs) and interspersed with conserved regions referred to as framework regions (FR). Each $V_H$ and $V_L$ region thus consists of three CDRs and four FRs which are arranged from the N terminus to the C terminus in the following order: FR1, CDR1, FR2, CDR2, FR3, CDR3, FR4. This structure is well-known to those skilled in the art.

As used herein, the term "CDR" refers to the complementarity determining region within antibody variable sequences. There are three CDRs in each of the variable regions of the heavy chain and of the tight chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al, Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Each complementarity determining region may comprise amino acid residues from a "complementarity region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop. For example, the CDRH1 of the human heavy chain of antibody 4D5 includes amino acids 26 to 35. Chothia and coworkers (Chothia & Lesk, J. Mol. Biol, 196:901-917 (1987) and Chothia et al., Nature 342:877-883 (-1989)) found that certain sub-portions within Kabat CDRs adopt nearly identical peptide backbone conformations, in spite of great diversity at the level of amino acid sequence. Mese sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB). 9:133439 (1995)) and MacCallum (J Mot Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs. As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)) Amino acid numbering of antibodies or antigen binding fragments is also according to that of Kabat.

Examples of antibody fragments encompassed by the terms antigen-binding fragment or "antigen-binding moiety" as described herein include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) a dAb fragment (Ward et al., Nature 341, 544-546 (1989)) which consists of a $V_H$ domain or a $V_L$ domain or of $V_H$, CH1, CH2, DH3, or $V_H$, CH2, CH3; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$—$C_H1$-$V_H$-$C_H1$) which, together with complementary light chain polypeptides, form a pair of antigen binding regions (Zapata et al. Protein Eng. 8(10): 1057-1062 (1995); and U.S. Pat. No. 5,641,870); and modified versions of any of the foregoing (e.g., modified by the covalent attachment of polyalkylene glycol (e.g., polyethylene glycol, polypropylene glycol, polybutylene glycol) or other suitable polymer).

As used herein, an "epitope" can be formed both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope can also be formed from non-contiguous amino acids found on two different proteins, which occurs only when they are bound to each other, such as, for example, when LAP binds TGF-β. Accordingly, in some embodiments of the compositions and methods described herein, an anti-LAP antibody or antigen-binding fragment thereof binds to an epitope formed from non-contiguous amino acids found when LAP is bound to TGF-13. An epitope typically includes at least 3, and, more usually, at least 5, about 9, or about 8-10 amino acids in a unique spatial conformation. An "epitope" includes the unit of structure conventionally bound by an immunoglobulin $V_H/V_L$ pair. Epitopes define the minimum binding site for an antibody, and thus represent the target of specificity of an antibody or antigen-binding fragment thereof. In the case of a single domain antibody, an epitope represents the unit of structure bound by a variable domain in isolation. The terms "antigenic determinant" and "epitope" can also be used interchangeably herein.

With respect to a target or antigen, the term "ligand interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen. For example, in some embodiments, a ligand interaction site on LAP can be any site to which TGF-β binds or interacts, or any site to which integrins bind or interact, or any site to which LTBP binds or interacts. More generally, a "ligand interaction site" can be any site, epitope, antigenic determinant, part, domain or stretch of amino acid residues on a target or antigen to which a binding site of a LAP binding agent described herein can bind such that the interaction or binding between LAP and the ligand (and/or any pathway, interaction, signalling, biological mechanism or biological effect mediated by LAP binding to a ligand is involved) is modulated. See, for example, Mittl et al., Protein Sci. 5: 1261-1271(1996), "The crystal structure of TGFβ3 and comparison to TGFβ2: implications for receptor binding," the contents of which are herein incorporated by reference in their entireties.

In the context of an antibody or antigen-binding fragment thereof, the term "specificity" or "specific for" refers to the number of different types of antigens or antigenic determinants to which a particular antibody or antigen-binding fragment thereof can bind. The specificity of an antibody or antigen-binding fragment or portion thereof can be determined based on affinity and/or avidity. The affinity, represented by the equilibrium constant for the dissociation ($K_D$) of an antigen with an antigen-binding protein, is a measure for the binding strength between an antigenic determinant and an antigen-binding site on the antigen-binding protein: the lesser the value of the $K_D$, the stronger the binding strength between an antigenic determinant and the antigen-binding molecule. Alternatively, the affinity can also be expressed as the affinity constant ($K_A$), which is $1/K_D$. As will be clear to the skilled person, affinity can be determined in a manner known per se, depending on the specific antigen of interest. Accordingly, an antibody or antigen-binding fragment thereof as defined herein is said to be "specific for" a first target or antigen compared to a second target or antigen when it binds to the first antigen with an affinity (as described above, and suitably expressed, for example as a $K_D$ value) that is at least 50 times, such as at least 100 times, and preferably at least 1000 times, and up to 10,000 times or more better than the affinity with which said amino acid sequence or polypeptide binds to another target or polypeptide. Preferably, when an antibody or antigen-binding fragment thereof is "specific for" a target or antigen, compared to another target or antigen, it can bind the target or antigen, but does not bind the other target or antigen.

However, as understood by one of ordinary skill in the art, in some embodiments, where a binding site on a target is shared or partially shared by multiple, different ligands, an antibody or antigen binding fragment thereof can specifically bind to a target, such as LAP, and have the functional effect of inhibiting/preventing binding of multiple, different ligands.

Avidity is the measure of the strength of binding between an antigen-binding molecule and the pertinent antigen. Avidity is related to both the affinity between an antigenic determinant and its antigen binding site on the antigen-binding molecule, and the number of pertinent binding sites present on the antigen-binding molecule. Typically, antigen-binding proteins will bind to their cognate or specific antigen with a dissociation constant ($K_D$ of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ $M^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction is, the lower is its $K_D$. Preferably, a binding site on an anti-LAP antibody or antigen-binding fragment thereof described herein will bind with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

In some embodiments of the methods described herein, the LAP binding agent is an anti-LAP monoclonal antibody.

The term "monoclonal antibody," as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each antibody in a monoclonal preparation is directed against the same, single determinant on the antigen. It is to be understood that the term "monoclonal antibody" refers to an antibody that is derived from a single clone, including any eukaryotic, prokaryotic, or phage clone, and not the method by which it is produced. The term "monoclonal antibody" as used herein is not limited to antibodies produced through hybridoma technology, and the modifier "monoclonal" is not to be construed as requiring production of the antibody by any particular method. For example, the monoclonal antibodies to be used in accordance with the invention can be made by the hybridoma method first described by Kohler et al., Nature 256:495 (1975), or later adaptations thereof, or can be made by recombinant DNA methods (see, e.g., U.S. Pat. No. 4,816,567). The "monoclonal antibodies" can also be isolated from phage antibody libraries using the techniques described in Clackson et al., Nature 352:624-628 (1991) or Marks et al., J. Mol. Biol. 222:581-597 (1991), for example.

In some embodiments of the compositions and methods described herein, the LAP binding agent is an anti-LAP monoclonal antibody produced by any one of hybridoma clones TW4-9E7, TW4-5A8, TW4-3E5, TW4-4E5, TW4-12B12, TW4-13B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11 (deposited on Jul. 18, 2017 with the American Type Culture Collection (ATCC), 10801 University Boulevard, Manassas, Va. 20110-2209; ATCC Accession No. PTA-124319), TW7-7H4, and TW7-20B9.

In some embodiments of the compositions and methods described herein, the LAP binding agent is an anti-LAP monoclonal having one or more biological characteristics of an antibody produced by any one of hybridoma clones TW4-9E7, TW4-5A8, TW4-4E5, TW4-12B12, TW4-13B12, TW4-1G12, TW4-3E5, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9.

As used herein, an antibody having a "biological characteristic" of a designated antibody, such as the TW7-28G11 antibody or the TW7-16B4, is one that possesses one or more of the biological characteristics of that antibody which distinguish it from other antibodies that bind to the same antigen. For example, a biological characteristics of the TW7-28G11 monoclonal antibody includes having an $ED_{50}$ value (i.e., the dose therapeutically effective in 50% of the population) at or around the $ED_{50}$ value of the TW7-28G11 antibody for the given population; having an $EC_{50}$ value (i.e., the dose that achieves a half-maximal inhibition of a given parameter or phenotype) at or around the $EC_{50}$ value of the TW7-28G11 antibody for a given parameter or phenotye. The effects of any particular dosage can be monitored by a suitable bioassay. For example, in some embodiments of these aspects, the given parameter or phenotype to be inhibited by the anti-LAP antibody that specifically binds to LAP and has one or more biological characteristics of the TW7-28G11 antibody can include, but is not limited to, the ability to specifically bind both human and mouse LAP and/or prevent or inhibit release of TGF-β from the small latent complex, and/or selectively deplete regulatory T cell populations, such as CD4+ regulatory T cells expressing LAP and/or CD103+CD8 T cells.

In some embodiments of the aspects described herein, anti-LAP antibodies for use in the compositions and methods described herein include monoclonal antibodies that bind to the same epitope or epitopes of LAP as the monoclonal antibody produced by any one of hybridoma clones TW4-9E7, TW4-5A8, TW4-3E5, TW4-4E5, TW4-12B12, TW4-13B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9.

In some aspects, the anti-LAP monoclonal antibody is the monoclonal anti-LAP antibody TW7-28G11 produced or expressed by the hybridoma TW7-28G11 described herein, and referred to as the "TW7-28G11 antibody" or "TW7-28G11 anti-LAP antibody" and derivatives or antigen-binding fragments thereof, including, for example, a "TW7-28G11 variable heavy chain," or a "TW7-28G11 variable light chain."

As described herein, the TW7-28G11 hybridoma produces a monoclonal antibody termed herein as the "TW7-28G11 anti-LAP antibody" or "TW7-28G11 antibody," or the "variant TW7-28G11 anti-LAP monoclonal antibody" that is highly specific for LAP and can potently inhibit LAP biological activity and provide highly therapeutic effects in the treatment of cancer. As shown herein, the TW7-28G11 anti-LAP antibody binds both human and mouse LAP and prevents or inhibits release of TGF-β from the small latent complex and selectively depletes regulatory T cell populations, such as CD4+ regulatory T cells expressing LAP and/or CD103+CD8 T cells when administered in vivo. The biological characteristics of the TW7-28G11 anti-LAP antibody, and any antigen-binding fragments derived or generated therefrom, render it particularly useful for the compositions and methods described herein, including therapeutic and diagnostic applications. Accordingly, sequence analysis of the TW7-28G11 antibody was performed, as described herein, to identify the heavy and light chain variable domain sequences, and complementarity determining region (CDR) sequences, of the TW7-28G11 antibody for use in the compositions and methods described herein.

Throughout the present specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), which is also available on the world wide web, and is expressly incorporated herein in its entirety by reference. The "EU index as in Kabat" refers to the residue numbering of the human IgG1 EU antibody. As used herein, "Kabat sequence numbering" or "Kabat labeling" refer to numbering of the sequence encoding a variable region according to the EU index as in Kabat. For the heavy chain variable region, the hypervariable region ranges from amino acid positions 31 to 35 for CDR1, amino acid positions 50 to 65 for CDR2, and amino acid positions 95 to 102 for CDR3, according to the Kabat numbering. For the light chain variable region, the hypervariable region ranges from amino acid positions 24 to 34 for CDR1, amino acid positions 50 to 56 for CDR2, and amino acid positions 89 to 97 for CDR3, according to the Kabat numbering. In some embodiments, IMGT (INTERNATIONAL IMMUNOGENETICS INFORMATION SYSTEM) numbering of variable regions can also be used, which is the numbering of the residues in an immunoglobulin variable heavy or light chain according to the methods of the IIMGT, as described in Lefranc, M.-P., "The IMGT unique numbering for immunoglobulins, T cell Receptors and Ig-like domains", The Immunologist, 7, 132-136 (1999), and is expressly incorporated herein in its entirety by reference. As used herein, "IMGT sequence numbering" refers to numbering of the sequence encoding a variable region according to the IMGT.

The nucleotide sequence encoding a $V_H$ or variable domain of the heavy chain of the TW7-28G11 antibody, as obtained by analysis of sequences obtained from the TW7-28G11 hybridoma, is:

(SEQ ID NO: 7)
ATGAAGTTGTGGCTGAACTGGATTTTCCTTGTAACACTTTTAAATGATAT

CCAGTGTGAGGTGAAGCTGGTGGAGTCTGGAGGAGGCTTGGTACAGCCTG

GGGGTTCTCTGAGTCTCTCCTGTGCAGCTTCTGGATTCACCTTCACTGAT

TACTACATGAGCTGGGTCCGCCAGCCTCCAGGGAAGGCACTTGAGTGGTT

GGGTTTTATTAGAAACAAACCTAATGGTTACACAACAGAGTACAGTGCAT

CTGTGAAGGGTCGGTTCACCATCTCCAGAGATAATTCCCAAAGCATCCTC

TATCTTCAAATGAATGTCCTGAGAGCTGAGGACAGTGCCACTTATTACTG

TGCAAGATATACGGGGGGGGGTTACTTTGACTACTGGGGCCAAGGCACCA

CTCTCACAGTCTCCTCA.

The amino acid sequence of the $V_H$ domain of the TW7-28G11 antibody corresponding to SEQ ID NO: 7 is:

(SEQ ID NO: 8)
MKLWLNWIFLVTLLNDIQCEVKLVESGGGLVQPGGSLSLSCAASGFTFTD

YYMSWVRQPPGKALEWLGFIRNKPNGYTTEYSASVKGRFTISRDNSQSIL

YLQMNVLRAEDSATYYCARYTGGGYFDYWGQGTTLTVSS.

The amino acid sequence of the complementarity determining region 1 or CDR1 of the $V_H$ domain of SEQ ID NO: 8 of the TW7-28G11 antibody according to the Kabat sequence numbering is: DYYMS (SEQ ID NO: 9). The amino acid sequence of the CDR2 of the $V_H$ domain of SEQ ID NO: 8 of the TW7-28G11 antibody according to the Kabat sequence numbering is: FIRNKPNGYTTEYSASVKG (SEQ ID NO: 10). The amino acid sequence of the CDR3 of the $V_H$ domain of SEQ ID NO: 8 of the TW7-28G11 antibody according to the Kabat sequence numbering is: YTGGGYFDY (SEQ ID NO: 11).

The nucleotide sequence encoding a $V_L$ or variable domain of the light chain of the TW7-28G11 antibody, as obtained by analysis of sequences obtained from the TW7-28G11 hybridoma, is:

(SEQ ID NO: 12)
ATGATGTCCTCTGCTCAGTTCCTTGGTCTCCTGTTGCTCTGTTTTCAAGG

TACCAGATGTGATATCCAGATGACACAGACTACATCCTCCCTGTCTGCCT

CTCTGGGAGACAGACTCACCATCAGTTGCAGGGCAAGTCAGGACATTAGC

AATTATTTAAACTGGTATCAGCAGAAACCAGATGGAACTGTTAAACTCCT

-continued
GATCTACTACACATCAAGATTACACTCAGGAGTCCCATCAAGGTTCAGTG

GCAGTGGGTCTGGAACAGATTATTCTCTCACCATTAGCAACCTGGAGCAA

GCAGATATTGCCACTTACTTTTGCCAACAGGGTGATACACTTCCGTGGAC

GTTCGGTGGAGGCACCAAGCTGGAAATCAAA.

The amino acid sequence of the $V_L$ domain of the TW7-28G11 antibody corresponding to SEQ ID NO: 12 is:

(SEQ ID NO: 13)
MMSSAQFLGLLLLCFQGTRCDIQMTQTTSSLSASLGDRLTISCRASQDIS

NYLNWYQQKPDGTVKLLIYYTSRLHSGVPSRFSGSGSGTDYSLTISNLEQ

ADIATYFCQQGDTLPWTFGGGTKLEIK.

The amino acid sequence of the complementarity determining region 1 or CDR1 of the $V_L$ domain of SEQ ID NO: 13 of the TW7-28G11 antibody according to the Kabat sequence numbering is: RASQDISNYLN (SEQ ID NO: 14). The amino acid sequence of the CDR2 of the $V_L$ domain of SEQ ID NO: 13 of the TW7-28G11 antibody according to the Kabat sequence numbering is: YTSRLHS (SEQ ID NO: 15). The amino acid sequence of the CDR3 of the $V_L$ domain of SEQ ID NO: 13 of the TW7-28G11 antibody according to the Kabat sequence numbering is: QQGDTLPWT (SEQ ID NO: 16).

The amino acid sequence of the framework 1 or FR1 region of the $V_H$ domain of SEQ ID NO: 8 of the TW7-28G11 antibody according to the Kabat sequence numbering is: EVKLVESGGGLVQPGGSLSLSCAASGFTFT (SEQ ID NO: 17). The amino acid sequence of the framework 2 or FR2 region of the $V_H$ domain of SEQ ID NO: 8 of the TW7-28G11 antibody according to the Kabat sequence numbering is: WVRQPPGKALEWLG (SEQ ID NO: 18). The amino acid sequence of the framework 3 or FR3 region of the $V_H$ domain of SEQ ID NO: 8 of the TW7-28G11 antibody according to the Kabat sequence numbering is: RFTISRDNSQSILYLQMNVLRAEDSATYYCAR (SEQ ID NO: 19). The amino acid sequence of the framework 4 or FR4 region of the $V_H$ domain of SEQ ID NO: 8 of the TW7-28G11 antibody according to the Kabat sequence numbering is: WGQGTTLTVSS (SEQ ID NO: 20).

The amino acid sequence of the framework 1 or FR1 region of the $V_L$ domain of SEQ ID NO: 13 of the TW7-28G11 antibody according to the Kabat sequence numbering is: DIQMTQTTSSLSASLGDRLTISC (SEQ ID NO: 21). The amino acid sequence of the framework 2 or FR2 region of the $V_L$ domain of SEQ ID NO: 13 of the TW7-28G11 antibody according to the Kabat sequence numbering is: WYQQKPDGTVKLLIY (SEQ ID NO: 22). The amino acid sequence of the framework 3 or FR3 region of the $V_L$ domain of SEQ ID NO: 13 of the TW7-28G11 antibody according to the Kabat sequence numbering is: GVPSRFSGSGSGTDYSLTISNLEQADIATYFC (SEQ ID NO: 23). The amino acid sequence of the framework 2 or FR2 region of the $V_L$ domain of SEQ ID NO: 13 of the TW7-28G11 antibody according to the Kabat sequence numbering is: FGGGTKLEIK (SEQ ID NO: 24).

Accordingly, in some embodiments of the aspects provided herein, the heavy and/or light chain variable domain(s) sequence(s) of the TW7-28G11 antibody, i.e., SEQ ID NO: 8, and/or SEQ ID NO: 13, and their respective CDR sequences SEQ ID NOs: 9-11 and SEQ ID NOs: 14-16 can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies or antigen-binding fragments derived from the TW7-28G11 antibody or any one of the antibodies produced by hybrodimas TW4-9E7, TW4-5A8, TW4-3E5, TW4-4E5, TW4-12B12, TW4-13B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9 useful in the compositions and methods described herein will maintain the ability to immunospecifically bind LAP, such that the variant, CDR-grafted, chimeric, humanized, or composite antibody or antigen-binding fragment thereof has at least 50%, at least 60%, at least 70%, at least 80%, at least 90%, at least 95% or more binding to LAP relative to the original antibody from which it is derived.

In some embodiments of the aspects described herein, an anti-LAP antibody or an antigen-binding fragment thereof described herein, which specifically binds to LAP (e.g., human LAP), comprises a light chain variable region ($V_L$) comprising $V_L$ CDR1 of SEQ ID NO: 14, $V_L$ CDR2 of SEQ ID NO: 15, and $V_L$ CDR3 of SEQ ID NO: 14, or the $V_L$ CDR1, $V_L$ CDR2, and $V_L$ CDR3 of any one of the antibodies produced by hybrodimas TW4-9E7, TW4-5A8, TW4-3E5, TW4-4E5, TW4-12B12, TW4-13B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9. In some embodiments, the anti-LAP antibody or antigen-binding fragment thereof comprises $V_L$ framework regions of the TW7-28G11 antibody. In some embodiments of the aspects described herein, the anti-LAP antibody or antigen-binding fragment thereof comprises a light chain variable region sequence comprising one, two, three or four of the framework regions of the light chain variable region sequence of SEQ ID NO: 13. In some embodiments of the aspects described herein, the anti-LAP antibody or antigen-binding fragment thereof comprises one, two, three or four of the framework regions of a light chain variable region sequence which is at least 75%, 80%, 85%, 90%, 95%, or 100% identical to one, two, three or four of the framework regions of the light chain variable region sequence of SEQ ID NO: 13. In some embodiments of the aspects described herein, the light chain variable framework region that is derived from said amino acid sequence consists of said amino acid sequence but for the presence of up to 10 amino acid substitutions, deletions, and/or insertions, preferably up to 10 amino acid substitutions. In some embodiments of the aspects described herein, the light chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human light chain variable framework region.

In some embodiments of the aspects described herein, an anti-LAP antibody or antigen-binding fragment thereof described herein that specifically binds to LAP comprises the $V_L$ CDR1, $V_L$ CDR2, and $V_L$ CDR3 of SEQ ID NOS: 14, 15, and 16, respectively. In some embodiments of the aspects described herein, the antibody or antigen-binding fragment further comprises one, two, three or all four $V_L$ framework regions derived from the $V_L$ of a human or primate antibody. The primate or human light chain framework region of the antibody selected for use with the light chain CDR sequences described herein, can have, for example, at least 70% identity with a light chain framework region of the non-human parent antibody, for example, SEQ ID NOs: 21-24. The primate or human antibody selected can have the same or substantially the same number of amino acids in its light chain complementarity determining regions to that of the light chain complementarity determining regions of the TW7-28G11 antibody, i.e., SEQ ID NOs: 14-16. In some embodiments of the aspects described herein, the primate or human light chain framework region amino acid residues are from a natural primate or human antibody light chain framework region having at least 75% identity, at least 80% identity, at least 85% identity (or more) with the light chain framework regions of the TW7-28G11 antibody, namely SEQ ID NOs: 20-24. In some embodiments, the anti-LAP antibody or antigen-binding fragment further comprises one, two, three or all four $V_L$ framework regions derived from a human light chain variable kappa subfamily. In some embodiments, the anti-LAP antibody or antigen-binding fragment further comprises one, two, three or all four VL framework regions derived from a human light chain variable lambda subfamily.

In some embodiments of the aspects described herein, an anti-LAP antibody or fragment thereof described herein that specifically binds to LAP comprises the heavy chain variable region ($V_H$) comprising $V_H$ CDR1, $V_H$ CDR2, and $V_H$ CDR3 of SEQ ID NOS: 9, 10, and 11, respectively, or the $V_H$ CDR1, $V_H$ CDR2, and $V_H$ CDR3 of any one of the antibodies produced by hybrodimas TW4-9E7, TW4-5A8, TW4-3E5, TW4-4E5, TW4-12B12, TW4-13B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9. In some embodiments of the aspects described herein, the anti-LAP antibody or antigen-binding fragment thereof comprises one, two, three or all four of the framework regions of the heavy chain variable region sequence of SEQ ID NO: 8. In some embodiments of the aspects described herein, the anti-LAP antibody or antigen-binding fragment thereof comprises one, two, three, or four of the framework regions of a heavy chain variable region sequence which is at least 75%, 80%, 85%, 90%, 95% or 100% identical to one, two, three or four of the framework regions of the heavy chain variable region sequence of SEQ ID NO: 8. In some embodiments of the aspects described herein, the heavy chain variable framework region that is derived from said amino acid sequence consists of said amino acid sequence but for the presence of up to 10 amino acid substitutions, deletions, and/or insertions, preferably up to 10 amino acid substitutions. In some embodiments of the aspects described herein, the heavy chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human heavy chain variable framework region.

In some embodiments of the aspects described herein, an anti-LAP antibody or fragment thereof described herein that specifically binds to LAP comprises the $V_H$ CDR1, $V_H$ CDR2, and $V_H$ CDR3 of SEQ ID NOS: 9, 10, and 11, respectively. In some embodiments of the aspects described herein, the anti-LAP antibody or antigen-binding fragment further comprises one, two, three or all four $V_H$ framework regions derived from the $V_H$ of a human or primate antibody. The primate or human heavy chain framework region of the antibody selected for use with the heavy chain CDR sequences described herein, can have, for example, at least 70% identity with a heavy chain framework region of the non-human parent antibody, for example, SEQ ID NOs: 17-20. Preferably, the primate or human antibody selected can have the same or substantially the same number of amino acids in its heavy chain complementarity determining regions to that of the light chain complementarity determining regions of the TW7-28G11 antibody, i.e., SEQ ID NOs: 9-11. In some embodiments of the aspects described herein, the primate or human heavy chain framework region amino acid residues are from a natural primate or human antibody heavy chain framework region having at least 75% identity, at least 80% identity, at least 85% identity (or more) with the heavy chain framework regions of the TW7-28G11 antibody, namely SEQ ID NOs: 17-20. In specific embodiments, the antibody or antigen-binding fragment further comprises one, two, three or all four $V_H$ framework regions derived from a human heavy chain variable subfamily (e.g., one of subfamilies 1 to 7).

In some embodiments of the aspects described herein, an anti-LAP antibody or fragment thereof described herein that specifically binds to LAP comprises (i) a heavy chain variable region ($V_H$) comprising $V_H$ CDR1, $V_H$ CDR2, and $V_H$ CDR3 of of SEQ ID NOS: 9, 10, and 11, respectively and (ii) a light chain variable region ($V_L$) comprising $V_L$ CDR1, $V_L$ CDR2, and $V_L$ CDR3 of SEQ ID NOS: 14, 15, and 16, respectively. In some embodiments of the aspects described herein, the anti-LAP antibody or antigen-binding fragment thereof described herein comprises one, two, three or four framework regions of a heavy chain variable region sequence which is at least 75%, 80%, 85%, 90%, 95% or 100% identical to one, two, three or four of the framework regions of a heavy chain variable region sequence of SEQ ID NO: 8. In some embodiments of the aspects described herein, the heavy chain variable framework region that is derived from said amino acid sequence consists of said amino acid sequence but for the presence of up to 10 amino acid substitutions, deletions, and/or insertions, preferably up to 10 amino acid substitutions. In some embodiments of the aspects described herein, the heavy chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human heavy chain variable framework region. In some embodiments of the aspects described herein, the anti-LAP antibody or antigen-binding fragment thereof comprises a light chain variable region sequence comprising one, two, three or four of the framework regions of the light chain variable region sequence of SEQ ID NO: 13. In some embodiments of the aspects described herein, the anti-LAP antibody or antigen-binding fragment thereof comprises one, two, three or four framework regions of a light chain variable region sequence which is at least 75%, 80%, 85%, 90%, 95%, or 100% identical to one, two, three or four of the framework regions of a light chain variable region of SEQ ID NO: 13. In some embodiments of the aspects described herein, the light chain variable framework region that is derived from said amino acid sequence consists of said amino acid sequence but for the presence of up to 10 amino acid substitutions, deletions, and/or insertions, preferably up to 10 amino acid substitutions. In some embodiments of the aspects described herein, the light chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human light chain variable framework region. The primate or human light chain framework region of the antibody selected for use with the light chain CDR sequences described herein, can have, for example, at least 70% identity with a light chain framework region of the non-human parent antibody, for example, SEQ ID NOs: 21-24. The primate or human antibody selected can have the same or substantially the same number of amino acids in its light chain complementarity determining regions to that of the light chain complementarity determining regions of the TW7-28G11 antibody, i.e., SEQ ID NOs: 14-16. In some embodiments of the aspects described herein, the primate or human light chain framework region amino acid residues are from a natural primate or human antibody light chain framework region having at least 75% identity, at least 80% identity, at least 85% identity (or more) with the light chain framework regions of the TW7-28G11 antibody, namely SEQ ID NOs: 20-24. The primate or human heavy chain framework region of the antibody selected for use with the heavy chain CDR sequences described herein, can have, for example, at least 70% identity with a heavy chain framework region of the non-human parent antibody, for example, SEQ ID NOs: 17-20. Preferably, the primate or human antibody selected can have the same or substantially the same number of amino acids in its heavy chain complementarity determining regions to that of the light chain complementarity determining regions of the TW7-28G11 antibody, i.e., SEQ ID NOs: 9-11. In some embodiments of the aspects described herein, the primate or human heavy chain framework region amino acid residues are from a natural primate or human antibody heavy chain framework region having at least 75% identity, at least 80% identity, at least 85% identity (or more) with the heavy chain framework regions of the TW7-28G11 antibody, namely SEQ ID NOs: 17-20. In specific embodiments, the antibody or antigen-binding fragment further comprises one, two, three or all four VH framework regions derived from a human heavy chain variable subfamily (e.g., one of subfamilies 1 to 7).

In some embodiments of the aspects described herein, an anti-LAP antibody or fragment thereof that specifically binds to LAP comprises the $V_L$ CDR1, $V_L$ CDR2, $V_L$ CDR3, $V_H$ CDR1, $V_H$ CDR2, and $V_H$ CDR3 of SEQ ID NOS: 14, 15, 16, 9, 10, and 11, respectively. In certain embodiments, the anti-LAP antibody or antigen-binding fragment further comprises one, two, three or all four $V_L$ framework regions derived from the $V_L$ of a human or primate antibody and one, two, three or all four $V_H$ framework regions derived from the $V_H$ of a human or primate antibody. The primate or human light chain framework region of the antibody selected for use with the light chain CDR sequences described herein, can have, for example, at least 70% identity with a light chain framework region of the non-human parent antibody, for example, SEQ ID NOs: 21-24. The primate or human antibody selected can have the same or substantially the same number of amino acids in its light chain complementarity determining regions to that of the light chain complementarity determining regions of the TW7-28G11 antibody, i.e., SEQ ID NOs: 14-16. In some embodiments of the aspects described herein, the primate or human light chain framework region amino acid residues are from a natural primate or human antibody light chain framework region having at least 75% identity, at least 80% identity, at least 85% identity (or more) with the light chain framework regions of the TW7-28G11 antibody, namely SEQ ID NOs: 20-24. The primate or human heavy chain framework region of the antibody selected for use with the heavy chain CDR sequences described herein, can have, for example, at least 70% identity with a heavy chain framework region of the non-human parent antibody, for example, SEQ ID NOs: 17-20. Preferably, the primate or human antibody selected can have the same or substantially the same number of amino acids in its heavy chain complementarity determining regions to that of the light chain complementarity determining regions of the TW7-28G11 antibody, i.e., SEQ ID NOs: 9-11. In some embodiments of the aspects described herein, the primate or human heavy chain framework region amino acid residues are from a natural primate or human antibody heavy chain framework region having at least 75% identity, at least 80% identity, at least 85% identity (or more) with the heavy chain framework regions of the TW7-28G11 antibody, namely SEQ ID NOs: 17-20. In specific embodiments, the anti-LAP antibody or antigen-binding fragment further comprises one, two, three or all four $V_H$ framework regions derived from a human heavy chain variable subfamily (e.g., one of subfamilies 1 to 7).

In some embodiments of the aspects described herein, an antibody or fragment thereof that specifically binds to LAP comprises the amino acid sequence of a $V_L$ domain of SEQ ID NO: 13. In some embodiments of the aspects described herein, an antibody or fragment thereof that specifically binds to LAP comprises a $V_L$ domain consisting of or consisting essentially of the amino acid sequence of SEQ ID NO: 13.

In some embodiments of the aspects described herein, an anti-LAP antibody or fragment thereof that specifically binds to LAP comprises the amino acid sequence of a $V_H$ domain comprising the amino acid sequence of a $V_H$ domain of SEQ ID NO: 8. In some embodiments of the aspects described herein, an anti-LAP antibody or fragment thereof that specifically binds to LAP comprises a $V_H$ domain consisting of or consisting essentially of the amino acid sequence of SEQ ID NO: 8.

In some embodiments of the aspects described herein, an anti-LAP antibody or fragment thereof that specifically binds to LAP comprises a $V_H$ domain comprising the amino acid sequence of a $V_H$ domain of SEQ ID NO: 8 and a $V_L$ domain comprising the amino acid sequence of SEQ ID NO: 13. some embodiments of the aspects described herein, an anti-LAP antibody or fragment thereof that specifically binds to LAP comprises a $V_H$ domain consisting of or consisting essentially of the amino acid sequence of SEQ ID NO: 8 and a $V_L$ domain consisting of or consisting essentially of the amino acid sequence of SEQ ID NO: 13.

An antibody or antigen-binding fragment described herein can be described by its $V_L$ domain alone, or its $V_H$ domain alone, or by its 3 $V_L$ CDRs alone, or its 3 $V_H$ CDRs alone. See, for example, Rader C et al., (1998) PNAS 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also, Clackson T et al., (1991) Nature 352: 624-628, which is incorporated herein by reference in its entirety, describing methods of producing antibodies that bind a specific antigen by using a specific $V_L$ domain (or $V_H$ domain) and screening a library for the complementary variable domains.

In some embodiments of the aspects described herein, the position of one or more CDRs along the $V_H$ (e.g., CDR1, CDR2, or CDR3) and/or VL (e.g., CDR1, CDR2, or CDR3) region of an antibody described herein can vary by one, two, three, four, five, or six amino acid positions so long as immunospecific binding to LAP (e.g., human LAP) is maintained (e.g., substantially maintained, for example, at least 50%, at least 60%, at least 70%, at least 80%, at least 90%, at least 95% of the binding of the original antibody from which it is derived). For example, in some embodiments, the position defining a CDR of any antibody described herein (e.g., any one of the antibodies produced by hybrodimas TW4-9E7, TW4-5A8, TW4-3E5, TW4-4E5, TW4-12B12, TW4-13B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9) can vary by shifting the N-terminal and/or C-terminal boundary of the CDR by one, two, three, four, five, or six amino acids, relative to the CDR position of any one of the antibodies described herein, so long as immunospecific binding to LAP (e.g., human LAP) is maintained (e.g., substantially maintained, for example, at least 50%, at least 60%, at least 70%, at least 80%, at least 90%, at least 95% of the binding of the original antibody from which it is derived). In another embodiment, the length of one or more CDRs along the $V_H$ (e.g., CDR1, CDR2, or CDR3) and/or $V_L$ (e.g., CDR1, CDR2, or CDR3) region of an antibody described herein can vary (e.g., be shorter or longer) by one, two, three, four, five, or more amino acids, so long as immunospecific binding to LAP (e.g., human LAP) is maintained (e.g., substantially maintained, for example, at least 50%, at least 60%, at least 70%, at least 80%, at least 90%, at least 95% of the binding of the original antibody from which it is derived).

Accordingly, in some embodiments of the aspects described herein, a $V_L$ CDR1, $V_L$ CDR2, $V_L$ CDR3, $V_H$ CDR1, $V_H$ CDR2, and/or $V_H$ CDR3 described herein may be one, two, three, four, five or more amino acids shorter than one or more of the CDRs described herein (e.g., SEQ ID NO: 14-16, and 9-11) so long as immunospecific binding to LAP (e.g., human LAP) is maintained (e.g., substantially maintained, for example, at least 50%, at least 60%, at least 70%, at least 80%, at least 90%, at least 95% relative to the binding of the original antibody from which it is derived). In some embodiments of the aspects described herein, a $V_L$ CDR1, $V_L$ CDR2, $V_L$ CDR3, $V_H$ CDR1, $V_H$ CDR2, and/or $V_H$ CDR3 described herein may be one, two, three, four, five or more amino acids longer than one or more of the CDRs described herein (e.g., SEQ ID NO: 14-16, and 9-11) so long as immunospecific binding to LAP (e.g., human LAP) is maintained (e.g., substantially maintained, for example, at least 50%, at least 60%, at least 70%, at least 80%, at least 90%, at least 95% relative to the binding of the original antibody from which it is derived). In some embodiments of the aspects described herein, the amino terminus of a $V_L$ CDR1, $V_L$ CDR2, $V_L$ CDR3, $V_H$ CDR1, $V_H$ CDR2, and/or $V_H$ CDR3 described herein can be extended by one, two, three, four, five or more amino acids compared to one or more of the CDRs described herein (e.g., SEQ ID NO: 14-16, and 9-11) so long as immunospecific binding to LAP (e.g., human LAP) is maintained (e.g., substantially maintained, for example, at least 50%, at least 60%, at least 70%, at least 80%, at least 90%, at least 95% relative to the binding of the original antibody from which it is derived). In some embodiments of the aspects described herein, the carboxy terminus of a $V_L$ CDR1, $V_L$ CDR2, $V_L$ CDR3, $V_H$ CDR1, $V_H$ CDR2, and/or $V_H$ CDR3 described herein can be extended by one, two, three, four, five or more amino acids compared to one or more of the CDRs described herein (e.g., SEQ ID NO: 14-16, and 9-11) so long as immunospecific binding to LAP (e.g., human LAP) is maintained (e.g., substantially maintained, for example, at least 50%, at least 60%, at least 70%, at least 80%, at least 90%, at least 95 relative to the binding of the original antibody from which it is derived). In some embodiments of the aspects described herein, the amino terminus of a $V_L$ CDR1, $V_L$ CDR2, $V_L$ CDR3, $V_H$ CDR1, $V_H$ CDR2, and/or $V_H$ CDR3 described herein can be shortened by one, two, three, four, five or more amino acids compared to one or more of the CDRs described herein (e.g., SEQ ID NO: 14-16, and 9-11) so long as immunospecific binding to LAP (e.g., human LAP) is maintained (e.g., substantially maintained, for example, at least 50%, at least 60%, at least 70%, at least 80%, at least 90%, at least 95 relative to the binding of the original antibody from which it is derived). In some embodiments of the aspects described herein, the carboxy terminus of a $V_L$ CDR1, $V_L$ CDR2, $V_L$ CDR3, $V_H$ CDR1, $V_H$ CDR2, and/or $V_H$ CDR3 described herein can be shortened by one, two, three, four, five or more amino acids compared to one or more of the CDRs described herein (e.g., SEQ ID NO: 14-16, and 9-11) so long as immunospecific binding to LAP (e.g., human LAP) is maintained (e.g., substantially maintained, for example, at least 50%, at least 60%, at least 70%, at least 80%, at least 90%, at least 95 relative to the binding of the original antibody from which it is derived). Any method known in the art can be used to ascertain whether immunospecific binding to LAP (e.g., human LAP) is maintained, for example, the binding assays and conditions described in the "Examples" section provided herein.

With respect to the heavy chain, in some embodiments of the aspects described herein, the heavy chain of an antibody described herein can be an alpha (α), delta (Δ), epsilon (ε), gamma (γ) or mu (μ) heavy chain. In some embodiments of the aspects described herein, the heavy chain of an antibody described can comprise a human alpha (α), delta (Δ), epsilon (ε), gamma (γ) or mu (μ) heavy chain. In a particular embodiment, an antibody described herein comprises a heavy chain wherein the amino acid sequence of the $V_H$ domain comprises SEQ ID NO: 8, and wherein the constant region of the heavy chain comprises the amino acid sequence of a human gamma (γ) heavy chain constant region, such as any known in the art. Non-limiting examples of human constant region sequences have been described in the art, e.g., see U.S. Pat. No. 5,693,780 and Kabat E A et al., (1991) supra.

In some embodiments of the aspects described herein, an anti-LAP antibody comprises a $V_L$ domain and a $V_H$ domain comprising SEQ ID NO: 13 and/or SEQ ID NO: 8, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In some embodiments of the aspects described herein, an anti-LAP antibody comprises a $V_L$ domain and a $V_H$ domain comprising SEQ ID NO: 13 and/or SEQ ID NO: 8, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. Non-limiting examples of human constant regions are described in the art, e.g., see Kabat E A et al., (1991) supra.

In some embodiments of the aspects described herein, one, two or more mutations (e.g., amino acid substitutions) are introduced into the Fc region of an anti-LAP antibody described herein or a fragment thereof (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to alter one or more functional properties of the antibody, such as serum half-life, complement fixation, Fc receptor binding and/or antigen-dependent cellular cytotoxicity.

In some embodiments of the aspects described herein, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody.

In some embodiments of the aspects described herein, one, two or more mutations (e.g., amino acid substitutions) are introduced into the Fc region of an anti-LAP antibody described herein or a fragment thereof (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody or fragment thereof that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments of the aspects described herein, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments of the aspects described herein, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-LAP antibody in vivo. In some embodiments of the aspects described herein, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments of the aspects described herein, the antibodies can have one or more amino acid mutations (e.g., substitutions) in the second constant (CH2) domain (residues 231-340 of human IgG1) and/or the third constant (CH3) domain (residues 341-447 of human IgG1), with numbering according to the EU index in Kabat (Kabat E A et al., (1991) supra). In some embodiments of the aspects described herein, the constant region of the IgG1 of an antibody or antigen-binding fragment thereof described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments of the aspects described herein, an antibody or antigen-binding fragment thereof comprises an IgG constant domain comprising one, two, three or more amino acid substitutions of amino acid residues at positions 251-257, 285-290, 308-314, 385-389, and 428-436, numbered according to the EU index as in Kabat.

In some embodiments of the aspects described herein, one, two or more amino acid substitutions are introduced into an IgG constant domain Fc region to alter the effector function(s) of the anti-LAP antibody. For example, one or more amino acids selected from amino acid residues 234, 235, 236, 237, 297, 318, 320 and 322, numbered according to the EU index as in Kabat, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260. In some embodiments of the aspects described herein, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments of the aspects described herein, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604). In some embodiments of the aspects described herein, one or more of the following mutations in the constant region of an antibody described herein can be made: an N297A substitution; an N297Q substitution; a L235A substitution and a L237A substitution; a L234A substitution and a L235A substitution; a E233P substitution; a L234V substitution; a L235A substitution; a C236 deletion; a P238A substitution; a D265A substitution; a A327Q substitution; or a P329A substitution, numbered according to the EU index as in Kabat. In some embodiments of the aspects described herein, an antibody or antigen-binding fragment thereof described herein comprises the constant domain of an IgG1 with an N297Q or N297A amino acid substitution.

In some embodiments of the aspects described herein, one or more amino acids selected from amino acid residues 329, 331 and 322 in the constant region of an anti-LAP antibody described herein, numbered according to the EU index as in Kabat, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al). In some embodiments of the aspects described herein, one or more amino acid residues within amino acid positions 231 to 238 in the N-terminal region of the CH2 domain of an antibody described herein are altered to thereby alter the ability of the antibody to fix complement. This approach is described further in International Publication No. WO 94/29351. In some embodiments of the aspects described herein, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439, numbered according to the EU index as in Kabat. This approach is described further in International Publication No. WO 00/42072.

In some embodiments of the aspects described herein, an anti-LAP antibody described herein comprises the constant region of an IgG4 antibody and the serine at amino acid residue 228 of the heavy chain, numbered according to the EU index as in Kabat, is substituted for proline.

Antibodies with reduced fucose content have been reported to have an increased affinity for Fc receptors, such as, e.g., FcγRIIIa. Accordingly, in certain embodiments, the anti-LAP antibodies or antigen-binding fragments thereof described herein have reduced fucose content or no fucose content. Such antibodies can be produced using techniques known to one skilled in the art. For example, the antibodies can be expressed in cells deficient or lacking the ability of fucosylation. In a specific example, cell lines with a knockout of both alleles of α1,6-fucosyltransferase can be used to produce antibodies with reduced fucose content. The POTELLIGENTR' system (Lonza) is an example of such a system that can be used to produce antibodies with reduced fucose content. Alternatively, antibodies or antigen-binding fragments with reduced fucose content or no fucose content can be produced by, e.g.: (i) culturing cells under conditions which prevent or reduce fucosylation; (ii) posttranslational removal of fucose (e.g., with a fucosidase enzyme); (iii) post-translational addition of the desired carbohydrate, e.g., after recombinant expression of a non-glycosylated glycoprotein; or (iv) purification of the glycoprotein so as to select for antibodies or antigen-binding fragments thereof which are not fucsoylated. See, e.g., Longmore G D & Schachter H (1982) Carbohydr Res 100: 365-92 and Imai-Nishiya H et al., (2007) BMC Biotechnol. 7: 84 for methods for producing antibodies or antigen-binding fragments thereof with no fucose content or reduced fucose content.

In some embodiments of the aspects described herein, anti-LAP antibodies or antigen-binding fragments thereof described herein have an increased affinity for CD32B (also known as FcγRIIB or FCGR2B), e.g., as compared to an antibody with a wild-type Fc region, e.g., an IgG1 Fc. In some embodiments of the aspects described herein, anti-LAP antibodies or antigen-binding fragments thereof described herein have a selectively increased affinity for CD32B (FcγRIIB) over both CD32A (FcγRIIA) and CD16 (FcγRIIIA) Sequence alterations that result in increased affinity for CD32B are provided, for example, in Mimoto et al., Protein Engineering, Design & Selection 10: 589-598 (2013), Chu et al., Molecular Immunology 45: 3926-3933 (2008), and Strohl, Current Opinion in Biology 20: 685-691 (2009), each of which is herein incorporated by reference in its entirety. In some embodiments of the aspects described herein, the antibody or antigen-binding fragment with an increased affinity for CD32B comprises a heavy chain constant region, e.g., an IgG1 constant region, or fragment thereof comprising a mutation selected from the group consisting of: G236D, P238D, S239D, S267E, L328F, L328E, an arginine inserted after position 236, and combinations thereof, numbered according to EU index (Kabat et al., Sequences of Proteins of Immunological Interest, U.S. Department of Health and Human Services, Bethesda (1991)). In some embodiments of the aspects described herein, the antibody or antigen-binding fragment with an increased affinity for CD32B comprises a heavy chain constant region, e.g., an IgG1 constant region, or fragment thereof comprising S267E and L328F substitutions. In some embodiments of the aspects described herein, the antibody or antigen-binding fragment with an increased affinity for CD32B comprises a heavy chain constant region, e.g., an IgG1 constant region, or fragment thereof comprising P238D and L328E substitutions. In some embodiments of the aspects described herein, the antibody or antigen-binding fragment with an increased affinity for CD32B comprises a heavy chain constant region, e.g., an IgG1 constant region, or fragment thereof comprising a P238D substitution and substitution selected from the group consisting of E233D, G237D, H268D, P271G, A330R, and combinations thereof. In some embodiments of the aspects described herein, the antibody or antigen-binding fragment with an increased affinity for CD32B comprises a heavy chain constant region, e.g., an IgG1 constant region, or fragment thereof comprising P238D, E233D, G237D, H268D, P271G, and A330R substitutions. In some embodiments of the aspects described herein, the antibody or antigen-binding fragment with an increased affinity for CD32B comprises a heavy chain constant region, e.g., an IgG1 constant region, or fragment thereof comprising G236D and S267E. In some embodiments of the aspects described herein, the antibody or antigen-binding fragment with an increased affinity for CD32B comprises a heavy chain constant region, e.g., an IgG1 constant region, or fragment thereof comprising S239D and S267E. In some embodiments of the aspects described herein, the antibody or antigen-binding fragment with an increased affinity for CD32B comprises a heavy chain constant region, e.g., an IgG1 constant region, or fragment thereof comprising S267E and L328F. In some embodiments of the aspects described herein, the antibody or antigen-binding fragment with an increased affinity for CD32B comprises a heavy chain constant region, e.g., an IgG1 constant region, or fragment thereof comprising an arginine inserted after position 236 and L328R.

In some embodiments of the aspects described herein, an anti-LAP antibody or antigen-binding fragment thereof that specifically binds to LAP (e.g., human LAP) comprises VL framework regions (FRs) having at least 80%, at least 85%, at least 90%, at least 95%, or at least 98% sequence identity to one, two, three, or four of the VL framework regions described herein as SEQ ID NOs: 21-24. In some embodiments of the aspects described herein, an anti-LAP antibody or antigen-binding fragment thereof that specifically binds to LAP (e.g., human LAP) comprises VH framework regions (FRs) having at least 80%, at least 85%, at least 90%, at least 95%, or at least 98% sequence identity to one, two, three, or four of the VH framework regions described herein as SEQ ID NOs: 17-20. In some embodiments of the aspects described herein, an antibody or antigen-binding fragment thereof that specifically binds to LAP (e.g., human LAP) comprises (i) VH framework regions (FRs) having at least 80%, at least 85%, at least 90%, at least 95%, or at least 98% sequence identity to one, two, three, or four of the VH framework regions described herein as SEQ ID NOs: 17-20, and (ii) VL framework regions (FRs) having at least 80%, at least 85%, at least 90%, at least 95%, or at least 98% sequence identity to one, two, three, or four of the VL framework regions described herein as SEQ ID NOs: 21-24.

The determination of percent identity between two sequences (e.g., amino acid sequences or nucleic acid sequences) can also be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877. Such an algorithm is incorporated into the NBLAST and XBLAST programs of Altschul S F et al., (1990) J Mol Biol 215: 403. BLAST nucleotide searches can be performed with the NBLAST nucleotide program parameters set, e.g., for score=100, wordlength=12 to obtain nucleotide sequences homologous to a nucleic acid molecule described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi nlm nih.gov). Another specific, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In some aspects, provided herein are anti-LAP antibodies or antigen-binding fragments thereof that bind the same or an overlapping epitope of LAP (e.g., an epitope of human LAP) as any one of the antibodies produced by hybridomas TW4-9E7, TW4-5A8, TW4-3E5, TW4-4E5, TW4-12B12, TW4-13B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9. In some embodiments of these aspects, the anti-LAP antibodies or antigen-binding fragments thereof bind the same or overlapping epitope of LAP as the antibody produced by hybridoma TW7-28G11 having a $V_H$ domain of SEQ ID NO: 8 and a $V_L$ domain of SEQ ID NO: 13. As known to one of ordinary skill in the art, the epitope of an antibody can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giege R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals can be studied using well known X-ray diffraction techniques and can be refined using computer software such as X-PLOR (Yale University, 1992, distributed by Molecular Simulations, Inc.; see e.g. Meth Enzymol (1985) volumes 114 & 115, eds Wyckoff H W et al., U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In addition, antibodies that recognize and bind to the same or overlapping epitopes of LAP (e.g., human LAP) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as LAP. Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using 1-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified antigen (e.g., LAP) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389. A competition assay can be performed, for example, using surface plasmon resonance (BIACORE) e.g., by an 'in tandem approach' such as that described by Abdiche Y N et al., (2009) Analytical Biochem 386: 172-180, whereby LAP antigen is immobilized on the chip surface, for example, a CMS sensor chip and the anti-LAP antibodies are then run over the chip. To determine if an antibody competes with an anti-LAP antibody or antigen-binding fragment thereof described herein, the anti-LAP antibody is first run over the chip surface to achieve saturation and then the potential, competing antibody is added. Binding of the competing antibody can then be determined and quantified relative to a non-competing control.

Competition binding assays can be used to determine whether an antibody is competitively blocked, e.g., in a dose dependent manner, by another antibody for example, an antibody that binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody.

Accordingly, in some embodiments of the aspects described herein, an anti-LAP antibody can be tested in competition binding assays with any one of the antibodies produced by hybridomas TW4-9E7, TW4-5A8, TW4-3E5, TW4-4E5, TW4-12B12, TW4-13B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9 described herein, or a chimeric or Fab antibody thereof, or an anti-LAP antibody comprising one or more $V_H$ CDRs and one or more $V_L$ CDRs of any one of the antibodies produced by hybridomas TW4-9E7, TW4-5A8, TW4-3E5, TW4-4E5, TW4-12B12, TW4-13B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9 described herein.

In some embodiments of the methods described herein, the LAP binding agent is a chimeric antibody derivative of an anti-LAP antibody or antigen-binding fragment thereof that specifically binds LAP.

As used herein, the term "chimeric antibody" refers to an antibody molecule in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). Chimeric antibody molecules can include, for example, one or more $V_H$ and/or $V_L$ antigen binding domains from an antibody of a mouse, rat, or other species, with human constant regions. A variety of approaches for making chimeric antibodies have been described and can be used to make chimeric antibodies containing the immunoglobulin variable region which recognizes the desired antigen, e.g., LAP. See, for example, Takeda et al., 1985, Nature 314:452; Cabilly et al., U.S. Pat. No. 4,816,567; Boss et al.; Tanaguchi et al., European Patent Publication EP171496; European Patent Publication 0173494, United Kingdom patent GB 2177096B).

In some embodiments of the methods described herein, the LAP binding agent is a CDR-grafted antibody derivative of an anti-LAP antibody or antigen-binding fragment thereof that specifically binds LAP.

The term "CDR-grafted antibody" refers to antibodies which comprise heavy and light chain variable region sequences from one species, but in which the sequences of one or more of the CDR regions of $V_H$ and/or $V_L$ are replaced with CDR sequences of another species, such as antibodies having human heavy and light chain variable regions in which one or more of the human CDRs (e.g., CDR3) has been replaced with mouse CDR sequences. CDR-grafted antibodies described herein comprise heavy and light chain variable region sequences from a human antibody wherein one or more of the CDR regions of $V_H$ and/or $V_L$ are replaced with CDR sequences of the murine antibodies described herein, such as SEQ ID NOs: 9-11 and 14-16, or the CDR sequences of any one of the antibodies produced by hybridomas TW4-9E7, TW4-5A8, TW4-3E5, TW4-4E5, TW4-12B12, TW4-13B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9. A framework sequence from any human antibody can serve as the template for CDR grafting. However, straight chain replacement onto such a framework often leads to some loss of binding affinity to the antigen. The more homologous a human antibody is to the original non-human, or murine antibody, the less likely the possibility that combining the non-human CDRs with the human framework will introduce distortions in the CDRs that could reduce affinity. Therefore, the human variable framework chosen to replace the murine variable framework apart from the CDRs have, for example, at least a 65% sequence identity with the murine antibody variable region framework. The human and murine variable regions apart from the CDRs have, for example, at least 70% sequence identity, at least 75% sequence identity, at least 80% sequence identity, or at least 85% sequence identity. Methods for producing chimeric antibodies are known in the art. (See, for example, EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,352), the contents of each of which are herein incorporated by reference in their entireties.

In some embodiments of the methods described herein, the LAP binding agent is a humanized antibody derivative of an anti-LAP antibody or antigen-binding fragment thereof that specifically binds LAP.

Humanized forms of non-human (e.g., murine) antibodies are chimeric antibodies which contain minimal sequence derived from non-human immunoglobulin. For the most part, humanized antibodies are human immunoglobulins (recipient antibody) in which residues from a CDR or hypervariable region of the recipient are replaced by residues from a CDR or hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin consensus sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

The humanized antibody can be selected from any class of immunoglobulins, including IgM, IgG, IgD, IgA and IgE, and any subclass, including without limitation IgG1, IgG2, IgG3 and IgG4.

The framework and CDR regions of a humanized antibody need not correspond precisely to the parental sequences, e.g., the donor antibody CDR or the consensus framework can be mutagenized by substitution, insertion and/or deletion of at least one amino acid residue so that the CDR or framework residue at that site does not correspond exactly to either the donor antibody or the consensus framework. In preferred embodiments, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see e.g., Winnaker, From Genes to Clones (Veriagsgesellschaft, Weinheim, Germany 1987). In a family of immunoglobulins, each position in the consensus sequence is occupied by the amino acid occurring most frequently at that position in the family. Where two amino acids occur equally frequently, either can be included in the consensus sequence.

As used herein, "Vernier zone" refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and can impact on the structure of CDRs and the affinity of the antibody.

Known human immunoglobulin (Ig) sequences that can be used with the CDR sequences described herein are disclosed, for example, on the worldwide web at www.ncbi nlm nih.gov/entrez-/query.fcgi; www.atcc.org/phage/hdb.html; www.sciquest.com/; www.abcam.com/; www.antibodyresource.com/onlinecomp.html; www.public.iastate.eduLabout.pedro/research_tools.html; www.mgen.uniheidelberg.de/SD/IT/IT.html; www.whfreeman com/immunology/CH-05/kuby05.htm; www.library.thinkquest.org/12429/Immune/Antibody.html; www.hhmi.org/grants/lectures/1996/vlab/; www.path.cam.ac.uk/.about.mrc7/m-ikei-mages.html; www.antibodyresource.com/; mcb.harvard.edu/BioLinks/Immunology.html. www.immunologylink com/; pathbox.wustl.edu/.about.h-center/index.-html; www.biotech.ufl.edu/.about.hcl/; www.pebio.com/pa/340913/340913.html-; www.nal.usda.gov/awic/pubs/antibody/; www.m.ehime-u.acjp/.about.yas-uhito-/Elisa.html; www.biodesign.com/table.asp; www.ic-net.uk/axp/facs/davies/lin-ks.html; www.biotech.ufl.edu/.about.fccl/protocol.html; www.isac-net.org/sites_geo.html; aximtl.imt.uni-marburg.de/.about.rek/AEP-Start.html; baserv.uci.kun.nl/.about.jraats/linksl html; www.recab.uni-hd.de/immuno.bme.nwu.edu/; www.mrc-cpe.cam.ac.uk/imt-doc/pu-blic/INTRO.html; www.ibt.unam.mx/virN_mice.html; imgt.cnusc.fr:8104/; www.biochem.ucl.ac.uk/.about.martin/abs/index.html; anti-body.bath.ac.uk/; abgen.cvm.tamu.edu/lab/wwwabgen.html; www.unizh.ch/.abouthonegger/AHOsem-inar/Slide01.html; www.cryst.bbk.ac.uk/.about.ubcg07s/; www.nimr mrc.ac.uk/CC/ccaewg/ccaewg.htm; www.path.cam.ac.ukhabout.mrc7/h-umanisation/TAHHP.html; www.ibt.unam.na/vir/structure/stat_aim.html; www.biosci.missouri.edu/smithgp/index.html; www.cryst.bioc.cam.ac.uk/.abo-utimolina/Web-pages/Pept/spottech.html; www.jerini.de/fr roducts.htm; www.patents.ibm.com/ibm.html.Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions can be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, including, but not limited to, those described in Jones et al., Nature 321:522 (1986); Verhoeyen et al., Science 239:1534 (1988), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, each entirely incorporated herein by reference.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98 or 100% of the amino acid sequences of one or more of the framework regions. In accordance with this embodiment, an acceptor may contain at least 1, at least 2, at least 3, least 4, at least 5, or at least 10 amino acid residues not occurring at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol, 227:799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In some embodiments of the compositions and methods described herein, the donor antibody is an antibody from a species different from the antibody from which the framework regions are obtained or derived. In the context of a humanized antibody, the term "donor antibody" refers to a non-human antibody providing one or more CDRs.

As used herein, the term "key" residues refers to certain residues within the variable region that more impact on the binding specificity and/or affinity of an antibody, in particular a humanized antibody. A key residue includes, but is not limited to, one or more of the following: a residue that is adjacent to a CDR, a potential glycosylation site (which can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

In some embodiments of the compositions and methods comprising any of the anti-LAP antibodies or antigen-binding fragments thereof described herein, the anti-LAP antibody or antigen-binding fragment is an antibody derivative. For example, but not by way of limitation, antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

The anti-LAP antibodies and antigen-binding fragments thereof described herein can be generated by any suitable method known in the art. Monoclonal and polyclonal antibodies against, for example, LAP, are known in the art. To the extent necessary, e.g., to generate antibodies with particular characteristics or epitope specificity, the skilled artisan can generate new monoclonal or polyclonal anti-LAP antibodies as briefly discussed herein or as known in the art.

Polyclonal antibodies can be produced by various procedures well known in the art. For example, LAP or fragments thereof comprising one or more of the LAP ligand interaction sites, can be administered to various host animals including, but not limited to, rabbits, mice, rats, etc. to induce the production of sera containing polyclonal antibodies specific for the protein. Polyclonal antibodies are preferably raised in animals by multiple subcutaneous (sc) or intraperitoneal (ip) injections of the relevant antigen and an adjuvant. It can be useful to conjugate the antigen to a protein that is immunogenic in the species to be immunized, e.g., keyhole limpet hemocyanin, serum albumin, bovine thyroglobulin, or soy-bean trypsin inhibitor using a bifunctional or derivatizing agent, for example, maleimidobenzoyl sulfosuccinimide ester (conjugation through cysteine residues), N-hydroxy-succinimide (through lysine residues), glutaraldehyde, succinic anhydride, $SOCl_2$, or $R^1N=C=NR$, where R and $R^1$ are different alkyl groups. Various other adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Suitable adjuvants are also well known to one of skill in the art.

Monoclonal antibodies can be prepared using a wide variety of techniques known in the art including the use of hybridoma, recombinant, and phage display technologies, or a combination thereof. Various methods for making monoclonal antibodies described herein are available in the art. For example, the monoclonal antibodies can be made using the hybridoma method first described by Kohler et al., Nature, 256:495 (1975), or any later developments thereof, or by recombinant DNA methods (U.S. Pat. No. 4,816,567). For example, monoclonal antibodies can be produced using hybridoma techniques including those known in the art and taught, for example, in Harlow et al., Antibodies: A Laboratory Manual, (Cold Spring Harbor Laboratory Press, 2nd ed., 1988); Hammer-ling, et al., in: Monoclonal Antibodies and T-Cell Hybridomas 563-681 (Elsevier, N.Y., 1981) (said references incorporated by reference in their entireties). Methods for producing and screening for specific antibodies using hybridoma technology are routine and well known in the art. In another example, antibodies useful in the methods and compositions described herein can also be generated using various phage display methods known in the art, such as isolation from antibody phage libraries generated using the techniques described in McCafferty et al., Nature, 348: 552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

In some embodiments of the compositions, methods, and uses described herein, completely human antibodies are used as LAP binding agents, which are particularly desirable for the therapeutic treatment of human patients.

Human antibodies can be made by a variety of methods known in the art, including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741, the contents of which are herein incorporated by reference in their entireties.

Human antibodies can also be produced using transgenic mice which express human immunoglobulin genes, and upon immunization are capable of producing a full repertoire of human antibodies in the absence of endogenous immunoglobulin production. For an overview of this technology for producing human antibodies, see, Lonberg and Huszar, 1995, Int. Rev. Immunol. 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, the contents of which are herein incorporated by reference in their entireties. In addition, companies such as Abgenix, Inc. (Freemont, Calif.) and Medarex (Princeton, N.J.) can be engaged to provide human antibodies directed against a selected antigen using technology similar to that described above. See also, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and Duchosal et al. Nature 355:258 (1992), the contents of which are herein incorporated by reference in their entireties. Alternatively, phage display technology (McCafferty et al., Nature 348:552-553 (1990)) can be used to produce human antibodies and antibody fragments in vitro, from immunoglobulin variable (V) domain gene repertoires from unimmunized donors. Human antibodies can also be generated by in vitro activated B cells (see U.S. Pat. Nos. 5,567,610 and 5,229,275, the contents of which are herein incorporated by reference in their entireties). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1994, Bio/technology 12:899-903).

"An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

"Humanized antibodies," as the term is used herein, refer to antibody molecules from a non-human species, where the antibodies that bind the desired antigen, i.e., LAP or LAP bound to a ligand, have one or more CDRs from the non-human species, and framework and constant regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., 1988, Nature 332:323. Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology, 1991, 28(4/5):489-498; Studnicka et al., 1994, Protein Engineering 7(6):805-814; Roguska. et al, 1994, PNAS 91:969-973), and chain shuffling (U.S. Pat. No. 5,565,332), the contents of which are herein incorporated by reference in their entireties. Accordingly, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), the contents of which are herein incorporated by reference in their entireties, by substituting rodent CDRs or CDR sequences for the corresponding sequences of a human antibody. Accordingly, such "humanized" antibodies are chimeric antibodies (U.S. Pat. No. 4,816,567, the contents of which are herein incorporated by reference in its entirety) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The "Fab" fragment contains a variable and constant domain of the light chain and a variable domain and the first constant domain ($C_H1$) of the heavy chain. $F(ab')_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

The expression "linear antibodies" refers to the antibodies described in Zapata et al., Protein Eng., 8(10):1057-1062 (1995). Briefly, these antibodies comprise a pair of tandem Fd segments ($V_H$-$C_H1$-$V_H$-$C_H1$) which, together with complementary light chain polypeptides, form a pair of antigen binding regions. Linear antibodies can be bispecific or monospecific.

Various techniques have been developed for the production of antibody or antigen-binding fragments. The antibodies described herein can be fragmented using conventional techniques and the fragments screened for utility in the same manner as described above for the whole antibodies. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). For example, Fab and $F(ab')_2$ fragments of the bispecific and multispecific antibodies described herein can be produced by proteolytic cleavage of immunoglobulin molecules, using enzymes such as papain (to produce Fab fragments) or pepsin (to produce F(ab') 2 fragments). F(ab') 2 fragments contain the variable region, the light chain constant region and the $C_H1$ domain of the heavy chain. However, these fragments can now be produced directly by recombinant host cells. For example, the antibody fragments can be isolated from the antibody phage libraries discussed above. Alternatively, Fab'-SH fragments can be directly recovered from E. coli and chemically coupled to form $F(ab')_2$ fragments (Carter et al., Bio/Technology 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

Examples of techniques which can be used to produce single-chain Fvs and antibodies include those described in U.S. Pat. Nos. 4,946,778 and 5,258,498; Huston et al., 1991, Methods in Enzymology 203:46-88; Shu et al., 1993, PNAS 90:7995-7999; and Skerra et al., 1988, Science 240:1038-1040. For some uses, including the in vivo use of antibodies in humans as described herein and in vitro proliferation or cytotoxicity assays, it is preferable to use chimeric, humanized, or human antibodies.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by $V_H$ and $V_L$ domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al., J. Mol. Biol. 226:889-896 (1992).

As used herein "complementary" refers to when two immunoglobulin domains belong to families of structures which form cognate pairs or groups or are derived from such families and retain this feature. For example, a $V_H$ domain and a $V_L$ domain of a natural antibody are complementary; two $V_H$ domains are not complementary, and two $V_L$ domains are not complementary. Complementary domains can be found in other members of the immunoglobulin superfamily, such as the $V_\alpha$ and $V_\beta$ (or γ and δ) domains of the T-cell receptor. Domains which are artificial, such as domains based on protein scaffolds which do not bind epitopes unless engineered to do so, are non-complementary. Likewise, two domains based on, for example, an immunoglobulin domain and a fibronectin domain are not complementary.

In some embodiments of the compositions, methods, and uses described herein, the LAP binding agent is a small molecule inhibitor, agent, or compound.

In some embodiments of the methods described herein, a LAP small molecule binding agent for use in the methods described herein can bind or physically interact with a LAP ligand interaction site, e.g., a site that interacts with mature TGF-β, a site that interacts with integrins, and/or a site that interacts with LTBP.

In some embodiments of the methods described herein, a LAP small molecule binding agent binds or physically interacts with R189 of SEQ ID NOs: 1 and 4, R196 of SEQ ID NOs: 2 and 5, and/or R192 of SEQ ID NOs: 3 and 6. In some embodiments of the methods described herein, a LAP small molecule binding agent binds or physically interacts with amino acids 215-217 of SEQ ID NOs: 1 and 4, amino acids 241-243 of SEQ ID NOs: 2 and 5, and/or amino acids 238-240 of SEQ ID NOs: 3 and 6. In some embodiments of the methods described herein, a LAP small molecule binding agent binds or physically interacts with Cys4 of any of SEQ ID NOs: 1-6.

In some embodiments of the methods described herein, a LAP small molecule binding agent for use in the methods described herein can bind or physically interact with a LAP homodimerization site, i.e., a site that interacts with another LAP molecule. Accordingly, in some embodiments of the methods described herein, a LAP small molecule binding agent binds or physically interacts with Cys194 and/or Cys196 of SEQ ID NOs: 1 and 4, Cys206 and/or Cys208 of SEQ ID NOs: 2 and 5, and/or Cys204 and/or Cys206 of SEQ ID NOs: 3 and 6.

Such small molecule inhibitors include, but are not limited to, small peptides or peptide-like molecules, soluble peptides, and synthetic non-peptidyl organic or inorganic compounds. A small molecule inhibitor or antagonist can have a molecular weight of any of about 100 to about 20,000 daltons (Da), about 500 to about 15,000 Da, about 1000 to about 10,000 Da.

In some embodiments of the compositions, methods, and uses described herein, a LAP binding agent is an RNA or DNA aptamer that binds or physically interacts with LAP, and modulates interactions between LAP and any of its ligands.

In some embodiments of the methods described herein, a LAP RNA or DNA aptamer for use in the methods described herein can bind a LAP ligand interaction site, e.g. a site that interacts with mature TGFβ, a site that interacts with integrins, and/or a site that interacts with LTBP.

In some embodiments of the methods described herein, a LAP RNA or DNA aptamer binds R189 of SEQ ID NOs: 1 and 4, R196 of SEQ ID NOs: 2 and 5, and/or R192 of SEQ ID NOs: 3 and 6. In some embodiments of the methods described herein, a LAP RNA or DNA aptamer binds or physically interacts with amino acids 215-217 of SEQ ID NOs: 1 and 4, amino acids 241-243 of SEQ ID NOs: 2 and 5, and/or amino acids 238-240 of SEQ ID NOs: 3 and 6. In some embodiments of the methods described herein, a RNA or DNA aptamer binds or physically interacts with Cys4 of any of SEQ ID NOs: 1-6.

In some embodiments of the methods described herein, a LAP RNA or DNA aptamer for use in the methods described herein can bind or physically interact with a LAP homodimerization site, i.e., a site that interacts with another LAP molecule. Accordingly, in some embodiments of the methods described herein, a LAP RNA or DNA aptamer binds or physically interacts with Cys194 and/or Cys196 of SEQ ID NOs: 1 and 4, Cys206 and/or Cys208 of SEQ ID NOs: 2 and 5, and/or Cys204 and/or Cys206 of SEQ ID NOs: 3 and 6.

LAP binding agents for use in the compositions and methods described herein can be identified or characterized using methods known in the art, such as protein-protein binding assays, biochemical screening assays, immunoassays, and cell-based assays, which are well known in the art, including, but not limited to, those described herein in the Examples and Figures.

For the clinical use of the methods and uses described herein, administration of the compositions comprising LAP-binding agents can include formulation into pharmaceutical compositions or pharmaceutical formulations for parenteral administration, e.g., intravenous; mucosal, e.g., intranasal; ocular, or other mode of administration. In some embodiments, the LAP binding agents described herein, can be administered along with any pharmaceutically acceptable carrier compound, material, or composition which results in an effective treatment in the subject. Thus, a pharmaceutical formulation for use in the methods described herein can contain LAP binding agents as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of a LAP binding agent. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alchols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

The LAP binding agents described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a LAP-binding agent can be implanted into a patient or injected using a drug delivery system. See, for example, Urquhart, et al., Ann. Rev. Pharmacol. Toxicol. 24: 199-236

(1984); Lewis, ed. "Controlled Release of Pesticides and Pharmaceuticals" (Plenum Press, New York, 1981); U.S. Pat. No. 3,773,919; and U.S. Pat. No. 35 3,270,960.

Further embodiments of the formulations and modes of administration of the compositions comprising LAP binding agents that can be used in the methods described herein are described below.

Parenteral Dosage Forms.

Parenteral dosage forms of the LAP binding agents can also be administered to a subject by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Aerosol Formulations.

The LAP binding agents can be packaged in a pressurized aerosol container together with suitable propellants, for example, hydrocarbon propellants like propane, butane, or isobutane with conventional adjuvants. A LAP binding agent described herein, can also be administered in a non-pressurized form such as in a nebulizer or atomizer. The LAP binding agents described herein, can also be administered directly to the airways in the form of a dry powder, for example, by use of an inhaler.

Suitable powder compositions include, by way of illustration, powdered preparations of the LAP binding agents described herein, thoroughly intermixed with lactose, or other inert powders acceptable for intrabronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The formulations of the LAP binding agents described herein, further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms.

In some embodiments of the aspects described herein, the LAP binding agents can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the LAP binding agents described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUO-LITE® A568 and DUOLITE® AP143 (Rohm&Haas, Spring House, Pa. USA).

In some embodiments of the methods described herein, the LAP binding agents for use in the methods described herein are administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has continuous or chronic symptoms of a viral infection. Each pulse dose can be reduced and the total amount of the LAP binding agents described herein administered over the course of treatment to the subject or patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Methods of Treatment and Uses of LAP Binding Agents

As demonstrated herein, intracranial and subcutaneous GBM tumor growth is lower and mice survive longer when treated with anti-LAP antibodies. Anti-LAP antibody treatment also affected both systemic and intra-tumor immunity as follows: (1) Tumors were infiltrated by increased numbers of cytotoxic CD8+ T cells and intra-tumor Foxp3 Tregs were decreased. CD4+ and CD8+ intra-tumor T cells had decreased expression of PD-1, LAG3 and CD103. (2) In the periphery, CD4+ and CD8+ T cells, expressing IFN-γ and granzyme B, were increased, respectively whereas CD103+ T cells were decreased. Finally, there were reduced numbers of tolerogenic dendritic cells expressing CD103 and PD-L1 whereas MHC II was elevated on splenic myeloid cells. Anti-LAP antibodies were also tested in a melanoma model and colorectal cancer model and similar intra-tumor and peripheral immune effects were observed. Thus, as demonstrated herein, inhibition of LAP strongly influences systemic and intra-tumor immune responses by activating both innate and adaptive immunity and overcomes the mechanisms suppressing tumor-specific immunity. In conclusion, LAP binding agents as monotherapies or combined with conventional anti-tumor modalities represent novel immunotherapeutic approaches for the treatment of various cancers, including, but not limited to, brain tumors, melanoma, and colorectal cancer.

Provided herein, in some aspects, are methods to treat cancer and tumors where LAP expression and/or activity is associated with suppression of cancer- or tumor-specific immunity comprising administering a therapeutically effective amount of a LAP binding agenty agent to a subject in need thereof.

In some aspects, provided herein are methods to increase tumor-specific immunity comprising administering a therapeutically effective amount of a LAP binding agenty agent to a subject in need thereof.

In some embodiments of these aspects and all such aspects described herein, the subject has or has been diagnosed with cancer.

A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastases. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; cholangiocarcinoma; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intraepithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; teratocarcinoma; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglubulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), tumors of primitive origins and Meigs' syndrome.

In some embodiments of these methods and all such methods described herein, the subject in need thereof has or has been diagnosed with a brain tumor. In some such embodiments, the brain tumor is glioblastoma.

In some embodiments of these methods and all such methods described herein, the subject in need thereof has or has been diagnosed with melanoma.

In some embodiments of these methods and all such methods described herein, the subject in need thereof has or has been diagnosed with a colorectal cancer.

In some embodiments of these methods and all such methods described herein, the subject in need thereof has or has been diagnosed with a brain tumor, a melanoma, or colorectal cancer. In some such embodiments, the brain tumor is glioblastoma.

In some embodiments of these methods and all such methods described herein, the methods further comprise admininstering an anti-cancer therapy or agent to a subject in addition to the LAP binding agent(s) described herein.

The term "anti-cancer therapy" refers to a therapy useful in treating cancer. Examples of anti-cancer therapeutic agents include, but are not limited to, e.g., surgery, chemotherapeutic agents, growth inhibitory agents, cytotoxic agents, radiotherapy and agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets PD1, PDL1, PDL2 (e.g., pembrolizumab; nivolumab; MK-3475; AMP-224; MPDL3280A; MEDI0680; MSB0010718C; and/or MEDI4736); CTLA4 (e.g., tremelimumab (PFIZER) and ipilimumab); LAG3 (e.g., BMS-986016); CD103; TIM-3 and/or other TIM family members; CEACAM-1 and/or other CEACAM family members, ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also specifically contemplated for the methods described herein.

In some embodiments of the methods described herein, an anti-cancer therapy to be administered with the LAP binding agents described herein comprises a PD1, PDL1, and/or PDL2 inhibitory agent, such as an antibody. Non-limiting examples of such PD1, PDL1, and PDL2 inhibitory agents include pembrolizumab (KEYTRUDA, MERCK); nivolumab (BRISTOL-MYERS SQUIBB); MK-3475; MPDL3280A (GENENTECH); MEDI0680 and MEDI4736 (MEDIMMUNE/ASTRAZENECA); AMP-224; and MSB0010718C. Additional non-limiting examples of anti-PD1 antibody reagents can include PD1 binding site sequences from monoclonal antibodies specific for human PD1, such as, MDX-1106 (ONO-4538), a fully human IgG4 anti-PD1 blocking antibody (Journal of Clinical Oncology, 2008 Vol 26, No 15S); CT-011 (CureTech, LTD, previously CT-AcTibody or BAT), a humanized monoclonal IgG1 antibody (Benson D M et al, Blood. 2010 May 11), or those obtained from, clone NAT (Abeam), clone EH12.2H7 (Biolegend), clone Jl 16 (eBioscience), clone MIH4 (eBioscience), clone J105 (eBioscience), or clone 192106 (R& D systems).

In some embodiments, an anti-cancer therapy comprises an immunotherapy such as adoptive cell transfer. "Adoptive cell transfer," as used herein, refers to immunotherapies involving genetically engineering a subject or patient's own T cells to produce special receptors on their surface called chimeric antigen receptors (CARs). CARs are proteins that allow the T cells to recognize a specific protein (antigen) on tumor cells. These engineered CAR T cells are then grown in the laboratory until they number in the billions. The expanded population of CAR T cells is then infused into the patient. After the infusion, the T cells multiply in the subject's body and, with guidance from their engineered receptor, recognize and kill cancer cells that harbor the antigen on their surfaces.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including active fragments and/or variants thereof.

In some embodiments of these methods and all such methods described herein, the methods further comprise admininstering a chemotherapeutic agent, such as, for example, temozolomide, to the subject being administered the LAP binding agent(s) described herein.

Non-limiting examples of chemotherapeutic agents can include include alkylating agents such as thiotepa and CYTOXAN® cyclosphosphamide; temozolomide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin;

spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE, vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB.); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above. In addition, the methods of treatment can further include the use of radiation, radiotherapy, or radiation therapy.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2, 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

In some embodiments of these methods and all such methods described herein, the methods further comprise admininstering a tumor or cancer antigen to a subject being administered the LAP binding agent(s) described herein. The antigen can be administered as a tumor antigen vaccine. In addition to known tumor antigen expressed by a subject's tumor, whole tumor antigen vaccination is also contemplated. See, e.g., Chiang et al, Vaccines 3: 344-372 (2015).

A number of tumor antigens have been identified that are associated with specific cancers. As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER-2, mucins (i.e., MUC-1), prostate-specific antigen (PSA), and prostatic acid phosphatase (PAP). In addition, viral proteins such as hepatitis B (HBV), Epstein-Barr (EBV), and human papilloma (HPV) have been shown to be important in the development of hepatocellular carcinoma, lymphoma, and cervical cancer, respectively. However, tumors use or benefit from a range of different immune evasion mechanisms, such that the immune systems of cancer patients often fail to respond to the tumor antigens. Some examples of cancer antigens that are normally associated with spermatocytes or spermatogonia of the testis, placenta, and ovary include the cancer-testis (CT) antigens BAGE, GAGE, MAGE-1 and MAGE-3, NY-ESO-1, SSX. These antigens are found in melanoma, lymphoma, lung, bladder, colon, and breast carcinomas (e.g., as described in Butterfield et al., J. Immunotherapy 2008; 31:294-309; Markowicz et al., J Clin Oncol 27:15s, 2009 (suppl; abstr 9039)). Cancer antigens normally found in melanocytes, epithelial tissues, prostate, and colon also include the differentiation antigens Gp100, Melan-A/Mart-1, Tyrosinase, PSA, CEA, and Mammaglobin-A. These antigens are found in melanoma, prostate cancer, and in colon and breast carcinomas. Some cancer antigens are shared antigens that are ubiquitously expressed at low levels but overespressed in cancers. Examples of overexpressed cancer antigens include p53, HER-2/neu, livin, and survivin, found in esophagus, liver, pancreas, colon, breast, ovary, bladder, and prostate carcinomas. Other cancer antigens are unique, such as β-catenin-m, β-Actin/4/m, Myosin/m, HSP70-2/m, and HLA-A2-R170J, which are associated with one or more of melanoma, non-small cell lung cancer, and renal cancer. Still other cancer antigens are the tumor-associated carbohydrate antigens that are normally found in epithelia tissues such as renal, intestinal, and colorectal tissues. These cancer antigens include GM2, GD2, GD3, MUC-1, sTn, abd globo-H, which can be found in melanoma, neuroblastoma, colorectal, lung, breast, ovarian, and prostate cancers. Additional tumor antigens, peptide epitopes, and descriptions thereof are described in U.S. Pat. Nos. 7,906,620; 7,910,692; 8,097,242; 7,935,531; 8,012,468; 8,097,256; 8,003,773; Tartour et al., Immunol Lett 2000; 74(1): 1-3, the contents of which are herein incorporated by reference in their entireties. In some embodiments, the intact cancer antigen is used, whereas in other embodiments, a peptide epitope of the cancer antigen (prepared either by proteolytic digestion or recombinantly) is used. Accordingly, non-limiting examples of tumor or cancer antigens for use with the compositions and methods described herein include, but are not limited to, Her2, prostate stem cell antigen (PSCA), PSMA (prostate-specific membrane antigen), β-catenin-m, B cell maturation antigen (BCMA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, Mammaglobin-A, melanoma-associated antigen (MAGE), CD34, CD45, CD99, CD117, chromogranin, cytokeratin, desmin, glial fibrillary acidic protein (GFAP), gross cystic disease fluid protein (GCDFP-15), EBV, gp100, HMB-45 antigen, protein melan-A (melanoma antigen recognized by T lymphocytes; MART-1), livin, survivin, myo-D1, muscle-specific actin (MSA), neurofilament, neuron-specific enolase (NSE), placental alkaline phosphatase, synaptophysin, thyroglobulin, thyroid transcription factor-1, the dimeric form of the pyruvate kinase isoenzyme type M2 (tumor M2-PK), CD19, CD22, CD27, CD30, CD70, GD2 (ganglioside G2), EphA2, CSPG4, CD138, FAP (Fibroblast Activation Protein), CD171, kappa, lambda, 5T4, $\alpha_v\beta_6$ integrin, B7-H3, B7-H6, CAIX, CD19, CD20, CD22, CD30, CD33, CD44, CD44v6, CD44v7/8, CD70, CD123, EGFR, EGP2, EGP40, EpCAM, fetal AchR, FRα, GAGE, GD3, HLA-A1+MAGE1, MAGE-3, HLA-A1+NY-ESO-1, IL-11Rα, IL-13Rα2, Lewis-Y, Muc16, NCAM, NKG2D Ligands, NY-ESO-1, PRAME, ROR1, SSX,Survivin, TAG72, TEMs, VEGFR2, EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), HSP70-2/m, and HLA-A2-R170J, tyrosinase, an abnormal ras protein, or an abnormal p53 protein.

In some embodiments of these methods and all such methods described herein, the methods further comprise admininstering a dendritic cell (DC) vaccination concurrently or in combination with the LAP binding agent(s) described herein.

As used herein "dendritic cell vaccination" or a "DC vaccine" refers to a form of immunotherapy designed to induce T cell-dependent immunity, such as cancer-specific T cell-dependent anti-tumor immunity, that can result in durable complete responses using DCs. Examples of "dendritic cell (DC) immunotherapies" or "dendritic cell vaccines," as used herein, include modified dendritic cells and any other antigen presenting cell, autologous or xeno, whether modified by multiple antigens, whole cancer cells, single antigens, by mRNA, phage display or any other modification, including, but not restricted to, ex vivo-generated, antigen-loaded dendritic cells (DCs) to induce antigen-specific T-cell immunity, ex vivo gene-loaded DCs to induce humoral immunity, ex vivo-generated, antigen-loaded DCs to induce tumour-specific immunity, ex vivo-generated immature DCs to induce tolerance, for example.

By "reduce," "inhibit" or "decrease" in terms of the values and cancer treatment methods described herein is meant the ability to cause an overall decrease preferably of 20% or greater, 30% or greater, 40% or greater, 45% or greater, more preferably of 50% or greater, of 55% or greater, of 60% or greater, of 65% or greater, of 70% or greater, and most preferably of 75% or greater, 80% or greater, 85% or greater, 90% or greater, or 95% or greater, for a given parameter or symptom. Reduce, inhibit or decrease can refer to, for example, the symptoms of the disorder being treated, the presence or size of metastases or micrometastases, the size of a primary tumor, the number or activity of a certain cell population, etc.

As used herein, "alleviating a symptom of a cancer or tumor" is ameliorating any condition or symptom associated with the cancer such as the symptoms of the cancer being treated, the presence or size of metastases or micrometastases, the size of the primary tumor, the presence or the size of the dormant tumor, etc. As compared with an equivalent untreated control, such as a subject prior to the administration of the LAP binding agents, such reduction or degree of prevention is at least 5%, 10%, 20%, 40%, 50%, 60%, 80%, 90%, 95%, or more as measured by any standard technique known to one of ordinary skill in the art. A patient or subject who is being treated for a cancer or tumor is one who a medical practitioner has diagnosed as having such a condition. Diagnosis can be by any suitable means.

As used herein, in regard to any of the compositions, methods, and uses comprising LAP binding agents described herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

The terms "subject," "patient," and "individual" as used in regard to any of the methods described herein are used interchangeably herein, and refer to an animal, for example a human, recipient of the inhibitos described herein. For treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e g dog, cat, horse, and the like. Production mammal, e.g. cow, sheep, pig, and the like are also encompassed in the term subject.

The term "effective amount" as used herein refers to the amount of a LAP binding agent described herein, needed to alleviate at least one or more symptom of the disease or disorder being treated, and relates to a sufficient amount of pharmacological composition to provide the desired effect, e.g., reduce or inhibit LAP-mediated tumor immune suppression. The term "therapeutically effective amount" therefore refers to an amount of the inhibitors or potentiators described herein, using the methods as disclosed herein, that is sufficient to provide a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions, methods, and uses that exhibit large therapeutic indices are preferred. A therapeutically effective dose can be estimated initially from cell culture assays. Also, a dose can be formulated in animal models to achieve a circulating plasma concentration range that includes the IC50, which achieves a half-maximal inhibition of measured function or activity) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

The LAP binding agents described herein can be administered to a subject in need thereof by any appropriate route which results in an effective treatment in the subject. As used herein, the terms "administering," and "introducing" are used interchangeably and refer to the placement of LAP binding agents into a subject by a method or route which results in at least partial localization of such agents at a desired site, such as a tumor site or site of inflammation, such that a desired effect(s) is produced.

In some embodiments, the LAP binding agents described herein can be administered to a subject by any mode of administration that delivers the agent systemically or to a desired surface or target, and can include, but is not limited to, injection, infusion, instillation, and inhalation administration. To the extent that polypeptide agents can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of LAP binding agents, other than directly into a target site, tissue, or organ, such that it enters the subject's circulatory system and, thus, is subject to metabolism and other like processes.

Some embodiments of the present invention may be defined in any of the following numbered paragraphs:

1. An isolated anti-LAP (latency associated peptide) antibody or antigen-binding fragment thereof that specifically binds to LAP comprising one or more heavy and light chain complimentarity determining regions (CDRs) selected from the group consisting of:
   a. a heavy chain CDR1 having the amino acid sequence of SEQ ID NO: 9;
   b. a heavy chain CDR2 having the amino acid sequence of SEQ ID NO: 10;
   c. a heavy chain CDR3 having the amino acid sequence of SEQ ID NO: 11;
   d. a light chain CDR1 having the amino acid sequence of SEQ ID NO: 14;
   e. a light chain CDR2 having the amino acid sequence of SEQ ID NO: 15; and
   f. a light chain CDR3 having the amino acid sequence of SEQ ID NO: 16.
2. The isolated anti-LAP antibody or antigen-binding fragment thereof of paragraph 1, comprising the heavy chain complimentarity determining regions (CDRs):

a. a heavy chain CDR1 having the amino acid sequence of SEQ ID NO: 9;
   b. a heavy chain CDR2 having the amino acid sequence of SEQ ID NO: 10; and
   c. a heavy chain CDR3 having the amino acid sequence of SEQ ID NO: 11.
3. The isolated anti-LAP antibody or antigen-binding fragment thereof of any one of paragraphs 1-2, comprising the light chain complimentarity determining regions (CDRs):
   a. a light chain CDR1 having the amino acid sequence of SEQ ID NO: 14;
   b. a light chain CDR2 having the amino acid sequence of SEQ ID NO: 15; and
   c. a light chain CDR3 having the amino acid sequence of SEQ ID NO: 16.
4. The isolated anti-LAP antibody or antigen-binding fragment thereof of any one of paragraphs 1-2, comprising the complimentarity determining regions (CDRs):
   a. a heavy chain CDR1 having the amino acid sequence of SEQ ID NO: 9;
   b. a heavy chain CDR2 having the amino acid sequence of SEQ ID NO: 10;
   c. a heavy chain CDR3 having the amino acid sequence of SEQ ID NO: 11;
   d. a light chain CDR1 having the amino acid sequence of SEQ ID NO: 14;
   e. a light chain CDR2 having the amino acid sequence of SEQ ID NO: 15; and
   f. a light chain CDR3 having the amino acid sequence of SEQ ID NO: 16.
5. The isolated anti-LAP antibody or antigen-binding fragment thereof of any one of paragraphs 1-4, comprising a heavy chain having the amino acid sequence of SEQ ID NO: 8.
6. The isolated anti-LAP antibody or antigen-binding fragment thereof of any one of paragraphs 1-5, comprising a light chain having the sequence of SEQ ID NO: 13.
7. An isolated anti-LAP antibody or antigen-binding fragment thereof that specifically binds LAP comprising:
   a. a heavy chain CDR1 having the amino acid sequence of SEQ ID NO: 9;
   b. a heavy chain CDR2 having the amino acid sequence of SEQ ID NO: 10;
   c. a heavy chain CDR3 having the amino acid sequence of SEQ ID NO: 11;
   d. a light chain CDR1 having the amino acid sequence of SEQ ID NO: 14;
   e. a light chain CDR2 having the amino acid sequence of SEQ ID NO: 15; and
   f. a light chain CDR3 having the amino acid sequence of SEQ ID NO: 16.
8. An isolated anti-LAP antibody or antigen-binding fragment thereof that specifically binds to LAP comprising one or more heavy chain complimentarity determining regions (CDRs) selected from the group consisting of:
   a. a heavy chain CDR1 having the amino acid sequence of SEQ ID NO: 9;
   b. a heavy chain CDR2 having the amino acid sequence of SEQ ID NO: 10; and
   c. a heavy chain CDR3 having the amino acid sequence of SEQ ID NO: 11.
9. An isolated anti-LAP antibody or antigen-binding fragment thereof that specifically binds to LAP comprising one or more light chain complimentarity determining regions (CDRs) selected from the group consisting of:
   a. a light chain CDR1 having the amino acid sequence of SEQ ID NO: 14;
   b. a light chain CDR2 having the amino acid sequence of SEQ ID NO: 15; and
   c. a light chain CDR3 having the amino acid sequence of SEQ ID NO: 16.
10. The isolated anti-LAP antibody or antigen-binding fragment thereof of any one of paragraphs 1-9, wherein the antibody is a chimeric, CDR-grafted, humanized, composite human or fully human antibody or dual antibody or antigen-binding fragment thereof.
11. The isolated anti-LAP antibody or antigen-binding fragment thereof of any one of paragraphs 1-10, wherein the antibody fragment is a Fab fragment, a Fab' fragment, a Fd fragment, a Fd' fragment, a Fv fragment, a dAb fragment, a F(ab')$_2$ fragment, a single chain fragment, a diabody, or a linear antibody.
12. The isolated anti-LAP antibody or antigen-binding fragment thereof of any one of paragraphs 1-10, wherein the antibody or antibody fragment thereof comprises a human acceptor framework.
13. A composition comprising a LAP-binding agent and an inhibitor of TGF-β signaling.
14. The composition of paragraph 13, wherein the LAP-binding agent comprises an anti-LAP antibody or antigen-binding fragment thereof.
15. The composition of paragraph 14, wherein the antibody is a monoclonal antibody.
16. The composition of paragraph 14, wherein the antibody is chimeric, CDR-grafted, humanized or fully human.
17. The composition of paragraph 14, wherein the anti-LAP antibody or antigen-binding fragment thereof is selected from those of paragraphs 1-12.
18. The composition of paragraph 13, wherein the inhibitor of TGF-β signaling is selected from the group consisting of an antibody or antigen-binding fragment thereof that binds TGF-β or a receptor therefor, a double-stranded RNA or nucleic acid encoding a double-stranded RNA, an aptamer, and a small molecule.
19. The composition of paragraph 18, wherein the small molecule is selected from the group consisting of 4-[4-(1,3-benzodioxol-5-yl)-5-pyridin-2-yl-1H-imidazol-2-yl]benzamide (SB431542), N-(oxan-4-yl)-4-[4-(5-pyridin-2-yl-1H-pyrazol-4-yl)pyridin-2-yl]benzamide (GW788388), 4-[3-(2-Pyridinyl)-1H-pyrazol-4-yl]-quinoline (LY364947), and 2-(3-(6-methylpyridin-2-yl)-1H-pyrazol-4-yl)-1,5-naphthyridine ("ALKS Inhibitor II").
20. A composition comprising a LAP-binding agent and an immunomodulatory or chemotherapeutic agent.
21. The composition of paragraph 20, wherein the LAP-binding agent comprises an antibody or antigen-binding fragment thereof.
22. The composition of paragraph 21, wherein the antibody or antigen-binding fragment thereof is a monoclonal antibody or antigen-binding fragment thereof.
23. The composition of paragraph 21, wherein the antibody or antigen-binding fragment thereof is chimeric, CDR-grafted, humanized or fully human.
24. The composition of paragraph 21, wherein the antibody or antigen-binding fragment thereof comprises an antibody composition of any one of paragraphs 1-12.
25. The composition of paragraph 20, wherein the immunomodulatory agent comprises an immune checkpoint modulator.
26. The composition of paragraph 25, wherein the immune checkpoint modulator modulates the effects of a polypeptide selected from the group consisting of PD-1, PD-L1, PDL2, CTLA4, LAG3, TIM3, TIGIT, and/or CD103.

27. The composition of paragraph 20, wherein the immunomodulatory agent comprises a tumor antigen vaccine.
28. The composition of paragraph 27, wherein the tumor antigen vaccine comprises a dendritic cell tumor antigen vaccine.
29. An antibody or antigen-binding fragment thereof that binds to LAP when complexed with TGF-β and inhibits release of TGF-β from the LAP/TGF-β complex.
30. The composition of paragraph 29, wherein the antibody or antigen-binding fragment thereof is a monoclonal antibody or antigen-binding fragment thereof.
31. The composition of paragraph 29, wherein the antibody or antigen-binding fragment thereof is chimeric, CDR-grafted, humanized or fully human.
32. The composition of paragraph 29, wherein the antibody or antigen-binding fragment thereof comprises an antibody composition of any one of paragraphs 1-12.
33. The antibody or antigen-binding fragment of paragraph 29, which binds an epitope formed by the binding of LAP to TGF-β.
34. The antibody or antigen-binding fragment of paragraph 29, which comprises the CDRs of the antibody of paragraph 7.
35. A pharmaceutical composition comprising the composition of any one of paragraphs 1-34, and a pharmaceutically acceptable carrier.
36. A method of decreasing the number or activity of a population of LAP+ T Regulatory cells in a subject, the method comprising administering a LAP-binding agent to the subject, whereby the number or activity of the population is decreased.
37. The method of paragraph 36, wherein the LAP-binding agent comprises an antibody or antigen-binding fragment thereof.
38. The method of paragraph 37, wherein the antibody or antigen-binding fragment thereof is a monoclonal antibody or antigen-binding fragment thereof.
39. The method of paragraph 37, wherein the antibody or antigen-binding fragment thereof is chimeric, CDR-grafted, humanized or fully human.
40. The method of paragraph 37, wherein the antibody or antigen-binding fragment thereof comprises an antibody composition of any one of paragraphs 1-12.
41. The method of paragraph 36, wherein the LAP-binding agent is conjugated to a cytotoxic drug.
42. A method of decreasing the number or activity of tumor-infiltrated immunosuppressive T cells in a tumor, the method comprising administering a LAP-binding agent to a subject with a tumor comprising tumor-infiltrated immunosuppressive T cells, whereby the number or activity of such cells is decreased.
43. The method paragraph 42, wherein the LAP-binding agent comprises an antibody or antigen-binding fragment thereof.
44. The method of paragraph 43, wherein the antibody or antigen-binding fragment thereof is a monoclonal antibody or antigen-binding fragment thereof.
45. The method of paragraph 43, wherein the antibody or antigen-binding fragment thereof is chimeric, CDR-grafted, humanized or fully human.
46. The method of paragraph 43, wherein the antibody or antigen-binding fragment thereof comprises an antibody composition of any one of paragraphs 1-12.
47. The method of paragraph 42, wherein the LAP-binding agent is conjugated to a cytotoxic drug.
48. A method of increasing tumor-specific immunity comprising administering a therapeutically effective amount of a LAP-binding agent to a subject in need thereof.
49. The method paragraph 48, wherein the LAP-binding agent comprises an antibody or antigen-binding fragment thereof.
50. The method of paragraph 49, wherein the antibody or antigen-binding fragment thereof is a monoclonal antibody or antigen-binding fragment thereof.
51. The method of paragraph 49, wherein the antibody or antigen-binding fragment thereof is chimeric, CDR-grafted, humanized or fully human.
52. The method of paragraph 49, wherein the antibody or antigen-binding fragment thereof comprises an antibody composition of any one of paragraphs 1-12.
53. A method of treating a cancer or tumor where LAP expression and/or activity is associated with suppression of cancer- or tumor-specific immunity comprising administering a therapeutically effective amount of a LAP-binding agent to a subject in need thereof.
54. The method paragraph 53, wherein the LAP-binding agent comprises an antibody or antigen-binding fragment thereof.
55. The method of paragraph 54, wherein the antibody or antigen-binding fragment thereof is a monoclonal antibody or antigen-binding fragment thereof.
56. The method of paragraph 54, wherein the antibody or antigen-binding fragment thereof is chimeric, CDR-grafted, humanized or fully human.
57. The method of paragraph 54, wherein the antibody or antigen-binding fragment thereof comprises an antibody composition of any one of paragraphs 1-12.
58. A method of increasing the number of CD8+ cytotoxic T cells in a tumor, the method comprising administering, to a subject with a tumor, a LAP-binding agent.
59. The method paragraph 58, wherein the LAP-binding agent comprises an antibody or antigen-binding fragment thereof.
60. The method of paragraph 59, wherein the antibody or antigen-binding fragment thereof is a monoclonal antibody or antigen-binding fragment thereof.
61. The method of paragraph 59, wherein the antibody or antigen-binding fragment thereof is chimeric, CDR-grafted, humanized or fully human.
62. The method of paragraph 59, wherein the antibody or antigen-binding fragment thereof comprises an antibody composition of any one of paragraphs 1-12.
63. A method of increasing peripheral CD4+ T cells expressing IFNγ in a subject in need thereof, the method comprising administering a LAP-binding agent to the subject.
64. The method paragraph 63 wherein the LAP-binding agent comprises an antibody or antigen-binding fragment thereof.
65. The method of paragraph 64 wherein the antibody or antigen-binding fragment thereof is a monoclonal antibody or antigen-binding fragment thereof.
66. The method of paragraph 64 wherein the antibody or antigen-binding fragment thereof is chimeric, CDR-grafted, humanized or fully human.
67. The method of paragraph 64 wherein the antibody or antigen-binding fragment thereof comprises an antibody composition of any one of paragraphs 1-12.
68. A method of increasing peripheral CD8+ T cells expressing granzyme B in a subject in need thereof, the method comprising administering a LAP-binding agent to the subject.

69. The method paragraph 68 wherein the LAP-binding agent comprises an antibody or antigen-binding fragment thereof.
70. The method of paragraph 69 wherein the antibody or antigen-binding fragment thereof is a monoclonal antibody or antigen-binding fragment thereof.
71. The method of paragraph 69 wherein the antibody or antigen-binding fragment thereof is chimeric, CDR-grafted, humanized or fully human.
72. The method of paragraph 69 wherein the antibody or antigen-binding fragment thereof comprises an antibody composition of any one of paragraphs 1-12.
73. A method of decreasing the number of FoxP3+ regulatory T cells in a tumor, the method comprising administering a LAP-binding agent to the subject.
74. The method paragraph 73 wherein the LAP-binding agent comprises an antibody or antigen-binding fragment thereof.
75. The method of paragraph 74 wherein the antibody or antigen-binding fragment thereof is a monoclonal antibody or antigen-binding fragment thereof.
76. The method of paragraph 74 wherein the antibody or antigen-binding fragment thereof is chimeric, CDR-grafted, humanized or fully human.
77. The method of paragraph 74 wherein the antibody or antigen-binding fragment thereof comprises an antibody composition of any one of paragraphs 1-12.
78. A method of inhibiting expression of an immunosuppressive factor or marker by CD8+ and/or CD4+ T cells in a tumor, the method comprising administering a LAP-binding agent to a subject with a tumor.
79. The method paragraph 78 wherein the LAP-binding agent comprises an antibody or antigen-binding fragment thereof.
80. The method of paragraph 79 wherein the antibody or antigen-binding fragment thereof is a monoclonal antibody or antigen-binding fragment thereof.
81. The method of paragraph 79 wherein the antibody or antigen-binding fragment thereof is chimeric, CDR-grafted, humanized or fully human.
82. The method of paragraph 79 wherein the antibody or antigen-binding fragment thereof comprises an antibody composition of any one of paragraphs 1-12.
83. The method of paragraph 78 wherein the immunosuppressive factor or marker comprises one or more of PD-1, LAG-3 and CD103.
84. A method of promoting an anti-tumor immune response, the method comprising vaccinating a subject in need of treatment for a tumor with a tumor antigen and administering a LAP-binding agent to the subject.
85. The method paragraph 84 wherein the LAP-binding agent comprises an antibody or antigen-binding fragment thereof.
86. The method of paragraph 85 wherein the antibody or antigen-binding fragment thereof is a monoclonal antibody or antigen-binding fragment thereof.
87. The method of paragraph 85 wherein the antibody or antigen-binding fragment thereof is chimeric, CDR-grafted, humanized or fully human.
88. The method of paragraph 85 wherein the antibody or antigen-binding fragment thereof comprises an antibody composition of any one of paragraphs 1-12.
89. A method of treating cancer that is refractory to treatment with an immune checkpoint inhibitor, the method comprising administering to a subject having such cancer a LAP-binding agent.
90. The method paragraph 89 wherein the LAP-binding agent comprises an antibody or antigen-binding fragment thereof.
91. The method of paragraph 90 wherein the antibody or antigen-binding fragment thereof is a monoclonal antibody or antigen-binding fragment thereof.
92. The method of paragraph 90 wherein the antibody or antigen-binding fragment thereof is chimeric, CDR-grafted, humanized or fully human.
93. The method of paragraph 90 wherein the antibody or antigen-binding fragment thereof comprises an antibody composition of any one of paragraphs 1-12.
94. The method of paragraph 89, further comprising administering an immune checkpoint inhibitor.
95. The method of paragraph 89, wherein the cancer is a glioblastoma, colorectal carcinoma or a melanoma.
96. The method of paragraph 89, wherein the cancer is refractory to a PD-1 or PD-L1 inhibitor before treatment with the LAP-binding agent.
97. A method for treating cancer, the method comprising analyzing a tumor sample from a subject to determine the presence of LAP+ T regulatory cells, and, if LAP+ T regulatory cells are present, administering to the subject a LAP-binding agent, thereby promoting an anti-tumor immune response.
98. The method paragraph 97 wherein the LAP-binding agent comprises an antibody or antigen-binding fragment thereof.
99. The method of paragraph 97 wherein the antibody or antigen-binding fragment thereof is a monoclonal antibody or antigen-binding fragment thereof.
100. The method of paragraph 97 wherein the antibody or antigen-binding fragment thereof is chimeric, CDR-grafted, humanized or fully human
101. The method of paragraph 97 wherein the antibody or antigen-binding fragment thereof comprises an antibody composition of any one of paragraphs 1-12.
102. A method of selecting a patient, from among a population of cancer patients, whose cancer is likely to respond to therapy with a LAP-binding agent, the method comprising analyzing a tumor sample from a patient for the presence of LAP+ T regulatory cells, wherein, if LAP+ T regulatory cells are found to be present in the patient's tumor, the patient's tumor is identified as likely to respond to therapy with a LAP-binding agent.
103. The method of paragraph 102, further comprising, when LAP+ T regulatory cells are found in said tumor, administering a LAP-binding agent to that patient, and when LAP+ T regulatory cells are not found in said tumor, administering an immunomodulatory or anti-tumor agent other than a LAP-binding agent to the patient.
104. The method paragraph 102 or 103 wherein the LAP-binding agent comprises an antibody or antigen-binding fragment thereof.
105. The method of paragraph 104 wherein the antibody or antigen-binding fragment thereof is a monoclonal antibody or antigen-binding fragment thereof.
106. The method of paragraph 104 wherein the antibody or antigen-binding fragment thereof is chimeric, CDR-grafted, humanized or fully human.
107. The method of paragraph 104 wherein the antibody or antigen-binding fragment thereof comprises an antibody composition of any one of paragraphs 1-12.
108. The method of paragraph 102, wherein the analysis of a tumor sample from the patient for the presence of LAP+ T regulatory cells comprises quantitative measurement of the amount of LAP+T regulatory cells present, and when LAP+ T regulatory cells are found to be present, comparing their amount to a reference, wherein a tumor with a higher relative level of LAP+ T regulatory cells is identified as more likely to respond to therapy with a LAP-binding agent.

109. The method of paragraph 103 wherein the immunomodulatory agent comprises an immune checkpoint inhibitor.

110. The method of paragraph 103 wherein the anti-tumor agent comprises gamma radiation or a chemotherapeutic agent.

111. A method of promoting the formation of memory T cells specific for an antigen of interest in a subject in need thereof, the method comprising administering a LAP-binding agent and the antigen of interest to the subject.

112. The method of paragraph 111 wherein CD44+ and/or IL7R+ T cells are increased following administration of the LAP-binding agent.

113. The method of paragraph 111 wherein the antigen of interest comprises a tumor antigen or an antigen expressed by an infectious pathogen.

114. The method of paragraph 113 wherein the tumor antigen is administered as a dendritic cell vaccine.

115. The method paragraph 111 wherein the LAP-binding agent comprises an antibody or antigen-binding fragment thereof.

116. The method of paragraph 115 wherein the antibody or antigen-binding fragment thereof is a monoclonal antibody or antigen-binding fragment thereof.

117. The method of paragraph 115 wherein the antibody or antigen-binding fragment thereof is chimeric, humanized or fully human 118. The method of paragraph 115 wherein the antibody or antigen-binding fragment thereof comprises an antibody composition of any one of paragraphs 1-12.

119. Use of a LAP-binding agent to treat a disease or disorder characterized by or involving an undesirable number or activity of LAP+ T regulatory cells.

120. Use of a LAP-binding agent to decrease the number or activity of tumor-infiltrated immunosuppressive T cells in a tumor, the use comprising administering a LAP-binding agent to a subject with a tumor comprising tumor-infiltrated immunosuppressive T cells, whereby the number or activity of such cells is decreased.

121. Use of a LAP-binding agent to increase tumor-specific immunity, the use comprising administering a therapeutically effective amount of a LAP-binding agent to a subject in need thereof.

122. Use of a LAP-binding agent for the treatment of a cancer or tumor where LAP expression and/or activity is associated with suppression of cancer- or tumor-specific immunity, the use comprising administering a therapeutically effective amount of a LAP-binding agent to a subject in need thereof.

123. Use of a LAP-binding agent for the treatment of a cancer or tumor by increasing the number of CD8+ cytotoxic T cells in a tumor, the usecomprising administering, to a subject with a tumor, a LAP-binding agent.

124. Use of a LAP-binding agent for the treatment of a cancer or tumor by increasing peripheral CD4+ T cells expressing IFNγ in a subject in need thereof, the use comprising administering a LAP-binding agent to the subject.

125. Use of a LAP-binding agent for the treatment of a cancer or tumor by increasing peripheral CD8+ T cells expressing granzyme B in a subject in need thereof, the use comprising administering a LAP-binding agent to the subject.

126. Use of a LAP-binding agent for the treatment of a cancer or tumor by decreasing the number of FoxP3+ regulatory T cells in a tumor, the use comprising administering a LAP-binding agent to the subject.

127. Use of a LAP-binding agent for the treatment of a cancer or tumor by inhibiting expression of an immunosuppressive factor by CD8+ and/or CD4+ T cells in a tumor, the use comprising administering a LAP-binding agent to a subject with a tumor.

128. Use of a LAP-binding agent for promoting an anti-tumor immune response, the use comprising vaccinating a subject in need of treatment for a tumor with a tumor antigen and administering a LAP-binding agent to the subject.

129. Use of a LAP-binding agent for treating cancer that is refractory to treatment with an immune checkpoint inhibitor, the use comprising administering to a subject having such cancer a LAP-binding agent.

130. Use of a LAP-binding agent for treating cancer, the use comprising analyzing a tumor sample from a subject to determine the presence of LAP+ T regulatory cells, and, if LAP+ T regulatory cells are present, administering to the subject a LAP-binding agent, thereby promoting an anti-tumor immune response.

131. Use of a LAP-binding agent promoting the formation of memory T cells specific for an antigen of interest for the treatment of cancer or an infection in a subject, the use comprising administering a LAP-binding agent and the antigen of interest to the subject.

132. The composition of any one of paragraphs 13-32 or the method of any one of paragraphs 36-118 or the use of any one of paragraphs 119-131 wherein the LAP-binding agent specifically binds a LAP molecule having the sequence set forth in any one of SEQ ID NOs: 1-3.

133. The composition of any one of paragraphs 13-28 or the method of any one of paragraphs 37, 43, 49, 54, 59, 64, 69, 74, 79, 85, 90, 98, 104 or 115 wherein the antibody or antigen-binding fragment thereof binds a LAP ligand interaction site.

134. The composition or method of paragraph 133, wherein the LAP ligand interaction site is a site that interacts with mature TGFβ, a site that interacts with integrins, and/or a site that interacts with latent TGFβ binding protein (LTBP).

135. The composition of any one of paragraphs 1-28 or the method of any one of paragraphs 36, 42, 48, 53, 58, 63, 68, 73, 78, 84, 89, 97, 102, 111 or the use of any one of paragraphs 119-131 wherein the LAP-binding agent binds LAP complexed with TGF-β and inhibits release of TGF-β from the complex.

136. The composition of any one of paragraphs 15, 22, 30, or the method of any one of paragraphs 38, 44, 50, 55, 60, 65, 70, 75, 80, 86, 91, 99, 105 or 116 wherein the monoclonal antibody is produced by any one of the hybridoma clones selected from TW4-9E7, TW4-5A8, TW4-3E5, TW4-4E5, TW4-12B12, TW4-13B12, TW4-1G12, TW4-3G5, TW4-2F8, TW4-6H10, TW4-1G2, TW4-1E1, TW4-16F4, TW4-8F10, TW4-3H6, TW4-2C9, TW7-16B4, TW7-28G11, TW7-7H4, and TW7-20B9.

137. The composition of any one of paragraphs 13, 20 or 35, or the method of any one of paragraphs 36, 42, 48, 53, 58, 63, 68, 73, 78, 84, 89, 97, 102, 111, or the use of any one of paragraphs 119-131, wherein the LAP-binding agent is a small molecule inhibitor, agent, or compound.
138. The composition of any one of paragraphs 13, 20 or 35, or the method of any one of paragraphs 36, 42, 48, 53, 58, 63, 68, 73, 78, 84, 89, 97, 102, 111, or the use of any one of paragraphs 119-131, wherein the LAP-binding agent is an RNA or DNA aptamer that binds or physically interacts with LAP.
139. The method of any one of paragraphs 36-101, 111-118 or the use of any one of paragraphs 120-131, wherein the subject has or has been diagnosed with cancer.
140. The method or use of paragraph 139, wherein the subject has or has been diagnosed with a brain tumor, a melanoma, or colorectal cancer.
141. The method or use of paragraph 140, wherein the brain tumor is a glioblastoma.
142. The method of any one of paragraphs 36, 42, 48, 53, 58, 63, 68, 73, 78, 84, 89, 97, 111 or the use of any one of paragraphs 119-131, wherein the method further comprises administering an anti-cancer therapy, chemotherapeutic or immunomodulatory agent to the subject.
143. The method or use of paragraph 142, wherein the immunomodulatory agent comprises an immune checkpoint inhibitor.
144. The method or use of paragraph 143, wherein the immune checkpoint inhibitor binds to one or more of the following: PD1, PDL1, PDL2, CTLA4, LAG3, TIM3, TIGIT and/or CD103.
145. The method or use of paragraph 143, wherein the immune checkpoint inhibitor is a PD1, PDL1, and/or PDL2 inhibitory agent selected from pembrolizumab; nivolumab; MK-3475; MPDL3280A; MEDI0680; MEDI4736; AMP-224; and MSB0010718C.
146. The method of or use of paragraph 142, wherein the method further comprises administering a tumor or cancer antigen to the subject.
147. The method or use of paragraph 146, wherein the method comprises administering the LAP binding agent concurrently or in combination with dendritic cell (DC) vaccination.
148. The method of paragraph 24, wherein the LAP-binding agent is an isolated antibody or antigen-binding fragment thereof of any one of paragraphs 1-11 or the pharmaceutical composition of paragraph 12.
149. The composition of any one of paragraphs 13, 20 or 35, or the method of any one of paragraphs 36, 42, 48, 53, 58, 63, 68, 73, 78, 84, 89, 97, 102, 111, or the use of any one of paragraphs 119-131, wherein the LAP-binding agent is an isolated antibody or antigen-binding fragment thereof of any one of paragraphs 1-11 or the pharmaceutical composition of paragraph 12.

It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Example 1

Membrane-bound LAP expression was up-regulated on FOXP3+CD4+ lymphocytes from tumors of head and neck cancer patients. LAP+CD4+ lymphocytes were found as enhanced suppressor T cells in both blood and tumor of colorectal cancer (CRC) patients. The blood-derived LAP+ CD4+ subset suppresses naive T cell proliferation in a TGF-β-dependent manner. In colorectal cancer, 30% of intratumor CD4+FOXP3− regulatory T cells are LAP and LAG positive. They secrete IL-10 and produce membrane-bound TGF-β. Although IFN-γ is slightly higher on LAP positive vs. LAP negative T cells in blood, tumor-infiltrating LAP positive T lymphocytes (LAP+ TILs) secrete significantly lower amounts of IFN-γ and higher IL-10 in comparison to LAP− TILs. Interestingly, these CD4+LAP+ TILs were found to be 50-fold more suppressive than CD4+LAP− cells and this was partially dependent on TGF-β.

Independently of TGF-β, LAP has biological functions that can promote cancer malignancy. Soluble LAP was shown to regulate trafficking of human monocytes by serving as a chemo-attractant. Thus, high levels of LAP in the brain tumor can attract monocytes from the periphery that become tumor-associated macrophages in the tumor milieu, thus contributing immunosuppression. In addition, immobilized LAP can induce expression of MMP-9 and promote migration and invasion of tumor cells through integrin signaling, while soluble LAP has the opposite effect.

Therapeutic Effects of Anti-LAP

Figures 55A, 55N:
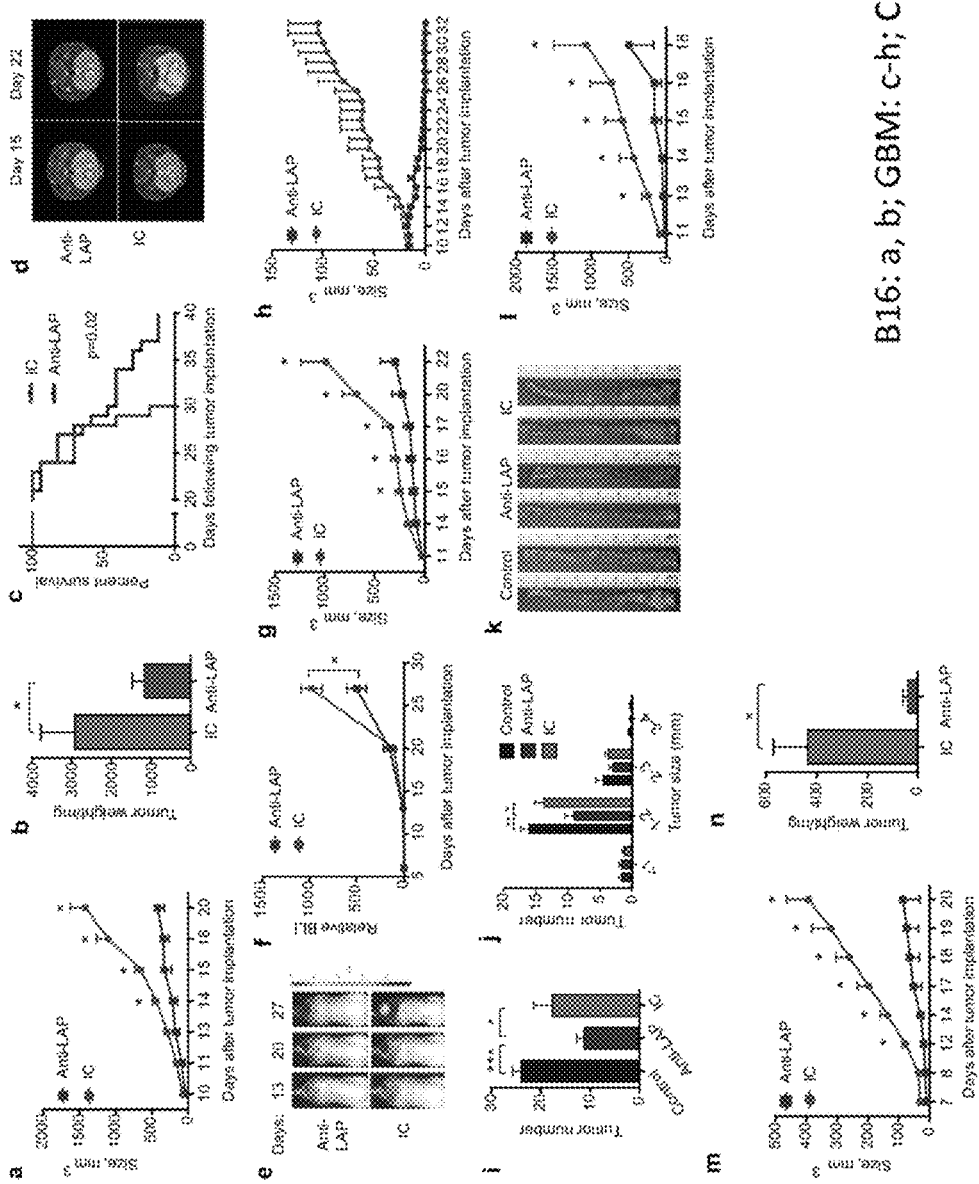
FIGS. 55A-55N depict therapeutic effects of anti-LAP antibodies in cancer models.

Given the important regulatory role of CD4+LAP+ T cells we developed monoclonal anti-LAP antibodies that recognize LAP expressed on the cell surface. We generated both mouse- and human-specific monoclonal anti-LAP antibodies that deplete CD4+LAP+ T cells in vivo and block TGF-release. Our results described herein show efficacy of the mouse antibodies in the decrease of melanoma, GBM and CRC tumor growth in syngeneic models (FIGS. 55A-55N). Specifically, B16 orthotopic tumor model was treated with anti-LAP (28G11 clone, FIGS. 55A, 55B). In addition, we tested anti-LAP in GBM/GL261 models: both orthotopic/intracranial and subcutaneous models. Intracraneous model was treated with 16B4 (FIGS. 55C-55F) and subcutaneous model was treated with either 16B4 (FIG. 55G) or 28G11 (FIG. 55H). Finally, colorectal carcinoma (CRC) models were treated with 28G11 (FIGS. 55I-55N) or 16B4 (not shown). AOM/DSS-induced orthotopic (FIGS. 55I-

55K) and subcutaneous MC38 (FIG. 55L) and CT26 (FIGS. 55M, 55N) CRC models were treated with anti-LAP. In all tumor models, anti-LAP treatment resulted in therapeutic effects. Thus, anti-LAP antibodies can be used to block the immunosuppression mediated by LAP in the models of melanoma, GBM and CRC.

We also acquired and tested syngeneic cancer models based on GL261 original glioma cells, B16 melanoma cells and cells constitutively expressing ovalbumin (GL261-OVA and B16-OVA) to study antigen-specific immune responses in both intracranial and subcutaneous mouse models.

We identified a novel LAP+γδ T cell regulatory subset that manifests an immunosuppressive phenotype, suppresses the proliferation of naïve T cells and induces FoxP3 expression further supporting the immunosuppression. (Rezende et al., Nature Comminications). In addition, we found that this cell population accumulates in the spleen of GBM bearing mice (FIG. 1E), indicating that these cells are involved in glioma-induced immunosuppression.

To study the role of LAP in the regulation of the immune response in GBM, we first analyzed LAP expression on different immune cells infiltrating GBM and in the periphery. We found that GBM-infiltrating lymphocytes and myeloid cells expressed high levels of LAP on their surface (FIGS. 1A-1D), indicating that it can play a role in immune suppression in GBM.

Figure 2B:
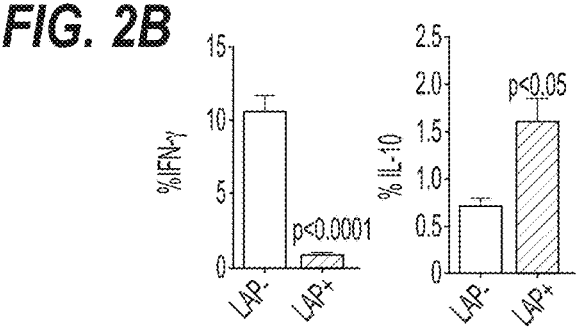
Figure 2C:
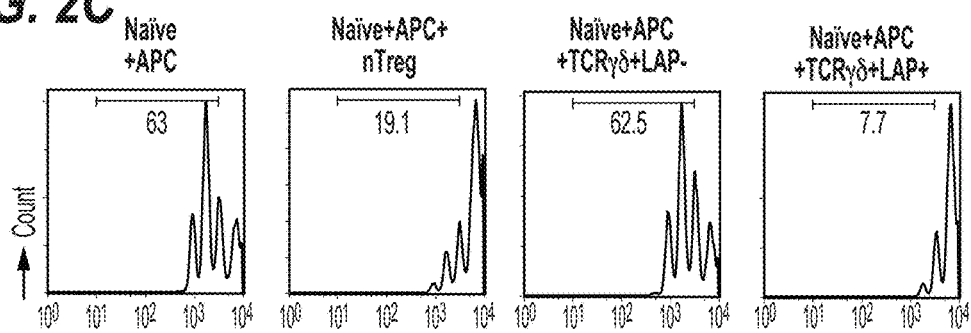
Figure 2D:
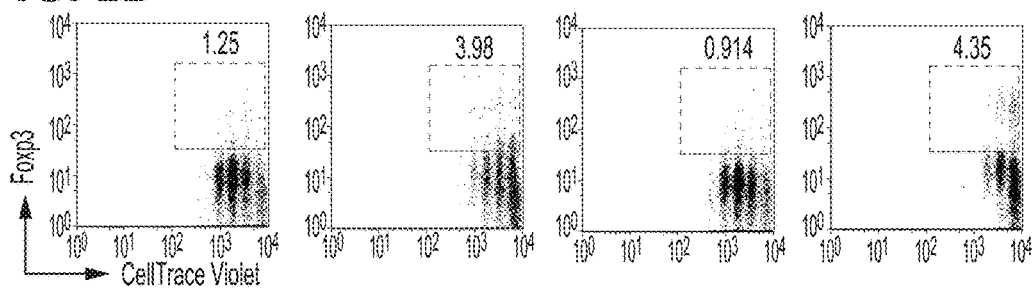

To investigate which populations of LAP+ immune cells are important in GBM-mediated immunosuppression we compared the frequencies of different LAP+ immune cells in GBM-bearing mice. Interestingly, we found that γδ+LAP+ T cells strongly accumulated in the spleen of GBM-bearing mice (FIG. 1E). Since this subset has not been described in the literature, we investigated its phenotype and function. We found that the γδ+LAP+ T lymphocytes possess a suppressive phenotype when compared to γδ+LAP- T cells isolated from naïve mice (FIG. 2A, 2B). Cytokine expression profile by both qRT-PCR and flow cytometry shows that a pro-inflammatory marker such as IFN-γ is down-regulated while immune suppressive cytokines (e.g., TGF-β and IL-10) are up-regulated. We then tested the function of the γδ+LAP+ T subset and found that these cells exhibit strong suppressive abilities and are able to induce FoxP3 expression in an in vitro assay (FIG. 2C).

Since we found high expression of LAP on γδ T lymphocytes isolated from tumor, we examined whether glioma cells can induce LAP expression on these cells. As FIGS. 3A-3B show, co-culturing γδ+LAP- T lymphocytes with glioma GL261 cells leads to increased LAP expression in vitro, indicating that glioma can cause immunosuppression by inducing LAP expression on γδ T cells. To abolish the suppressive LAP effects on immune system, we used anti-LAP antibodies to block LAP activity in vivo.

Figure 4A:
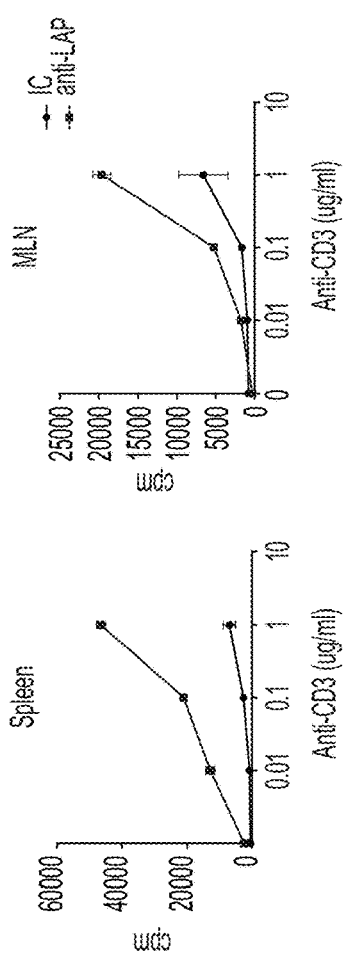
FIGS. 4A-4B demonstrate that Anti-LAP treatment skews the immune system towards pro-inflammatory responses. Naïve mice were treated with anti-LAP or IC antibodies. T cells were isolated from spleen and mesenteric lymph nodes (MLN) and T cell proliferation measured (FIG. 4A). The isolated T cells were activated and cytokine secretion to determine the potential of the cells to produce IFN-γ, IL17 and IL-2 was estimated by ELISA (FIG. 4B).
Figure 4B:
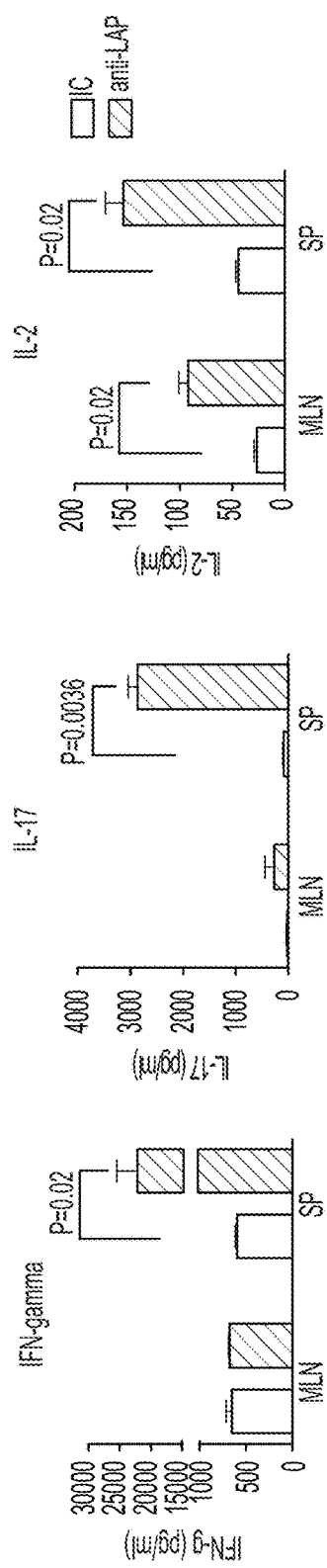
Figure 6:
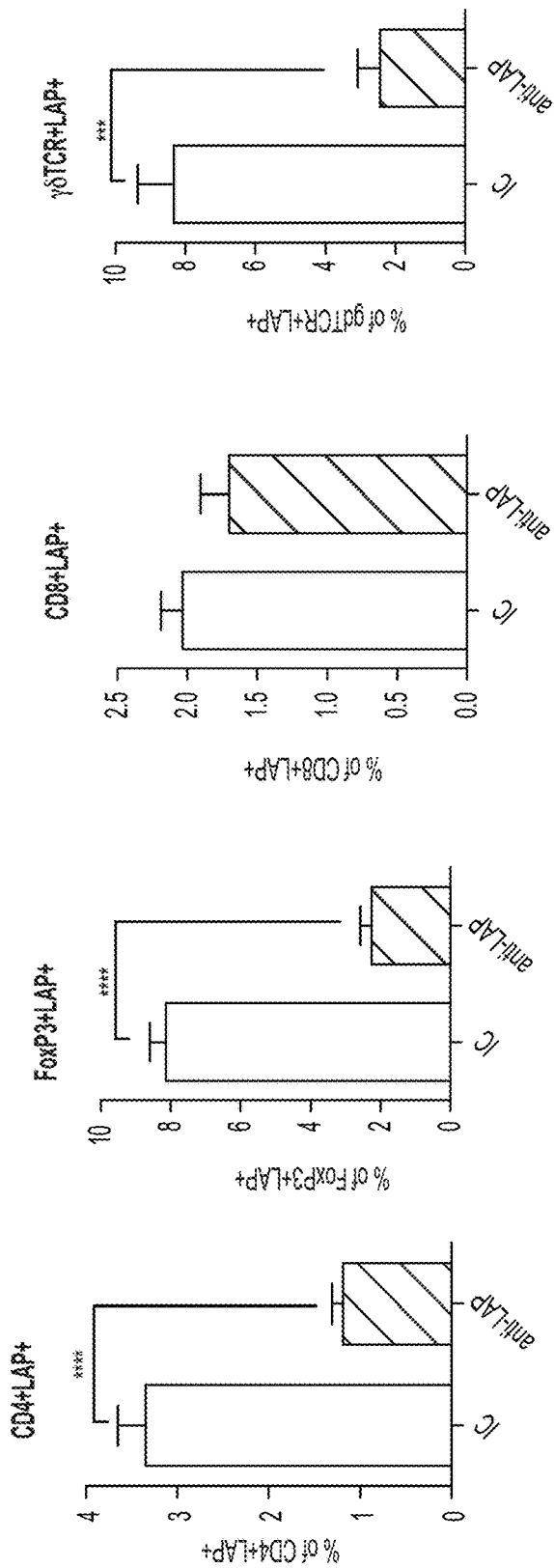
FIG. 6 demonstrates that LAP Expression is Reduced on T Cell Subsets in Anti-LAP Treated Melanoma-Bearing Mice.
Figure 7:
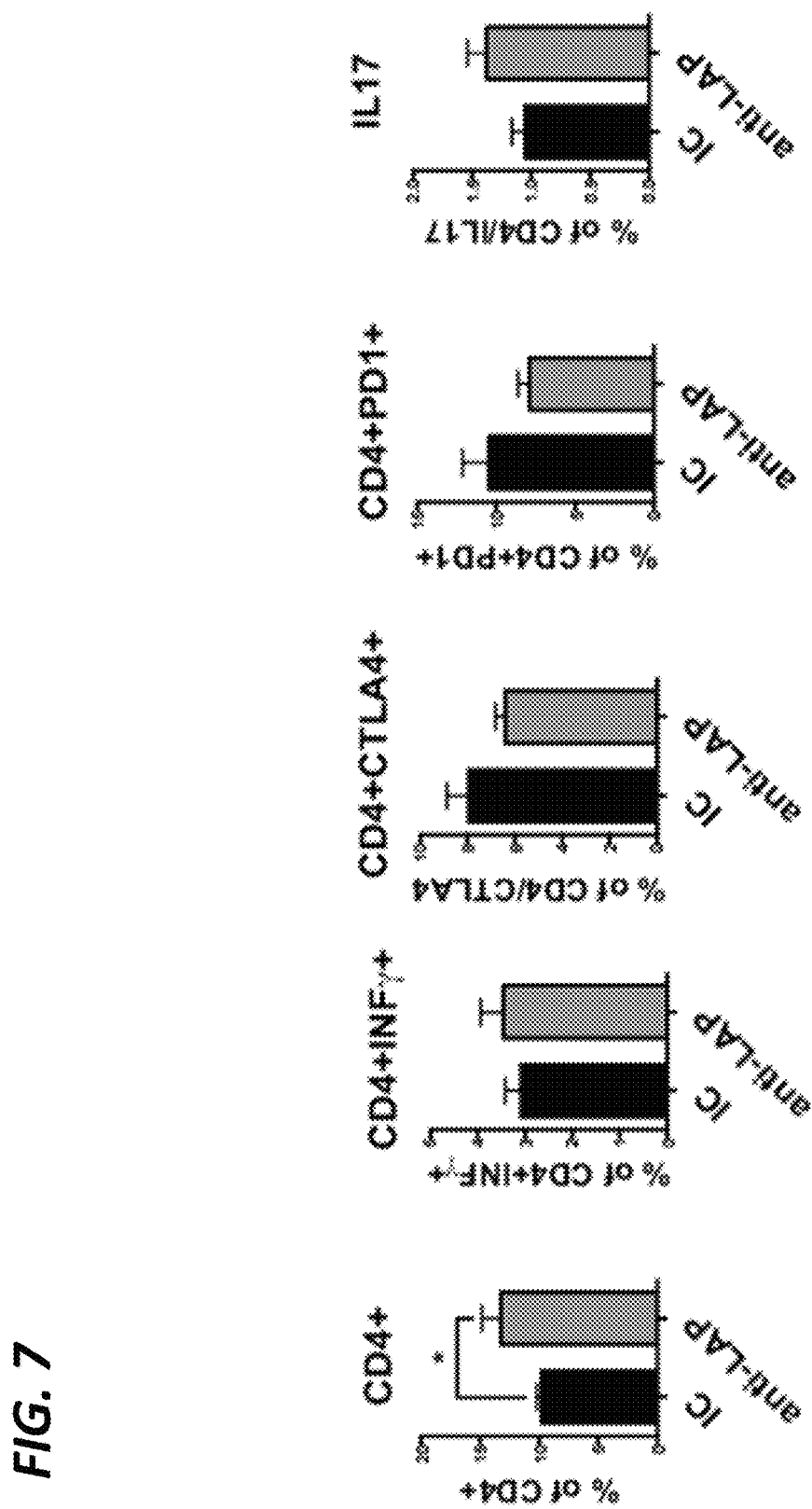
FIG. 7 demonstrates that CD4+ T Cells Exhibit Pro-Inflammatory Phenotype in Anti-LAP Treated Melanoma-Bearing Mice.
Figure 8:
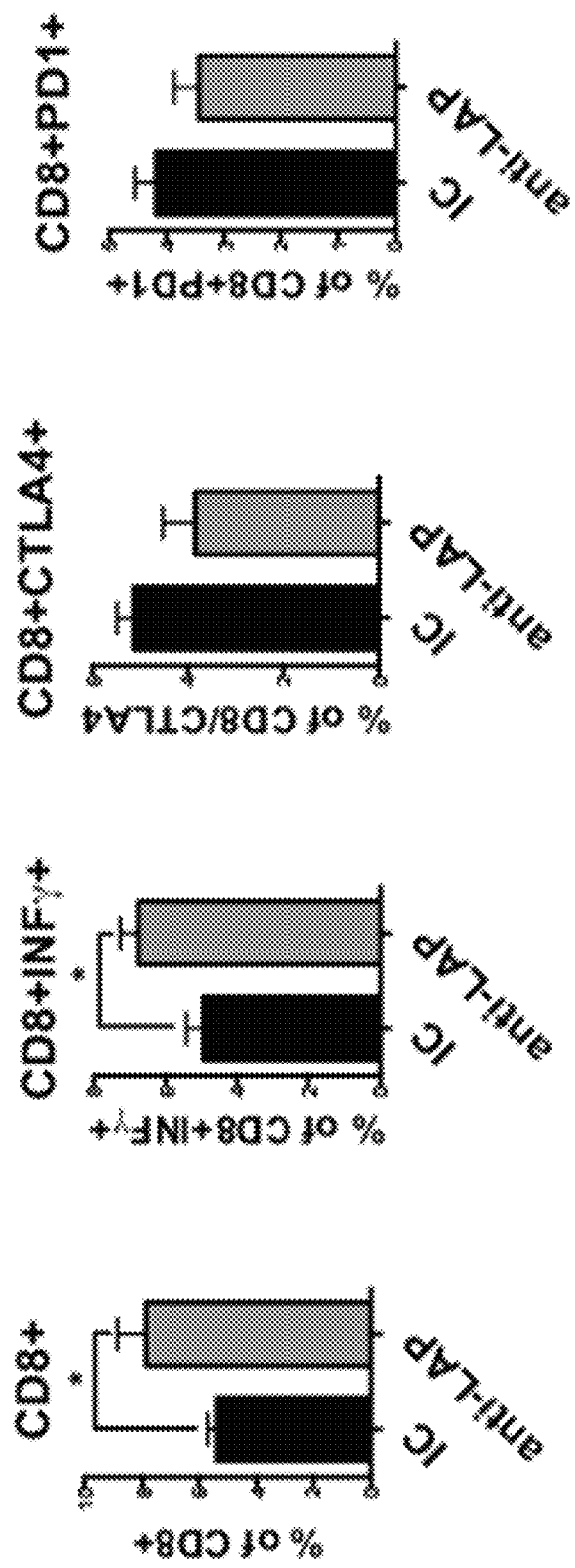
FIG. 8 demonstrates that CD8+ T Cells Exhibit Pro-Inflammatory Phenotype in Anti-LAP Treated Melanoma-Bearing Mice.
Figure 9:
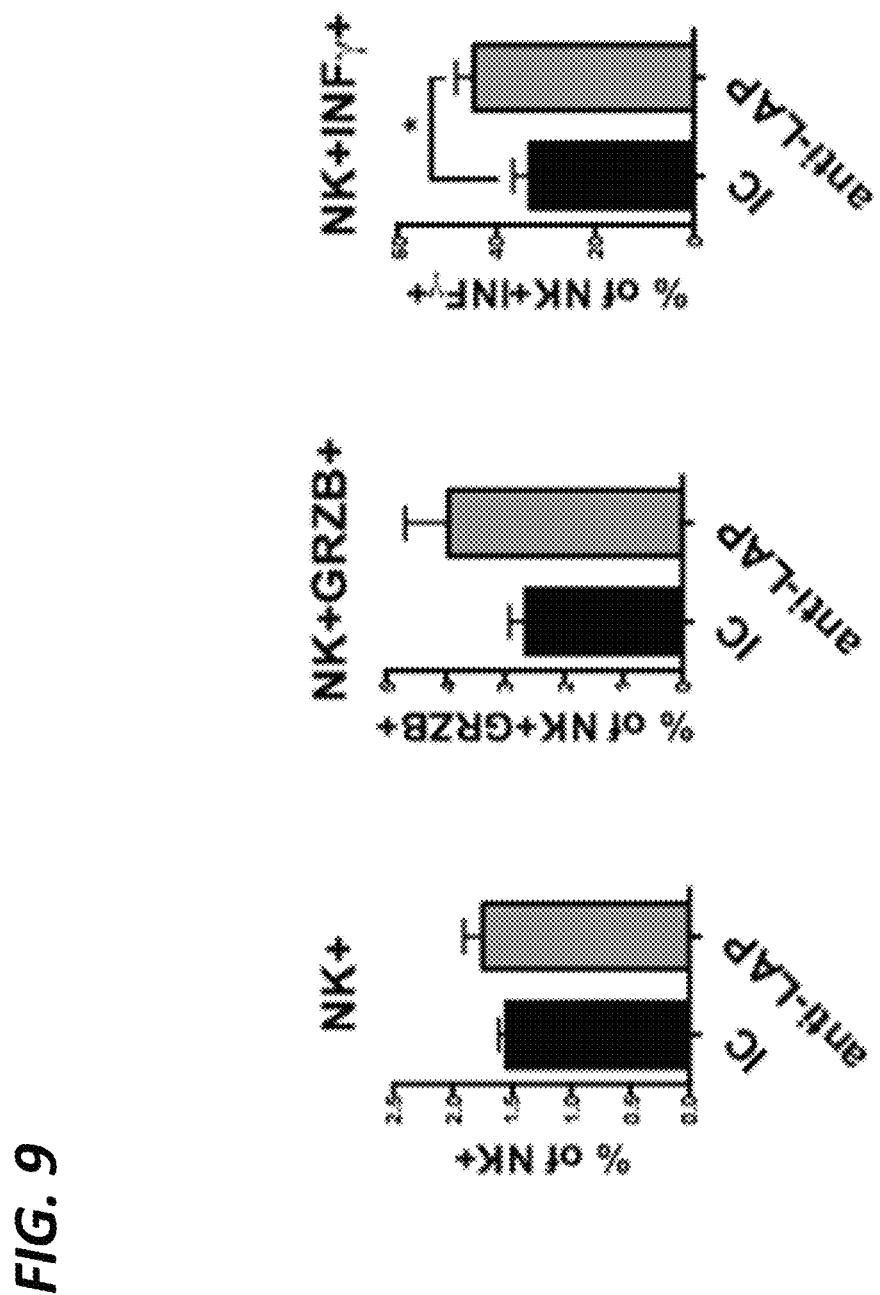
FIG. 9 demonstrates that NK Cells Exhibit Pro-Inflammatory Phenotype in Anti-LAP Treated Melanoma-Bearing Mice.
Figure 10:
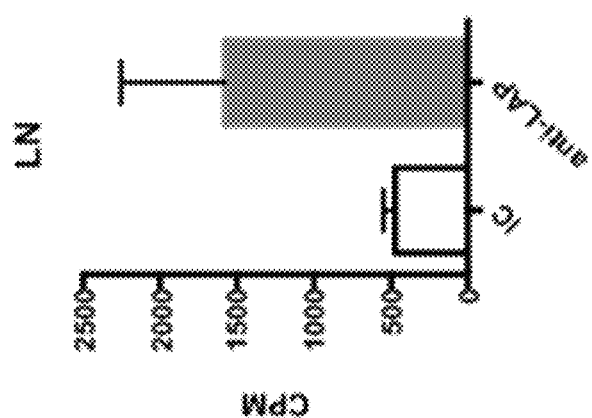
FIG. 10 demonstrates that Immune Cells isolated from LNs of Anti-LAP Treated Mice Proliferate Better. Proliferation of inguinal lymph node cells of OVA-melanoma tumor bearing mice after 3 days of in vitro stimulation with 100 µg/ml of OVA.
Figure 11:
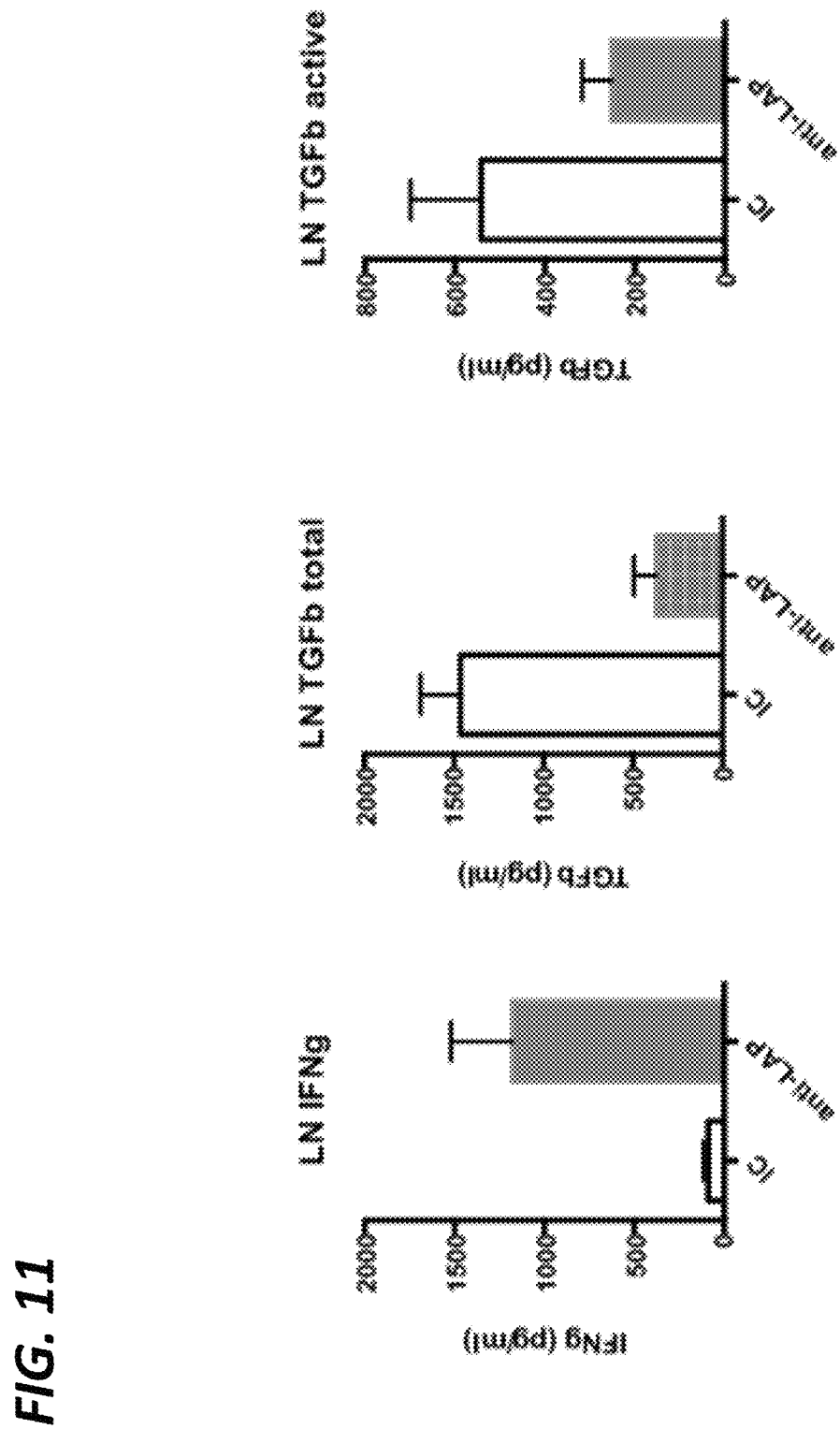
FIG. 11 demonstrates that immune Cells isolated from LNs of Anti-LAP Treated Mice Have Pro-Inflammatory Profile. Cytokine production of inguinal lymph node cells (by ELISA) of OVA-melanoma tumor bearing mice after 3 days of in vitro stimulation with 100 µg/ml of OVA.
Figure 12:
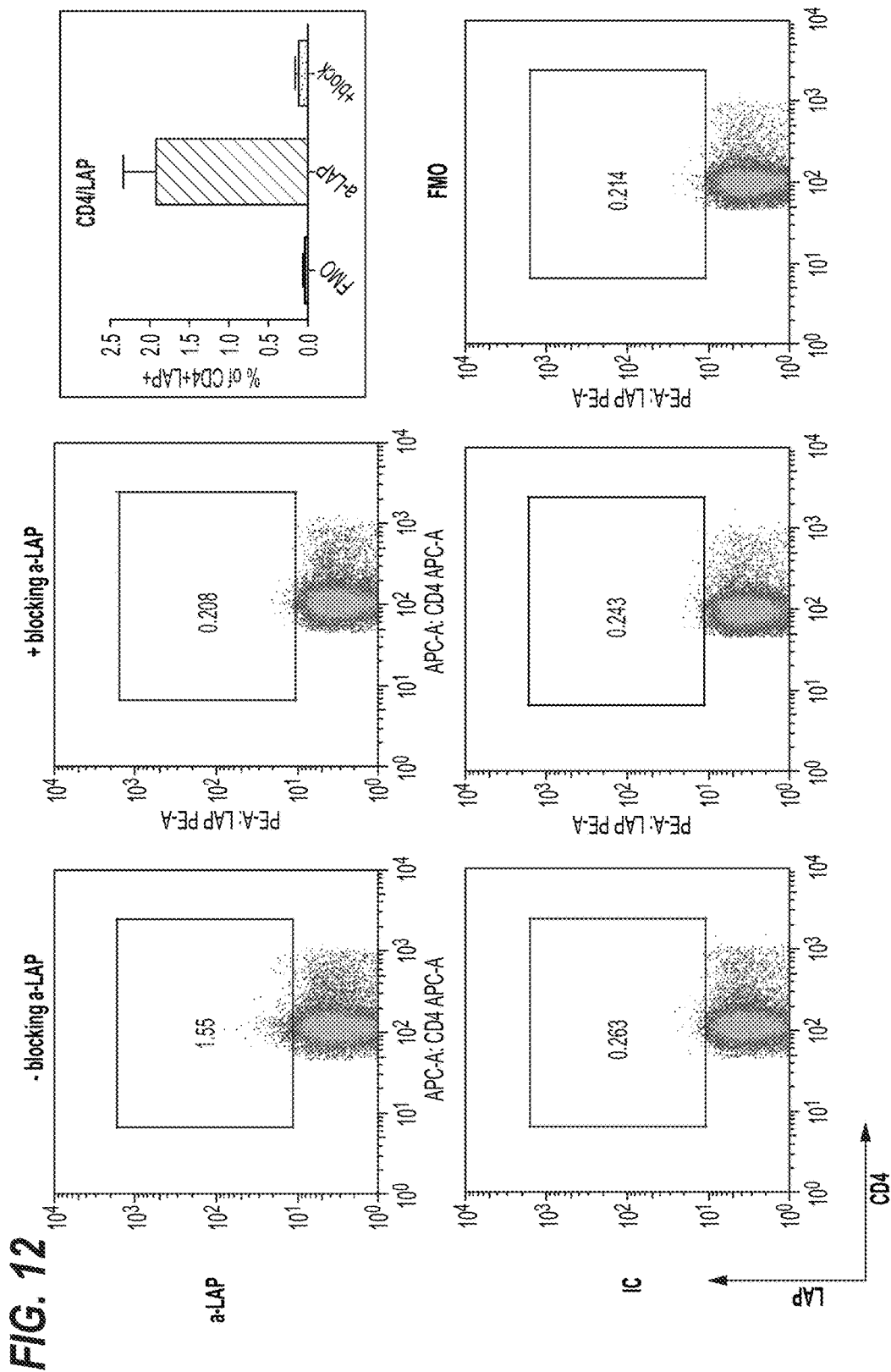
FIG. 12 demonstrates LAP Expression on CD4+ T Cells.
Figure 13:
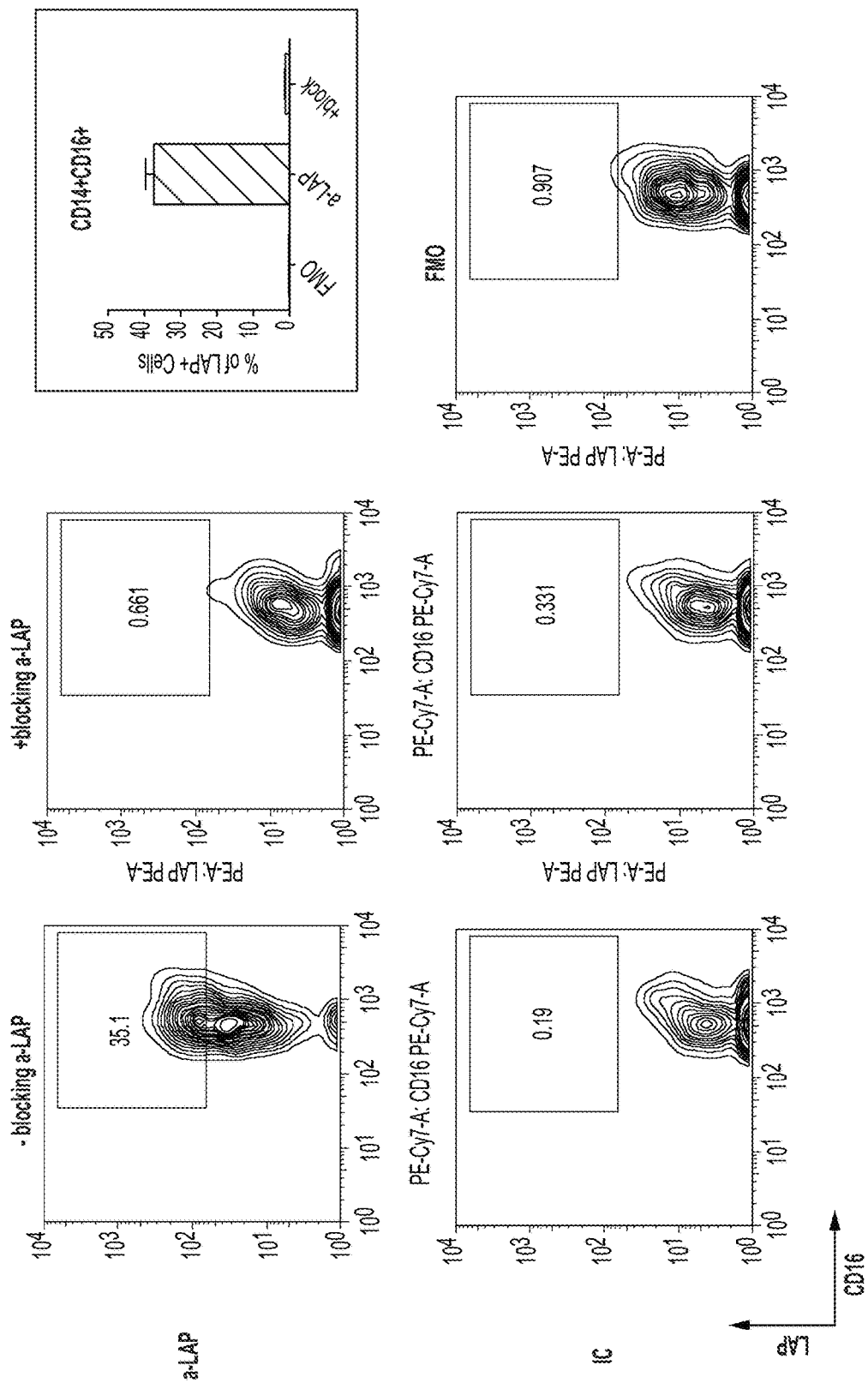
FIG. 13 demonstrates LAP Expression on CD16+CD14+.
Figure 14:
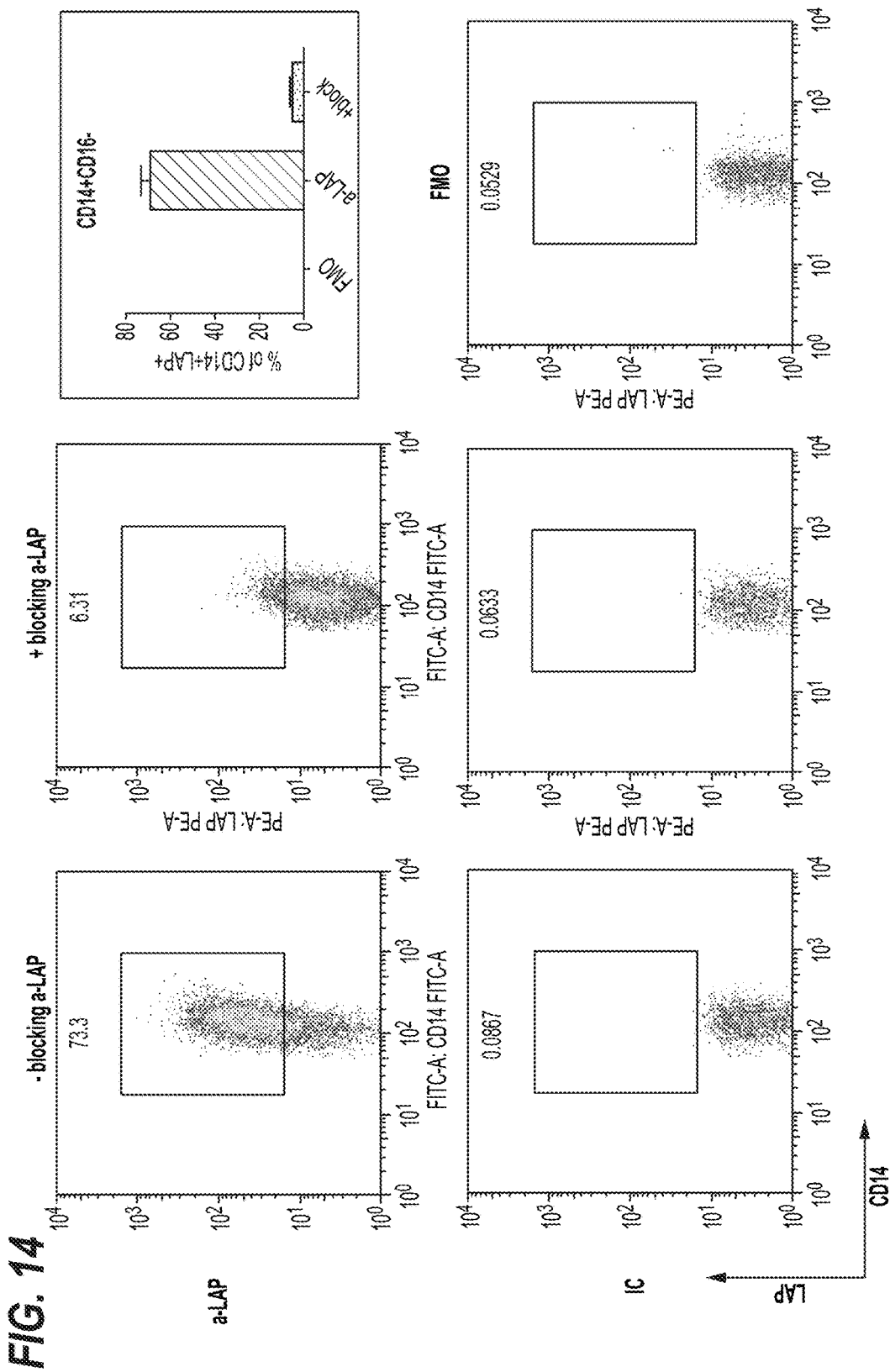
FIG. 14 demonstrates LAP Expression on CD11b+CD14+CD16—(Classical Monocytes, Resemble LyδC—hi).
Figure 15:
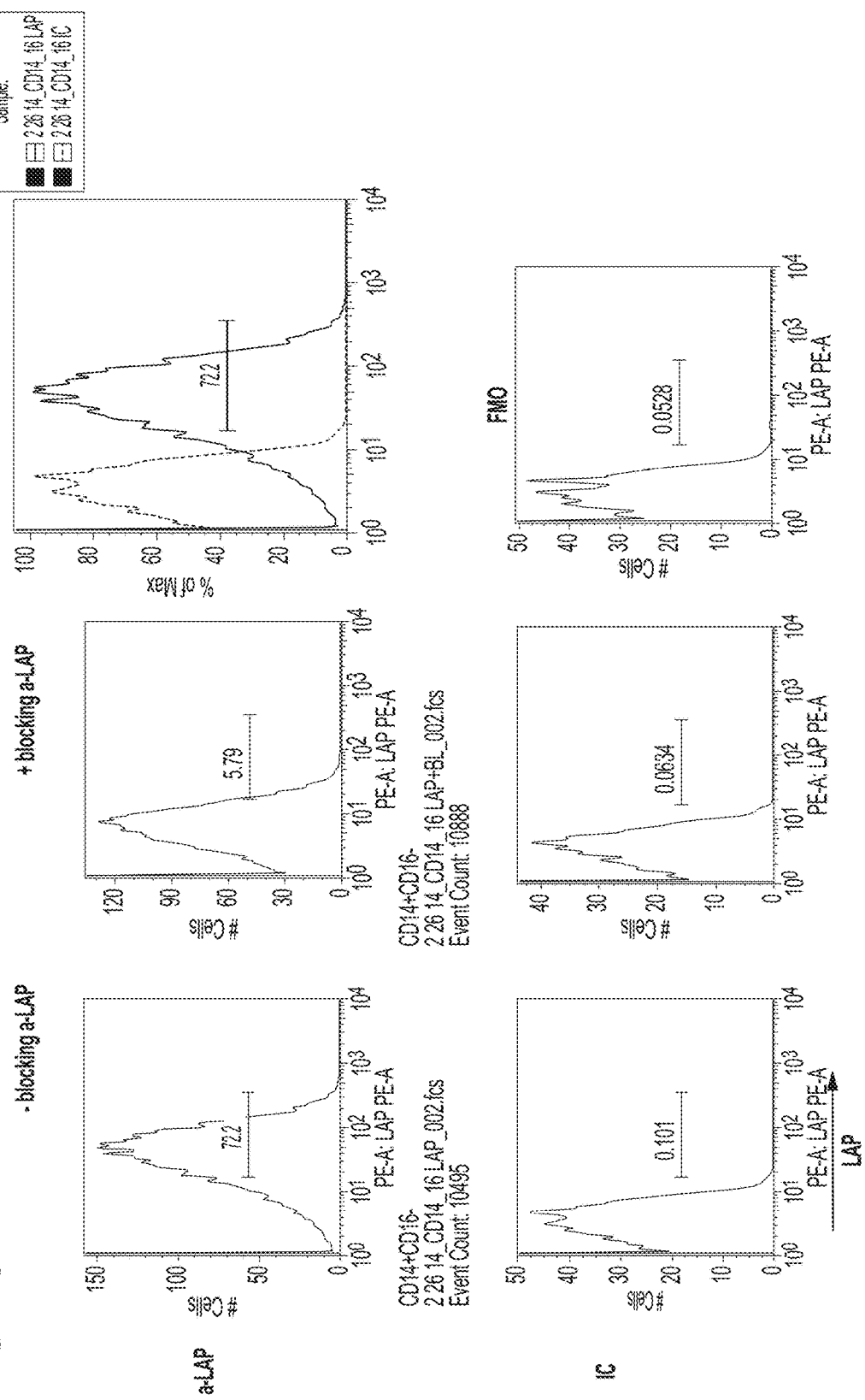
FIG. 15 demonstrates LAP Expression on CD11b+CD14+CD16—(Classical Monocytes, Resemble LyδC—hi).
Figure 16:
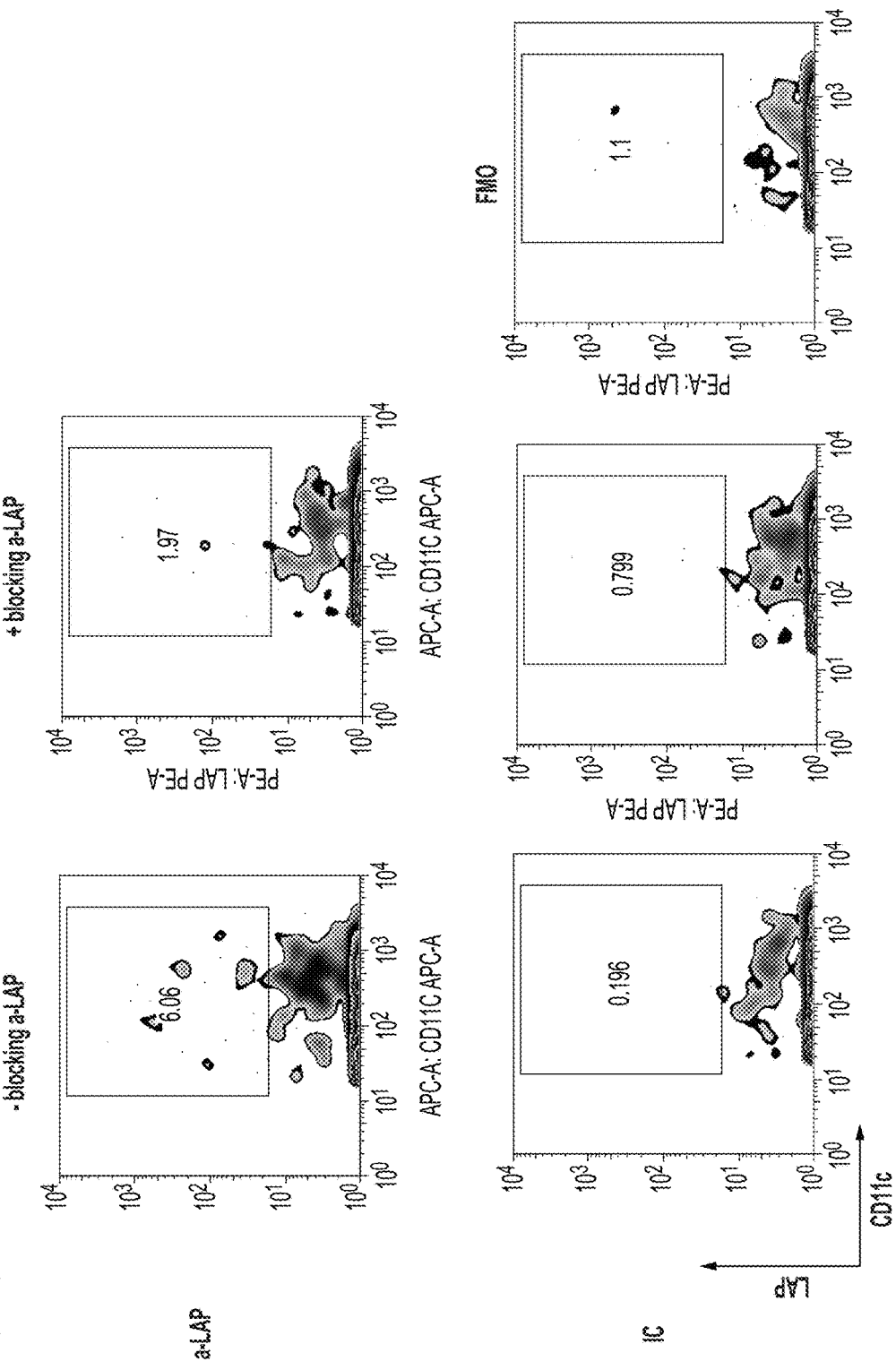
FIG. 16 demonstrates LAP Expression on Lin-CD11c+ (mDCs).
Figure 17:
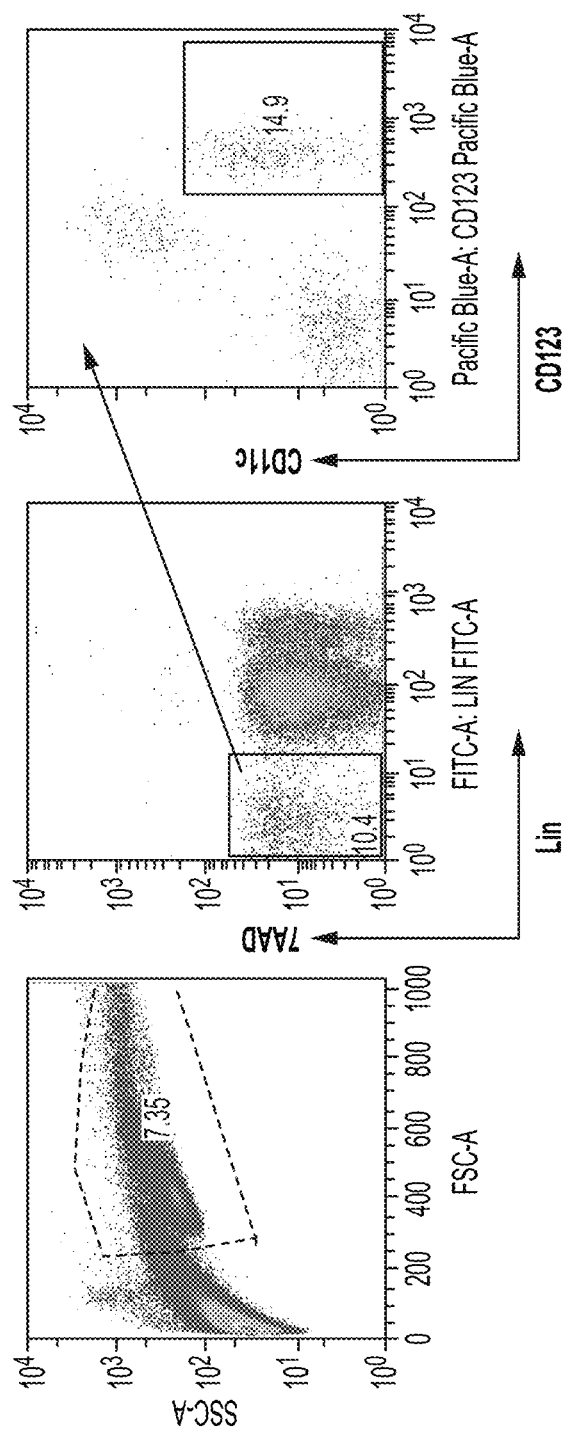
FIG. 17 demonstrates Gating for Lin-CD11c-CD123+ (pDCs).
Figure 18:
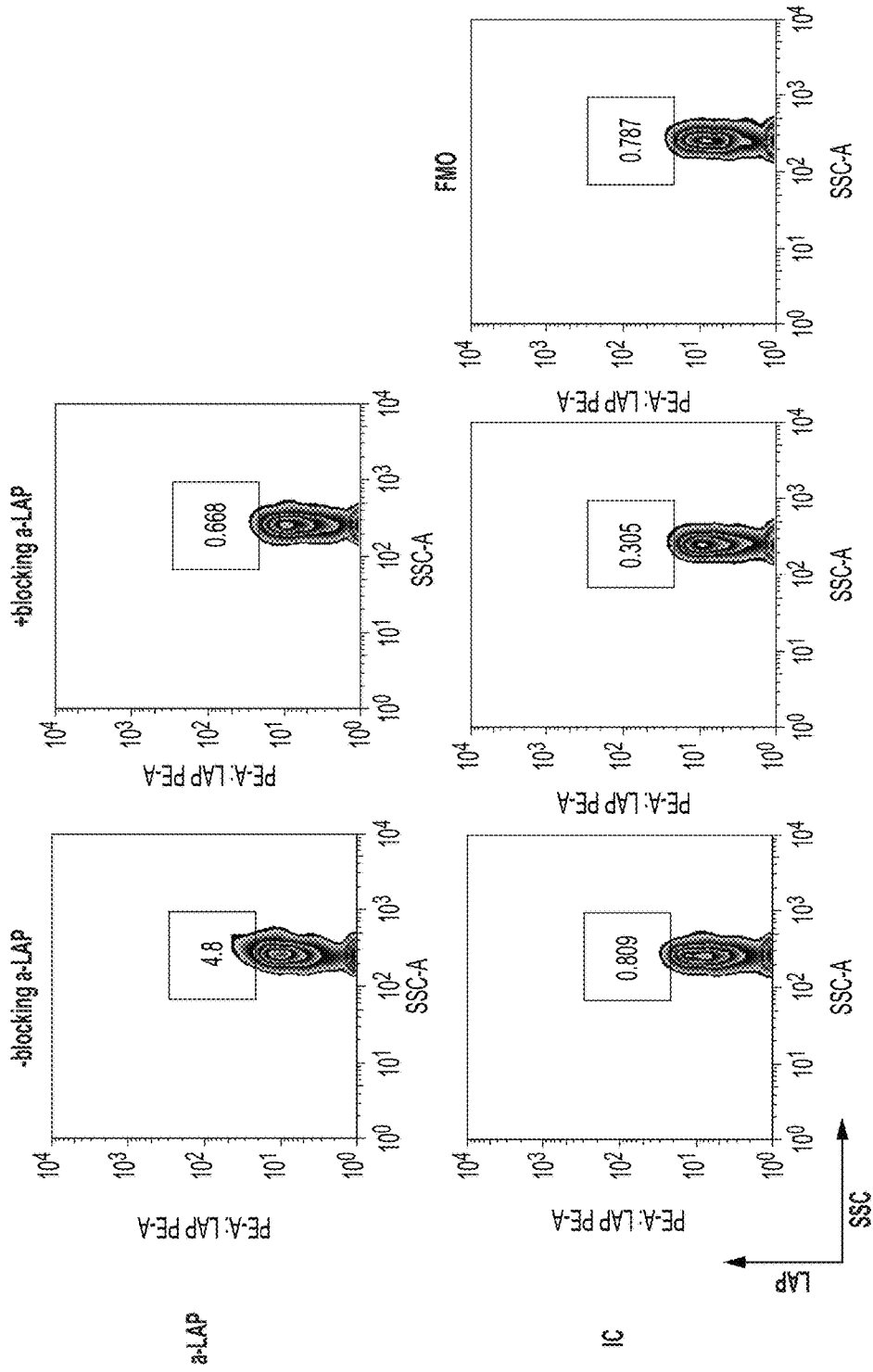
FIG. 18 demonstrates LAP Expression on Lin-CD11c-CD123+ (pDCs).
Figure 19:
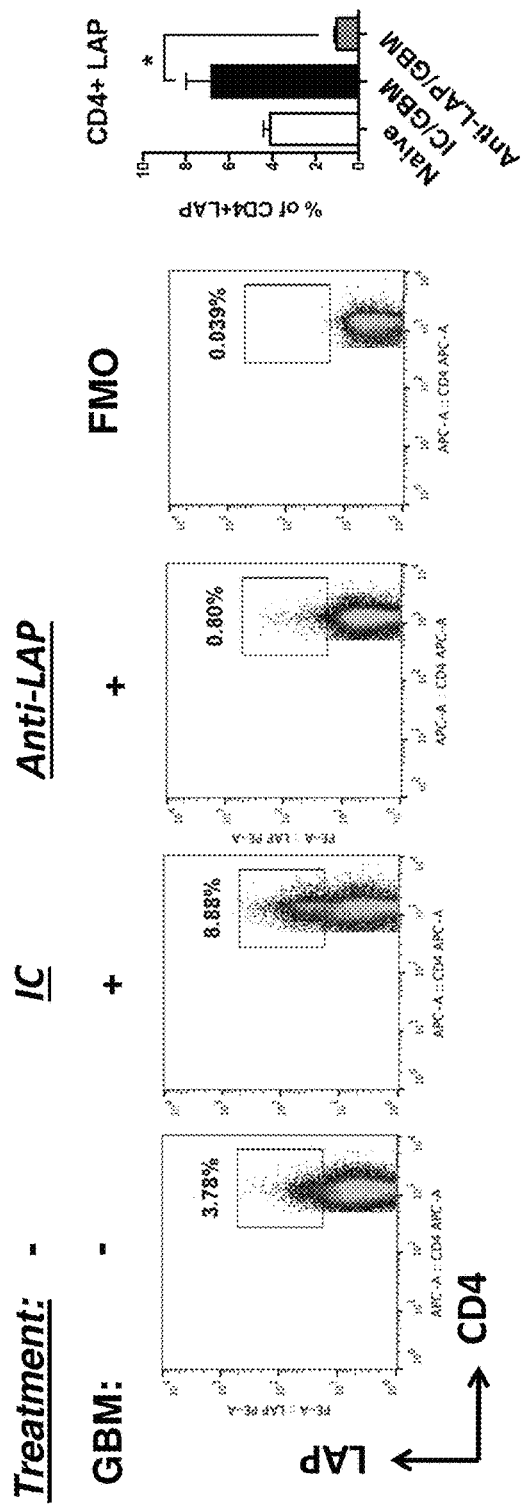
FIG. 19 depicts LAP expression on CD4+ T Cells in spleen.
Figure 20:
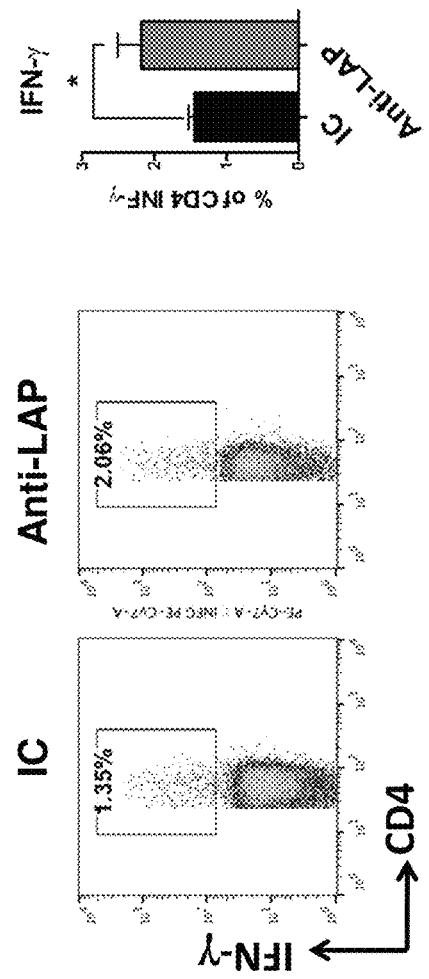
FIG. 20 demonstrates IFN-γ expression is higher on CD4+ T cells in spleen following anti-LAP treatment.
Figure 21:
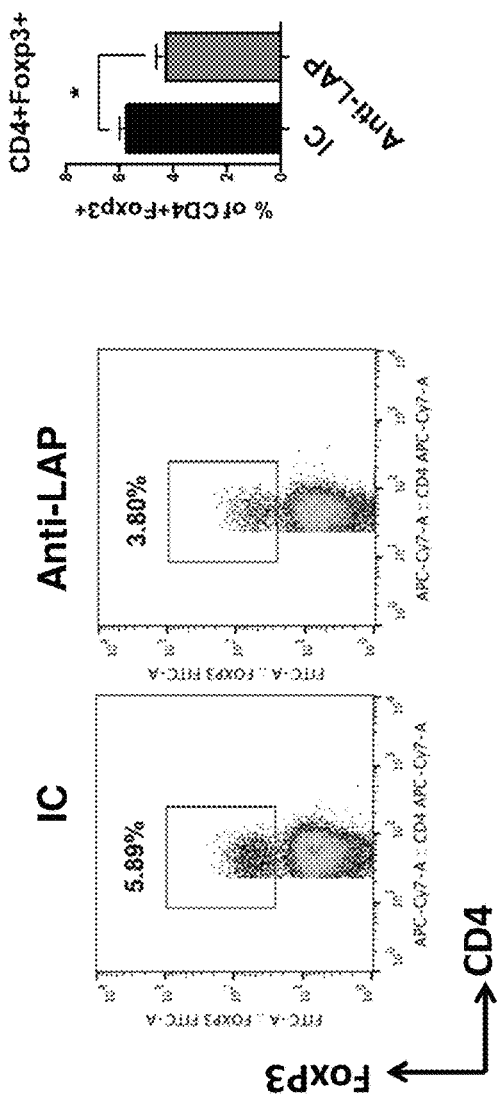
FIG. 21 demonstrates the Number of Regulatory CD4+ T Cells is Reduced in Spleen following anti-LAP treatment.
Figure 22:
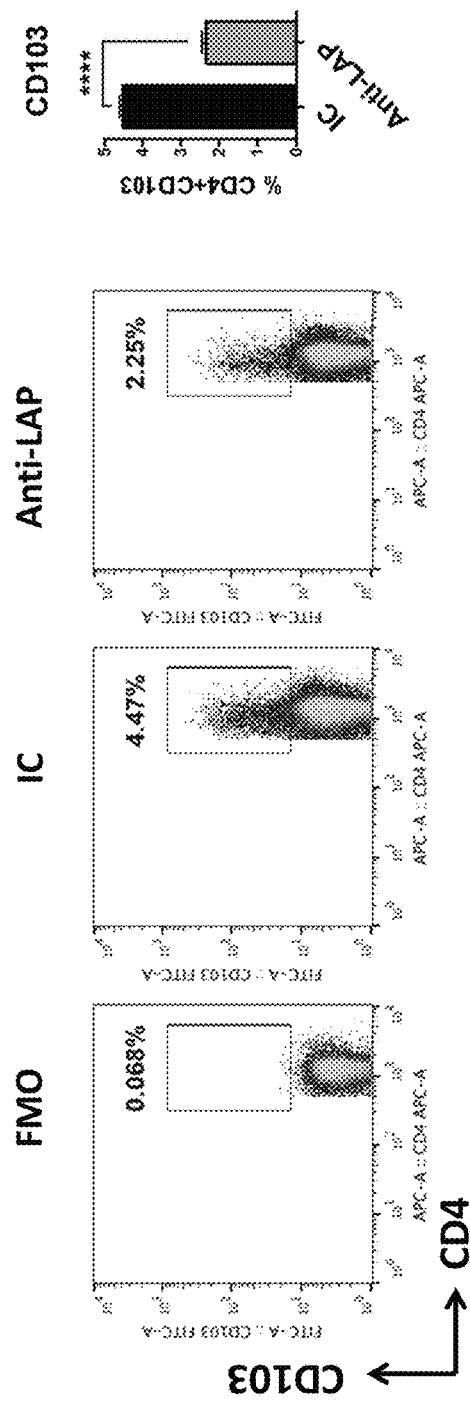
FIG. 22 demonstrates CD103 Expression is Decreased on CD4+ T Cells in Spleen following anti-LAP treatment.

To analyze the effects of anti-LAP antibodies on the immune system we treated naïve mice with anti-LAP antibodies. We found that T cell proliferation and pro-inflammatory cytokine production were higher in anti-LAP treated animals as compared to mice treated with isotype-matched control (FIGS. 4A-4B) indicating that anti-LAP has the ability to induce a pro-inflammatory immune response. (da Cunha, International Immunology, 2014)

To assess the therapeutic value of anti-LAP antibodies against tumor, we used a sub-cutaneous model of mouse glioma by implantation of GL261 cells in the flanks of C57BL/6 mice. Following tumor implantation, mice were treated intraperitoneally (i.p.) with anti-LAP antibodies and repeated treatments were given every other day. Isotype-matched non-specific antibodies (IC) were employed as a negative control. The tumors appeared around day 10 following implantation and grew initially in both treatment groups, and thereafter they markedly shrunk in the anti-LAP treated group after 14 days from the implantation when the immunity is fully developed (FIGS. 55H, 5B). When we investigated the immune response we found that anti-LAP blocked the tumor-induced immunosuppression that interferes with a proinflammatory immune response (FIGS. 5C-5K). Anti-LAP treatment led to higher expression of IFN-γ on CD4+ T cells and reduced FoxP3 on CD4+ T cells (FIGS. 5C and 5D, correspondingly). In addition, the treatment resulted in increased numbers of CD8+ T cells (FIG. 5G) and their cytotoxic phenotype (FIGS. 5H-5I).

Interestingly, the anti-LAP treatment resulted in a decreased frequency of CD11b-Hi myeloid subset while CD11b-Int cells increased (FIGS. 57A, 57B). Levels of tolerance-related markers PD-L1 and CD103 are reduced on CD11b-hi after anti-LAP treatment (FIG. 57C). LAP protein is mainly expressed on CD11b-hi cells, additionally indicating on a suppressive phenotype of this subset (FIG. 57D). We examined the immune profile of these two sub-populations. The subsets were sorted from naïve mice, stimulated with anti-CD40 antibody or lipopolysaccharide (LPS), followed by gene expression analysis. Upon activation, the CD11b-Hi population expressed higher levels of the immunosuppressive cytokines IL-10 and TGF-β and lower levels of the pro-inflammatory cytokine IL-12, indicating that this subset can have a regulatory role; anti-LAP treatment eliminated these cells. (FIG. 57E). CD8 cells, co-cultured with CD11b-hi, express lower levels of proinflammatory cytokines supporting anti-tumor immune responses, IFN-γ and TNF-α, as compared to CD11b-int subset (FIG. 57F). Moreover, the CD11b-Hi subset expressed low levels of antigen presentation markers (FIGS. 57G, 57H) indicating that these cells have lower capacity to support antigen-specific immune responses. Finally, CD11b-hi cells do not support CD8+ T cells growth when culture in vitro (FIG. 57I). Thus, we found that anti-LAP treatment reduces the number of myeloid cells with suppressive properties, which favors a stronger immune response and tumor elimination.

Since anti-LAP antibody treatment was very efficient in the elimination of the peripheral tumor, we performed experiments to assess its potential in an orthotopic mouse model of intracranial GBM. Following the implantation of GL261 glioma cells into the striatum using stereotactic surgery, mice were treated with anti-LAP every other day starting from day five following tumor implantation. As shown in FIGS. 55C-55F, despite aggressive tumor progression, mice treated with anti-LAP survived longer, and this was associated with increased infiltration of CD8+ T cells into the brain tumor. Considering the strong malignant nature of intracranial GBM, this result demonstrates a therapeutic potential of the anti-LAP antibodies against brain tumor and indicates the potential of a therapeutic effect of anti-LAP.

Figure 62:
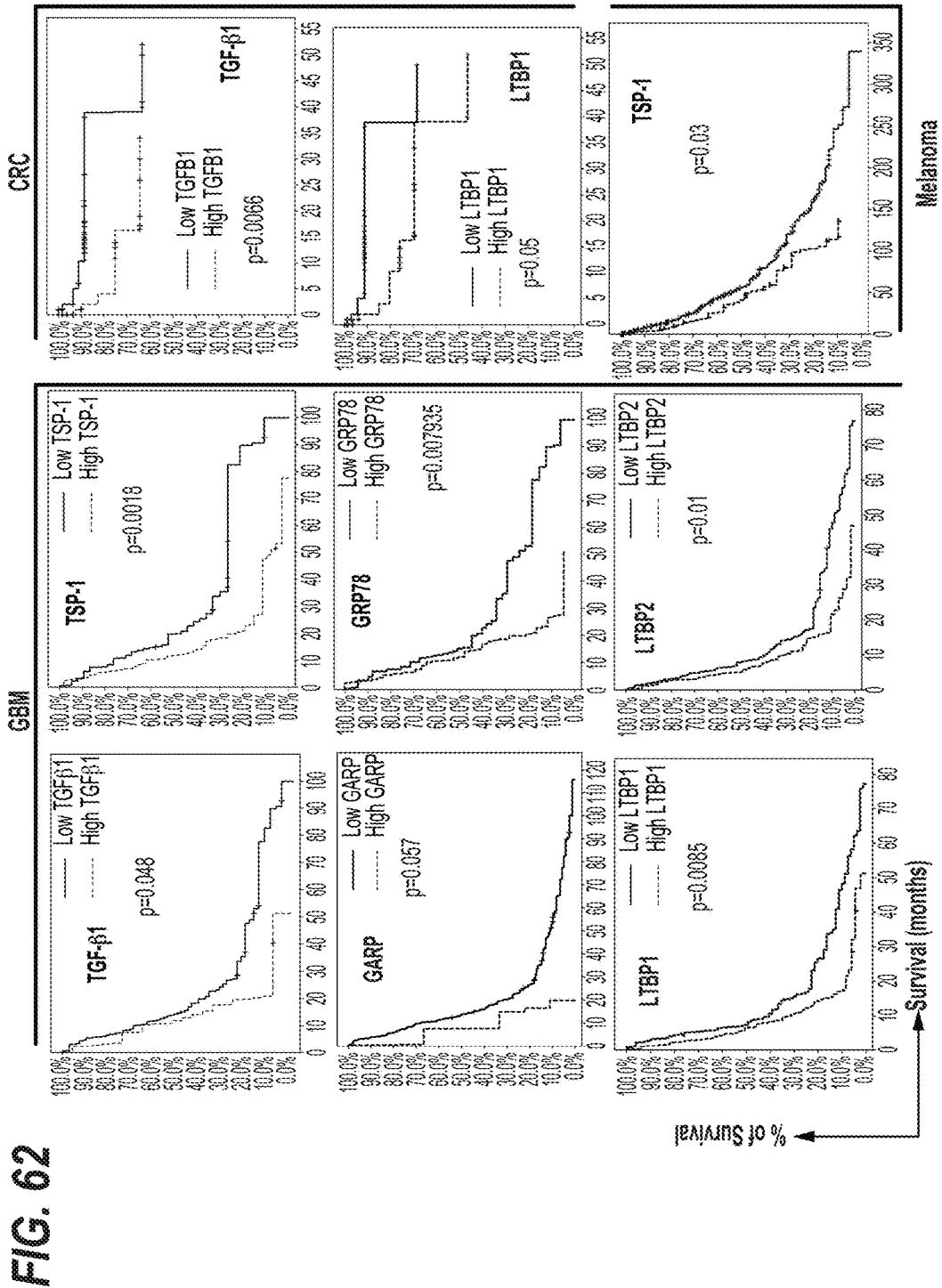
FIG. 62 demonstrates that high expression of TGF-β1/LAP and other LAP-related mRNAs correlate with better GBM, melanoma and CRC patients survival. Relationship between cancer patient survival and mRNA expression in tumors based on The Tumor Cancer Genome Atlas (TCGA) data.
Figure 63:
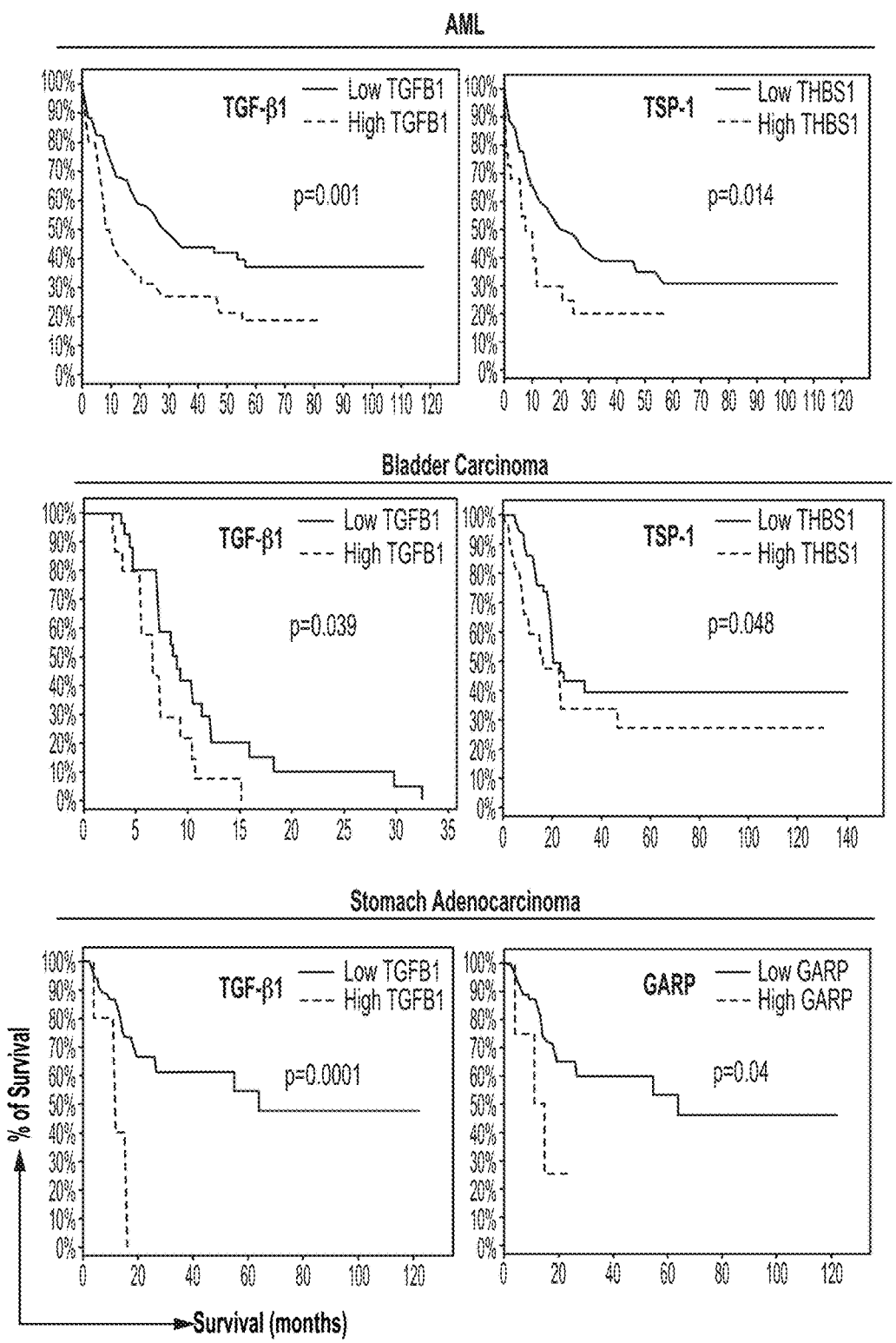
FIG. 63 depicts survival of other cancer patients (AML, bladder carcinoma, stomach adenocarcinoma) expressing low levels of LAP-associated genes (TCGA).
Figure 64:
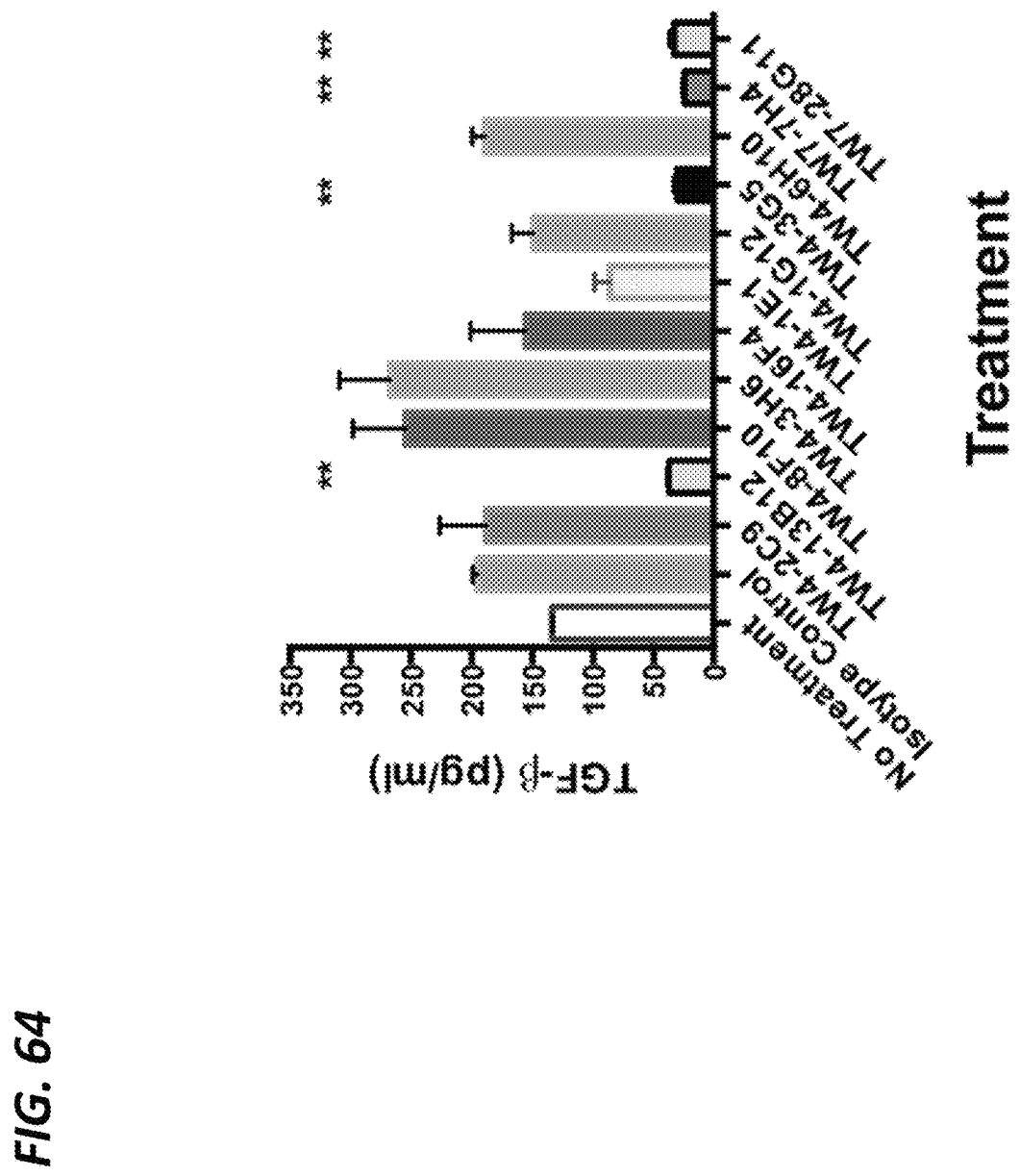
FIG. 64 depicts an exemplary screen for anti-LAP antibodies by their inhibition of TGF-β Release. Different clones of anti-LAP were tested by their treatment of P3U1 cells expressing a human TGF-β and measuring the level of secreted active/free TGF-β (non-acidified conditions) in the culture medium by ELISA.
Figure 65:
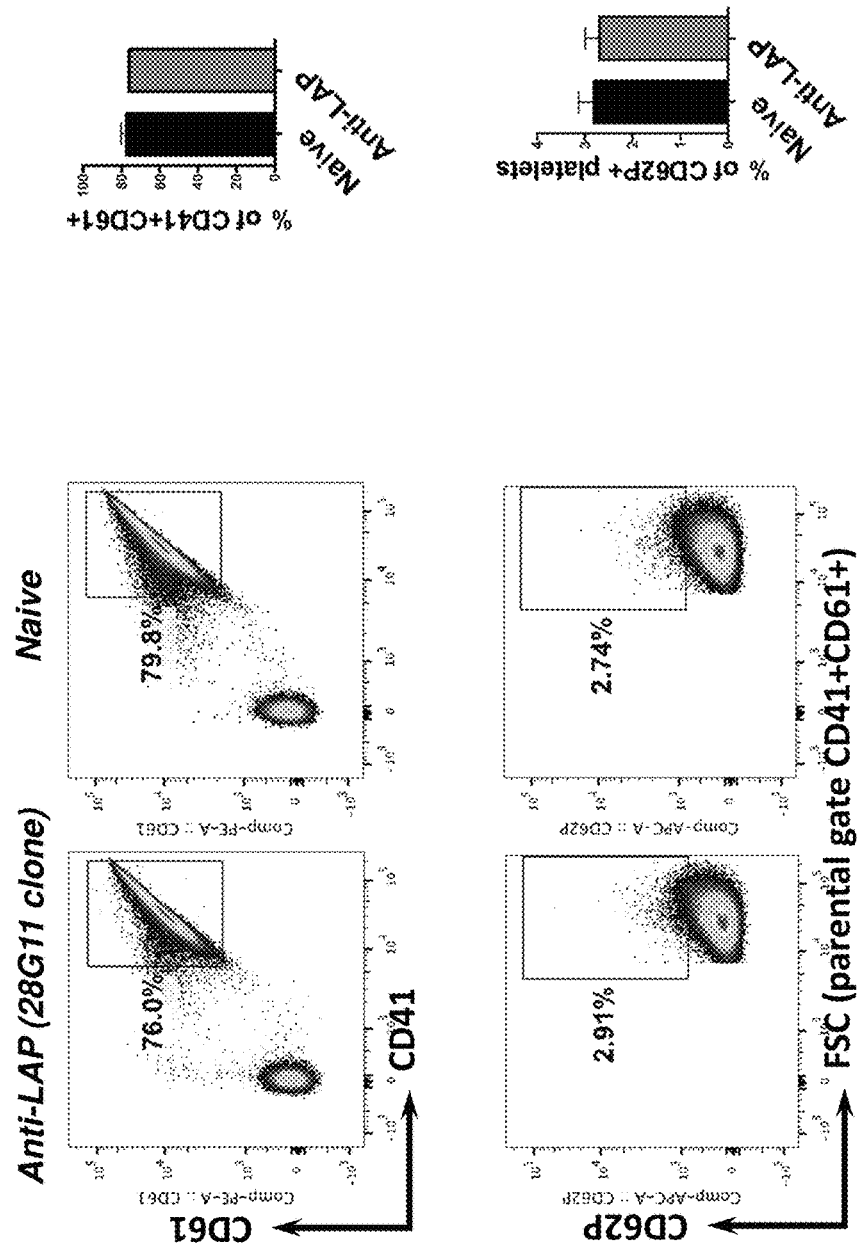
FIG. 65 demonstrates that anti-LAP treatment does not affect platelet counts and activity. Mice were treated with TW7-28G11 clone of anti-LAP (250 ug/mouse) and analysed 3 days later (n=3).

To investigate the role of LAP and TGF-β in human GBM, we analyzed TCGA (The Cancer Genome Atlas) data to determine if the expression of messenger RNA (common for both proteins) correlated with patients survival. We found an inverse correlation between high levels of the mRNA expression (marked as TGF-β) and the survival of GBM patients (FIG. 62) indicating that the gene encoding for LAP/TGF-β is involved in GBM pathogenesis. Similar results were observed for patients with other cancers, demonstrating a broad phenomenon of LAP expression machinery associated with malignancy (FIGS. 62, 63).

Investigating the Immunosuppressive Role of LAP in Cancer.

Figure 39:
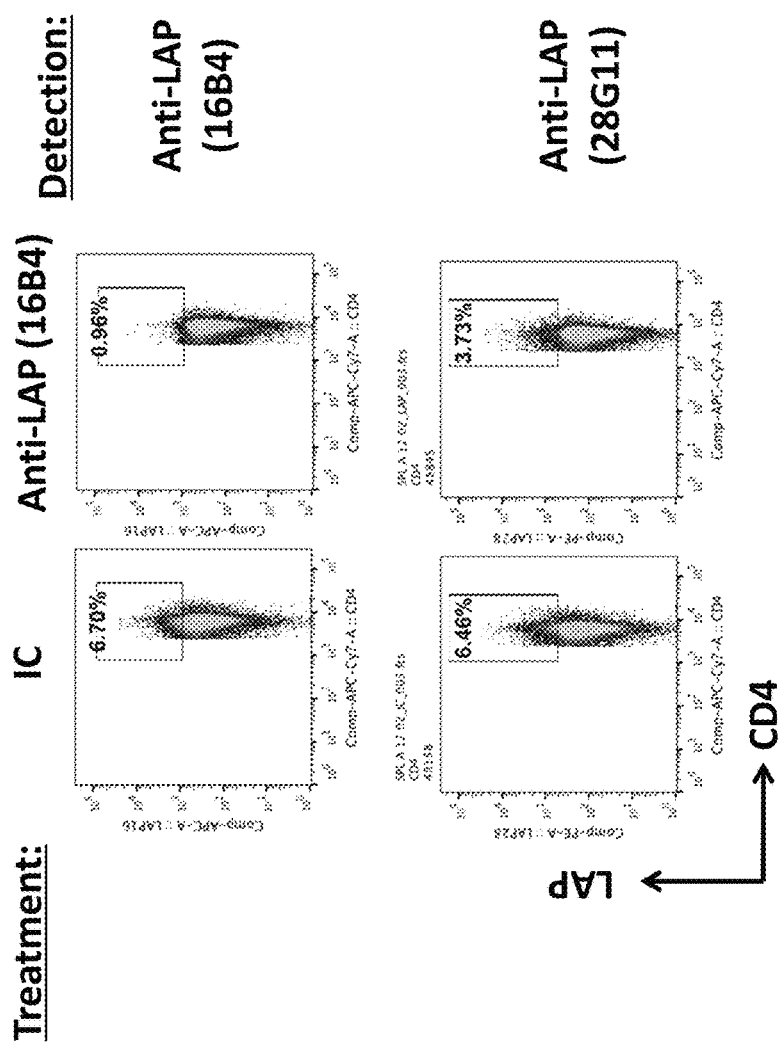
FIG. 39 demonstrates CD4+LAP+ T Cells are Downregulated Following Anti-LAP Treatment in Spleen.
Figures 40A, 40B:
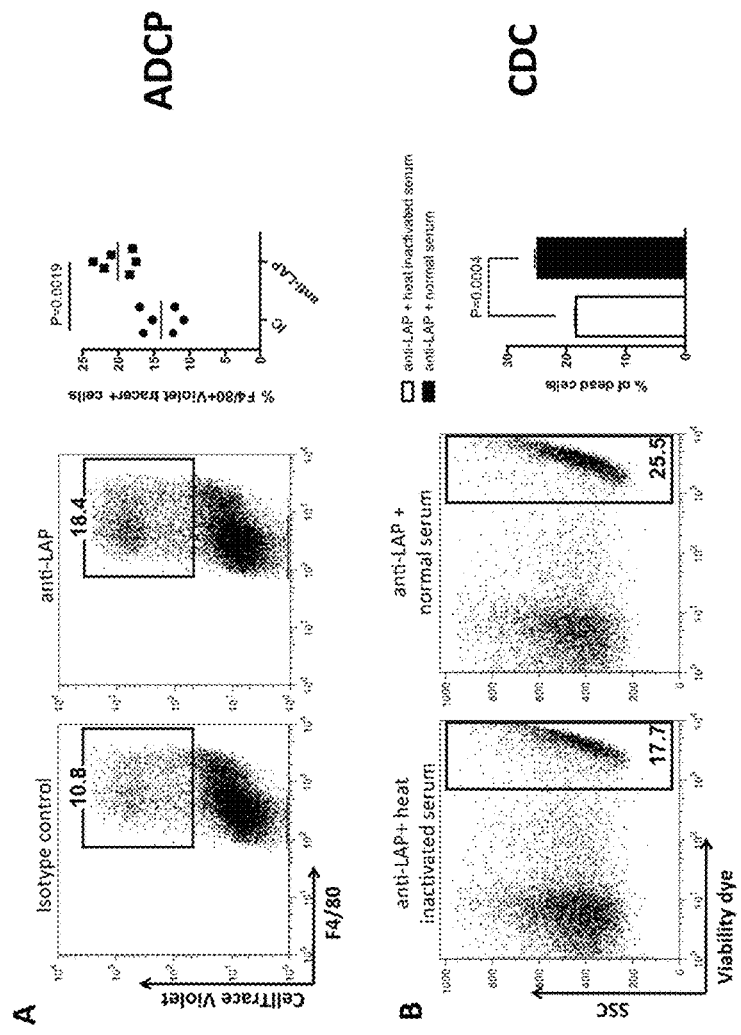
FIGS. 40A-40B demonstrates Anti-LAP Antibodies Mediate ADCP and CDC.
Figures 58A, 58B, 58C, 58D:
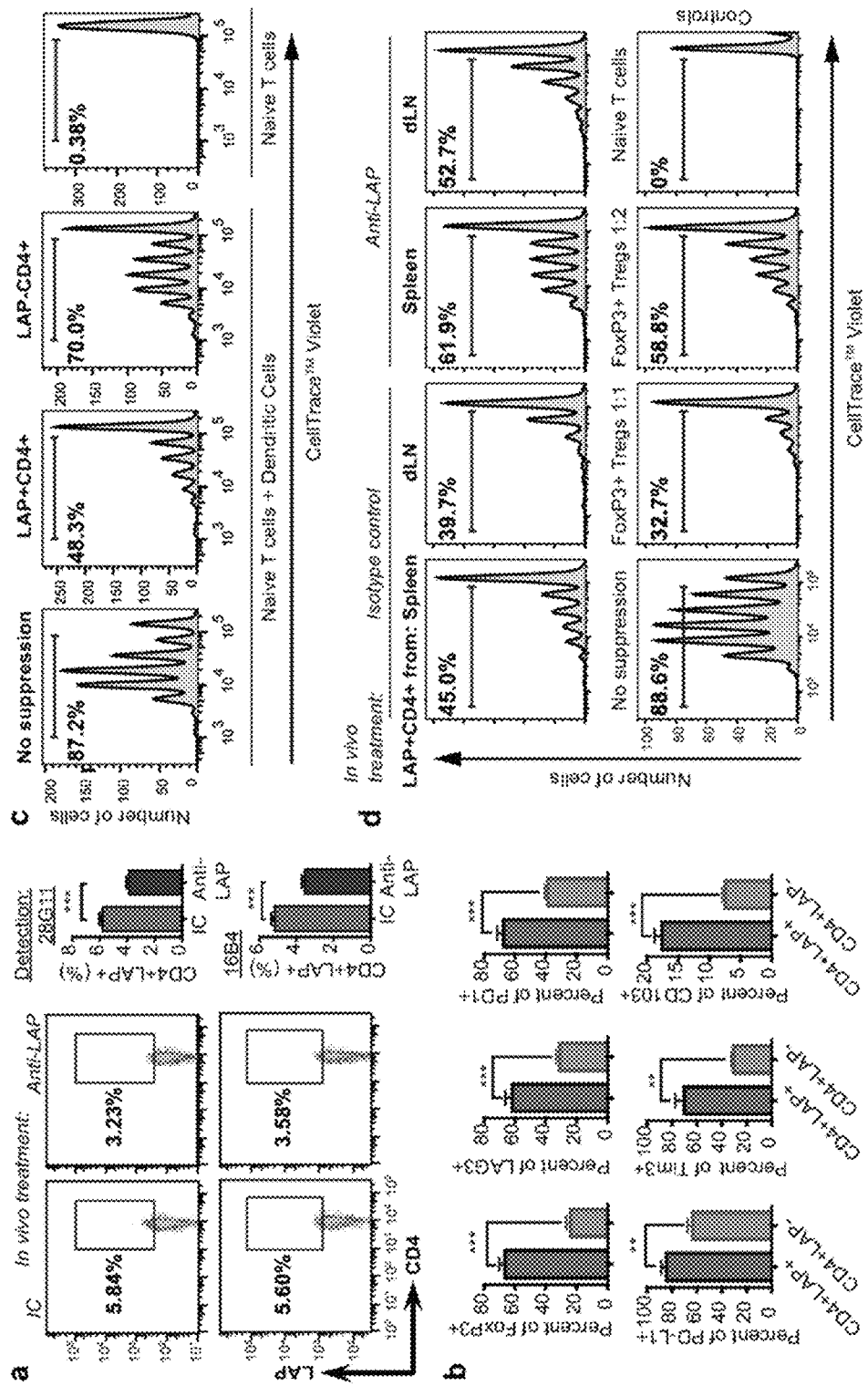
FIGS. 58A-58D demonstrate that anti-LAP antibodies deplete suppressive CD4+ T cells.

We found that treatment with anti-LAP antibodies, either TW7-28G11 (FIG. 58A) or TW7-16B4 (FIG. 39) result in a reduced accumulation of CD4+LAP+ T cells in mice as indicated by detection of these cells using a non-competing anti-LAP clone (FIG. 58A). These results demonstrate that anti-LAP treatment leads to depletion of CD4+LAP+ T cells in vivo. Recent studies indicate that LAP expressed by various immune cells can mediate immunosuppression. Using flow cytometry analysis we found that LAP+CD4+ T cells isolated from B16 melanoma express higher levels of immunosuppression markers, FoxP3, LAG3, PD1, PD-L1, Tim3, CD103 (FIG. 58B), suggesting suppressive abilities for these cells. To evaluate the suppression properties of LAP+CD4+ T cells in cancer, we sorted LAP+CD4+ T cells from the spleen of B16 tumor bearing mice (providing a sufficient amount of LAP+ cells for the assay) and co-cultured them with naïve CD4+ T cells in the presence of DCs. We observed almost two-fold reduced proliferation of the naïve T cells in the presence of LAP+CD4+ T cells in comparison to the condition where no suppression cells were added (FIG. 58C). As a negative control, we used LAP−CD4+ T cells that only slightly decreased the T cell proliferation presumably due to the presence of FoxP3+ T cells. Interestingly, CD4+LAP+ T cells isolated from either spleen or draining lymph nodes (dLNs) of mice bearing B16 melanoma had reduced suppression properties after anti-LAP treatment (FIG. 58D). Mice were treated with TW7-28G11 and CD4+LAP+ T cells were sorted by TW7-16B4 clone.

Figure 23:
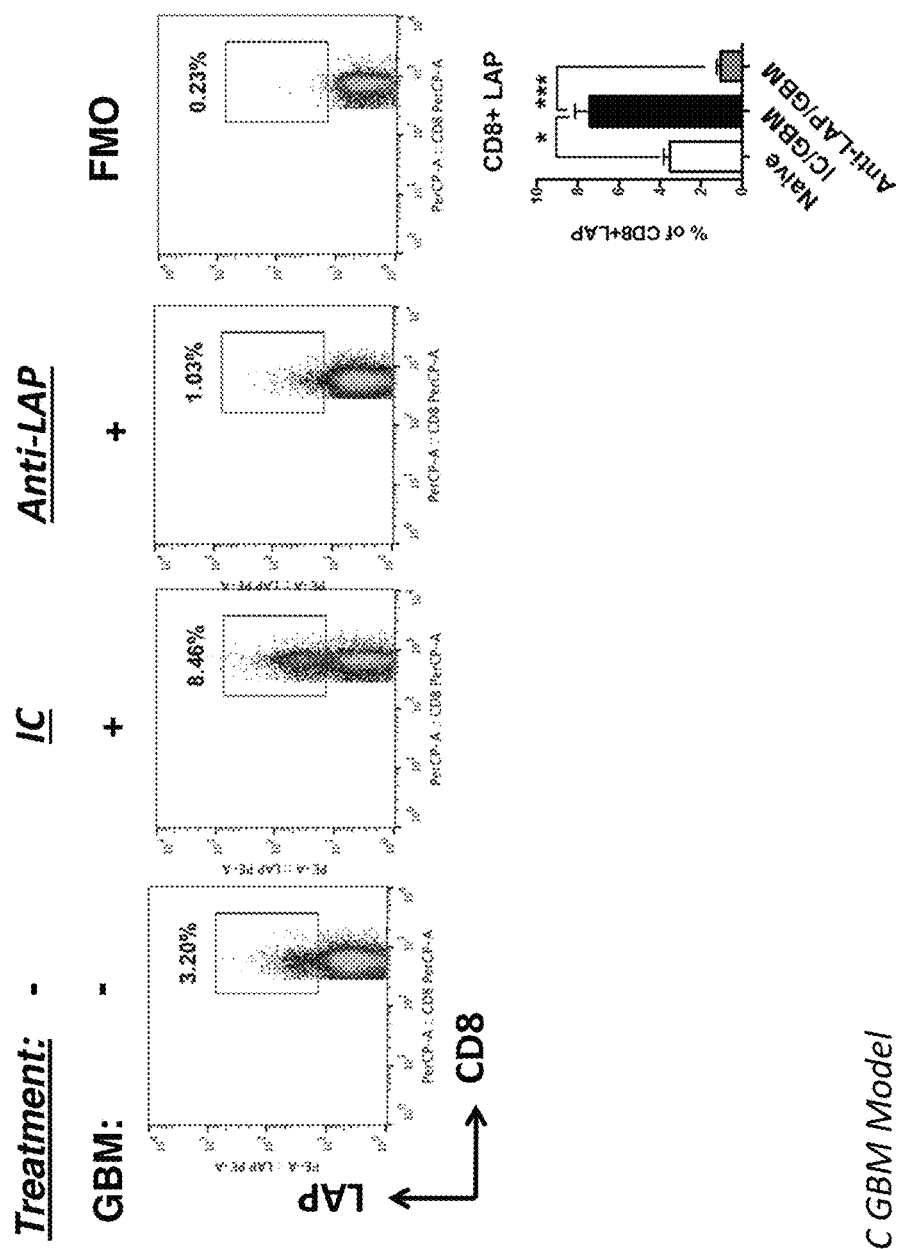
FIG. 23 demonstrates LAP Expression on CD8+ T Cells in Spleen following anti-LAP treatment.
Figure 24:
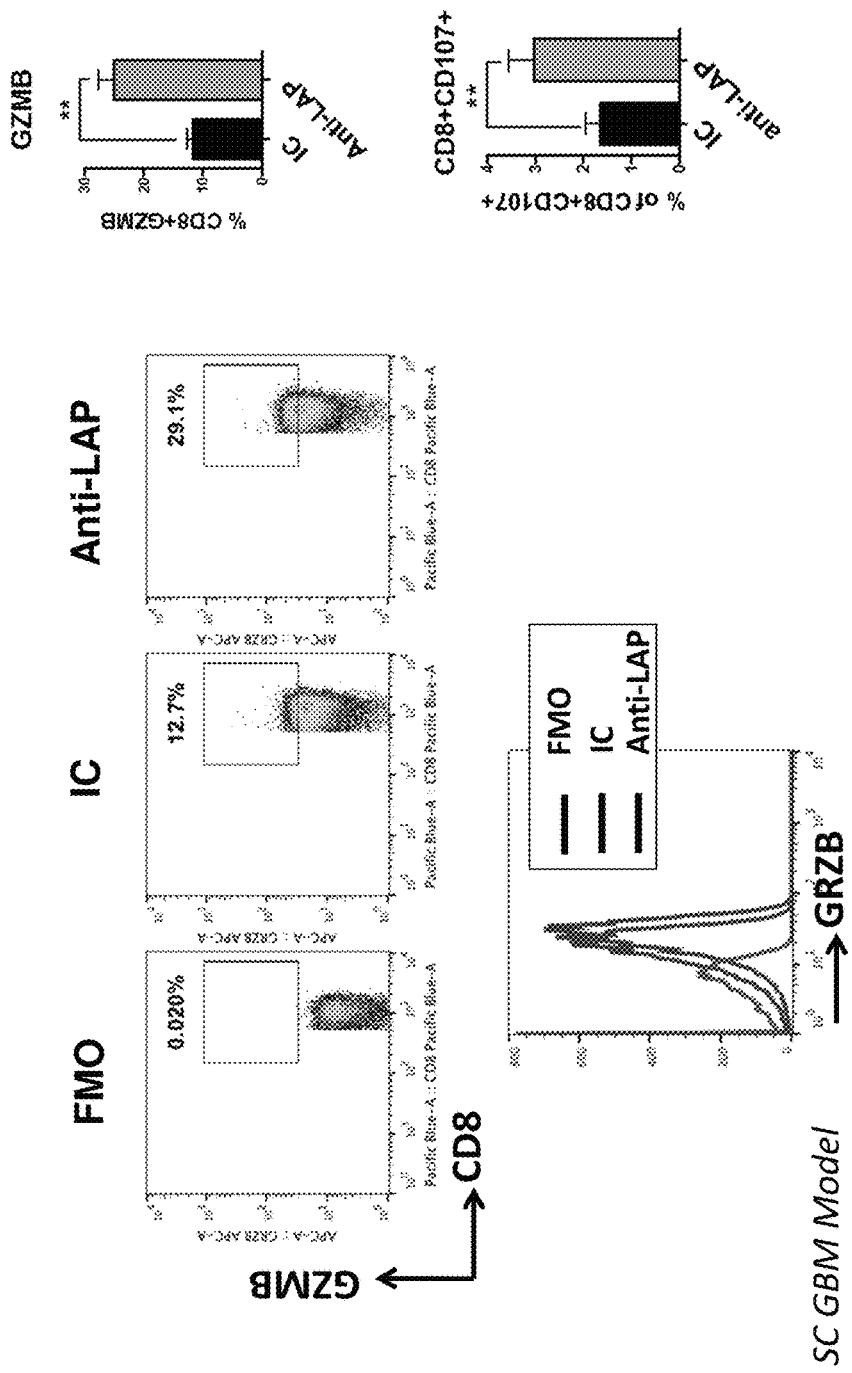
FIG. 24 demonstrates Increase in Cytotoxic Phenotype of CD8+ T Cells in Spleen following anti-LAP treatment.
Figure 25:
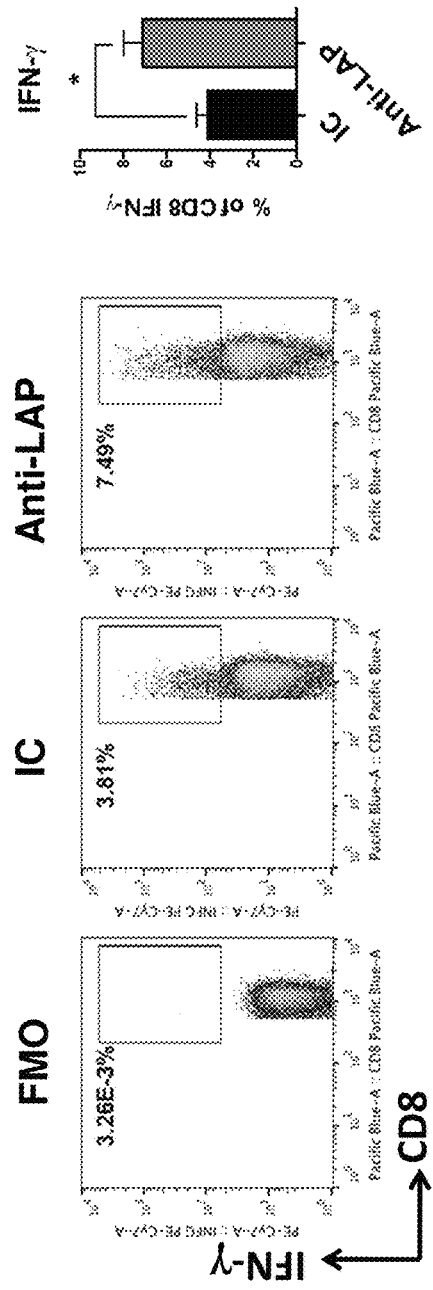
FIG. 25 demonstrates IFN-γ Expression on CD8+ T Cells is Higher in Spleen following anti-LAP treatment.
Figure 26:
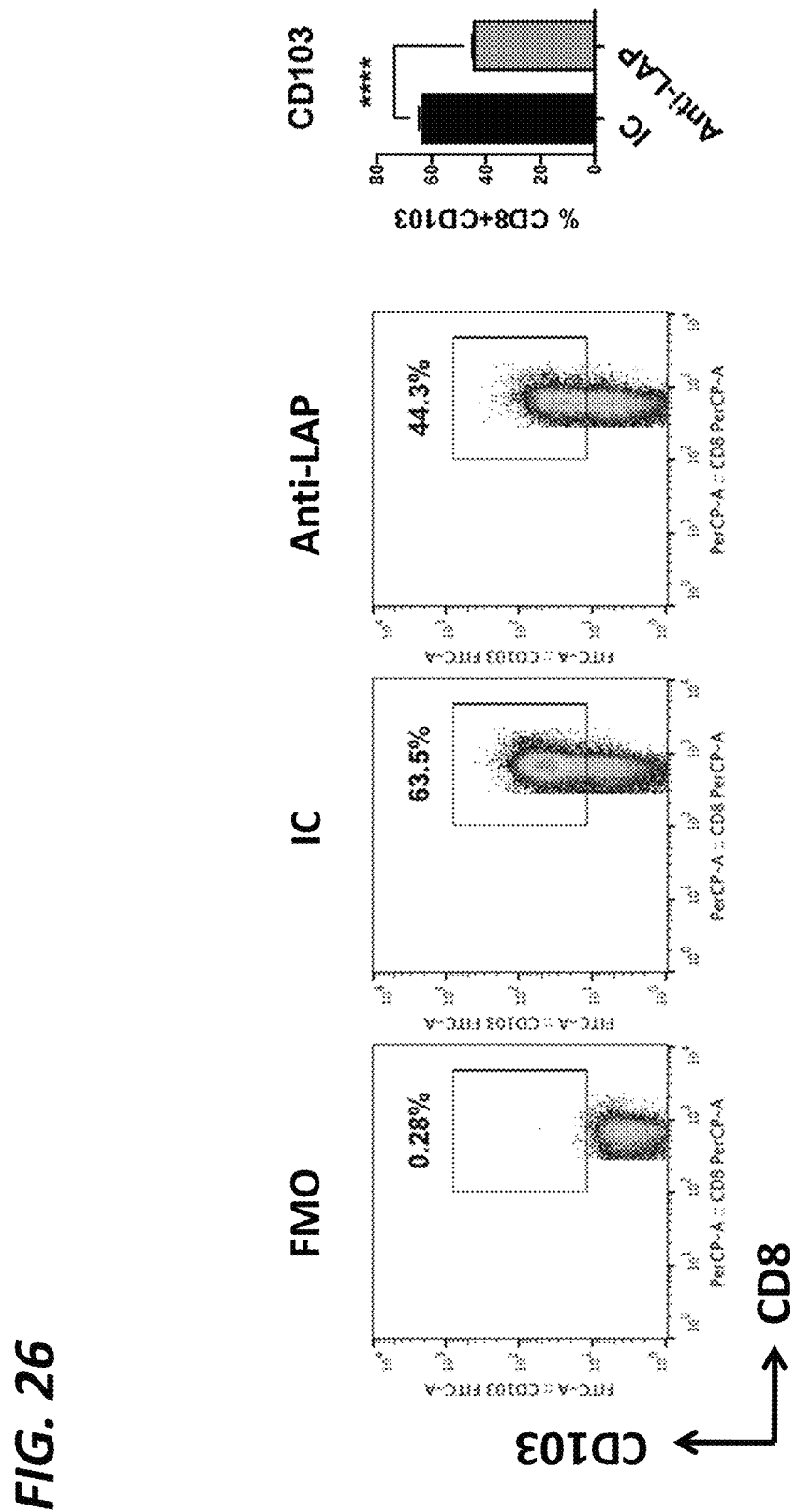
FIG. 26 demonstrates CD103 Expression is Lower on CD8+ T Cells in Spleen following anti-LAP treatment.
Figure 28:
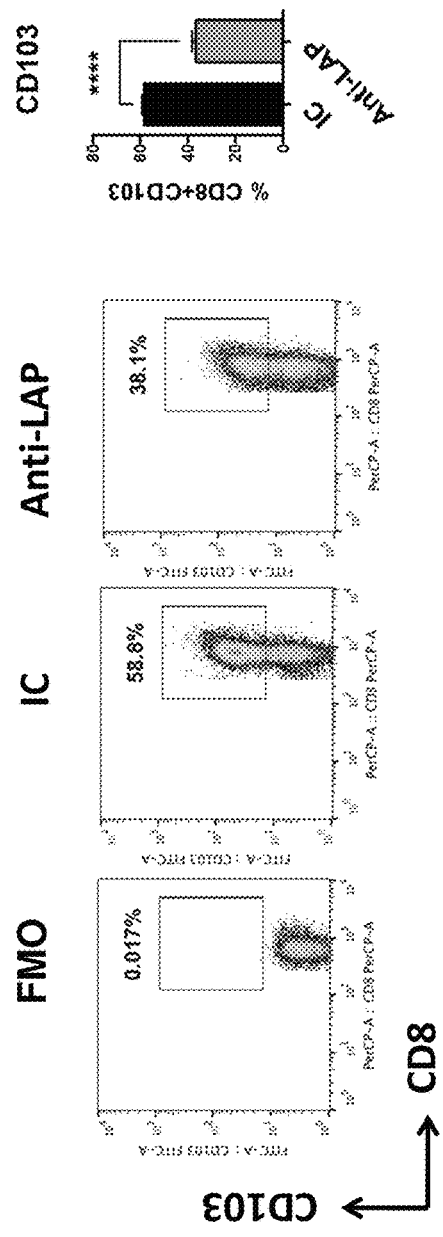
FIG. 28 demonstrates CD103 Expression is Lower on CD8+ T Cells in LN following anti-LAP treatment.
Figure 29:
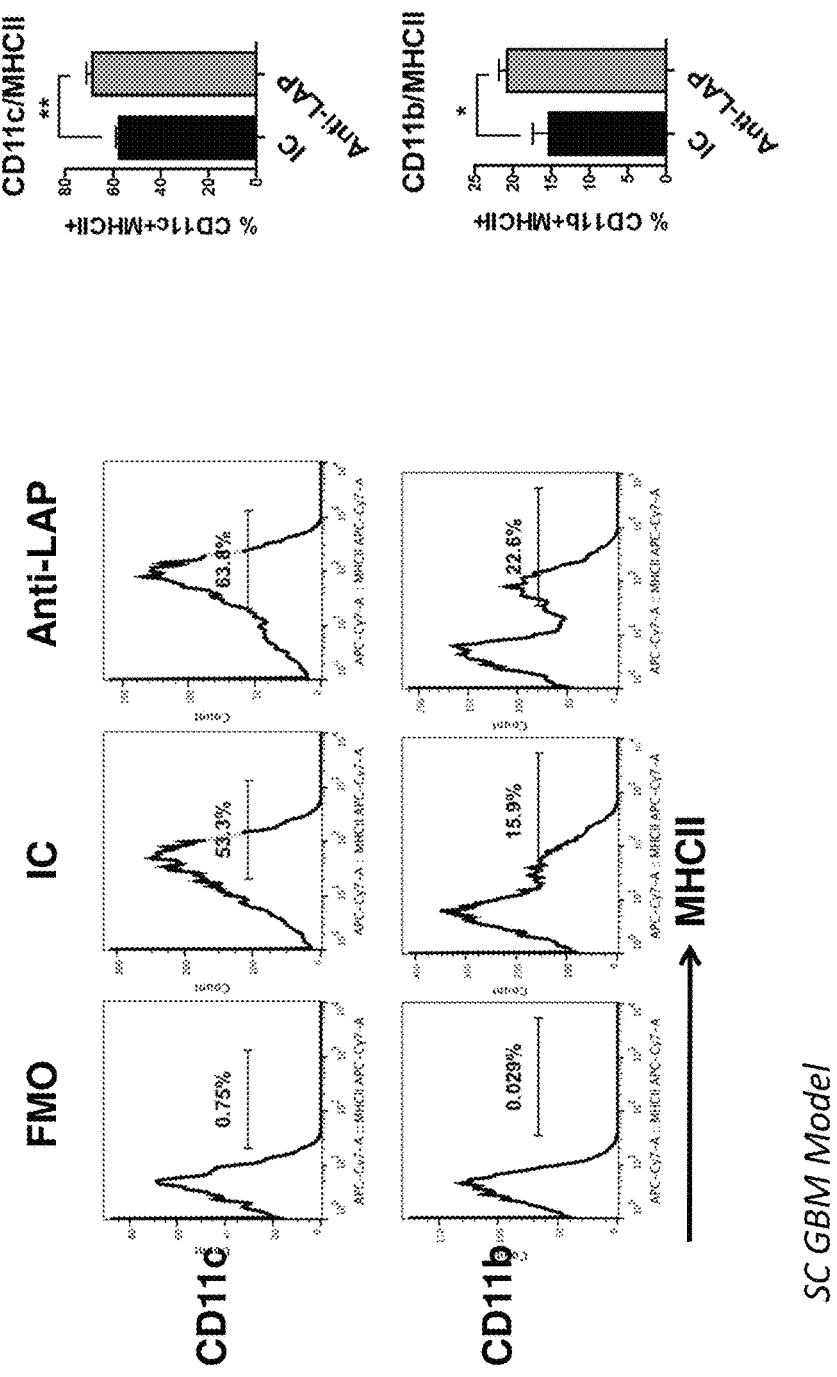
FIG. 29 demonstrates MHC Class II Expression is Increased on CD11c and CD11b Cells in Spleen following anti-LAP treatment.
Figure 30:
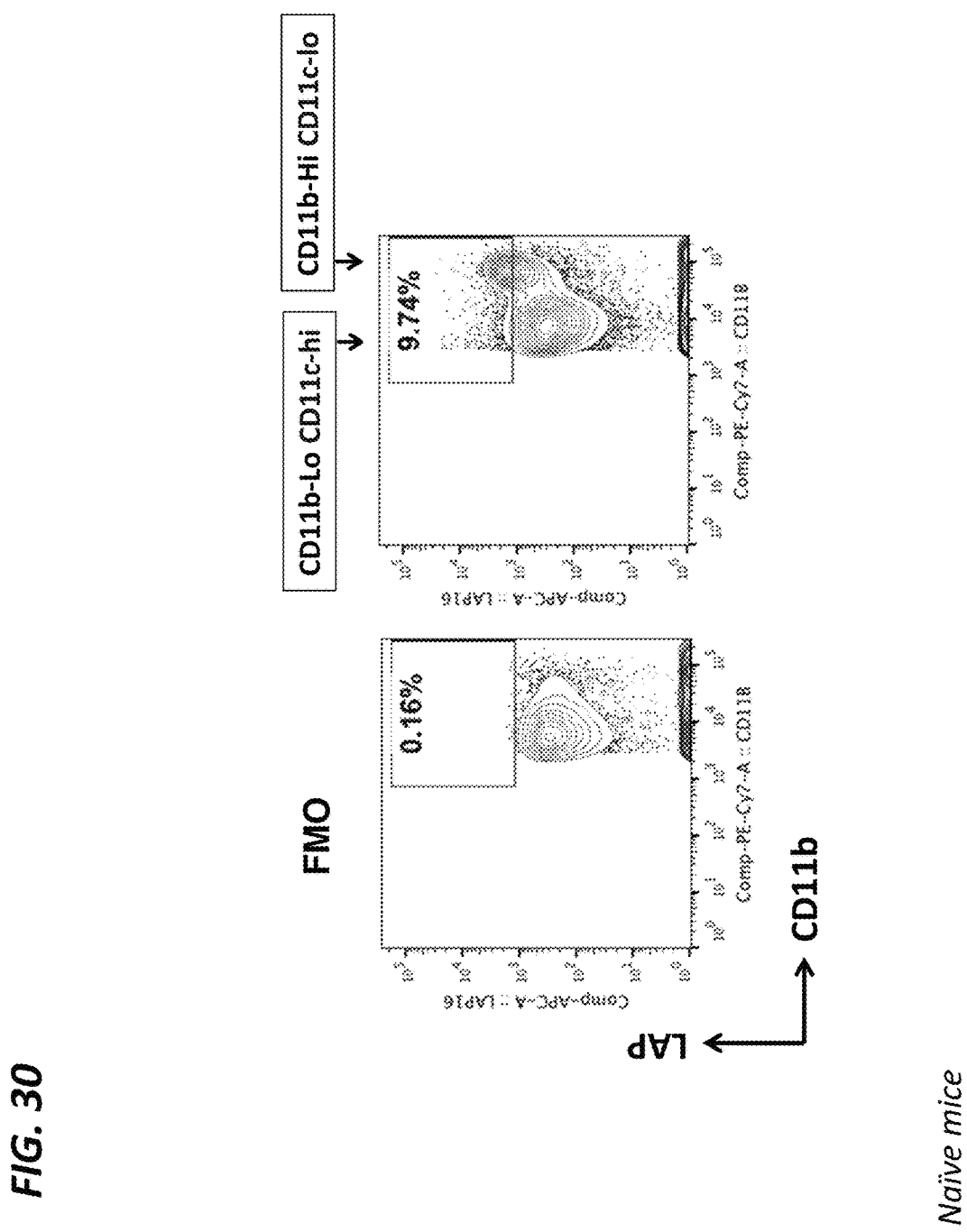
FIG. 30 demonstrates LAP Expression on Myeloid Cells in Spleen (Naïve Mice).
Figure 31:
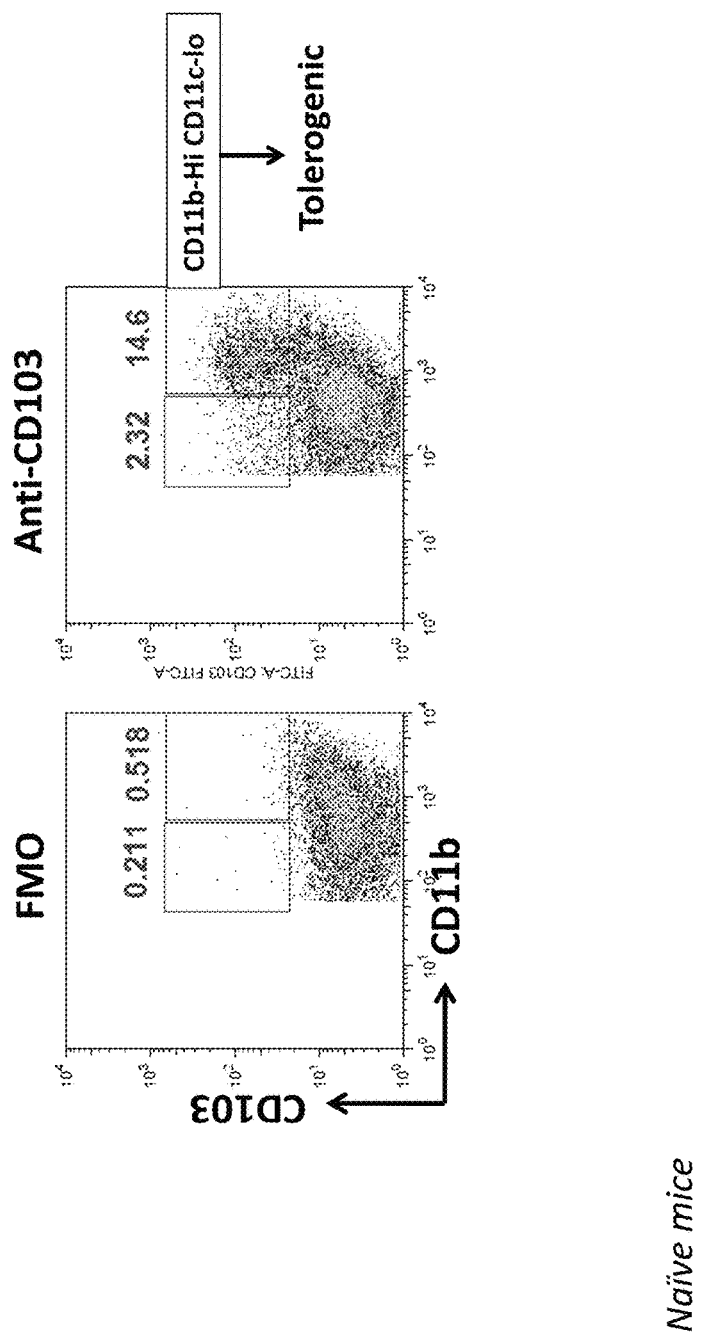
FIG. 31 demonstrates CD103 is Mainly Expressed by CD11b-Hi/CD11c-Lo (Naïve Mice).
Figure 32:
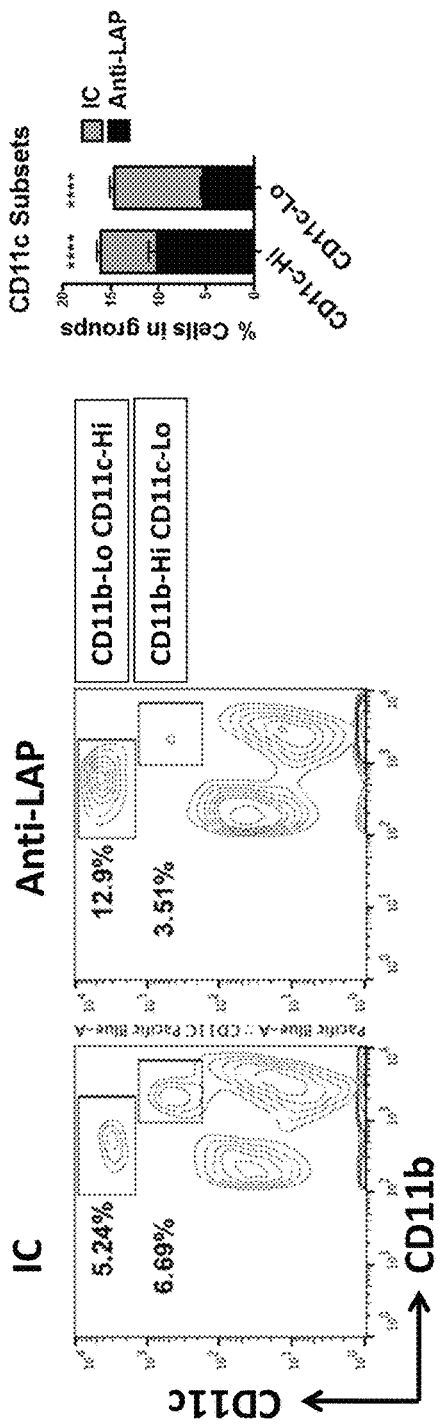
FIG. 32 demonstrates Anti-LAP (16B4) Treatment Leads to Changes in the Ratio of CD11c-Lo and CD11c-Hi subsets in spleen in a subcutaneous GL261 GBM model.
Figure 33:
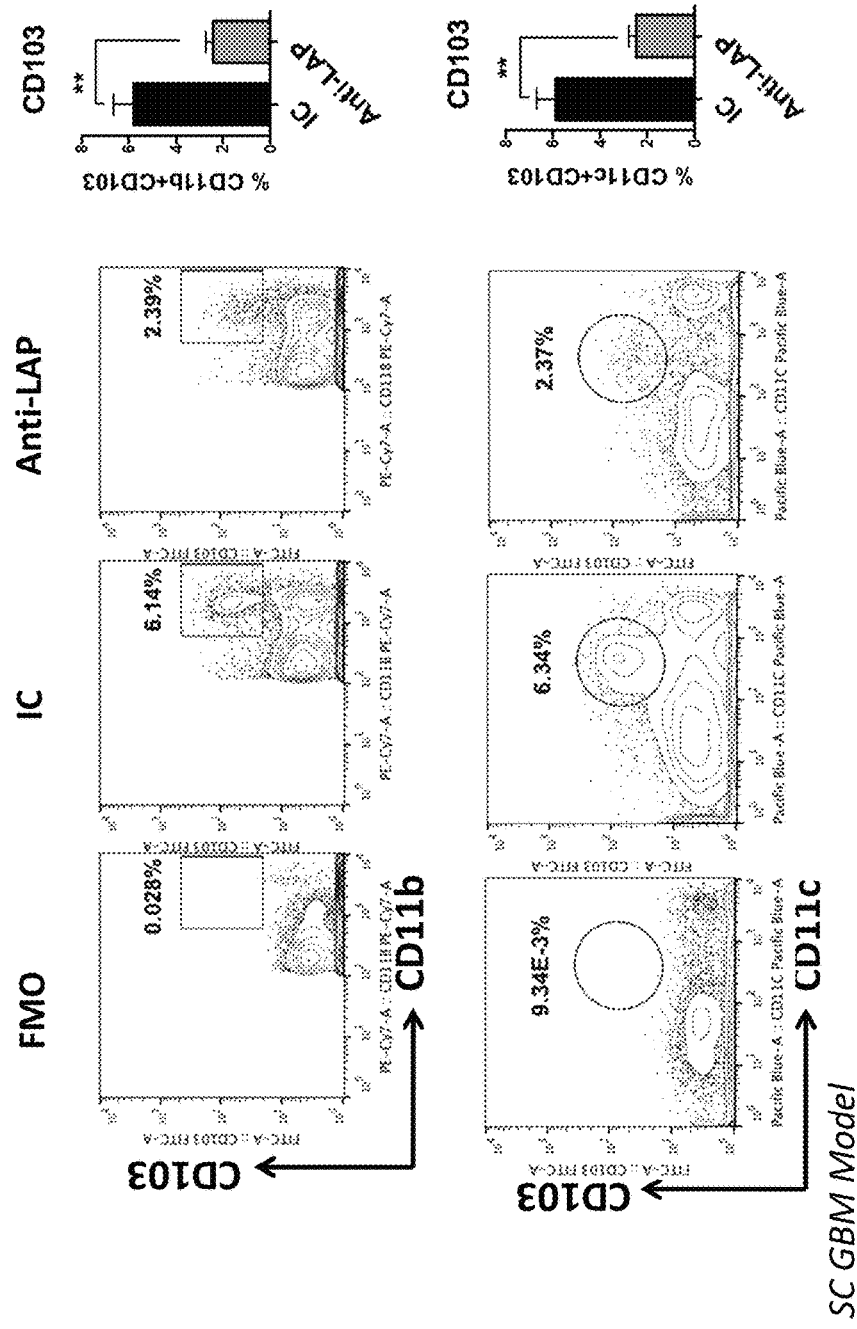
FIG. 33 demonstrates CD103 Expression on CD11b-Hi/CD11c-Lo Cells is Reduced by Anti-LAP in the Spleen in a subcutaneous GL261 GBM model.
Figure 34:
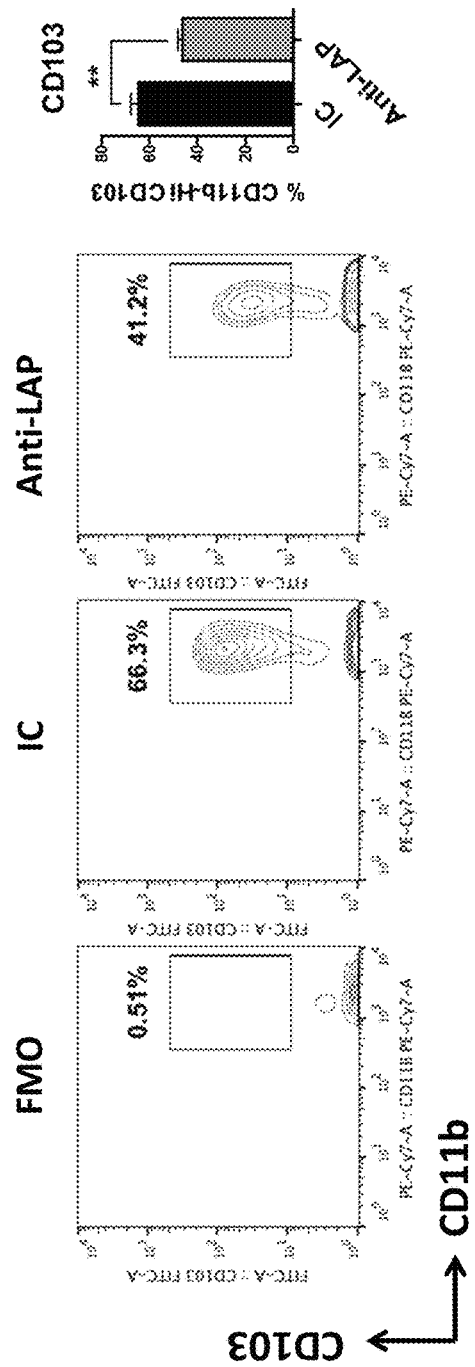
FIG. 34 demonstrates CD103 Expression on CD11b-Hi/CD11c-Lo Cells is Reduced by Anti-LAP in the Spleen in a subcutaneous GL261 GBM model.
Figure 35:
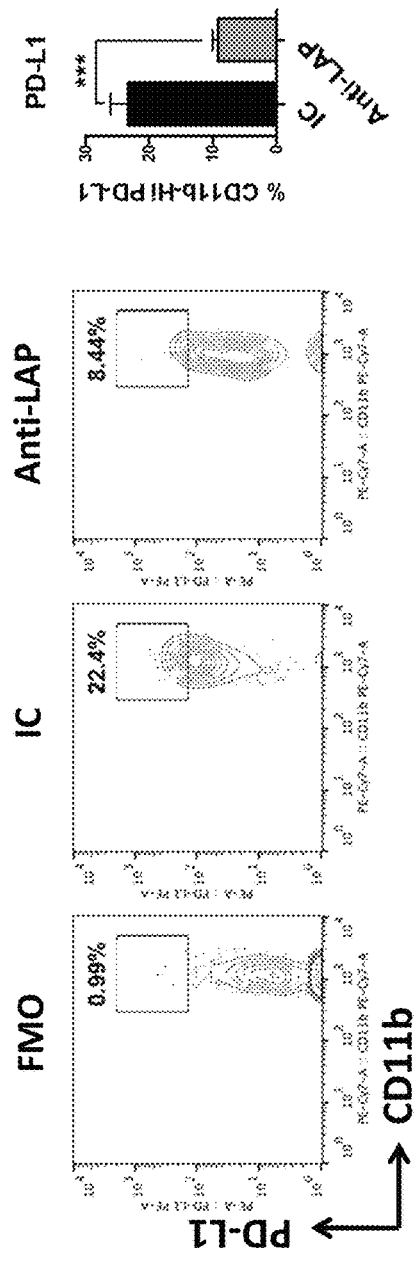
FIG. 35 demonstrates PD-L1 Expression on CD11b-Hi/CD11c-Lo Cells is Reduced by Anti-LAP in the Spleen in a subcutaneous GL261 GBM model.
Figure 36:
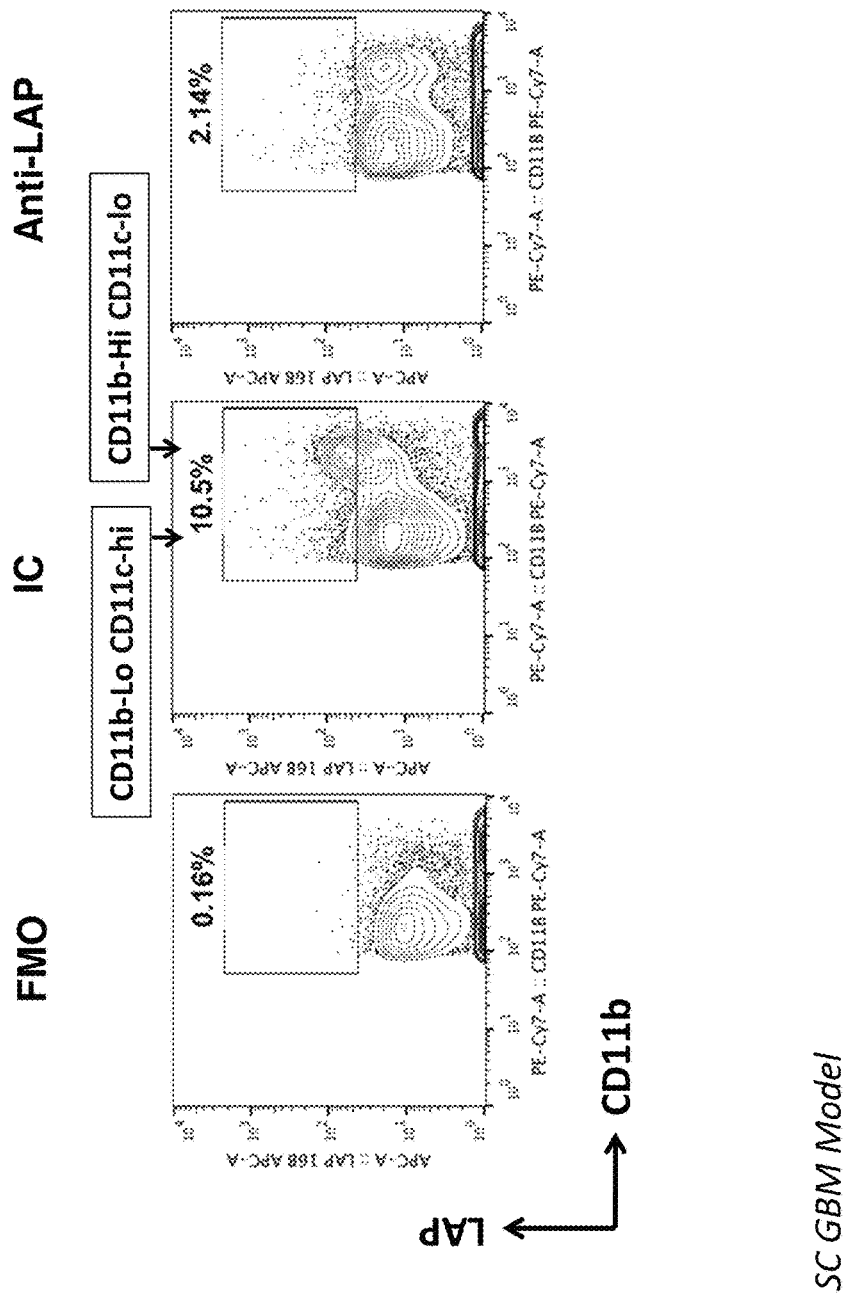
FIG. 36 demonstrates LAP Expression on Myeloid Cells in Spleen in GBM Mice in a subcutaneous GL261 GBM model.
Figure 37:
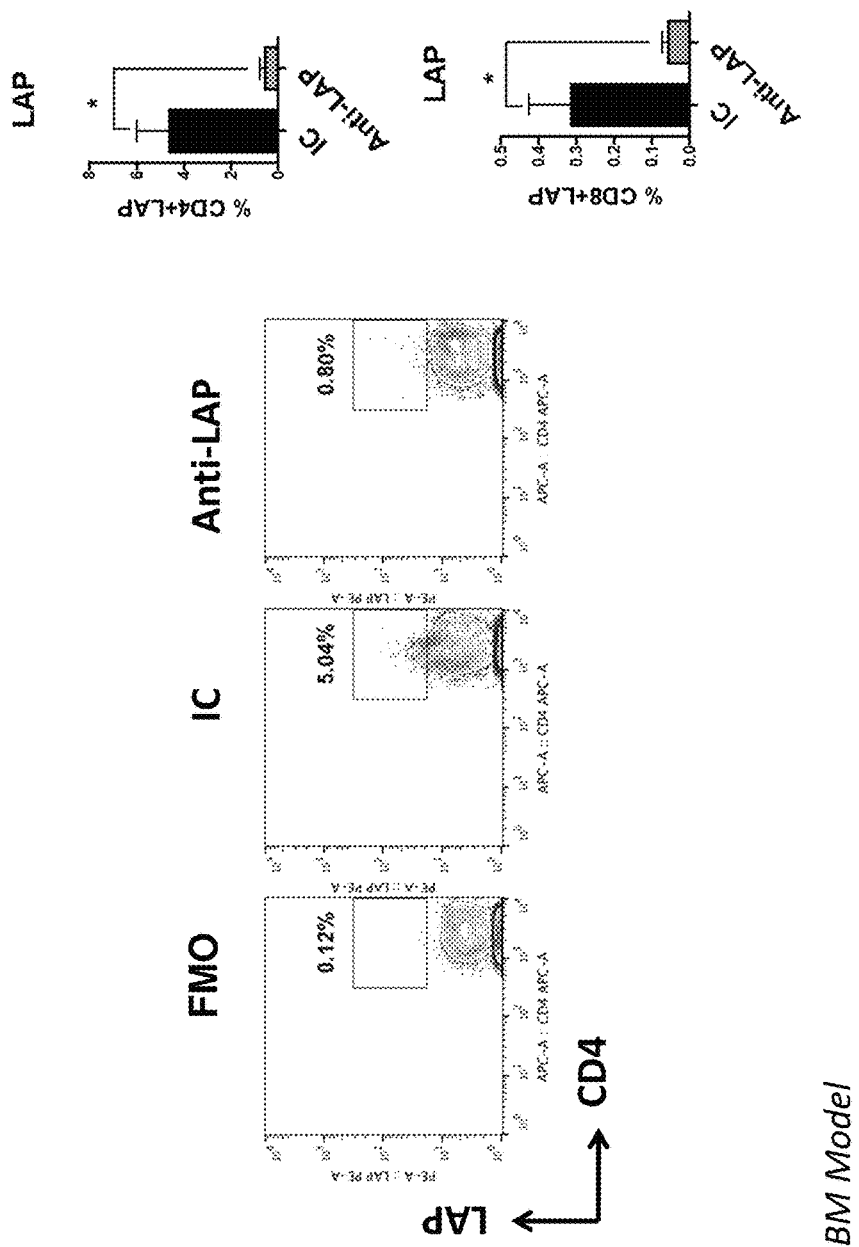
FIG. 37 demonstrates LAP Expression on CD4+ and CD8+ T Cells in Tumor a subcutaneous GL261 GBM model.
Figure 38:
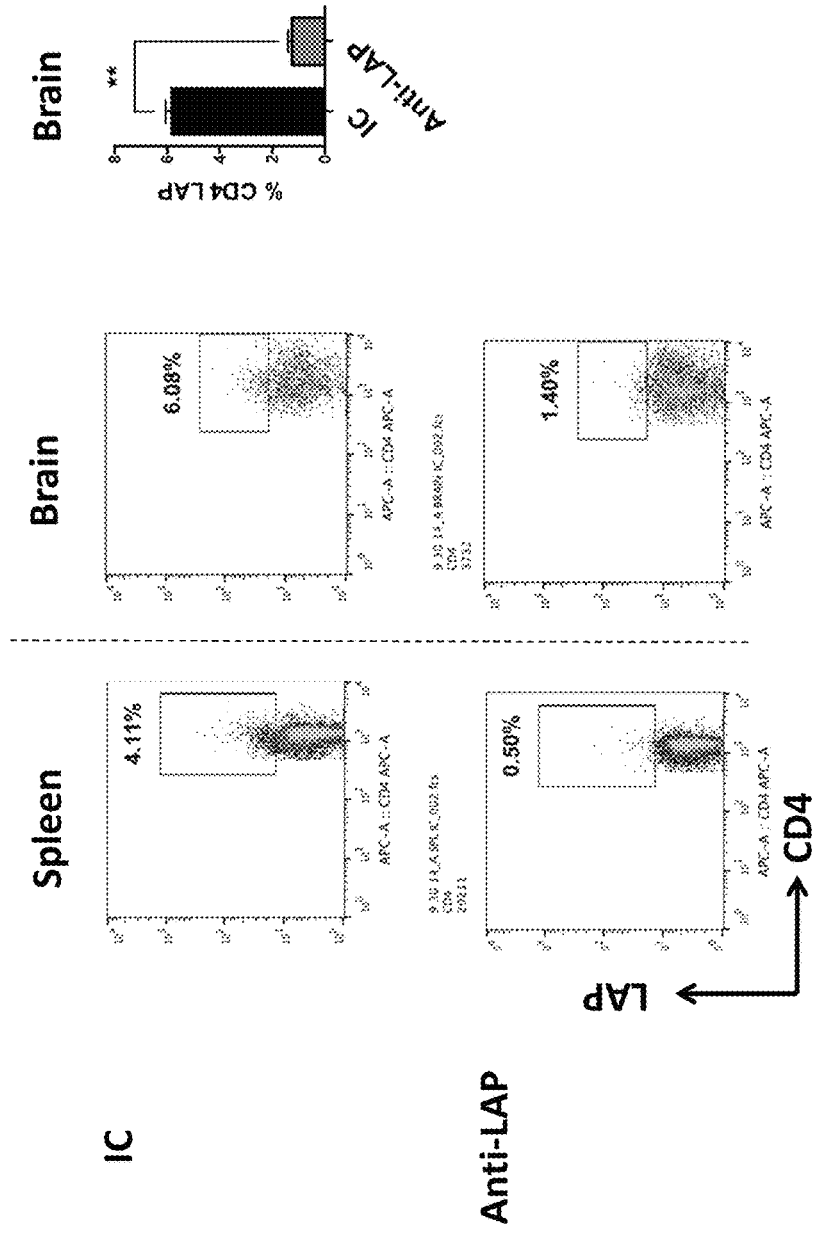
FIG. 38 demonstrates LAP Expression on CD4+ T Cells in vivo.
Figure 47:
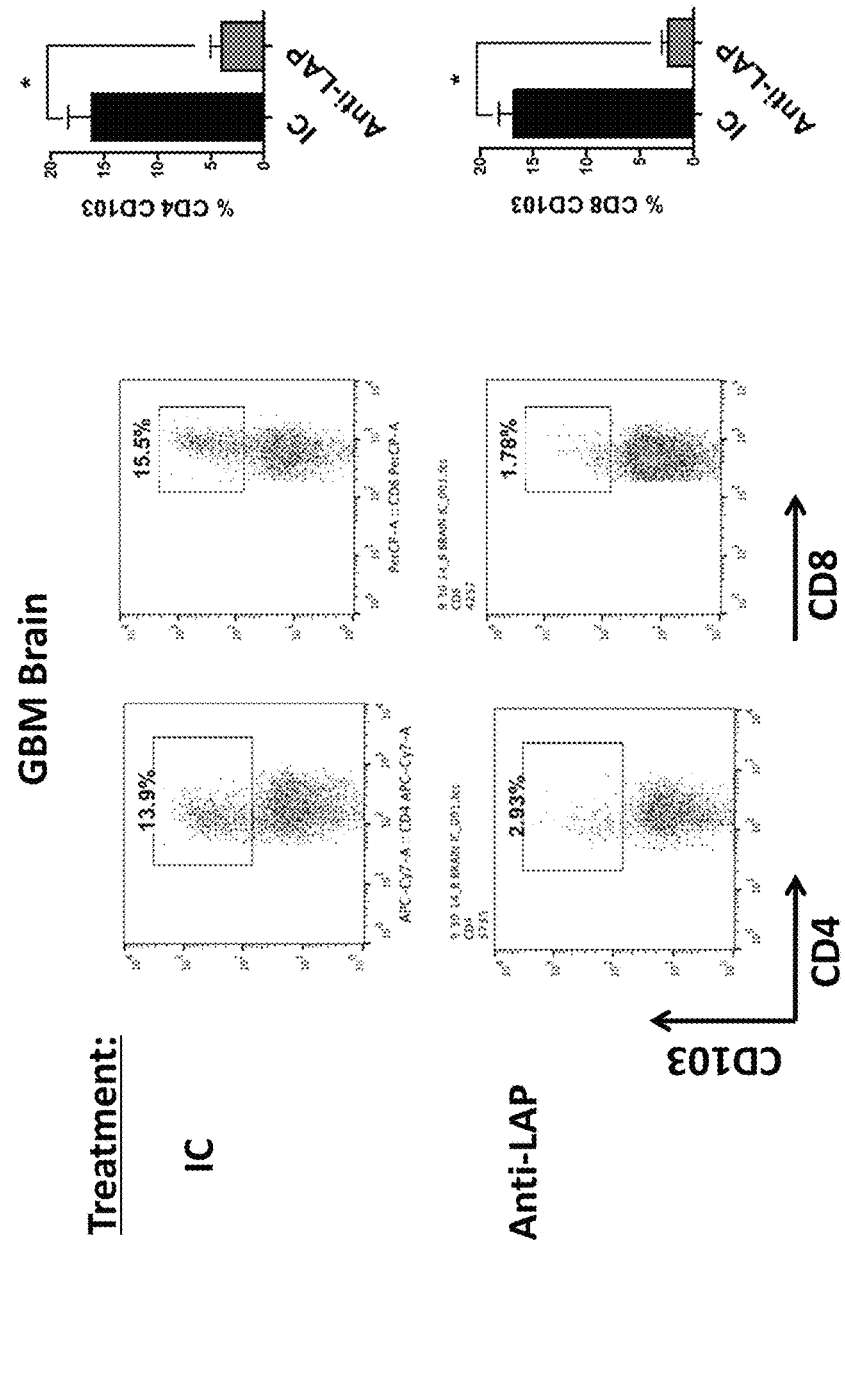
FIG. 47 demonstrates Decrease in CD103+ T Cells in GBM Following Anti-LAP Treatment.
Figure 48:
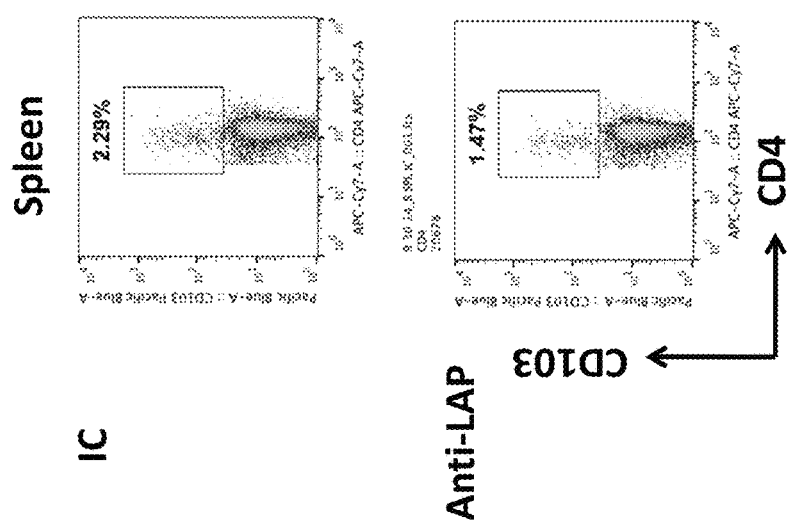
FIG. 48 demonstrates Decreased Numbers of CD103 on CD4+ T Cells in Spleen.
Figure 49:
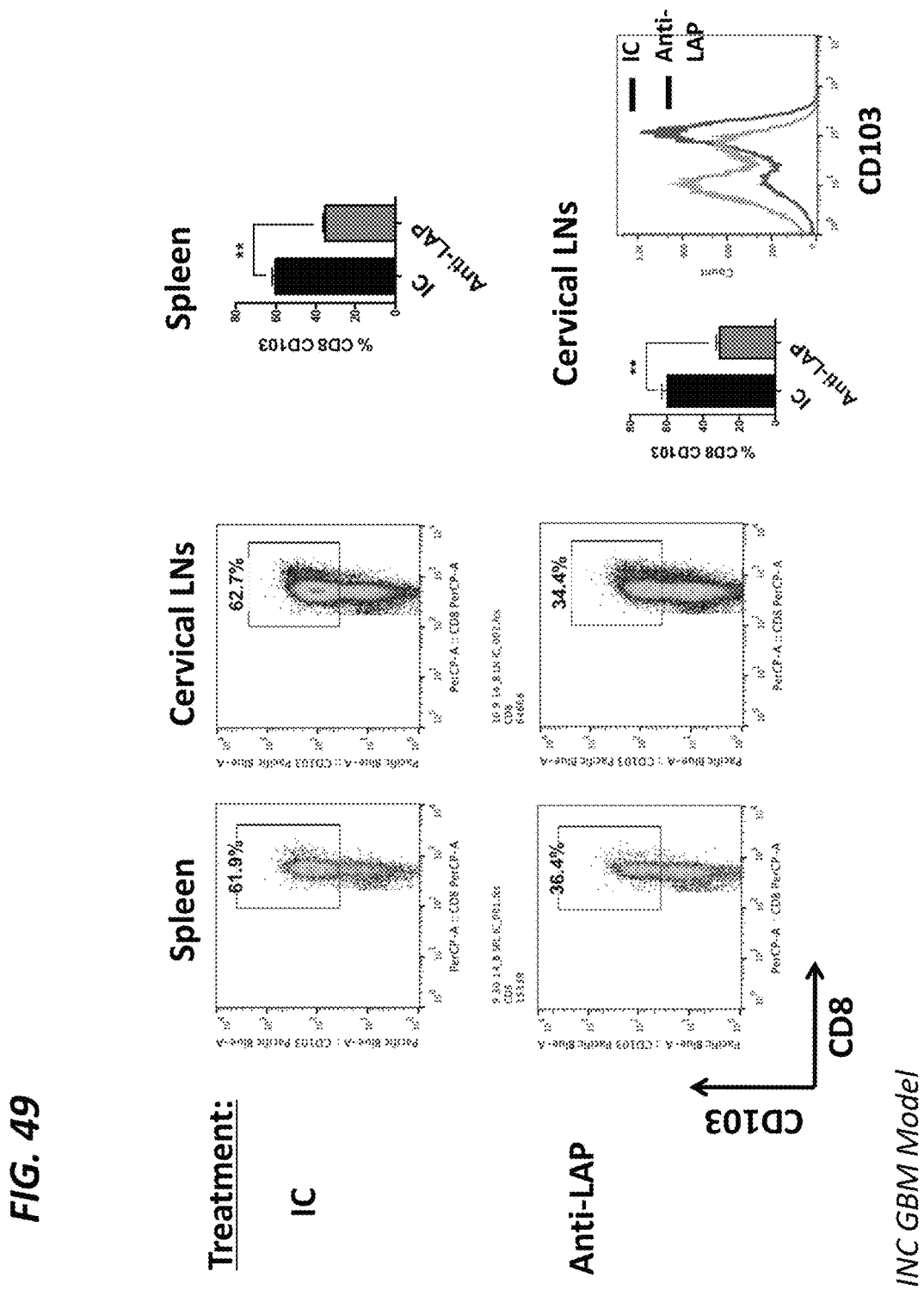
FIG. 49 demonstrates Decreased Numbers of CD103 on CD8+ T Cells in Spleen and LNs.
Figure 50:
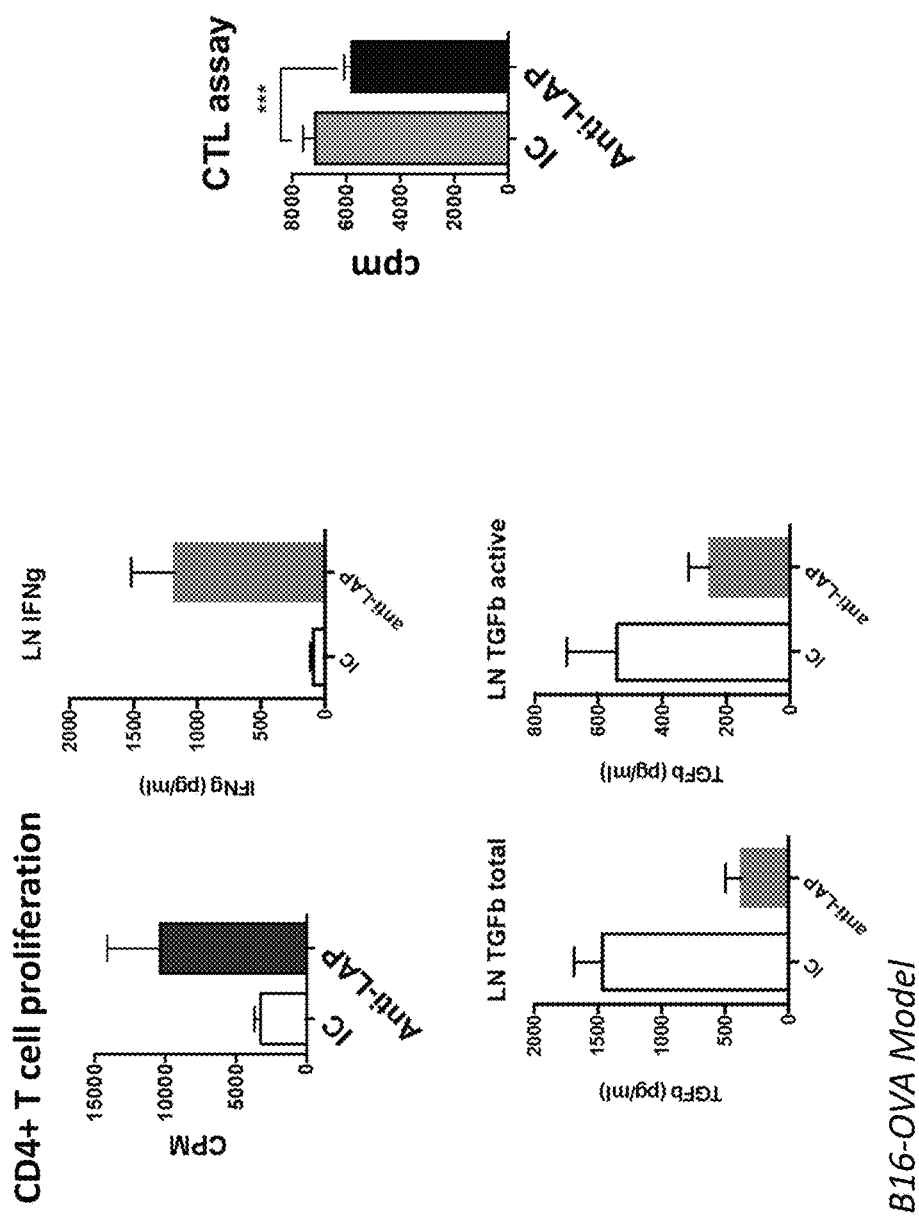
FIG. 50 demonstrates treatment with anti-LAP in B16-OVA bearing mice leads to a better T cell response to OVA stimulation.
Figure 51:
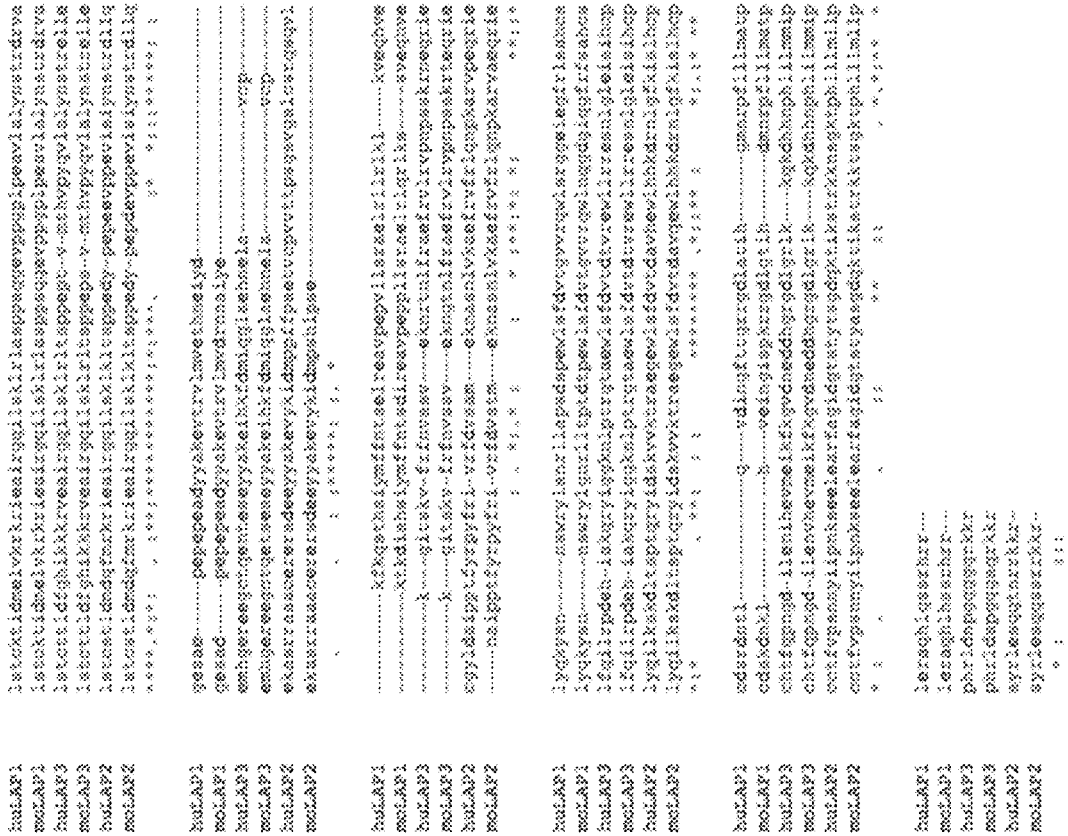
FIG. 51 depicts a sequence alignment and comparison between all human and mouse LAP isoforms.
Figures 59A, 59B, 59C, 59D, 59E:
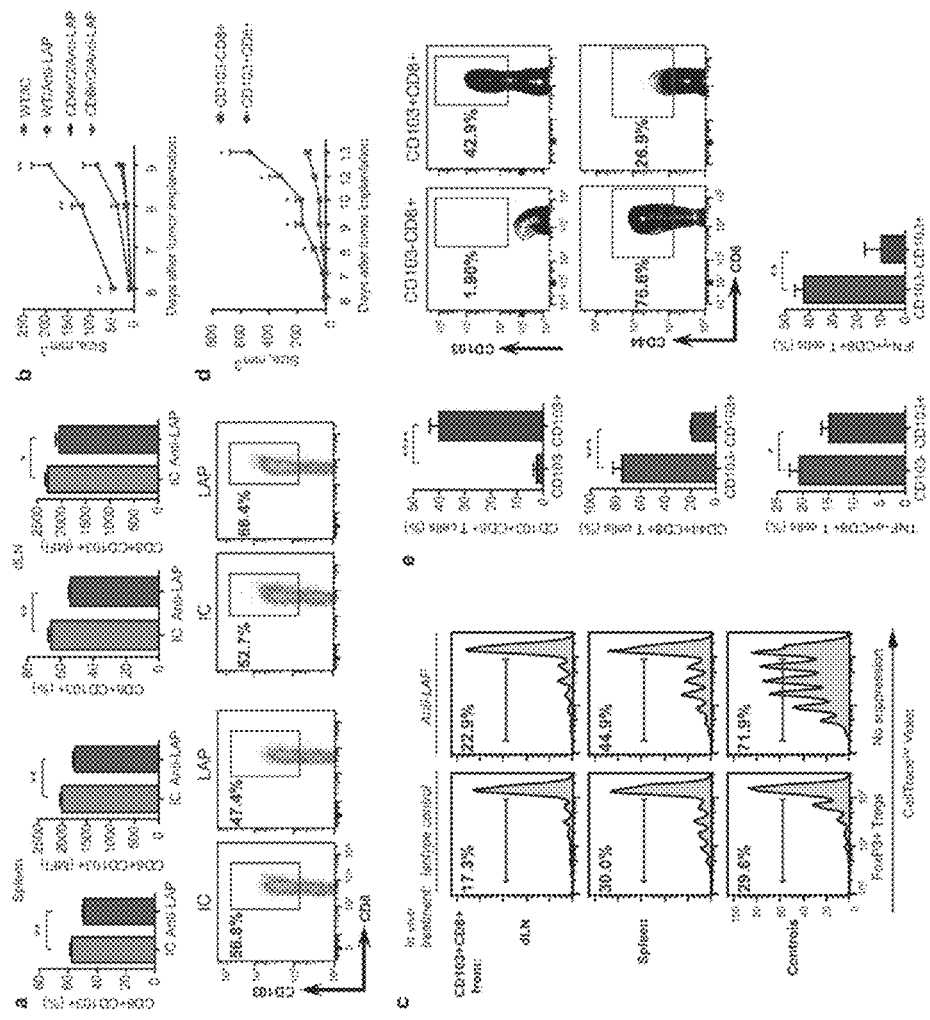
FIGS. 59A-59E demonstrate that anti-LAP antibodies reduce the numbers of suppressive CD103+CD8+ T cells in spleen and draining lymph nodes (dLNs, FIG. 59A). CD8+ but not CD4+ T cells are required for the therapeutic effect of anti-LAP (FIG. 59B). Anti-LAP antibodies reduce the suppressive abilities of CD103+CD8+ T cells in vitro (FIG. 59C). Adoptive transfer of CD103+CD8+ T cells to CD8KO mice abolishes the therapeutic effect of anti-LAP thus demonstrating their suppressive effect in vivo (FIG. 59D). CD103 expression is preserved on CD8+ T cells ater their adoptive transfer and CD103+CD8+ T express reduced levels of activation markers (FIG. 89E). Mice were treated with TW7-28G11.

We also found that anti-LAP treatment leads to a reduced accumulation of CD8+CD103+ T cells in tumor-bearing mice (subcutaneous GBM: FIGS. 23, 28); intracranial GBM: FIGS. 47, 49; melanoma: FIG. 59A), suggesting that these cells may possess suppressive abilities in tumor models. Indeed, while CD8+ T cells were nessesary to mediate the therapeutic effect of anti-LAP (FIG. 59B), CD103+CD8+ T cells isolated from spleen or dLNs of melanoma-bearing mice demonstrated suppressive abilities, which were decreased with anti-LAP treatment in an in vitro assay (FIG. 59C). Moreover, adoptive transfer of these cells to CD8KO mice implanted with melanoma caused worsening of tumor growth (FIG. 59D) indicating that CD103+CD8+ T cells suppress tumor-specific immunity in vivo. Phenotype analysis of these cells demonstrates that CD103+CD8+ T cells express lower pro-inflammatory markers than CD103− cells (FIG. 59E). Thus, anti-LAP is able to target a novel regulatory CD8+ T cell population in tumor.

To determine the levels of LAP expression on different immune cells in mice, intracranial GBM is induced in a syngeneic mouse model (GL261). The levels of LAP expression on the following immune subsets both in the periphery and the brain are examined: $\alpha\beta$ T lymphocytes (CD4+ and CD8+), $\gamma\delta$ T lymphocytes, macrophages (CD11b+) and dendritic cells (DCs, CD11c+).

Mononuclear cells are isolated from GBM using percoll gradient and stained with anti-CD4, -CD8, -$\gamma\delta$TCR, -CD11b, -CD11c antibodies each combined with anti-LAP antibodies for multiparametric flow cytometry analysis. Levels of LAP expression on tumor-infiltrating and peripheral immune cells isolated from the spleen of GBM-bearing and naïve mice are compared.

We previously demonstrated LAP expression on human T lymphocytes and dendritic cells in normal conditions. To analyze the expression of LAP on GBM-associated human immune cells, isolated peripheral blood mononuclear cells (PBMCs) from healthy donors and GBM subjects are stained for live T lymphocytes (CD4+), monocytes (CD11b+) and dendritic cells (mDCs, CD11c+Lin− and pDCs, CD11 c− Lin−CD123+) with human-specific anti-LAP antibodies, according to our published methods.

Phenotype of LAP+ Immune Cells Infiltrating Intracranial GBM Isolated at Different Stages of the Disease Progression in Mouse and Human.

To examine the phenotype of LAP+ immune cells ($\alpha\beta$+ and $\gamma\delta$+ T lymphocytes; CD11b+ and CD11c+ myeloid cells) gene profiling of LAP+ vs. LAP− immune cells is performed by employing Nanostring-based inflammatory arrays as we demonstrated earlier and then validating the expression of specific genes by qRT-PCR (e.g., TGF-$\beta$, TNF-$\alpha$, IL-10, and IL-12). The protein levels of inflammation-related and regulatory genes (e.g., IFN-$\gamma$, GRZB, CD107a, IL-10, FoxP3 on T cells and PD-L1, CD39, CD103 on myeloid cells) is determined under resting and stimulation conditions by flow cytometry and ELISA. To assess the antigen-presentation potential of the myeloid cells, the levels of MHCI, MHCII, CD80, CD86 and CD40 are measured. These studies are performed at different disease stages to determine how LAP expression and cell phenotype are linked to disease progression.

Complementary to our mice studies, the phenotype of LAP+ immune cells isolated from blood (PBMCs) and tumor of glioma patients compared to blood of healthy donors is examined. The expression of inflammation genes by Nanostring and qRT-PCR (e.g., TGF-$\beta$, TNF-$\alpha$, and IL-10) is determined. The protein levels of immune-related genes (e.g., IFN-$\gamma$, GRZB, IL-10, FoxP3 on T cells and PD-L1, CD39, CD103 on myeloid cells) under resting and stimulation conditions by flow cytometry is examined.

Functional Analysis of LAP+ Regulatory Immune Cells Isolated from Tumor

To study the function of immune cells expressing membrane-bound LAP, their ability to influence T cell function is determined. T lymphocytes and myeloid cells are examined. The following parameters are tested to analyze the suppressive abilities of corresponding LAP+ and LAP− cells: a) Function of lymphocytes: T cell proliferation in the presence of LAP+vs. LAP− T cells (both $\alpha\beta$+ and $\gamma\delta$+ T lymphocytes) is examined ex vivo. Two types of assays using non-specific responder T cell activation (with anti-CD3) and antigen-specific activation (with ovalbumin) using OT-II mice (OVA-TCR Tg) are performed.

To study the functional role of $\alpha\beta$+LAP+ and $\gamma\delta$+LAP+ T cells in vivo, adoptive transfer these cells into GBM-bearing mice is performed, and GBM progression followed by monitoring tumor growth (by MRI), assessing survival and examining local and systemic adaptive and innate immune responses.

Phagocytosis of CD11b+LAP+ cells is examined using a macrophage CytoSelect phagocytosis assay (with zymozan substrate). Effects on T cells are measured by co-culturing macrophages (CD11b+LAP+) and dendritic cells (CD11c+LAP+) with naïve T cells and by monitoring their growth by T cell proliferation assay. These experiments interrogate the antigenpresenting ability and suppressive effects of myeloid cells in GBM.

The function of human lymphocytes and myeloid cells isolated from PBMCs of GBM patients and healthy donors (by FACS sorting) is examined and their immune suppression potential evaluated using a T cell proliferation/suppression assay.

Given the immunosuppressive properties of LAP, immune cells expressing this protein express other suppressive markers (FIG. 58B) and demonstrate regulatory roles in the functional assays (FIGS. 58C, 58D). Most biologic roles of LAP described so far were attributed to the αβ+ T cell functions. As demonstrated herein, we found that γδ+LAP+ T cells also possess suppressive abilities (FIGS. 2A-2D) and are strongly upregulated systemically in GBM-bearing mice (FIG. 1E). Our experiments evaluate their pathological function in the context of GBM. In addition, our studies explore a previously uninvestigated role of LAP+ myeloid cells in immune suppression.

Evaluating the Therapeutic Potential of Anti-LAP Antibodies in the Treatment of a GBM Intracranial Mouse Model.

Our results demonstrate that anti-LAP antibodies eliminate tumor growth in a peripheral glioma model and show that they can increase survival in an intracranial GBM model (FIGS. 55C-55H). The effects of the anti-LAP antibodies developed in our lab on the immune system and whether this modulation has a therapeutic effect in an intracranial GBM model are systematically evaluated. Effects of the anti-LAP antibody treatment on the immune response in mice bearing tumor.

To study how anti-LAP influences the immune system, naïve and GBM mice bearing intracranial tumors are treated with anti-LAP and IC antibodies i.p. every other day for three weeks. Spleens and tumors are harvested and the adaptive and innate immune responses examined. The effects of anti-LAP antibody on both the adaptive and innate immune response are determined.

Figure 27:
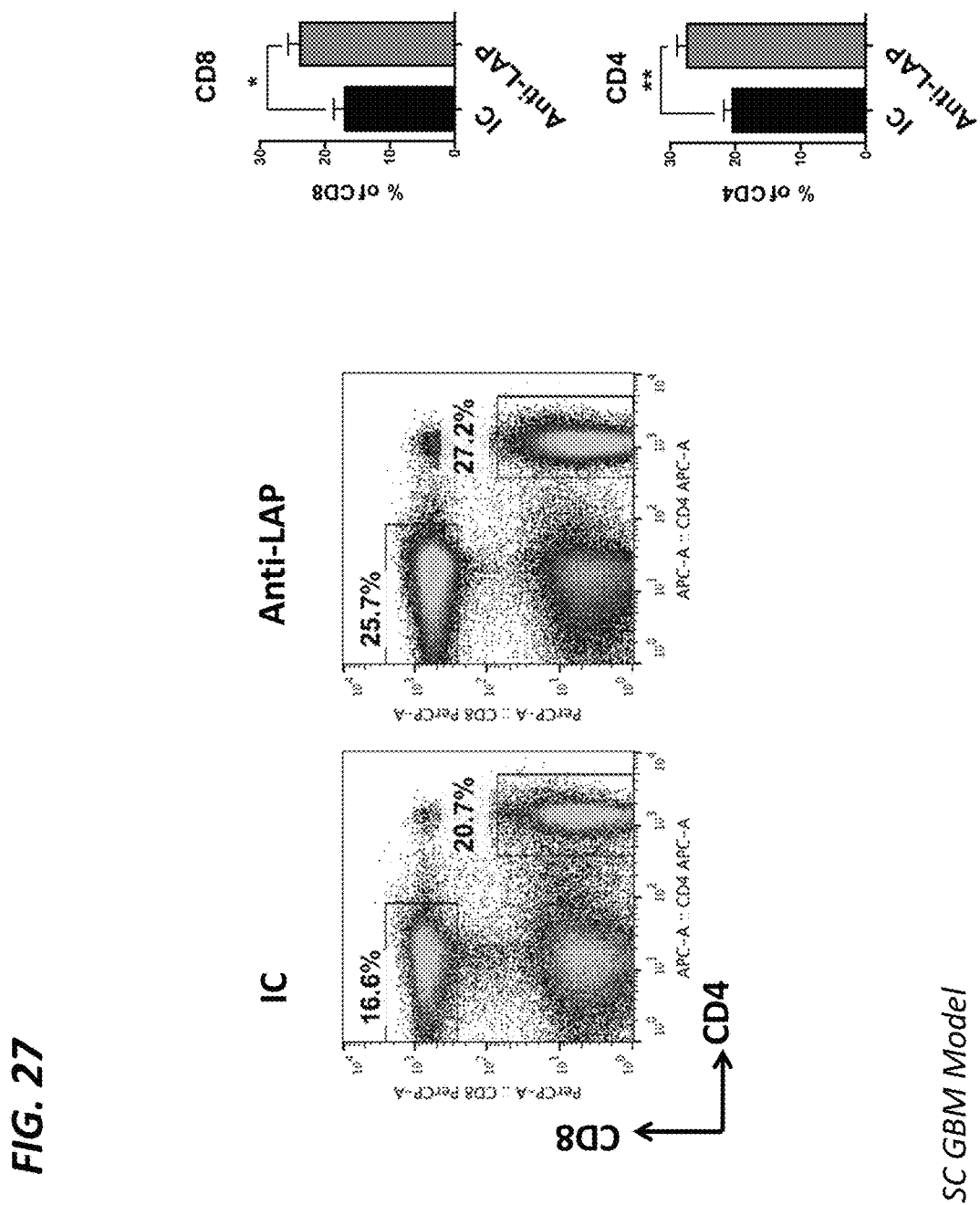
FIG. 27 demonstrates Proportion of T Cell Subsets in Draining lymph nodes (LNs) following anti-LAP treatment.
Figure 41:
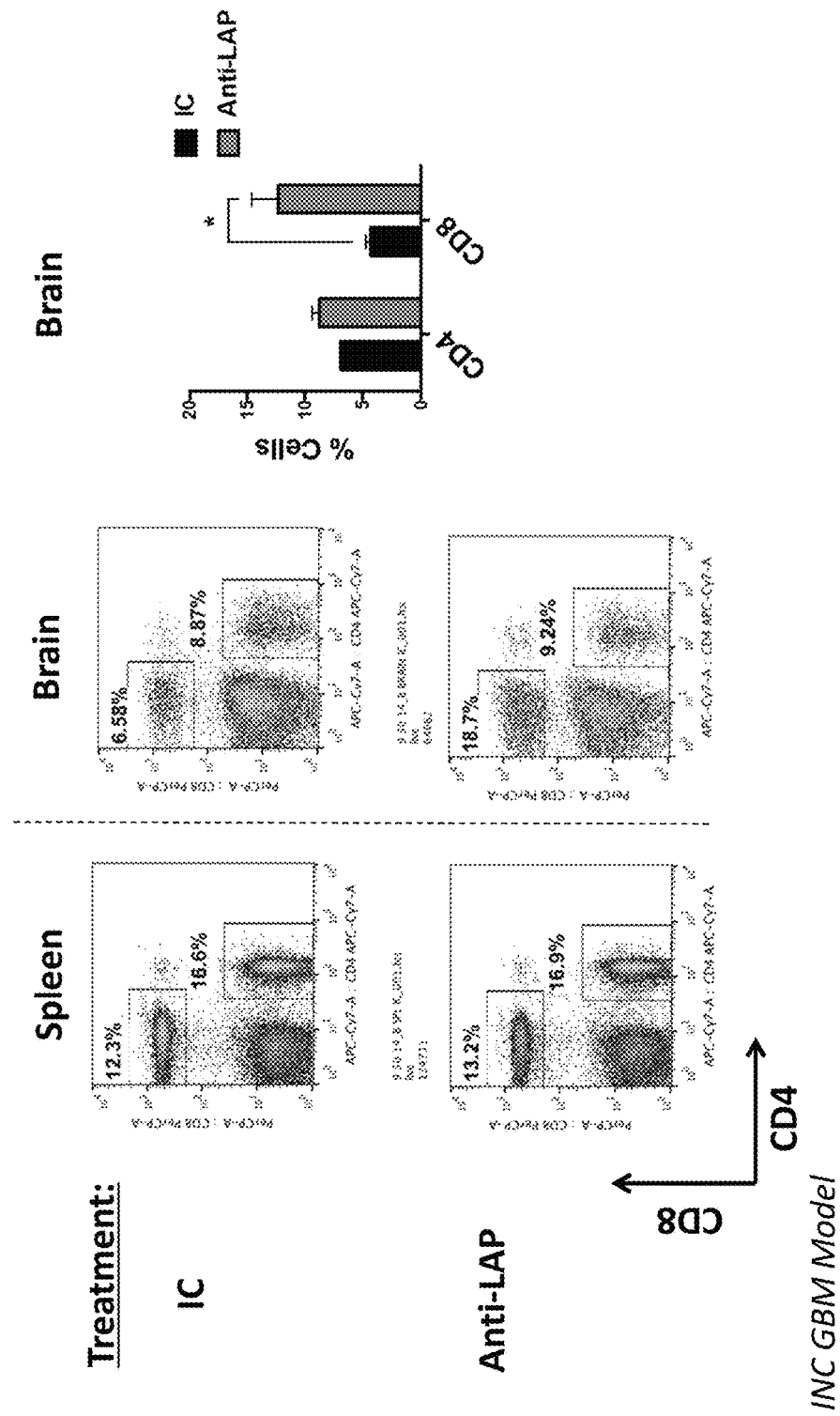
FIG. 41 demonstrates Accumulation of CD8+ T Lymphocytes in GBM Following Anti-LAP Treatment.
Figure 42:
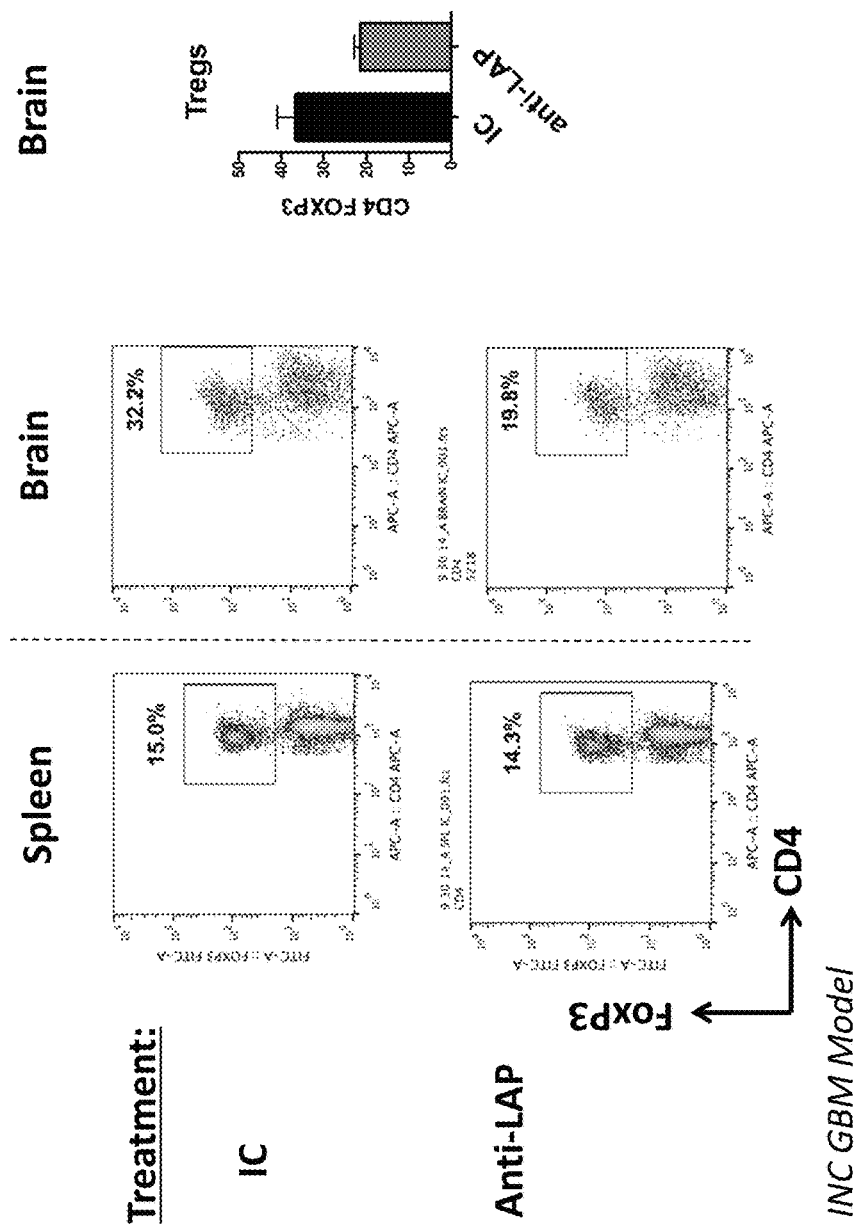
FIG. 42 demonstrates Decrease in CD4+FoxP3+ T Cells in GBM Following Anti-LAP Treatment.
Figure 43:
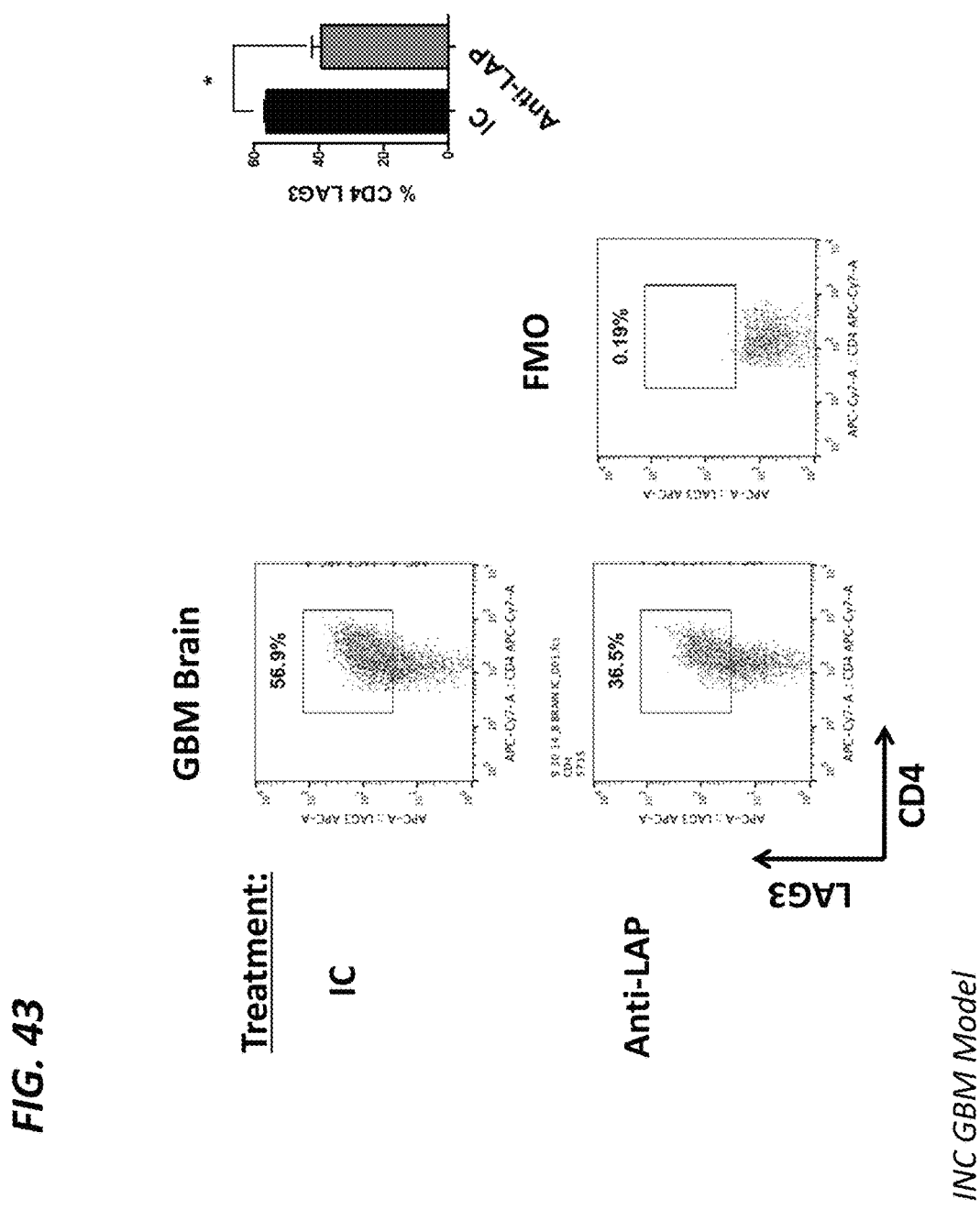
FIG. 43 demonstrates Decrease in LAG+CD4+ T Cells in GBM Following Anti-LAP Treatment.
Figure 44:
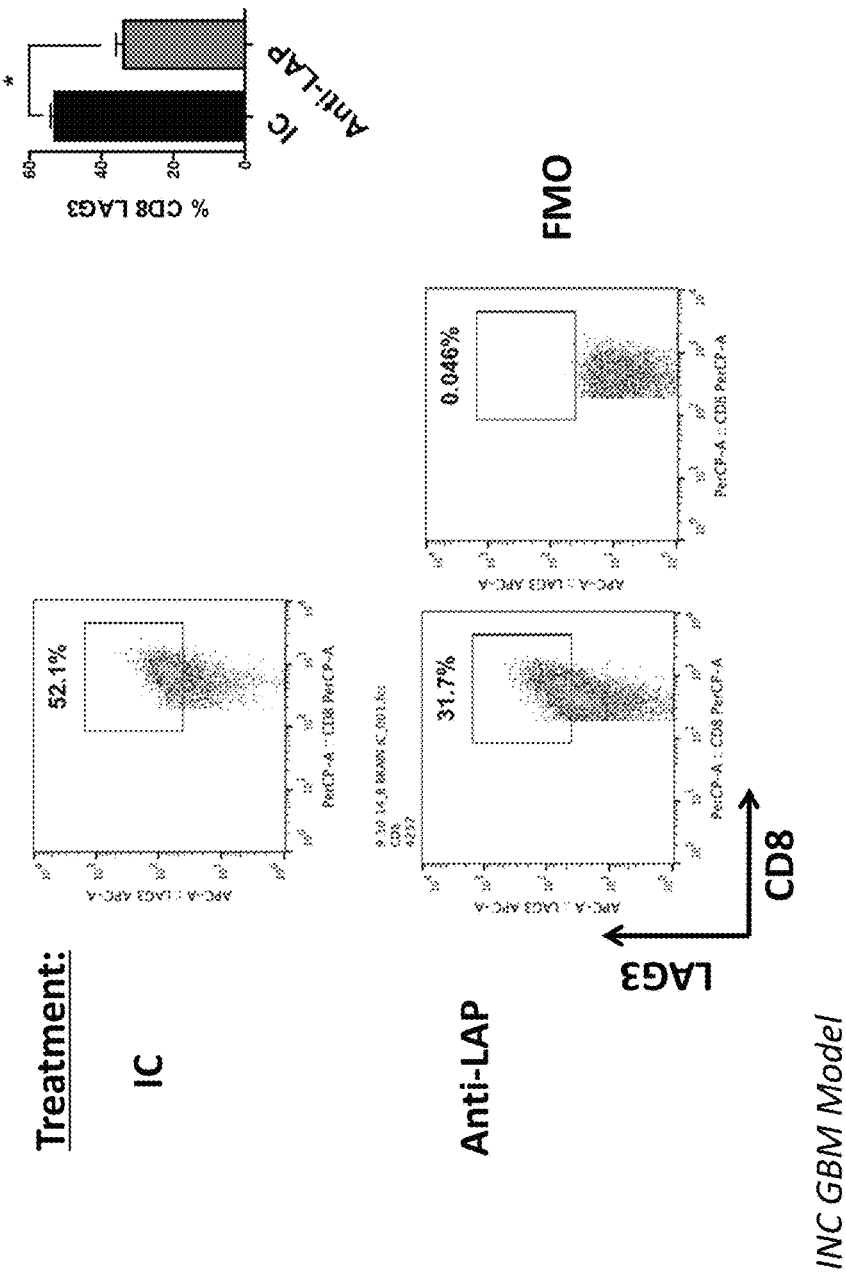
FIG. 44 demonstrates Decrease in LAG+CD8+ T Cells in GBM Following Anti-LAP Treatment.
Figure 45:
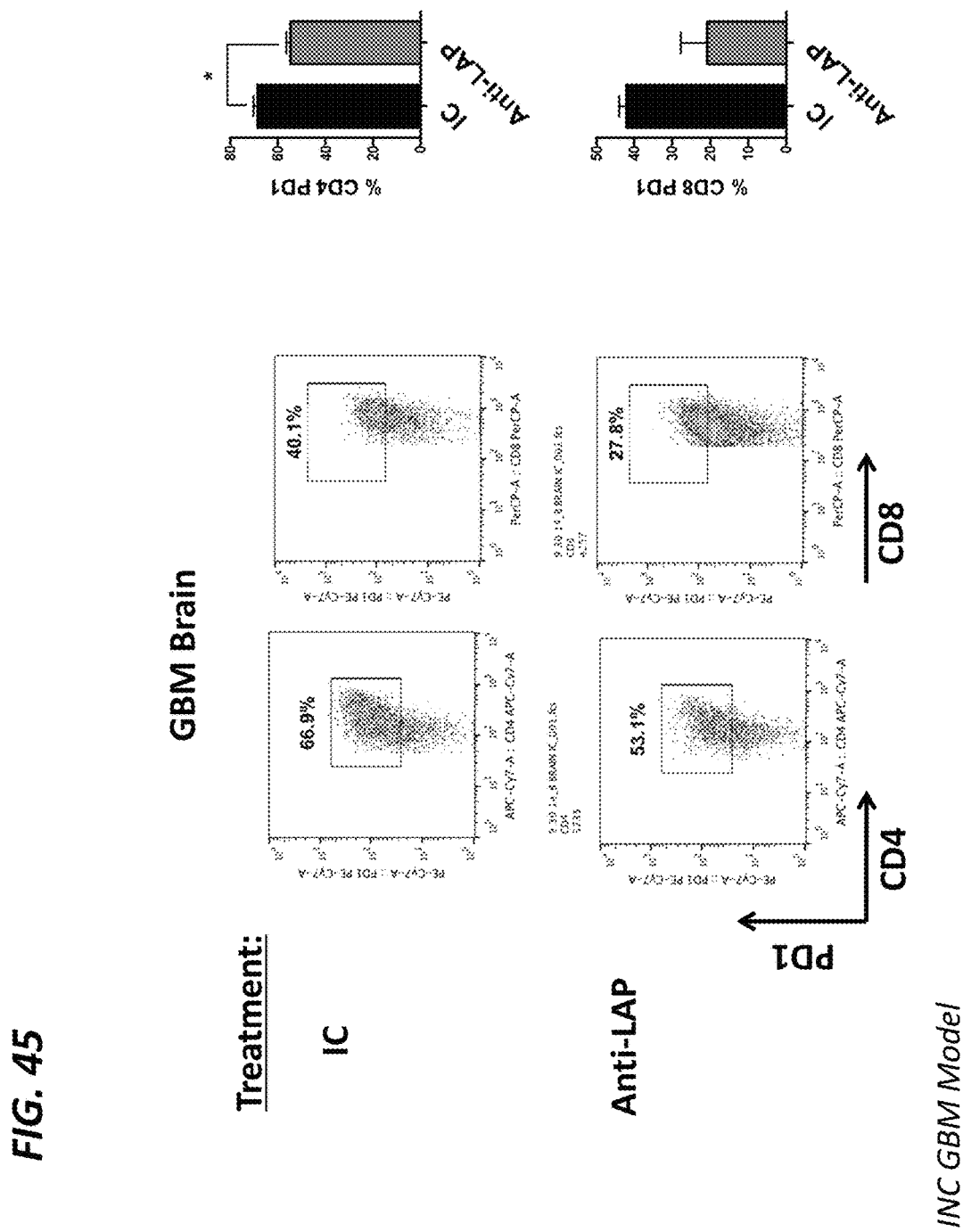
FIG. 45 demonstrates Decrease in PD1+ T Cells in GBM Following Anti-LAP Treatment.
Figure 46:
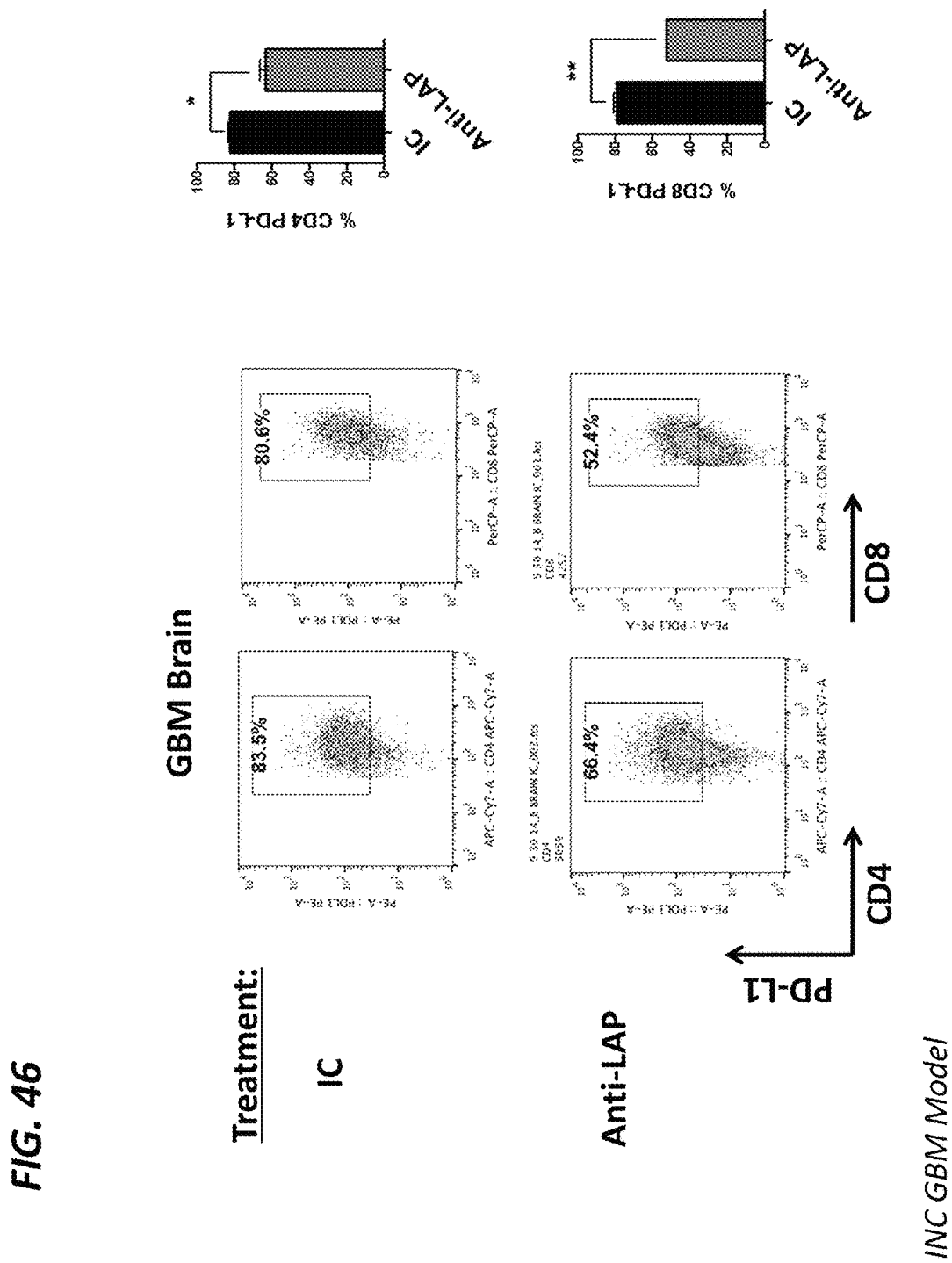
FIG. 46 demonstrates Decrease in PD-L1+ T Cells in GBM Following Anti-LAP Treatment.
Figures 56A, 56B:
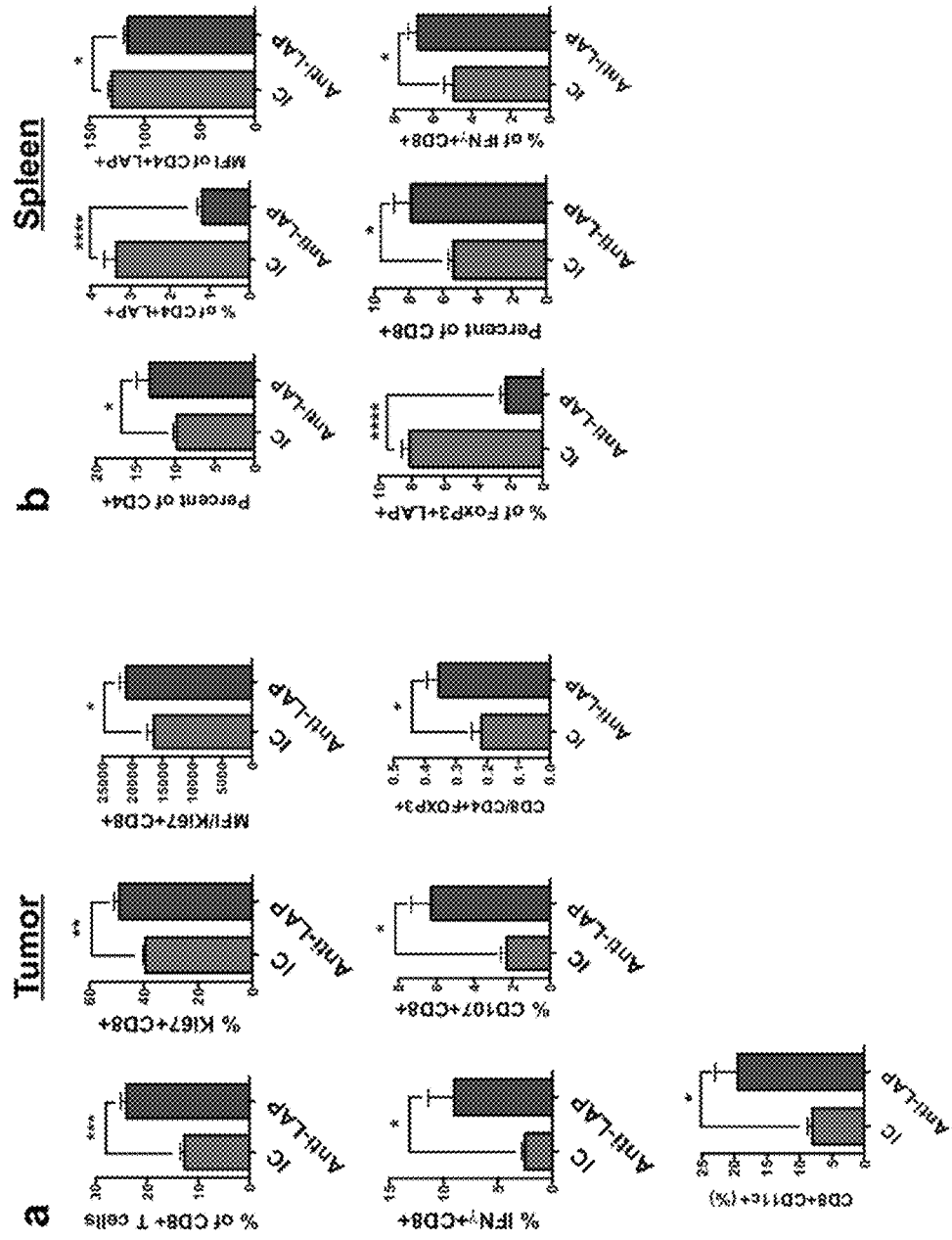
FIGS. 56A-56B depict effects of anti-LAP antibodies on adaptive immune responses using a melanoma tumor model. Effects in the intratumoral (FIG. 56A) and peripheral (FIG. 56B) immune responses are shown. Mice were treated with TW7-28G11.

1) Adaptive immune response. Th1/Th2 and cytotoxic T lymphocyte (CTL) responses are evaluated by analyzing the frequencies of T lymphocyte subsets (CD4+ and CD8+) in tumor and spleen. The expression of surface membrane-bound and intracellular immunomodulators, such as IFN-γ, on both subsets are examined; LAP, LAG, CD103, PD1, Tim3, IL-10, FoxP3, IL-17 and TGF-β on CD4+ T cells; CD107, GRZB and perforin on CD8+ T lymphocytes by flow cytometry. In GL261 glioma (FIGS. 27 and 41, treated by 16B4) and B16 melanoma (FIG. 56A, treated by 28G11) models, we found that tumors of mice treated with anti-LAP are infiltrated by increased numbers of CD8+ T cells. In the melanoma model, following anti-LAP treatment, CD8+ tumor-infiltrating T cells had better proliferation capacity, based on the expression of Ki67 and expressed higher levels of pro-inflammatory mediators (FIG. 56A). Moreover, the ratio of CD8+ T cells/Tregs was also higher after anti-LAP treatment. The number of CD8+ T cells and their pro-inflammatory phenotype was also higher in the periphery (FIG. 56B).

2) Innate immune response. Tumor-infiltrating antigen-presenting cells including dendritic cells (CD11c+) and macrophages (CD11b+) are investigated by examining their frequencies and expression of suppression markers (PD-L1, CD39, CD103), antigen-presentation markers (MHCI, MHCII) and co-stimulatory molecules (CD40, CD80, CD86) by flow cytometry. FIGS. 57A-57J.

The ability of these myeloid cell subsets to produce different cytokines (IL-1β, IL-6, IL10, IL-12, IL-23, and TGF-β) were assessed. Macrophages and DCs were sorted, stimulated with anti-CD40 antibody or lipopolysaccharide (LPS), followed by gene expression analysis.

To analyze functional immune response following anti-LAP in GBM, GL261 glioma cells expressing ovalbumin (GL261-OVA) are injected intracranially and mice treated with anti-LAP antibodies. OVA-specific CD4+ and CD8+ T cell immune response are measured in these mice.

Therapeutic Value of Anti-LAP Antibodies in the Experimental GBM Model.

Antibodies targeting GBM associated immunosuppression can be used as a treatment. The anti-LAP antibodies generated in our lab are used to test their therapeutic potential in GBM.

GL261 cells were implanted intracranially in C57BL/6 mice which were then treated with anti-LAP (100 µg/mouse) every other day starting from the second day following tumor implantation. GBM growth was monitored by magnetic resonance imaging (MRI) and survival (FIGS. 85A-85N). GBM invasion and angiogenesis is analyzed by hematoxylin and eosin (H&E) and immunohistochemical anti-CD31 staining, 3) transcriptional and functional profile of macrophages recruited to GBM is performed by Nanostring and their effects on T-cell proliferation in vitro; and 4) local and peripheral immune responses are evaluated by analyzing the frequency of cytotoxic and regulatory T cells and their function. Since LAP can induce cell invasion, whether GBM invasion is reduced by anti-LAP treatment is anaylzed in vitro (Boyden chambers) and in vivo (histopathology).

As described herein, using an aggressive intracranial GBM model, we observed enhanced survival of mice after treatment with anti-LAP. In some embodiments of the aspects described herein, higher doses of anti-LAP antibody and starting treatment early can be used to enhance the therapeutic effects of anti-LAP antibodies against GBM. In addition, given that LAP is produced by different immune cells in the intracranial GBM and can attract monocytes, the anti-LAP treatment can result in lower tumor infiltration by macrophages. Considering the pathological contribution of myeloid cells to GBM, anti-LAP treatment can lead to reduced invasion and local tumor immunosuppression, features significantly contributed by macrophages.

Enhanced Immune T Cells Memory Against Tumor-Associated Antigens.

Figure 61:
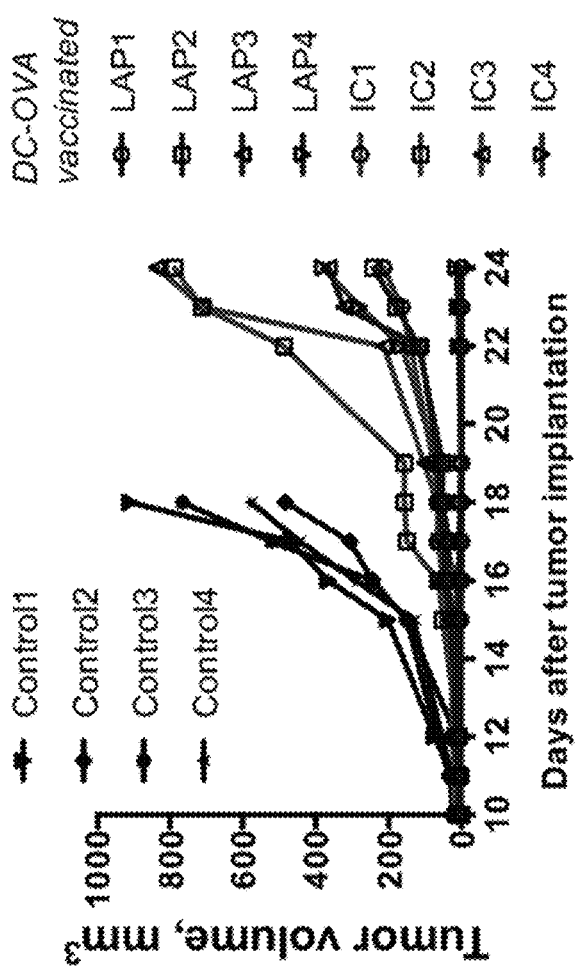
FIG. 61 demonstrates that anti-LAP treatment combined with dendritic cell vaccination improves treatment of B16 melanoma. Mice were prevaccinated with ovalbumin loaded DCs and treated with TW7-28G11. A week later, the mice were implanted with B16-OVA melanoma and tumor growth was measured. Naïve (non-vaccinated mice) were used as a control for vaccination.
Figure 67:
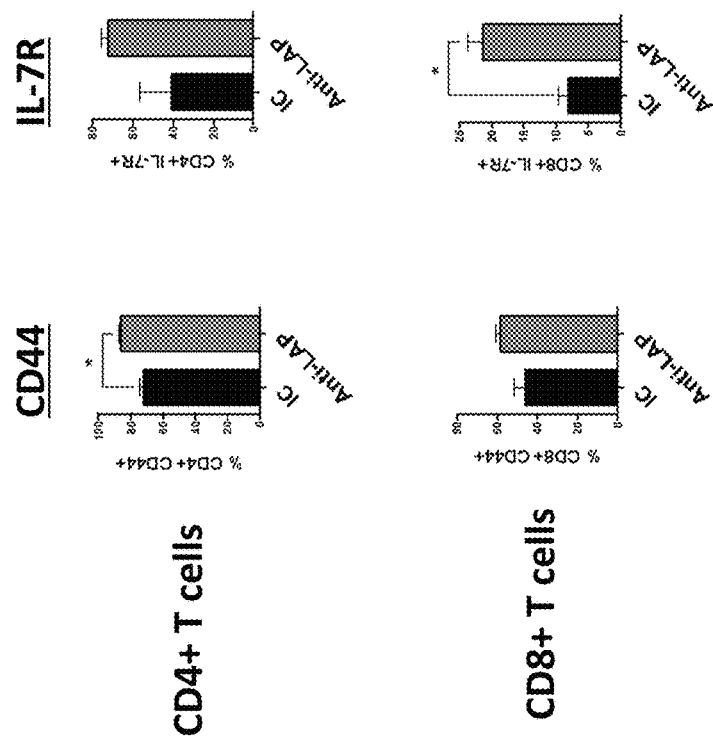
FIG. 67 demonstrates that markers of memory T Cells are up-regulated in GBM following anti-LAP treatment.

We found that tumor-infiltrating T cells in mice bearing intracranial GBM and treated with anti-LAP expressed higher levels of memory markers (IL7R and CD44, FIG. 67). Based on these results, we hypothesized that anti-LAP can enhance immune memory and benefit from prevaccination with a DC vaccine expressing a tumor-associated antigen. We tested this hypothesis by pre-vaccinating mice with ovalbumin loaded dendritic cells, treating the mice with anti-LAP (16B4 clone) and injecting intracranial tumors (GL261-OVA) a week later (FIG. 60A). We followed disease development by MRI imaging and survival. All mice treated with anti-LAP did not develop tumors, while four out of five IC treated mice developed GBM and had to be sacrificed thus supporting our hypothesis (FIGS. 60B, 60C). To test the long-term immunity, remaining mice were rechalenged three months later with subcutaneous GL261-OVA. These mice did not develop tumors indicating that they preserved immune memory against this tumor. Anti-LAP treated mice expressed higher levels of IL7R (FIGS. 60D, 60E) and tetramer signal was higher on CD8+ T cells (FIG. 60F) as comaped to naïve mice or the mouse treated with IC suggesting that anti-LAP increases CD8+ tumor-antigen-specific T cells. These observations were supported by similar observations in a melanoma model treated with 28G11 clone of anti-LAP (FIG. 61). Thus, anti-LAP may enhance immune memory and would potentially benefit from concomitant vaccination with tumor-associated antigens.

Example 2

Preparation of Anti-LAP Antibody Constructs

Total RNA was isolated from TW7-28G11 hybridoma cells using TRIZOL® Reagent (Thermo Fisher Scientific), according to the technical manual for TRIZOL® Reagent. The total RNA was analyzed by agarose gel electrophoresis.

Total RNA was reverse transcribed into cDNA using isotype-specific anti-sense primers or universal primers following the technical manual of PRIMESCRIPT™ 1st Strand cDNA Synthesis Kit. The antibody fragments of $V_H$ and $V_L$ from TW7-28G11 hybridoma cells were amplified according to the standard operating procedure of RACE of GenScript.

Amplified antibody fragments were separately cloned into a standard cloning vector using standard molecular cloning procedures.

Colony PCR screening was performed to identify clones with inserts of correct sizes. No less than five single colonies with inserts of correct sizes were sequenced for each antibody fragment.

Five single colonies from TW7-28G11 hybridoma cells with correct $V_H$ and $V_L$ insert sizes were sent for sequencing. The $V_H$ and $V_L$ genes of five different clones were found nearly identical. The consensus nucleotide sequence, listed herein as SEQ ID NO: 7 and SEQ ID NO: 12, are believed to be the sequence of the antibody produced by the hybridoma TW7-28G11.

The $V_H$ CDR1-CDR3 amino acid sequences of the TW7-28G11 antibody are provided herein as SEQ ID NOs: 9-11. The $V_L$ CDR1-CDR3 amino acid sequences of the TW7-28G11 antibody are provided herein as SEQ ID NOs: 14-16. Suitable framework sequences using the $V_H$ and/or $V_L$ CDR sequences of the TW7-28G11 antibody to generate humanized, CDR-grafted, and/or chimeric antibodies and/or antigen-binding fragments thereof can be identified and selected using techniques known to those of skill in the art and as described elsewhere herein.

Total RNA is isolated from TW7-16B4 hybridoma cells using, for example, TRIZOL® Reagent. The total RNA is analyzed using, for example, agarose gel electrophoresis.

Total RNA is reverse transcribed into cDNA using, for example, isotype-specific anti-sense primers or universal primers following the technical manual of PRIMESCRIPT™ 1st Strand cDNA Synthesis Kit. The antibody fragments of $V_H$ and $V_L$ from TW7-16B4 hybridoma cells are amplified using, for example, the standard operating procedure of RACE of GenScript.

Amplified antibody fragments are separately cloned into a standard cloning vector using standard molecular cloning procedures.

Colony PCR screening is performed to identify clones with inserts of correct sizes. For example, at least three or at least five single colonies with inserts of correct sizes are sequenced for each antibody fragment.

Single colonies from TW7-16B4 hybridoma cells with correct $V_H$ and $V_L$ insert sizes are sent for sequencing and a consensus nucleotide sequence identified from which the amino acid sequences of the $V_H$ and $V_L$ and corresponding CDR1-CDR3 regions are identified.

Suitable framework sequences using the $V_H$ and/or $V_L$ CDR sequences of the TW7-16B4 antibody to generate humanized, CDR-grafted, and/or chimeric antibodies and/or antigen-binding fragments thereof can be identified and selected using techniques known to those of skill in the art and as described elsewhere herein.

---

The invention claimed is:

1. A method of treating a cancer in a human subject in need thereof comprising administering a pharmaceutical composition comprising a humanized form of an antibody which binds latency-associated peptide (LAP), the antibody comprising the heavy chain complementarity determining regions CDR1, CDR2, and CDR3 and the light chain complementarity determining regions CDR1, CDR2, and CDR3 of the antibody produced by the hybridoma designated TW7-28G11 (ATCC Accession No. PTA-124319), or an antigen-binding fragment thereof, to said human subject in an effective amount to decrease the number or activity of immunosuppressive T cells, thereby treating the cancer.

2. The method of claim 1, wherein the humanized antibody or antigen-binding fragment thereof binds LAP on the surface of an immunosuppressive T cell associated with said cancer.

3. The method of claim 1, wherein said immunosuppressive T cells infiltrate a tumor associated with said cancer.

4. The method of claim 3, wherein said immunosuppressive T cells are regulatory T cells.

5. The method of claim 3, wherein said tumor is a glioblastoma, a colorectal carcinoma, or a melanoma.

6. The method of claim 1 further comprising administering a chemotherapeutic or immunomodulatory agent to said subject.

7. The method of claim 6, wherein the immunomodulatory agent comprises an immune checkpoint modulator.

8. The method of claim 7, wherein the immune checkpoint modulator modulates the effects of a polypeptide selected from the group consisting of PD-1, PD-L1, PDL2, CTLA4, LAG3, TIM3, TIGIT, and/or CD103.

9. The method of claim 1 further comprising selecting said human subject as a candidate for treatment with the humanized antibody or antigen-binding fragment thereof:
identifying LAP+ T cells in said tumor of said human subject; and
selecting said human subject for treatment with the humanized antibody or antigen-binding fragment thereof on the basis of said identifying LAP+ T cells in said tumor.

10. The method of claim 1, wherein binding of the humanized antibody or antigen-binding fragment thereof to a LAP-TGF-β complex inhibits release of TGF-β from said LAP-TGF-β complex.

11. The method of claim 1, wherein the cancer is refractory to treatment with an immune checkpoint inhibitor.

12. The method of claim 1, wherein the humanized antibody or antigen-binding fragment thereof is a Fab fragment, a Fab' fragment, a Fd fragment, a Fd' fragment, a Fv fragment, a dAb fragment, a F(ab')$_2$ fragment, a single chain fragment, a diabody, or a linear antibody.

13. The method of claim 1, wherein the antibody produced by TW7-28G11 comprises heavy chain complementarity determining region CDR1, CDR2, and CDR3 sequences set forth in SEQ ID NOs: 9, 10, and 11, respectively, and light chain complementarity determining region CDR1, CDR2, and CDR3 sequences set forth in SEQ ID NOs: 14, 15, and 16, respectively.

* * * * *

UNITED STATES PATENT AND TRADEMARK OFFICE
CERTIFICATE OF CORRECTION

PATENT NO. : 10,287,347 B2
APPLICATION NO. : 15/649373
DATED : May 14, 2019
INVENTOR(S) : Howard L. Weiner et al.

Page 1 of 1

It is certified that error appears in the above-identified patent and that said Letters Patent is hereby corrected as shown below:

In the Claims

In Claim 9, at Column 122, Line 39, the text:
"humanized antibody or antigen-binding fragment thereof:"
Should be replaced with:
-- humanized antibody or antigen-binding fragment thereof by: --.

Signed and Sealed this
Eighteenth Day of February, 2020

Andrei Iancu
*Director of the United States Patent and Trademark Office*